US011613760B2

(12) United States Patent
Oikawa

(10) Patent No.: US 11,613,760 B2
(45) Date of Patent: Mar. 28, 2023

(54) COMPOSITIONS AND METHODS FOR INCREASING PLANT GROWTH AND IMPROVING MULTIPLE YIELD-RELATED TRAITS

(71) Applicant: AFINGEN, INC., Emeryville, CA (US)

(72) Inventor: Ai Oikawa, Emeryville, CA (US)

(73) Assignee: AFINGEN, INC., Emeryville, CA (US)

( * ) Notice: Subject to any disclaimer, the term of this patent is extended or adjusted under 35 U.S.C. 154(b) by 139 days.

(21) Appl. No.: 16/965,809

(22) PCT Filed: Jan. 29, 2019

(86) PCT No.: PCT/US2019/015688

§ 371 (c)(1),
(2) Date: Jul. 29, 2020

(87) PCT Pub. No.: WO2019/148193

PCT Pub. Date: Aug. 1, 2019

(65) Prior Publication Data

US 2021/0054392 A1 Feb. 25, 2021

Related U.S. Application Data

(60) Provisional application No. 62/623,279, filed on Jan. 29, 2018.

(51) Int. Cl.
*C12N 15/82* (2006.01)
*C07K 14/47* (2006.01)

(52) U.S. Cl.
CPC .......... *C12N 15/8223* (2013.01); *C07K 14/47* (2013.01)

(58) Field of Classification Search
None
See application file for complete search history.

(56) References Cited

U.S. PATENT DOCUMENTS

| | | | |
|---|---|---|---|
| 4,237,224 | A | 12/1980 | Cohen et al. |
| 4,945,050 | A | 7/1990 | Sanford et al. |
| 5,100,792 | A | 3/1992 | Sanford et al. |
| 2012/0272406 | A1 | 10/2012 | Guan et al. |
| 2012/0322122 | A1 | 12/2012 | Shen et al. |
| 2013/0298282 | A1 | 11/2013 | Rouster et al. |
| 2014/0007287 | A1 | 1/2014 | Martin et al. |
| 2017/0298375 | A1 | 10/2017 | Han et al. |

FOREIGN PATENT DOCUMENTS

| | | | |
|---|---|---|---|
| JP | 5403206 | B2 | 1/2014 |
| WO | 2005/080580 | A2 | 9/2005 |
| WO | 2005/120215 | A1 | 12/2005 |
| WO | 2007141705 | A2 | 12/2007 |
| WO | 2012/103555 | A2 | 8/2012 |

OTHER PUBLICATIONS

Sequence Accession ADH50116, Oct. 16, 2008, sequence alignment attached at the end of the office action. (Year: 2008).*
Sequence Accession AD236916, Jun. 30, 2005, sequence alignment attached at the end of the office action. (Year: 2005).*
International Search Report of PCT/US2019/015688 dated Apr. 15, 2019, 2 pages.
Esau, Plant Anatomy (1965).
Cong et al., "Multiplex Genome Engineering Using CRISPR/Cas Systems," Science 339(6121): 819-23 (2013).
Wiedenheft et al., "RNA-Guided Genetic Silencing Systems in Bacteria and Archaea," Nat 482:331-338 (2012).
Turner and Somerville, "Collapsed Xylem Phenotype of *Arabidopsis* Identifies Mutants Deficient in Cellulose Deposition in the Secondary Cell Wall," Plant Cell 9(5):689-701 (1997).
Brown et al., "Identification of Novel Genes in *Arabidopsis* Involved in Secondary Cell Wall Formation Using Expression Profiling and Reverse Genetics," Plant Cell 17(8):2281-95 (2005).
Oikawa et al., "An Integrative Approach to the Identification of *Arabidopsis* and Rice Genes Involved in Xylan and Secondary Wall Development," PLoS ONE 5(11):e15481 (2010).
Hirano et al., "Survey of Genes Involved in Rice Secondary Cell Wall Formation Through a Co-Expression Network," Plant Cell Physiol. 54(1):1803-21 (2013).
Hao and Mohnen, "A Review of Xylan and Lignin Biosynthesis: Foundation for Studying *Arabidopsis* Irregular Xylem Mutants with Pleiotropic Phenotypes," Crit. Rev. Biochem. Mol. Biol. 49(3):212-41 (2014).
The Bio-Analytic Resource for Plant Biology, available online at http://bar.utoronto.ca/ and described in Toufighi et al., "The Botany Array Resource: e-Northerns, Expression Angling, and Promoter Analyses," The Plant Journal 43:153-63 (2005).
Oikawa et al., "Golgi-Localized Enzyme Complexes for Plant Cell Wall Biosynthesis," Trends Plant Sci. 18:49-58, (2013).
Jefferson et al., "GUS Fusions: b Glucuronidase as a Sensitive and Versatile Gene Fusion Marker in Higher Plants," EMBO J. 6:3901-3907 (1987).
Fan et al., "AtCesA8-driven OsSUS3 Expression Leads to Largely Enhanced Biomass Saccharification and Lodging Resistance by Distinctively Altering Lignocellulose Features in Rice,"Biotechnol. Biofuels 10:221 (2017).
Yang et al., "Engineering Secondary Cell Wall Deposition in Plants," Plant Biotechnol. J. 11(3):325-35 (2013).
Tak et al., "Overexpression of MusaMYB31, a R2R3 type MYB Transcription Factor Gene Indicate its Role as a Negative Regulator of Lignin Biosynthesis in Banana," PLoS ONE 12(2):e0172695 (2017).
Agarwal et al., "MYB31/MYB42 Syntelogs Exhibit Divergent Regulation of Phenylpropanoid Genes in Maize, Sorghum and Rice," Sci Rep. 6:28502 (2016).
Poovaiah et al., "Sugarcane Transgenics Expression MYB Transcription Factors Show Improved Glucose Release," Biotechnol Biofuels 9:143 (2016).
Zhou et al., "Changing a Conserved Amino Acid in R2R3-MYB Transcription Repressors Results in Cytoplasmic Accumulation and Abolishes Their Repressive Activity in *Arabidopsis*," Plant J. 84(2):395-403 (2015).

(Continued)

*Primary Examiner* — Elizabeth F McElwain
(74) *Attorney, Agent, or Firm* — Brooks Kushman P.C.

(57) ABSTRACT

The present invention relates to transgenic plants with vascular xylem tissue-targeting overexpression of tissue factors involved in vascular xylem cell development.

9 Claims, 29 Drawing Sheets

Specification includes a Sequence Listing.

(56) References Cited

OTHER PUBLICATIONS

Handakumbura and Hazen, "Transcriptional Regulation of Grass Secondary Cell Wall Biosynthesis: Playing Catch-Up With *Arabidopsis thaliana*," Front. Plant Sci. 3:74 (2012).
Shen et al., "Functional Characterization of the Switchgrass (*Panicum virgatum*) R2R3-MYB Transcription Factor PvMYB4 for Improvement of Lignocellulosic Feedstocks," New Phytol. 193:121-36 (2012).
Wang and Dixon, "On-Off Switches for Secondary Cell Wall Biosynthesis," Mol. Plant. 5(2):297-303 (2012).
Bedon et al., "Subgroup 4 R2R3-MYBs in Conifer Trees: Gene Family Expansion and Contribution to the Isoprenoid- and Flavonoid-Oriented Responses," Journal of Experimental Botany 61(14):3847-3864 (2010).
Fornalé et al., "ZmMYB31 Directly Represses Maize Lignin Genes and Redirects the Phenylpropanoid Metabolic Flux," Plant J. 64(4):633-44 (2010).
Sonbol et al., "The Maize ZmMYB42 Represses the Phenylpropanoid Pathway and Affects the Cell Wall Structure, Composition and Degradability in *Arabidopsis thaliana*," Plant Mol. Biol. 70:283-96 (2009).
Legay et al., "Molecular Characterization of EgMYB1, a Putative Transcriptional Repressor of the Lignin Biosynthetic Pathway," Plant Sci. 173:542-9 (2007).
Fornalé et al., "Down-Regulation of the Maize and *Arabidopsis thaliana* Caffeic Acid O-methyl-transferase Genes by Two New Maize R2R3-MYB Transcription Factors," Plant Mol. Biol. 62(6):809-23 (2006).
Preston et al., "AtMYB32 is Required for Normal Pollen Development in *Arabidopsis thaliana*," Plant J. 40(6):979-95 (2004).
Xu et al., "Overexpression of the Transcription Factors GmSHN1 and GmSHN9 Differentially Regulates Wax and Cutin Biosynthesis, Alters Cuticle Properties, and Changes Leaf Phenotypes in *Arabidopsis*," Int. J. Mol. Sci. 17(4):E587 (2016).
Djemal and Khoudi, Isolation and Molecular Characterization of a Novel WIN/SHN1 Ethylene-Responsive Transcription Factor TdSHN1 From Durum Wheat (*Triticum turgidum* L. subsp. durum) Protoplasma 252(6):1461-73 (2015).
Al-Abdallat et al., "Over-Expression of SISHN1 Gene Improves Drought Tolerance by Increasing Cuticular Wax Accumulation in Tomato," Int. J Mol. Sci. 15(11):19499-515 (2014).
Sela et al., "Overexpression of AtSHN1/WIN1 provokes Unique Defense Responses," PLoS One 8(7):e70146 (2013).
Wang et al., "An Ethylene Response Factor OsWR1 Responsive to Drought Stress Transcriptionally Activate Wax Synthesis Related Genes and Increases Wax Production in Rice," Plant Mol Biol. 78(3):275-88 (2012).
Shi et al., "SHINE Transcription Factors Act Redundantly to Pattern the Archetypal Surface of *Arabidopsis* Flower Organs," PLoS Genet. 7(5):e1001388 (2011).
Kannangara et al., "The Transcription Factor WIN1/SHN1 Regulates Cutin Biosynthesis in *Arabidopsis thaliana*," Plant Cell 19(4):1278-94 (2007).
Fromm et al., "Expression of Genes Transferred into Monocot and Dicot Plant Cells by Electroporation," Proc. Natl. Acad. Sci. USA 82:5824 (1985).
Aharoni et al., "The SHINE clade of AP2 Domain Transcription Factors Activates Wax Biosynthesis, Alters Cuticle Properties, and Confers Drought Tolerance When Overexpressed in *Arabidopsis*," Plant Cell 16(9):2463-80 (2004).
Hussey et al., "Navigating the Transcriptional Roadmap Regulating Plant Secondary Cell Wall Deposition," Front. Plant Sci. 4:325 (2013).
Yang and Wang, "Molecular Mechanisms for Vascular Development and Secondary Cell wall Formation," Front. Plant Sci. 7:356 (2016).
Ambavaram et al., "Coordinated Activation of Cellulose and Repression of Lignin Biosynthesis Pathways in Rice," Plant Physiol. 155(2):916-31 (2011).
Legay et al., "EgMYB1, an R2R3 MYB Transcription Factor from Eucalyptus Negatively Regulates Secondary Cell Wall Formation in *Arabidopsis* and Poplar," New Phytol. 188(3):774-86 (2010).
Wang et al., "Mutation of WRKY Transcription Factors Initiates Pith Secondary Wall Formation and Increases Stem Biomass in Dicotyledonous Plants," Proc. Natl. Acad. Sci. U. S. A. 107(51):22338-43 (2010).
Yang et al., "PtrWRKY19, a Novel WRKY Transcription Factor, Contributes to the Regulation of Pith Secondary Wall Formation in Populus trichocarpa," Sci. Rep. 6:18643 (2016).
Bourouis et al., "Vectors Containing a Prokaryotic Dihydrofolate Reductase Gene Transform *Drosophila* Cells to Methotrexate-resistance," EMBO J. 2:1099-1104 (1983).
Fraley et al., "Expression of Bacterial Genes in Plant Cells," Proc. Nat'l Acad. Sci. USA 80:4803-4807 (1983).
Odell et al., "Identification of DNA Sequences Required for Activity of the Cauliflower Mosaic Virus 35S Promoter," Nature 313(6005):810-812 (1985).
Coruzzi et al., "Tissue-specific and light-regulated expression of a pea nuclear gene encoding the small subunit of ribulose-1,5-bisphosphate carboxylase," EMBO J. 3(8):1671-1679 (1984).
Joung & Sander, "TALENs: A Widely Applicable Technology for Targeted Genome Editing," Nat Rev Mol Cell Biol. 14:49-55 (2013).
Studier et al., "Use of T7 RNA Polymerase to Direct Expression of Cloned Genes," Gene Expression Technology vol. 185 (1990).
Sambrook et al., Molecular Cloning: A Laboratory Manual, Second Edition, Cold Spring Harbor, NY:Cold Spring Harbor Press (1989).
Orlando: Acad. Press; and Fitch et al., "Somatic Embryogenesis and Plant Regeneration from Immature Zygotic Embryos of Papaya (*Carica papaya* L.)," Plant Cell Rep. 9:320 (1990).
Fraley et al., "Liposome-mediated Delivery of Tobacco Mosaic Virus RNA Into Tobacco Protoplasts: A Sensitive Assay for Monitoring Liposome-protoplast Interactions," Proc. Natl. Acad. Sci. USA 79:1859-63 (1982).
Bevan, "Binary Agrobacterium Vectors for Plant Transformation," Nucleic Acids Res. 12:8711-8721 (1984).
Frisch et al., "Complete Sequence of the Binary Vector Bin19," Plant Mol. Biol. 27:405-409 (1995).
Gaj et al., "ZFN, TALEN, and CRISPR/Cas-based Methods for Genome Engineering," Cell 31(7):397-405 (2013).
Esau, Anatomy of Seed Plants (1977).
Meylan and Butterfield, Three-Dimensional Structure of Wood (1972).
Stratagene Cloning Systems Catalog (1993) from Stratagene, La Jolla, CA.
Evans et al., Handbook of Plant Cell Cultures, vol. 1, New York, New York: MacMillan Publishing Co. (1983).
Vasil, ed., Cell Culture and Somatic Cell Genetics of Plants, vol. I (1984) and vol. III (1986).
Emerschad et al., "Somatic Embryogenesis and Plant Development from Immature Zygotic Embryos of Seedless Grapes (*Vitis vinifera*)," Plant Cell Reports 14:6-12 (1995).
Senior, "Uses of Plant Gene Silencing," Biotechnology and Genetic Engineering Reviews 15:79-119 (1998).
Urnov et al., "Genome Editing with Engineered Zinc Finger Nucleases," Nat Rev Genet. 11: 636-646 (2010).
Ausubel et al., Current Protocols in Molecular Biology, New York, N.Y.:John Wiley & Sons (1989).

* cited by examiner

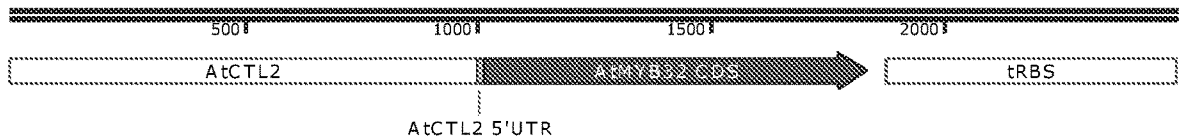

001 pAtCTL2-AtMYB32-tRBS V2
2496 bp

```
acgtacctcgtgtccaccggtgactctatccccggcgttagaagtgatgatagtctcgttcccaagggaaatcag
ccttcgaattggaattgatccctccggacatttgtgccgttcgtgtgccagacttgccatccatataatgcatc
ttcttctttttttcccgcagatggcatgtccgttggtctttcctgtatcatttatttacaaaagaaaaataaatt
aaacatttattaagttcccccgtaaaaaaaaaatatatatatatatatatataacacatgcatcataattgg
tatgtccgtaggtgtttccttatcataactgaaccattggtaaactatcggttccgttaaagcataagactagaa
aaggctcggtgcgactcgctaccacgtttctaaagatttatttagcaaattaaccccaatatatattttgctat
gagggtctaaacaaactggtatatgagccatttacttaccacttattagttccaagtatttatttttgggttaa
ttaatgtttaaattattggttgacaaaaaatataaaaataatggttaagttattgaaatgacttgagcaatctga
tgcaactgcggataacatgaactcattcgaagtgacgtcccaaatatttgattctttgttttattccttttgt
caaggtcaagattggccaaacattttcaatatctaaatatattgacattcatagcctggaaaagaaaaaatatat
ggttaaattagttccaaagtattctagcagcaacaaaaccgctccaataaacgatttccaatttctatctcaaac
ttgtttcccaatcattagttataatccgtcccctaaaccaaaaaaaaatctaattgtaaaggtgttgcaatagat
taaccattttttattttatttggtaaaatagattaaccattttgttagaaaaatgaagtttaaaacatttacagt
tctacgtgtacatgcttcgaccaatatgcttcgaccaatatggcaaggtctccttgctgtgagaaagaccacaca
aacaaaggagcttggactaaggaagaagacgataagctcatctcttacatcaaagctcacggtgaaggttgttgg
cgttctcttcctagatccgccggtcttcaacgttgcggaaaaagctgtcgtctccgatggattaactatctccga
cctgatctcaagaggggtaacttcaccctcgaagaagatgatctcatcatcaaactacatagccttctcggtaac
aagtggtctcttattgcgacgagattaccaggaagaacagataacgagattaagaattactggaacacacatgtt
aagaggaagctattaagaaaagggattgatccggcgactcatcgacctatcaacgagaccaaaacttctcaagat
tcgtctgattctagtaaaacagaggaccctcttgtcaagattctctcttttggtcctcagctggagaaaatagca
aatttcggggacgagagaattcaaaagagagttgagtactcagttgttgaagaaagatgtctggacttgaatctt
gagcttaggatcagtccaccatggcaagacaagctccatgatgagaggaacctaaggtttgggagagtgaagtat
aggtgcagtgcgtgccgttttggattcgggaacggcaaggagtgtagctgtaataatgtgaaatgtcaaacagag
gacagtagtagcagcagttattcttcaaccgacattagtagtagcattggttatgacttcttgggtctaaacaac
actagggttttggatttagcactttggaaatgaaatgacacgtgtgaattacaggtgaccagctcgaatttccc
cgatagctttcgttcgtatcatcggtttcgacaacgttcgtcaagttcaatgcatcagtttcattgcgcacacac
cagaatcctactgagttcgagtattatggcattgggaaacatgtttttcttgtaccatttgttgtgcttgtaatt
tactgtgtttttttattcggttttcgctatcgaactgtgaaatggaaatggatggagaagagttaatgaatgatat
ggtcctttttgttcattctcaaattaatattatttgtttttttctcttatttgttgtgtgttgaatttgaaaatata
agagatatgcaaacatttttgttttgagtaaaaatgtgtcaaatcgtggcctctaatgaccgaagttaatatgagg
agtaaaacacttgtagttgtaccattatgcttattcactaggcaacaaatatatttttcagacctagaaaagctgc
aaatgttactgaatacaagtatgtcctcttgtgttttagacatttatgaactttcctttatgtaattttccagaa
tccttgtcagattctaatcattgctttataattatagttatactcatggatttgtagttgagtatgaaaatattt
tttaatgcattttatgacttg
```

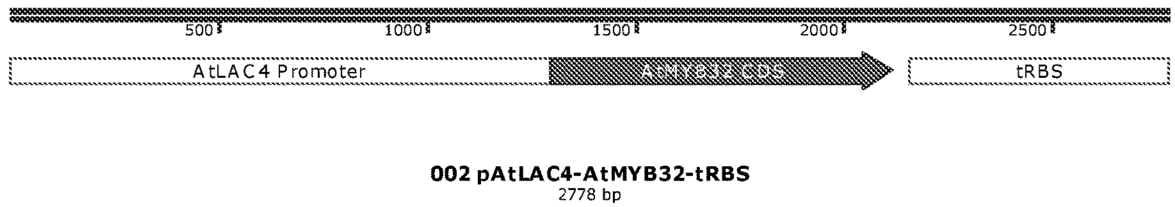

```
atacatgtcatgatttataattatgtatatataaatactaattgatgtatgaagtacgtagataatgttacgat
ctattaatctatttacattaacttttaattagtgttgagtagggaaaattaacatataaacctttagcagttggt
tgtattattaaaaataatttgaacttaaaatccaccttcgaaaagataaatcaaacaagtataaaaaatgctata
aatccagaatatttacctaaggttttattcttctacttaataatgtaagataaaaccggcacaatacttgttac
gtatgcatggtaggtaccgcaattgtgtaagcaaatcggcacaatactaaggttacatatactaactaaataaaa
caatctgatttcagtgacaccgtatatctaacctttattcaaatccaagggaacatgacttgacttcttctgttg
gaactaactcgatccctcaaccatctccagggatagaagagttagtaaaatcaaacttgaagtgaggaagtaagc
agtttaacgactccatatgactacagttatatacaaagttgggcacaaagtacaagtactaaatactcaaagtca
gataataatttaataagtacaaactatatatatgcagtacaattattgagtatatataaacgagactggtgatt
tggggcattgtccaccagggtgttatatcccaattgaaatttgaaaatttaagtgtgtgagtgttacgacaaaaa
aaagtgtgtgaattgtaggcgcggtgaaaaggtaaattaagattggaactagaaaaatagttgaatatcctttac
taaaagttgtcaattccggttttagtaaaaaaaaatttaaaatagaaattttatccaaaagacttcaaacacac
atattcgcatatataacataagatatcatttttttgtaaacagttaaaaagaaaaacacatgtttttttttttaat
ttagaaaaaaacatgttattatacaaaacagagttttgcccacttttaatatgttatgaaaagaaaaatgatttt
cttgggtttggtcagagagattggttgtggtaagaatgggaatcttaattacaaagaattggatttgggtcgac
ctaccacctaaaacgacgtcgcctccatctctggtttccaaatctctttctcctctccctttataagcttgcgtt
ggccagtcgctcatctcgaaaacagagagaaaaagactaaaaacacagtttaagaagaaggagagatagagagag
aagagaaagatagagagggagatggcaaggtctccttgctgtgagaaagaccacacaaacaaaggagcttggact
aaggaagaagacgataagctcatctcttacatcaaagctcacggtgaaggttgttggcgttctcttcctagatcc
gccggtcttcaacgttgcggaaaaagctgtcgtctccgatggattaactatctccgacctgatctcaagaggggt
aacttcaccctcgaagaagatgatctcatcatcaaactacatagccttctcggtaacaagtggtctcttattgcg
acgagattaccaggaagaacagataacgagattaagaattactggaacacacatgttaagaggaagctattaaga
aaagggattgatccggcgactcatcgacctatcaacgagaccaaaacttctcaagattcgtctgattctagtaaa
acagaggaccctcttgtcaagattctctctttggtcctcagctggagaaaatagcaaatttcggggacgagaga
attcaaaagagagttgagtactcagttgttgaagaaagatgtctggacttgaatcttgagcttaggatcagtcca
ccatggcaagacaagctccatgatgagaggaacctaaggtttgggagagtgaagtataggtgcagtgcgtgccgt
tttggattcgggaacggcaaggagtgtagctgtaataatgtgaaatgtcaaacagaggacagtagtagcagcagt
tattcttcaaccgacattagtagtagcattggttatgacttcttgggtctaaacaacactagggttttggatttt
agcactttggaaatgaaatgacacgtgtgaattacaggtgaccagctcgaatttccccgatagctttcgttcgta
tcatcggtttcgacaacgttcgtcaagttcaatgcatcagtttcattgcgcacacaccagaatcctactgagttc
gagtattatggcattgggaaacatgtttttcttgtaccatttgttgtgcttgtaatttactgtgtttttttattcg
gttttcgctatcgaactgtgaaatggaaatggatggagaagagttaatgaatgatatggtcctttttgttcattct
caaattaatattatttgtttttttctcttatttgttgtgtgttgaatttgaaaatataagagatatgcaaacattt
tgttttgagtaaaaatgtgtcaaatcgtggcctctaatgaccgaagttaatatgaggagtaaaacacttgtagtt
gtaccattatgcttattcactaggcaacaaatatatttcagacctagaaaagctgcaaatgttactgaatacaa
gtatgtcctcttgtgttttagacatttatgaactttcctttatgtaattttccagaatccttgtcagattctaat
cattgctttataattatagttatactcatggatttgtagttgagtatgaaaatatttttaatgcattttatgac
ttg          2778
```

FIG. 2

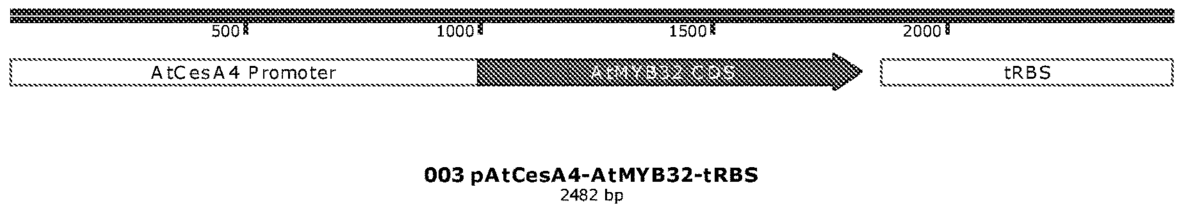

003 pAtCesA4-AtMYB32-tRBS
2482 bp

```
aactagaacacttcagataaatttgtcgttctgttgacttcatttattctctaaacacaaagaactatagacca
taatcgaaataaaaaccctaaaaaccaaatttatctatttaaaacaaacattagctatttgagtttcttttaggt
aagttatttaaggttttggagactttaagatgttttcagcatttatggttgtgtcattaatttgtttagtttagt
aaagaaagaaaagatagtaattaaagagttggttgtgaaatcatatttaaaacattaataggtatttatgtctaa
tttggggacaaaatagtggaattctttatcatatctagctagttcttatcgagtttgaactcgggttatgattat
gttacatgcattggtccatataaatctatgagcaatcaatataattcgagcattttggtataacataatgagcca
agtataacaaaagtatcaaacctatgcaggggagaagatgatgaaaagaagagtgtgagccaatacaaagcagat
ttgaggacatggcttacaagtcttgggtacagagtttggggagtgatgggtgcacaatggaacagcttctctggt
tgtccagttcccaagagaaccttcaagctccctaactccatctactatgtcgcctgattaaatcttatttactaa
caaaacaataagatcagagtttcattctgattcttgagtctttttttctctctccctcttttcatttctggttt
atataaccaattcaaatgcttatgatccatgcatgaaccatgatcatctttgtgtttttttttccttctgtatta
ccattttgggcctttgtgaaattgattttgggctttttgttatataatctcctctttctctttctctacctgattg
gattcaagaacatagccagatttggtaaagtttataagatacaaaatattaagtaagactaaagtagaaatacat
aataacttgaaagctactctaagttatggcaaggtctccttgctgtgagaaagaccacacaaacaaaggagcttg
gactaaggaagaagacgataagctcatctcttacatcaaagctcacggtgaaggttgttggcgttctcttcctag
atccgccggtcttcaacgttgcggaaaaagctgtcgtctccgatggattaactatctccgacctgatctcaagag
gggtaacttcaccctcgaagaagatgatctcatcatcaaactacatagccttctcggtaacaagtggtctcttat
tgcgacgagattaccaggaagaacagataacgagattaagaattactggaacacacatgttaagaggaagctatt
aagaaaagggattgatccggcgactcatcgacctatcaacgagaccaaaacttctcaagattcgtctgattctag
taaaacagaggaccctcttgtcaagattctctctttggtcctcagctggagaaaatagcaaatttcggggacga
gagaattcaaaagagagttgagtactcagttgttgaagaaagatgtctggacttgaatcttgagcttaggatcag
tccaccatggcaagacaagctccatgatgagaggaacctaaggtttgggagagtgaagtataggtgcagtgcgtg
ccgtttggattcgggaacggcaaggagtgtagctgtaataatgtgaaatgtcaaacagaggacagtagtagcag
cagttattcttcaaccgacattagtagtagcattggttatgacttcttgggtctaaacaacactagggttttgga
ttttagcactttggaaatgaaatgacacgtgtgaattacaggtgaccagctcgaatttccccgatagctttcgtt
cgtatcatcggtttcgacaacgttcgtcaagttcaatgcatcagtttcattgcgcacacaccagaatcctactga
gttcgagtattatggcattgggaaacatgtttttcttgtaccatttgttgtgcttgtaatttactgtgtttttta
ttcggttttcgctatcgaactgtgaaatggaaatggatggagaagagttaatgaatgatatggtcctttttgttca
ttctcaaattaatattatttgtttttttctcttatttgttgtgtgttgaatttgaaaatataagagatatgcaaac
attttgttttgagtaaaaatgtgtcaaatcgtggcctctaatgaccgaagttaatatgaggagtaaaacacttgt
agttgtaccattatgcttattcactaggcaacaaatatattttcagacctagaaaagctgcaaatgttactgaat
acaagtatgtcctcttgtgttttagacatttatgaactttcctttatgtaattttccagaatccttgtcagattc
taatcattgctttataattatagttatactcatggatttgtagttgagtatgaaaatattttttaatgcatttta
tgacttg    2482
```

FIG. 3

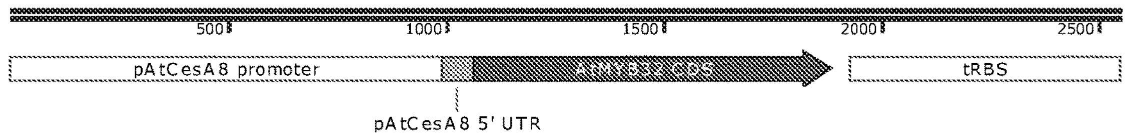

004 pAtCesA8-AtMYB32-tRBS
2546 bp

```
aacccataactttagtattcttcaacccttacaacttatctgagcaaaatcagaaggtcgaatttgatggatggt
tttgctgtatttggtcaacggttttatttgagacagtagaccagaggaaactcagatgtgatgatgcaaagactg
aattggttaagagtgtagattgatttgttctaacattgcaaatgtagagtagaattatgcaaaaaacgttaatga
acagagaagtgattaagcagaaacaaaattagagaagtgatattatatctcaaaatttattttggtacagctaa
agctcaaattgttatagagattagagatattaaaccaaatgacgagtgttttctttagtagtaaacggtgaaaat
tctcttctgacaaagacaattaaaatttaggtttaagactttaatatttgtcacaaattgtcatttacctaaat
aaaaaaaaaactaaatatttttttagatacatatgtgtcttataattttaactataaattttaattttatgtct
taaataattgtttacactataaatttaaatattttaatgctaaaattaatttgattcaaaaaagtgattttaatt
cttatttttcttatagaaagttggtgattgaaaagatttacttaaaaattataacaacttcaatggtgaataacc
cgacccgaataaaccggatataacaacttcaatgttagcttgatatagaaagtacggtgacgcttaggaggcaag
caagctagtatctgccgctggttagagacaaagaacatgtgtcactcctctcaactaaaactttccttcactttc
ccgcaaaatcatttcaaaaaagctccaaatttagcttacccatcagctttctcagaaaaccagtgaaagaaactt
ctcaacttccgatttttcacaatccaccaaactttttttaataactttttttcctcttattacaaaacctccact
ctcatggcttctcaaacttgttatccatccaaatctcaatccctaattagggttcatttctctgtttctccaaac
aggggaattcgaagatggcaaggtctccttgctgtgagaaagaccacacaaacaaaggagcttggactaaggaag
aagacgataagctcatctcttacatcaaagctcacggtgaaggttgttggcgttctcttcctagatccgccggtc
ttcaacgttgcggaaaaagctgtcgtctccgatggattaactatctccgacctgatctcaagaggggtaacttca
ccctcgaagaagatgatctcatcatcaaactacatagccttctcggtaacaagtggtctcttattgcgacgagat
taccaggaagaacagataacgagattaagaattactggaacacacatgttaagaggaagctattaagaaaggga
ttgatccggcgactcatcgacctatcaacgagaccaaaacttctcaagattcgtctgattctagtaaaacagagg
accctcttgtcaagattctctctttggtcctcagctggagaaaatagcaaatttcggggacgagagaattcaaa
agagagttgagtactcagttgttgaagaaagatgtctggacttgaatcttgagcttaggatcagtccaccatggc
aagacaagctccatgatgagaggaacctaaggtttgggagagtgaagtataggtgcagtgcgtgccgttttggat
tcgggaacggcaaggagtgtagctgtaataatgtgaaatgtcaaacagaggacagtagtagcagcagttattctt
caaccgacattagtagtagcattggttatgacttcttgggtctaaacaacactagggttttggattttagcactt
tggaaatgaaatgacacgtgtgaattacaggtgaccagctcgaatttccccgatagctttcgttcgtatcatcgg
tttcgacaacgttcgtcaagttcaatgcatcagtttcattgcgcacacaccagaatcctactgagttcgagtatt
atggcattgggaaacatgtttttcttgtaccatttgttgtgcttgtaatttactgtgtttttttattcggttttcg
ctatcgaactgtgaaatggaaatggatggagaagagttaatgaatgatatggtcctttttgttcattctcaaatta
atattatttgtttttttctcttatttgttgtgtgttgaatttgaaaatataagagatatgcaaacattttgttttg
agtaaaaatgtgtcaaatcgtggcctctaatgaccgaagttaatatgaggagtaaaacacttgtagttgtaccat
tatgcttattcactaggcaacaaatatattttcagacctagaaaagctgcaaatgttactgaatacaagtatgtc
ctcttgtgttttagacatttatgaactttcctttatgtaattttccagaatccttgtcagattctaatcattgct
ttataattatagttatactcatggatttgtagttgagtatgaaaatatttttttaatgcattttatgacttg 2546
```

FIG. 4

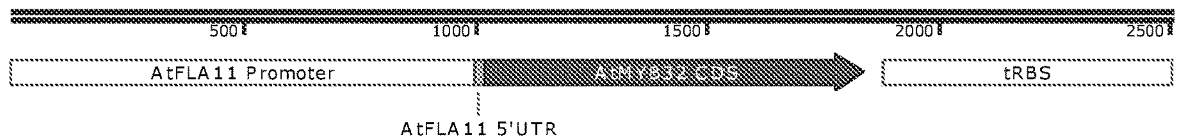

005 pAtFLA11-AtMYB32-tRBS
2501 bp

```
tcttcttgcatcaatgatatcaacaacaatgggtaataaagaagctacttcgaaattatatatttttcgtattc
tatattgatcatcagtcttaagtggtttggtttgttgcagtgaagaagaactatgtatggatctacgccaccgtt
cagttcggttttgtggtccttttcgctcagcttttctacagagttgtaagatttgatgtaatgtcacagagaaac
cttactttgttgtcacagagaaaccttactttgttgaagagttttgattcctcacactctctctcattaacttg
tgtgtaggtgaagcagccggtaatgtgcattgtcttagccactatgatcggatttggactcaccatgaccggcac
aacagctattaacgagtatttgaaatggaggagaagcaattcccacctgccagaagagccagcaagtactcaggt
ggtttgacagcagcgtagatcttttgagtgaagctagagtccctaaagggttggatcggttttcaattaaccggt
cgggattcggttttcggtttagctttaatcgacttgtctaggttgagatcagatttggttttcaatacttccaag
tcttttttttttgccaactaaaatataaggaatgatgataggcacacacatgacacataaaatcataatgaaca
gtagtatgattagcaatccatatttcttggataacacttcttcacagctttttgacaggtcactataacacctt
tttcagttcatttttcattttcaatcctcacccacccaaactctcccttcaaagcaatgtctctcctctctcttt
ctcaattcaaacaaactttattaaacctaaaagaaacatttccaatctctaatgacttagttgatagaatctcat
ttagttacctagtaataatcttcacactagtaagagaatcctactcttcaccaaactacatctctctctatataa
caaaccccaaaacatctcaacatacacacacaacaactacaacaatggcaaggtctccttgctgtgagaaagacc
acacaaacaaaggagcttggactaaggaagaagacgataagctcatctcttacatcaaagctcacggtgaaggtt
gttggcgttctcttcctagatccgccggtcttcaacgttgcggaaaaagctgtcgtctccgatggattaactatc
tccgacctgatctcaagaggggtaacttcaccctcgaagaagatgatctcatcatcaaactacatagccttctcg
gtaacaagtggtctcttattgcgacgagattaccaggaagaacagataacgagattaagaattactggaacacac
atgttaagaggaagctattaagaaaagggattgatccggcgactcatcgacctatcaacgagaccaaaacttctc
aagattcgtctgattctagtaaaacagaggaccctcttgtcaagattctctctttggtcctcagctggagaaaa
tagcaaatttcggggacgagagaattcaaaagagagttgagtactcagttgttgaagaaagatgtctggacttga
atcttgagcttaggatcagtccaccatggcaagacaagctccatgatgagaggaacctaaggtttgggagagtga
agtataggtgcagtgcgtgccgttttggattcgggaacggcaaggagtgtagctgtaataatgtgaaatgtcaaa
cagaggacagtagtagcagcagttattcttcaaccgacattagtagtagcattggttatgacttcttgggtctaa
acaacactagggttttggattttagcactttggaaatgaaatgacacgtgtgaattacaggtgaccagctcgaat
ttccccgatagctttcgttcgtatcatcggtttcgacaacgttcgtcaagttcaatgcatcagtttcattgcgca
cacaccagaatcctactgagttcgagtattatggcattgggaaacatgtttttcttgtaccatttgttgtgcttg
taatttactgtgtttttattcggttttcgctatcgaactgtgaaatggaaatggatggagaagagttaatgaat
gatatggtccttttgttcattctcaaattaatattatttgtttttctcttatttgttgtgtgttgaatttgaaa
atataagagatatgcaaacattttgttttgagtaaaaatgtgtcaaatcgtggcctctaatgaccgaagttaata
tgaggagtaaaacacttgtagttgtaccattatgcttattcactaggcaacaaatatattttcagacctagaaaa
gctgcaaatgttactgaatacaagtatgtcctcttgtgtttagacatttatgaactttcctttatgtaatttc
cagaatccttgtcagattctaatcattgctttataattatagttatactcatggatttgtagttgagtatgaaaa
tattttttaatgcattttatgacttg
```

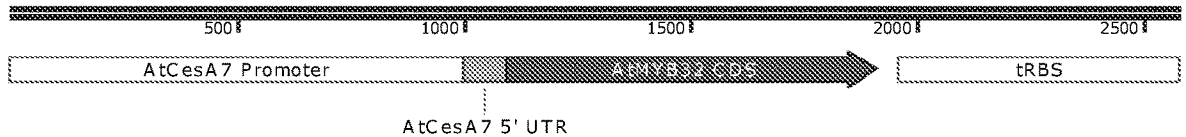

006 pAtCesA7-AtMYB32-tRBS
2575 bp

```
tgcgaacagtttgattctgtttttctttttcctttttttgggtaatttttcttataactttttcatagtttcgat
tatttggataaaatttcagattgaggatcatttatttatttattagtgtagtctaatttagttgtataactat
aaaattgttgtttgtttccgaatcataagttttttttttttttggttttgtattgataggtgcaagagactcaaa
attctggtttcgatgttaacagaattcaagtagctgcccacttgattcgatttgttttgtatttggaaacaacca
tggctggtcaaggcccagcccgttgtgcttctgaacctgcctagtcccatggactagatctttatccgcagactc
caaaagaaaaaggattggcgcagaggaattgtcatggaaacagaatgaacaagaaagggtgaagaagatcaaagg
catatatgatctttacattctctttagcttatgtatgcagaaaattcacctaattaaggacagggaacgtaactt
ggcttgcactcctctcaccaaaccttacccccctaactaatttaattcaaaattactagtattttggccgatcac
tttatataataagataccagatttattatatttacgaattatcagcatgcatatactgtatatagttttttttt
gttaaagggtaaaataataggatcctttttgaataaaatgaacatatataattagtataatgaaaacagaaggaaa
tgagattaggacagtaagtaaaatgagagagacctgcaaaggataaaaaagagaagcttaaggaaaccgcgacga
tgaaagaaagacatgtcatcagctgatggatgtgagtgatgagtttgttgcagttgtgtagaaatttttactaaa
acagttgtttttacaaaaaagaaataatataaaacgaaagcttagcttgaaggcaatggagactctacaacaaac
tatgtaccatacagagagagaaactaaaagctttcacacataaaaaccaaacttattcgtctctcattgatcac
cgttttgttctctcaagatcgctgctaatctccggccgtccctatggcaaggtctccttgctgtgagaaagacca
cacaaacaaaggagcttggactaaggaagaagacgataagctcatctcttacatcaaagctcacggtgaaggttg
ttggcgttctcttcctagatccgccggtcttcaacgttgcggaaaaagctgtcgtctccgatggattaactatct
ccgacctgatctcaagaggggtaacttcaccctcgaagaagatgatctcatcatcaaactacatagccttctcgg
taacaagtggtctcttattgcgacgagattaccaggaagaacagataacgagattaagaattactggaacacaca
tgttaagaggaagctattaagaaaagggattgatccggcgactcatcgacctatcaacgagaccaaacttctca
agattcgtctgattctagtaaaacagaggaccctcttgtcaagattctctctttggtcctcagctggagaaaat
agcaaatttcggggacgagagaattcaaaagagagttgagtactcagttgttgaagaaagatgtctggacttgaa
tcttgagcttaggatcagtccaccatggcaagacaagctccatgatgagaggaacctaaggtttgggagagtgaa
gtataggtgcagtgcgtgccgttttggattcgggaacggcaaggagtgtagctgtaataatgtgaaatgtcaaac
agaggacagtagtagcagcagttattcttcaaccgacattagtagtagcattggttatgacttcttgggtctaaa
caacactagggtttggattttagcactttggaaatgaaatgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgtttttcttgtaccatttgttgtgcttgt
aatttactgtgtttttttattcggttttcgctatcgaactgtgaaatggaaatggatggagaagagttaatgaatg
atatggtccttttgttcattctcaaattaatattatttgtttttttctcttatttgttgtgtgttgaatttgaaaa
tataagagatatgcaaacattttgttttgagtaaaaatgtgtcaaatcgtggcctctaatgaccgaagttaatat
gaggagtaaaacacttgtagttgtaccattatgcttattcactaggcaacaaatatatttcagacctagaaaag
ctgcaaatgttactgaatacaagtatgtcctcttgtgttttagacatttatgaactttcctttatgtaattttcc
agaatccttgtcagattctaatcattgctttataattatagttatactcatggatttgtagttgagtatgaaaat
atttttttaatgcattttatgacttg
```

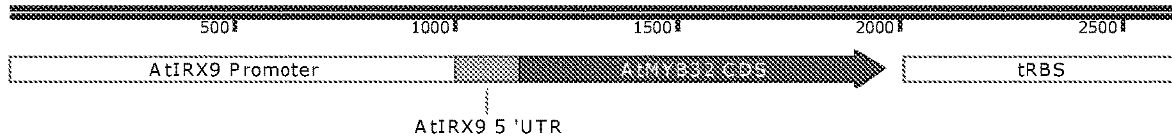

007 pAtIRX9-AtMYB32-tRBS
2628 bp tctctaattgtcaagtatcttagtctagagttaattacttaaatactaaaaggctgtcgacaaaatcaagcttga
atctccttgtggtatcttcaactcttcgttgtctgcttacgagtggtttactcagtaattatctataatatgtta
tttttttccctcatcttttagttgttgtttcattacattgaaaagcttgtaatgtctttatatggtatatatgg
atcttatgagtgaggcaagatccatgatgtttttgatcttagaatgtatatgatgatcttagaatgtatttgacc
gcccacaaattattgttcattgggattatatctctagtccaactccaagcaatcgaaatgggtcctgcttttaag
aacaacagtatatgtttaagaataataactttatatattctcgattttaagatcttttgacaaaacctcctttc
gttaggagcgtactaatttccaagtgtttgattagtggggtctccgtaaatttatttagagtttctatctattta
ttaatagctcaattaattaatctatactgtatctaaacatcaatttatatatttactcttgagaccaaaactgtc
aatttataacattggatagtttcttaattcttattatatattttcaaacacttttcaagactaatctccacatt
aggtactctctctagagataaaaatatttatcaaaaacattttatttatttattaagtagtagataaactactg
tggcaaaatcgtaaatgtctaaatgctgatgaatttttttgctgctccaatctggtttagtgctccatatacat
ccacggccaaaatgaatctatggcggcattaagattcattagtaagcaacgattatattaatataattgtttta
gcaatgattttccgtaatttcccaaatatgtttcagttaatgtgttccaatcccaacaactggttgttgcaaaag
accaccaacgcaagcaatcatcaaacatcaaaataatcttaccttagcgaacaaacaataactacacaattctca
taaagctcttatatatcactaacttcacacatttgtttccacaaaaataaaaacggaactcactcaagaaacc
ttcttccttgaagagagggttatggcaaggtctccttgctgtgagaaagaccacacaaacaaaggagcttggact
aaggaagaagacgataagctcatctcttacatcaaagctcacggtgaaggttgttggcgttctcttcctagatcc
gccggtcttcaacgttgcggaaaaagctgtcgtctccgatggattaactatctccgacctgatctcaagaggggt
aacttcaccctcgaagaagatgatctcatcatcaaactacatagccttctcggtaacaagtggtctcttattgcg
acgagattaccaggaagaacagataacgagattaagaattactggaacacacatgttaagaggaagctattaaga
aaagggattgatccggcgactcatcgacctatcaacgagaccaaaacttctcaagattcgtctgattctagtaaa
acagaggaccctcttgtcaagattctctctttggtcctcagctggagaaaatagcaaatttcggggacgagaga
attcaaaagagagttgagtactcagttgttgaagaaagatgtctggacttgaatcttgagcttaggatcagtcca
ccatggcaagacaagctccatgatgagaggaacctaaggtttgggagagtgaagtataggtgcagtgcgtgccgt
tttggattcgggaacggcaaggagtgtagctgtaataatgtgaaatgtcaaacagaggacagtagtagcagcagt
tattcttcaaccgacattagtagtagcattggttatgacttcttgggtctaaacaacactagggttttggatttt
agcactttggaaatgaaatgacacgtgtgaattacaggtgaccagctcgaatttccccgatagctttcgttcgta
tcatcggtttcgacaacgttcgtcaagttcaatgcatcagtttcattgcgcacacaccagaatcctactgagttc
gagtattatggcattgggaaacatgtttttcttgtaccatttgttgtgcttgtaatttactgtgtttttattcg
gttttcgctatcgaactgtgaaatggaaatggatggagaagagttaatgaatgatatggtcctttgttcattct
caaattaatattatttgtttttctcttatttgttgtgtgttgaatttgaaaatataagagatatgcaaacattt
tgttttgagtaaaaatgtgtcaaatcgtggcctctaatgaccgaagttaatatgaggagtaaaacacttgtagtt
gtaccattatgcttattcactaggcaacaaatatatttcagacctagaaaagctgcaaatgttactgaatacaa
gtatgtcctcttgtgttttagacatttatgaactttcctttatgtaattttccagaatccttgtcagattctaat
cattgctttataattatagttatactcatggatttgtagttgagtatgaaaatatttttaatgcattttatgac
ttg 2628

FIG. 7

Figure 8:
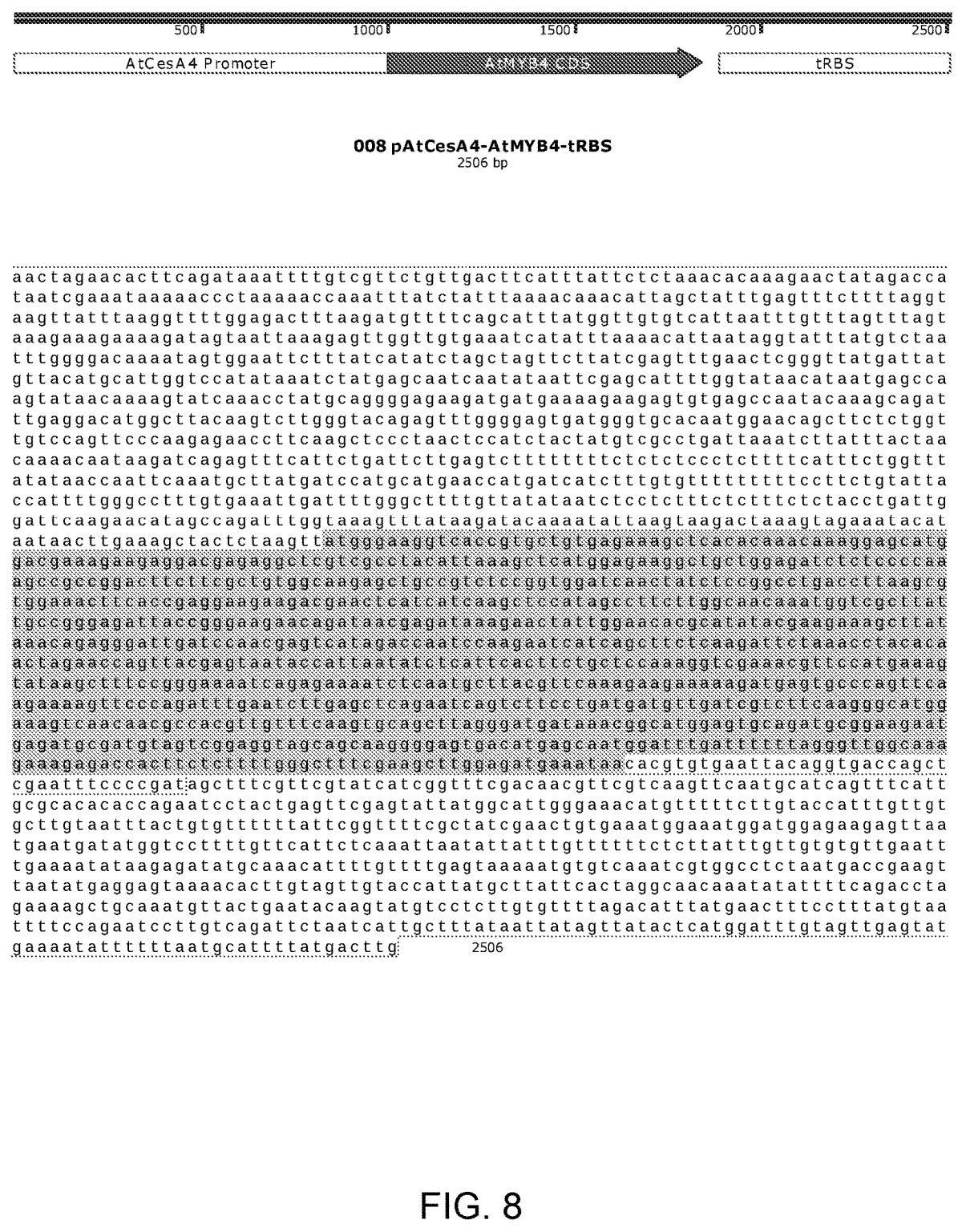

008 pAtCesA4-AtMYB4-tRBS
2506 bp

```
aactagaacacttcagataaatttgtcgttctgttgacttcatttattctctaaacacaaagaactatagacca
taatcgaaataaaaaccctaaaaaccaaatttatctatttaaaacaaacattagctatttgagtttcttttaggt
aagttatttaaggttttggagactttaagatgtttcagcatttatggttgtgtcattaatttgtttagtttagt
aaagaaagaaaagatagtaattaaagagttggttgtgaaatcatatttaaaacattaataggtatttatgtctaa
tttggggacaaaatagtggaattctttatcatatctagctagttcttatcgagtttgaactcgggttatgattat
gttacatgcattggtccatataaatctatgagcaatcaatataattcgagcattttggtataacataatgagcca
agtataacaaaagtatcaaacctatgcaggggagaagatgatgaaaagaagagtgtgagccaatacaaagcagat
ttgaggacatggcttacaagtcttgggtacagagtttggggagtgatgggtgcacaatggaacagcttctctggt
tgtccagttcccaagagaaccttcaagctccctaactccatctactatgtcgcctgattaaatcttatttactaa
caaaacaataagatcagagtttcattctgattcttgagtctttttttctctctccctcttttcatttctggttt
atataaccaattcaaatgcttatgatccatgcatgaaccatgatcatctttgtgttttttttccttctgtatta
ccattttgggcctttgtgaaattgattttgggctttttgttatataatctcctctttctctttctctacctgattg
gattcaagaacatagccagatttggtaaagtttataagatacaaaatattaagtaagactaaagtagaaatacat
aataacttgaaagctactctaagttatgggaaggtcaccgtgctgtgagaaagctcacacaaacaaaggagcatg
gacgaaagaagaggacgagaggctcgtcgcctacattaaagctcatggagaaggctgctggagatctctccccaa
agccgccggacttcttcgctgtggcaagagctgccgtctccggtggatcaactatctccggcctgaccttaagcg
tggaaacttcaccgaggaagaagacgaactcatcatcaagctccatagccttcttggcaacaaatggtcgcttat
tgccgggagattaccgggaagaacagataacgagataaagaactattggaacacgcatatacgaagaaagcttat
aaacagagggattgatccaacgagtcatagaccaatccaagaatcatcagcttctcaagattctaaacctacaca
actagaaccagttacgagtaataccattaatatctcattcacttctgctccaaaggtcgaaacgttccatgaaag
tataagctttccgggaaaatcagagaaaatctcaatgcttacgttcaaagaagaaaaagatgagtgcccagttca
agaaaagttcccagatttgaatcttgagctcagaatcagtcttcctgatgatgttgatcgtcttcaagggcatgg
aaagtcaacaacgccacgttgtttcaagtgcagcttagggatgataaacggcatggagtgcagatgcggaagaat
gagatgcgatgtagtcggaggtagcagcaaggggagtgacatgagcaatggatttgatttttagggttggcaaa
gaaagagaccacttctctttgggctttcgaagcttggagatgaaataacacgtgtgaattacaggtgaccagct
cgaatttccccgatagctttcgttcgtatcatcggtttcgacaacgttcgtcaagttcaatgcatcagtttcatt
gcgcacacaccagaatcctactgagttcgagtattatggcattgggaaacatgtttttcttgtaccatttgttgt
gcttgtaatttactgtgtttttattcggttttcgctatcgaactgtgaaatggaaatggatggagaagagttaa
tgaatgatatggtcctttgttcattctcaaattaatattatttgtttttctcttatttgttgtgtgttgaatt
tgaaaatataagagatatgcaaacatttgttttgagtaaaaatgtgtcaaatcgtggcctctaatgaccgaagt
taatatgaggagtaaaacacttgtagttgtaccattatgcttattcactaggcaacaaatatattttcagaccta
gaaaagctgcaaatgttactgaatacaagtatgtcctcttgtgttttagacatttatgaactttcctttatgtaa
ttttccagaatccttgtcagattctaatcattgctttataattatagttatactcatggatttgtagttgagtat
gaaaatatttttttaatgcattttatgacttg
```

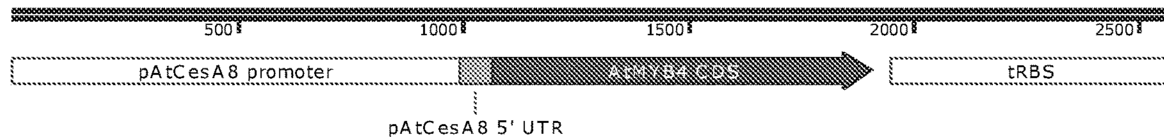

009 pAtCesA8-AtMYB4-tRBS
2570 bp

```
aacccataactttagtattcttcaacccttacaacttatctgagcaaaatcagaaggtcgaatttgatggatggt
tttgctgtatttggtcaacggttttatttgagacagtagaccagaggaaactcagatgtgatgatgcaaagactg
aattggttaagagtgtagattgatttgttctaacattgcaaatgtagagtagaattatgcaaaaaacgttaatga
acagagaagtgattaagcagaaacaaaattagagaagtgatattatatctcaaaatttatttttggtacagctaa
agctcaaattgttatagagattagagatattaaaccaaatgacgagtgttttctttagtagtaaacggtgaaaat
tctcttctgacaaagacaattaaaattttaggtttaagactttaatatttgtcacaaattgtcatttacctaaat
aaaaaaaaaactaaatatttttttagatacatatgtgtcttataattttaactataaatttaattttatgtct
taaataattgtttacactataaatttaaatatttaatgctaaaattaatttgattcaaaaaagtgattttaatt
cttatttttcttatagaaagttggtgattgaaaagatttacttaaaaattataacaacttcaatggtgaataacc
cgacccgaataaaccggatataacaacttcaatgttagcttgatatagaaagtacggtgacgcttaggaggcaag
caagctagtatctgccgctggttagagacaaagaacatgtgtcactcctctcaactaaaactttccttcactttc
ccgcaaaatcatttcaaaaaagctccaaatttagcttacccatcagctttctcagaaaaccagtgaaagaaactt
ctcaacttccgatttttcacaatccaccaaactttttttaataactttttttcctcttattacaaaacctccact
ctcatggcttctcaaacttgttatccatccaaatctcaatccctaattagggttcatttctctgtttctccaaac
aggggaattcgaagatgggaaggtcaccgtgctgtgagaaagctcacacaaacaaaggagcatggacgaaagaag
aggacgagaggctcgtcgcctacattaaagctcatggagaaggctgctggagatctctccccaaagccgccggac
ttcttcgctgtggcaagagctgccgtctccggtggatcaactatctccggcctgaccttaagcgtggaaacttca
ccgaggaagaagacgaactcatcatcaagctccatagccttcttggcaacaaatggtcgcttattgccgggagat
taccgggaagaacagataacgagataaagaactattggaacacgcatatacgaagaaagcttataaacagaggga
ttgatccaacgagtcatagaccaatccaagaatcatcagcttctcaagattctaaacctacacaactagaaccag
ttacgagtaataccattaatatctcattcacttctgctccaaaggtcgaaacgttccatgaaagtataagctttc
cgggaaaatcagagaaaatctcaatgcttacgttcaaagaagaaaaagatgagtgcccagttcaagaaaagttcc
cagatttgaatcttgagctcagaatcagtcttcctgatgatgttgatcgtcttcaagggcatggaaagtcaacaa
cgccacgttgtttcaagtgcagcttagggatgataaacggcatggagtgcagatgcggaagaatgagatgcgatg
tagtcggaggtagcagcaaggggagtgacatgagcaatggatttgatttttagggttggcaaagaaagagacca
cttctctttgggctttcgaagcttggagatgaaataacacgtgtgaattacaggtgaccagctcgaatttcccc
gatagctttcgttcgtatcatcggtttcgacaacgttcgtcaagttcaatgcatcagtttcattgcgcacacacc
agaatcctactgagttcgagtattatggcattgggaaacatgtttttcttgtaccatttgttgtgcttgtaattt
actgtgtttttttattcggttttcgctatcgaactgtgaaatggaaatggatggagaagagttaatgaatgatatg
gtccttttgttcattctcaaattaatattatttgtttttctcttatttgttgtgtgttgaatttgaaaatataa
gagatatgcaaacatttgttttgagtaaaaatgtgtcaaatcgtggcctctaatgaccgaagttaatatgagga
gtaaaacacttgtagttgtaccattatgcttattcactaggcaacaaatatattttcagacctagaaaagctgca
aatgttactgaatacaagtatgtcctcttgtgttttagacatttatgaactttcctttatgtaattttccagaat
ccttgtcagattctaatcattgctttataattatagttatactcatggatttgtagttgagtatgaaaatatttt
ttaatgcattttatgacttg          2570
```

FIG. 9

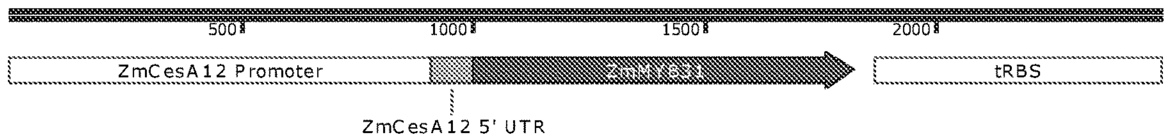

010 pZmCesA12-ZmMYB31-tRBS
2485 bp

```
aggcggggccggaggagggcaccagagaggctgctcaggagagagaaataatagaatatgtggtatagagtaaac
atgagtgcggatgattgtggtatagagtaaagaattttgctgactaggacagaatattctttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcgggggctcgaccgaccg
acccaacgcctccatctccaccgcgcgcaccaaatcgcactcccgtccgccccgccgatcgaacagccaccgctc
acctctcccacccgccaaaaacctccggcctcctctcatattcatatagctagcccctgccacaaggtagagcgt
cgctcacacctgcgtcgccctgcctcgcaatcgcgaatctgtcgagcacctgaggggtcggaggccgagagctag
cctagcacgccggcctccgcgcgcgatggggaggtcgccgtgctgcgagaaggcgcacaccaacaagggcgcgtg
gaccaaggaggaggacgagcgcctggtcgcgcacatcagggcgcacggcgaggggtgctggcgctcgctgcccaa
ggccgccggcctcctgcgctgcggcaagagctgccgcctccgctggatcaactacctccgccccgacctcaagcg
cggcaacttcacggaggaagaggacgagctcatcgtcaagctgcacagcgtcctcggcaacaagtggtccctgat
cgccggaaggctgcccggcaggacggacaacgagatcaagaactactggaacacgcacatccggaggaagctgct
gagcaggggggatcgacccggtgacgcaccgcccggtcacggagcaccacgcgtccaacatcaccatatcgttcga
gacggaagtggccgccgctgcccgtgatgataagaagggcgccgtcttccggttggaggacgaggaggaggagga
gcgcaacaaggcgacgatggtcgtcggccgcgaccggcagagccagagccacagccacagccacccccgccggcga
gtggggccaggggaagaggccgctcaagtgccccgacctcaacctggacctctgcatcagcccgccgtgccagga
ggaggaggagatggaggaggctgcgatgagagtgagaccggcggtgaagcgggaggccgggctctgcttcggctg
cagcctggggctccccaggaccgcggactgcaagtgcagcagcagcagcttcctcgggctcaggaccgccatgct
cgacttcagaagcctcgagatgaaatgacacgtgtgaattacaggtgaccagctcgaatttccccgatagctttc
gttcgtatcatcggtttcgacaacgttcgtcaagttcaatgcatcagtttcattgcgcacacaccagaatcctac
tgagttcgagtattatggcattgggaaacatgtttttcttgtaccatttgttgtgcttgtaatttactgtgtttt
ttattcggttttcgctatcgaactgtgaaatggaaatggatggagaagagttaatgaatgatatggtccttttgt
tcattctcaaattaatattatttgtttttctcttatttgttgtgtgttgaatttgaaaatataagagatatgca
aacattttgttttgagtaaaaatgtgtcaaatcgtggcctctaatgaccgaagttaatatgaggagtaaaacact
tgtagttgtaccattatgcttattcactaggcaacaaatatatttcagacctagaaaagctgcaaatgttactg
aatacaagtatgtcctcttgtgtttagacatttatgaactttcctttatgtaattttccagaatccttgtcaga
ttctaatcattgctttataattatagttatactcatggatttgtagttgagtatgaaaatatttttaatgcatt
ttatgacttg 2485
```

FIG. 10

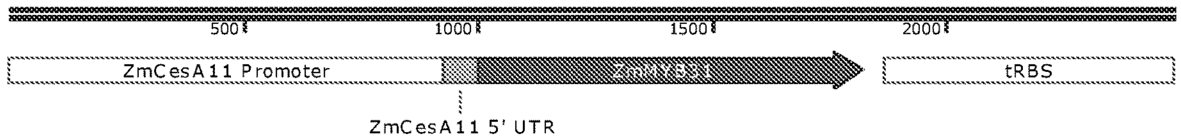

011 pZmCesA11-ZmMYB31-tRBS
2485 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatatttagcacaccgattttt
atatcatactgatgtttatcgttttgtatctatatttatatttgttttataataatattagatatttatttcgt
caatagaatattaatgttatgatgatactttactatattgattttacatatgatagtgatgttactccttccgta
tctatatttatattagtttttatctcctggcaacacggtcacaacagaagagaagtttttcagaccgattccag
gatcgatttttttttatatctgggctaagacatcaggtagagattgtttaacctttgcggctttccgcactgac
ggacccacccccaccgcatcaacggaacctaccaaccacccccgtgctccgacccccccatctgcccgtcttccag
gttacgccccgcgcggccgcgcgcgcggaagctgtatcaccccacccgtcgacgtcgtcttcgcttcgaaacccc
gcaaaaccccgcggaaaaaacccacctgctgcacgcacgcacccccctccctctccctccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctcccattctctcacacccaacacccagctatcacaccctgatccccgaggccg
cgcgtcggggtgaggaggaggggccatggggaggtcgccgtgctgcgagaaggcgcacaccaacaagggcgcgtg
gaccaaggaggaggacgagcgcctggtcgcgcacatcagggcgcacggcgaggggtgctggcgctcgctgcccaa
ggccgccggcctcctgcgctgcggcaagagctgccgcctccgctggatcaactacctccgccccgacctcaagcg
cggcaacttcacggaggaagaggacgagctcatcgtcaagctgcacagcgtcctcggcaacaagtggtccctgat
cgccggaaggctgcccggcaggacggacaacgagatcaagaactactggaacacgcacatccggaggaagctgct
gagcagggggatcgacccggtgacgcaccgcccggtcacggagcaccacgcgtccaacatcaccatatcgttcga
gacggaagtggccgccgctgcccgtgatgataagaagggcgccgtcttccggttggaggacgaggaggaggagga
gcgcaacaaggcgacgatggtcgtcggccgcgaccggcagagccagagccacagccacagccaccccgccggcga
gtggggccaggggaagaggccgctcaagtgccccgacctcaacctggacctctgcatcagcccgccgtgccagga
ggaggaggagatggaggaggctgcgatgagagtgagaccggcggtgaagcgggaggccgggctctgcttcggctg
cagcctggggctccccaggaccgcggactgcaagtgcagcagcagcagcttcctcgggctcaggaccgccatgct
cgacttcagaagcctcgagatgaaatgacacgtgtgaattacaggtgaccagctcgaatttccccgatagctttc
gttcgtatcatcggtttcgacaacgttcgtcaagttcaatgcatcagtttcattgcgcacacaccagaatcctac
tgagttcgagtattatggcattgggaaacatgtttttcttgtaccatttgttgtgcttgtaatttactgtgtttt
ttattcggttttcgctatcgaactgtgaaatggaaatggatggagaagagttaatgaatgatatggtcctttgt
tcattctcaaattaatattatttgtttttctcttatttgttgtgtgttgaatttgaaaatataagagatatgca
aacattttgttttgagtaaaaatgtgtcaaatcgtggcctctaatgaccgaagttaatatgaggagtaaaacact
tgtagttgtaccattatgcttattcactaggcaacaaatatattttcagacctagaaaagctgcaaatgttactg
aatacaagtatgtcctcttgtgtttagacatttatgaactttcctttatgtaattttccagaatccttgtcaga
ttctaatcattgctttataattatagttatactcatggatttgtagttgagtatgaaaatatttttaatgcatt
ttatgacttg
```
2485

FIG. 11

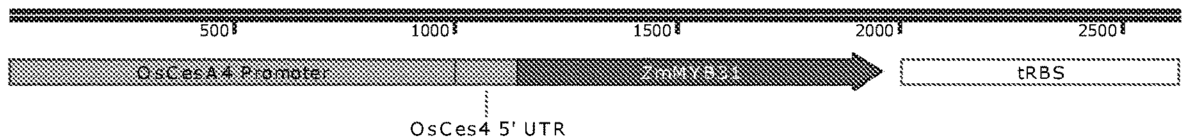

012 pOsCesA4-ZmMYB31-tRBS
2626 bp gagttaaattgatatggttttgtctgtcaaggtgccgtttctatggttggaggaggaaaatgaaattaggggaat
agaacagtcgcaatccaaaagctattgttctctcttctacggtagttgatagttcgatacgtgtgtttgatgtga
gagactgagaggagtgcacggtgcacctgccccgtaaggacgcggaactacattatcagaggctaggccggtact
gttatacgcgacgttcacgaatcacgatgcgtaaaaaagtgaagcatgaaacagtactaggctctccacgggcca
catcatgaaaaaactggtgcgacgccacgcttaacaatttgtcggtcgtaaactcgtaaagttaaaagccccacg
acattgtcaaccaatatctcagcacatgaacttctctaacgagtacaacgaaaccgcatccgcaaaagcgccgtg
aaccaaagctcttgccgtgctgtgccgtgccggtggccgtgaacatgtggaacacgaagaactcttgcgcgagat
cggagcacctgacctcccacctcgcgtccggcccgtcgccgtcgcagcaagcgggctgtcaaaaacgacgccaca
gcgcgagcgctctcgccgatccggcggacccaccctcctcacctcgcgcaccaaccgcccgttcgctagtccgat
cccccacccctcatccccccctacgccttgcaggttacgcgcctcgccgcggccaacgcaaaccaaaccaaatccc
ccgtcaccttcgcttcgaaaccccgcaaaaccccatggaagaaaacaccgaacacctgccgcgcgcacgcctcct
cctcccccgcctctcctcctctctcccgttccatgtccgctcaaccttgcttccattctttccatccacccgccg
atcgacgcgatgccgacgccccaaccccacccaccgcctgccagcgccaccccacctcgcgcctctgcggctatg
gctatatcaccatgcctccaacctccggtacgcttagcctctctctctctccccctcccattctgcgcattgctc
tctgcgcgcggtcgcgtgctgctgctcgcggcgccccggagcgtctcctttgggggagaggagaggagaggagag
gagagggggtgagccatggggaggtcgccgtgctgcgagaaggcgcacaccaacaagggcgcgtggaccaagga
ggaggacgagcgcctggtcgcgcacatcagggcgcacggcgaggggtgctggcgctcgctgcccaaggccgccgg
cctcctgcgctgcggcaagagctgccgcctccgctggatcaactacctccgccccgacctcaagcgcggcaactt
cacggaggaagaggacgagctcatcgtcaagctgcacagcgtcctcggcaacaagtggtccctgatcgccggaag
gctgcccggcaggacggacaacgagatcaagaactactggaacacgcacatccggaggaagctgctgagcagggg
gatcgacccggtgacgcaccgcccggtcacggagcaccacgcgtccaacatcaccatatcgttcgagacggaagt
ggccgccgctgcccgtgatgataagaagggcgccgtcttccggttggaggacgaggaggaggaggagcgcaacaa
ggcgacgatggtcgtcggccgcgaccggcagagccagagccacagccacagccaccccgccggcgagtggggcca
ggggaagaggccgctcaagtgccccgacctcaacctggacctctgcatcagcccgccgtgccaggaggaggagga
gatggaggaggctgcgatgagagtgagaccggcggtgaagcgggaggccgggctctgcttcggctgcagcctggg
gctccccaggaccgcggactgcaagtgcagcagcagcagcttcctcgggctcaggaccgccatgctcgacttcag
aagcctcgagatgaaatgacacgtgtgaattacaggtgaccagctcgaatttccccgatagctttcgttcgtatc
atcggtttcgacaacgttcgtcaagttcaatgcatcagtttcattgcgcacacaccagaatcctactgagttcga
gtattatggcattgggaaacatgtttttcttgtaccatttgttgtgcttgtaatttactgtgtttttattcggt
tttcgctatcgaactgtgaaatggaaatggatggagaagagttaatgaatgatatggtcctttgttcattctca
aattaatattatttgtttttctcttatttgttgtgtgttgaatttgaaaatataagagatatgcaaacatttg
ttttgagtaaaaatgtgtcaaatcgtggcctctaatgaccgaagttaatatgaggagtaaaacacttgtagttgt
accattatgcttattcactaggcaacaaatatattttcagacctagaaaagctgcaaatgttactgaatacaagt
atgtcctcttgtgtttagacatttatgaactttcctttatgtaattttccagaatccttgtcagattctaatca
ttgctttataattatagttatactcatggatttgtagttgagtatgaaaatatttttaatgcattttatgactt
g 2626

OsCesA7 Promoter | ZmMYB31 | tRBS

013 pOsCesA7-ZmMYB31-tRBS
2485 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttccgacctattgtgttgctttcctctctgatagcttatggtaaaagatacaaagatgtt
gaggagtttgtacgccacttaatttgctcgtaacatacattgacaatcaagaggagccatggcattgcgatctg
cttacacggcatattcttactggatggtgtacactacttacccttttaatgcaagcatcaatccattgctttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctccccccctgcaccatctcaccagaaaaacggtgaggcgtcaccgcaa
cccacccaccaaacacatccacgtcccttcaccgttggccttcgattttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggaggtcgccgtgctgcgagaaggcgcacaccaacaagggcgcgtg
gaccaaggaggaggacgagcgcctggtcgcgcacatcagggcgcacggcgaggggtgctggcgctcgctgcccaa
ggccgccggcctcctgcgctgcggcaagagctgccgcctccgctggatcaactacctccgccccgacctcaagcg
cggcaacttcacggaggaagaggacgagctcatcgtcaagctgcacagcgtcctcggcaacaagtggtccctgat
cgccggaaggctgcccggcaggacggacaacgagatcaagaactactggaacacgcacatccggaggaagctgct
gagcagggggatcgacccggtgacgcaccgcccggtcacggagcaccacgcgtccaacatcaccatatcgttcga
gacggaagtggccgccgctgcccgtgatgataagaagggcgccgtcttccggttggaggacgaggaggaggagga
gcgcaacaaggcgacgatggtcgtcggccgcgaccggcagagccagagccacagccacagccaccccgccggcga
gtggggccaggggaagaggccgctcaagtgccccgacctcaacctggacctctgcatcagcccgccgtgccagga
ggaggaggagatggaggaggctgcgatgagagtgagaccggcggtgaagcgggaggccgggctctgcttcggctg
cagcctggggctccccaggaccgcggactgcaagtgcagcagcagcagcttcctcgggctcaggaccgccatgct
cgacttcagaagcctcgagatgaaatgacacgtgtgaattacaggtgaccagctcgaatttccccgatagctttc
gttcgtatcatcggtttcgacaacgttcgtcaagttcaatgcatcagtttcattgcgcacacaccagaatcctac
tgagttcgagtattatggcattgggaaacatgtttttcttgtaccatttgttgtgcttgtaatttactgtgtttt
ttattcggttttcgctatcgaactgtgaaatggaaatggatggagaagagttaatgaatgatatggtcctttgt
tcattctcaaattaatattatttgtttttctcttatttgttgtgtgttgaatttgaaaatataagagatatgca
aacattttgttttgagtaaaaatgtgtcaaatcgtggcctctaatgaccgaagttaatatgaggagtaaaacact
tgtagttgtaccattatgcttattcactaggcaacaaatatattttcagacctagaaaagctgcaaatgttactg
aatacaagtatgtcctcttgtgtttagacatttatgaactttcctttatgtaattttccagaatccttgtcaga
ttctaatcattgctttataattatagttatactcatggatttgtagttgagtatgaaaatatttttaatgcatt
ttatgacttg
```

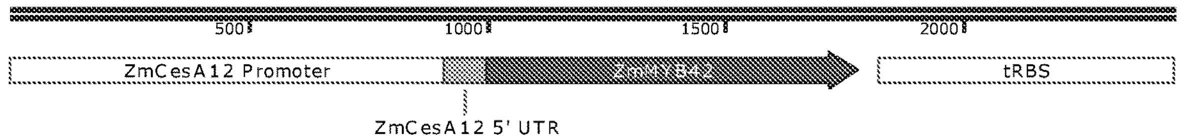

014 pZmCesA12-ZmMYB42-tRBS
2440 bp aggcggggccggaggagggcaccagagaggctgctcaggagagagaaataatagaatatgtggtatagagtaaac
atgagtgcggatgattgtggtatagagtaaagaattttgctgactaggacagaatattctttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcgggggctcgaccgaccg
acccaacgcctccatctccaccgcgcgcaccaaatcgcactcccgtccgccccgccgatcgaacagccaccgctc
acctctcccacccgccaaaaacctccggcctcctctcatattcatatagctagcccctgccacaaggtagagcgt
cgctcacacctgcgtcgccctgcctcgcaatcgcgaatctgtcgagcacctgaggggtcggaggccgagagctag
cctagcacgccggcctccgcgcgcgatggggcggtcgccgtgctgcgagaaggcgcacaccaacaggggcgcgtg
gaccaaggaggaggacgagcggctggtggcctacgtccgcgcgcacggcgaagggtgctggcgctcgctgcccag
ggcggcgggcctgctgcgctgcggcaagagctgccgcctgcgctggatcaactacctccgcccggacctcaagcg
aggcaacttcaccgccgacgaggacgacctcatcgtcaagctgcacagcctcctcgggaacaagtggtcgctcat
cgccgcgcggctcccggggcggacggacaacgagatcaagaactactggaacacgcacatccggcgcaagctgct
gggcagcggcatcgaccccgtcacgcaccgccgcgtcgcgggggcgccgcgaccaccatctcgttccagcccag
ccccaactccgccgccgccgccgccgccgcagaaacagcagcgcaggcgccgatcaaggccgaggagacggcggc
cgtcaaggcgcccaggtgccccgacctcaacctggacctctgcatcagcccgccgtgccagcatgaggacgacgg
cgaggaggaggacgaggagctggacctcaagcccgccttcgtcaagcgggaggcgctgcaggccggccacggcca
cggccacggcctctgcctcggctgcggcctgggcggacagaagggagcggccgggtgcagctgcagcaacggcca
ccacttcctggggctcaggaccagcgtgctcgacttcagaggcctggagatgaagtgacacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgtttttcttgtacc
atttgttgtgcttgtaatttactgtgtttttattcggttttcgctatcgaactgtgaaatggaaatggatggag
aagagttaatgaatgatatggtcctttgttcattctcaaattaatattatttgtttttctcttatttgttgtg
tgttgaatttgaaaatataagagatatgcaaacatttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatagttatactcatggatttgta
gttgagtatgaaaatatttttaatgcattttatgacttg 2440

FIG. 14

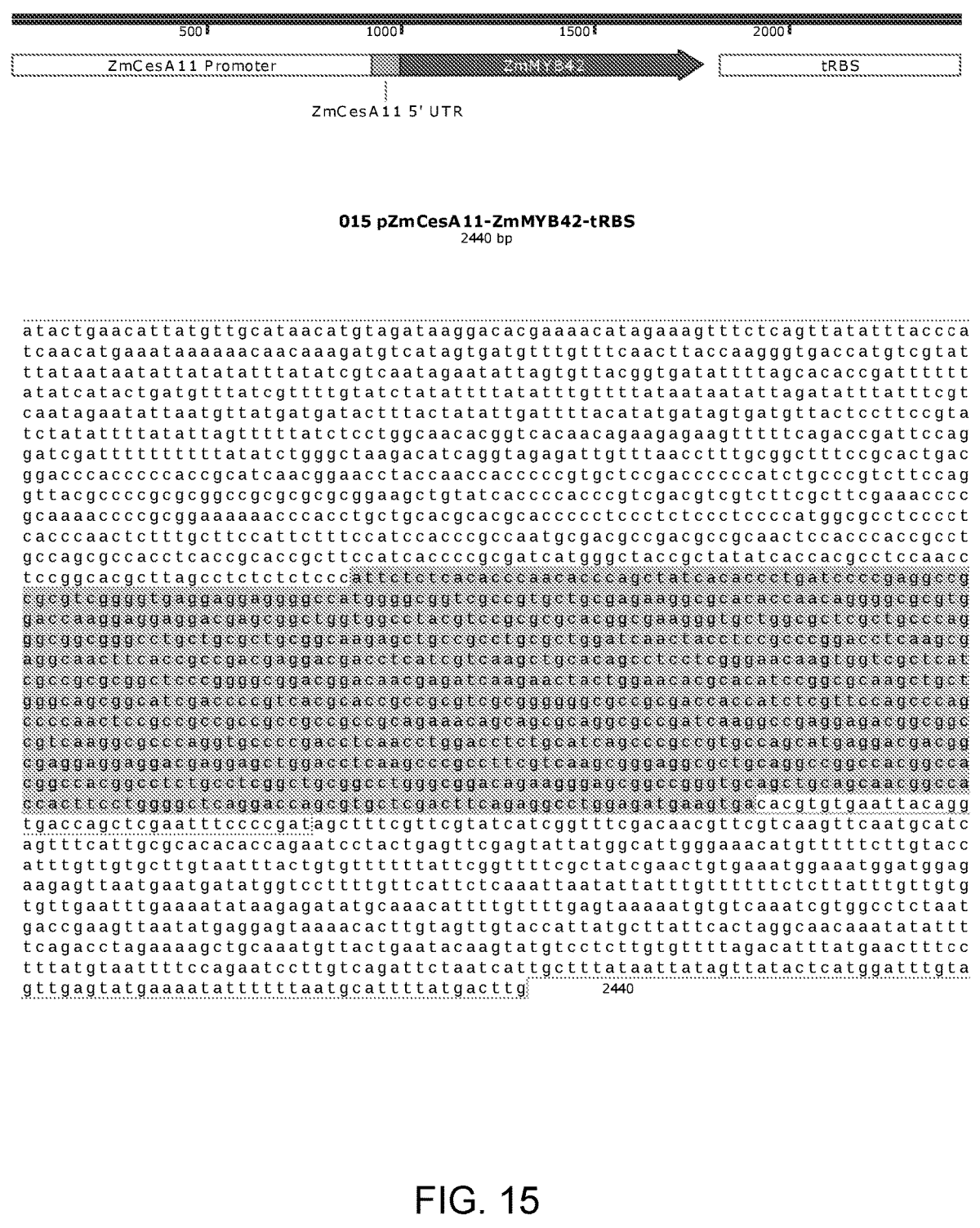

015 pZmCesA11-ZmMYB42-tRBS
2440 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatttatatcgtcaatagaatattagtgttacggtgatattttagcacaccgattttt
atatcatactgatgtttatcgttttgtatctatatttatatttgttttataataatattagatatttatttcgt
caatagaatattaatgttatgatgatactttactatattgattttacatatgatagtgatgttactccttccgta
tctatatttatattagttttatctcctggcaacacggtcacaacagaagagaagtttttcagaccgattccag
gatcgatttttttttatatctgggctaagacatcaggtagagattgtttaacctttgcggctttccgcactgac
ggacccacccccaccgcatcaacggaacctaccaaccaccccccgtgctccgacccccccatctgcccgtcttccag
gttacgccccgcgcggccgcgcgcgcggaagctgtatcaccccacccgtcgacgtcgtcttcgcttcgaaacccc
gcaaaaccccgcggaaaaaacccacctgctgcacgcacgcacccccctccctctccctccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctcccattctctcacacccaacacccagctatcacaccctgatccccgaggccg
cgcgtcggggtgaggaggaggggccatggggcggtcgccgtgctgcgagaaggcgcacaccaacaggggcgcgtg
gaccaaggaggaggacgagcggctggtggcctacgtccgcgcgcacggcgaagggtgctggcgctcgctgcccag
ggcggcgggcctgctgcgctgcggcaagagctgccgcctgcgctggatcaactacctccgcccggacctcaagcg
aggcaacttcaccgccgacgaggacgacctcatcgtcaagctgcacagcctcctcgggaacaagtggtcgctcat
cgccgcgcggctcccggggcggacggacaacgagatcaagaactactggaacacgcacatccggcgcaagctgct
gggcagcggcatcgaccccgtcacgcaccgccgcgtcgcgggggggcgccgcgaccaccatctcgttccagcccag
ccccaactccgccgccgccgccgccgccgcagaaacagcagcgcaggcgccgatcaaggccgaggagacggcggc
cgtcaaggcgcccaggtgccccgacctcaacctggacctctgcatcagcccgccgtgccagcatgaggacgacgg
cgaggaggaggacgaggagctggacctcaagcccgccttcgtcaagcgggaggcgctgcaggccggccacggcca
cggccacggcctctgcctcggctgcggcctgggcggacagaagggagcggccgggtgcagctgcagcaacggcca
ccacttcctggggctcaggaccagcgtgctcgacttcagaggcctggagatgaagtgacacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgtttttcttgtacc
atttgttgtgcttgtaatttactgtgtttttattcggttttcgctatcgaactgtgaaatggaaatggatggag
aagagttaatgaatgatatggtcctttgttcattctcaaattaatattatttgtttttctcttatttgttgtg
tgttgaatttgaaaatataagagatatgcaaacattttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatagttatactcatggatttgta
gttgagtatgaaaatatttttaatgcattttatgacttg 2440
```

FIG. 15

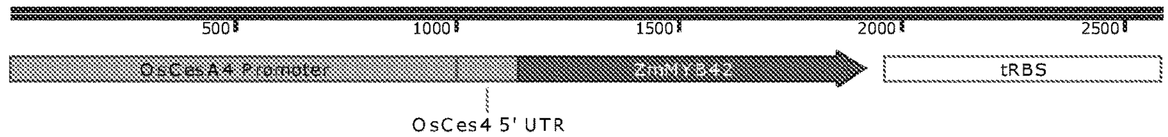

016 pOsCesA4-ZmMYB42-tRBS
2581 bp

```
gagttaaattgatatggttttgtctgtcaaggtgccgtttctatggttggaggaggaaaatgaaattaggggaat
agaacagtcgcaatccaaaagctattgttctctcttctacggtagttgatagttcgatacgtgtgtttgatgtga
gagactgagaggagtgcacggtgcacctgccccgtaaggacgcggaactacattatcagaggctaggccggtact
gttatacgcgacgttcacgaatcacgatgcgtaaaaaagtgaagcatgaaacagtactaggctctccacgggcca
catcatgaaaaaactggtgcgacgccacgcttaacaatttgtcggtcgtaaactcgtaaagttaaaagccccacg
acattgtcaaccaatatctcagcacatgaacttctctaacgagtacaacgaaaccgcatccgcaaaagcgccgtg
aaccaaagctcttgccgtgctgtgccgtgccggtggccgtgaacatgtggaacacgaagaactcttgcgcgagat
cggagcacctgacctcccacctcgcgtccggcccgtcgccgtcgcagcaagcgggctgtcaaaaacgacgccaca
gcgcgagcgctctcgccgatccggcggacccaccctcctcacctcgcgcaccaaccgcccgttcgctagtccgat
cccccacccctcatccccccctacgccttgcaggttacgcgcctcgccgcggccaacgcaaaccaaaccaaatccc
ccgtcaccttcgcttcgaaaccccgcaaaaccccatggaagaaaacaccgaacacctgccgcgcgcacgcctcct
cctcccccgcctctcctcctctctcccgttccatgtccgctcaaccttgcttccattctttccatccacccgccg
atcgacgcgatgccgacgccccaaccccacccaccgcctgccagcgccaccccacctcgcgcctctgcggctatg
gctatatcaccatgcctccaacctccggtacgcttagcctctctctctcccccctcccattctgcgcattgctc
tctgcgcgcggtcgcgtgctgctgctcgcggcgccccggagcgtctcctttgggggagaggagaggagaggagag
gagagggggggtgagccatggggcggtcgccgtgctgcgagaaggcgcacaccaacaggggcgcgtggaccaagga
ggaggacgagcggctggtggcctacgtccgcgcgcacggcgaagggtgctggcgctcgctgcccagggcggcggg
cctgctgcgctgcggcaagagctgccgcctgcgctggatcaactacctccgcccggacctcaagcgaggcaactt
caccgccgacgaggacgacctcatcgtcaagctgcacagcctcctcgggaacaagtggtcgctcatcgccgcgcg
gctcccggggcggacggacaacgagatcaagaactactggaacacgcacatccggcgcaagctgctgggcagcgg
catcgaccccgtcacgcaccgccgcgtcgcgggggggcgccgcgaccaccatctcgttccagcccagccccaactc
cgccgccgccgccgccgccgcagaaacagcagcgcaggcgccgatcaaggccgaggagacggcggccgtcaaggc
gcccaggtgccccgacctcaacctggacctctgcatcagcccgccgtgccagcatgaggacgacggcgaggagga
ggacgaggagctggacctcaagcccgccttcgtcaagcgggaggcgctgcaggccggccacggccacggccacgg
cctctgcctcggctgcggcctgggcggacagaagggagcggccgggtgcagctgcagcaacggccaccacttcct
ggggctcaggaccagcgtgctcgacttcagaggcctggagatgaagtgacacgtgtgaattacaggtgaccagct
cgaatttccccgatagctttcgttcgtatcatcggtttcgacaacgttcgtcaagttcaatgcatcagtttcatt
gcgcacacaccagaatcctactgagttcgagtattatggcattgggaaacatgtttttcttgtaccatttgttgt
gcttgtaatttactgtgtttttattcggttttcgctatcgaactgtgaaatggaaatggatggagaagagttaa
tgaatgatatggtcctttgttcattctcaaattaatattatttgtttttctcttatttgttgtgtgttgaatt
tgaaaatataagagatatgcaaacattttgttttgagtaaaaatgtgtcaaatcgtggcctctaatgaccgaagt
taatatgaggagtaaaacacttgtagttgtaccattatgcttattcactaggcaacaaatatatttcagaccta
gaaaagctgcaaatgttactgaatacaagtatgtcctcttgtgttttagacatttatgaactttcctttatgtaa
ttttccagaatccttgtcagattctaatcattgctttataattatagttatactcatggatttgtagttgagtat
gaaaatatttttaatgcattttatgacttg
```

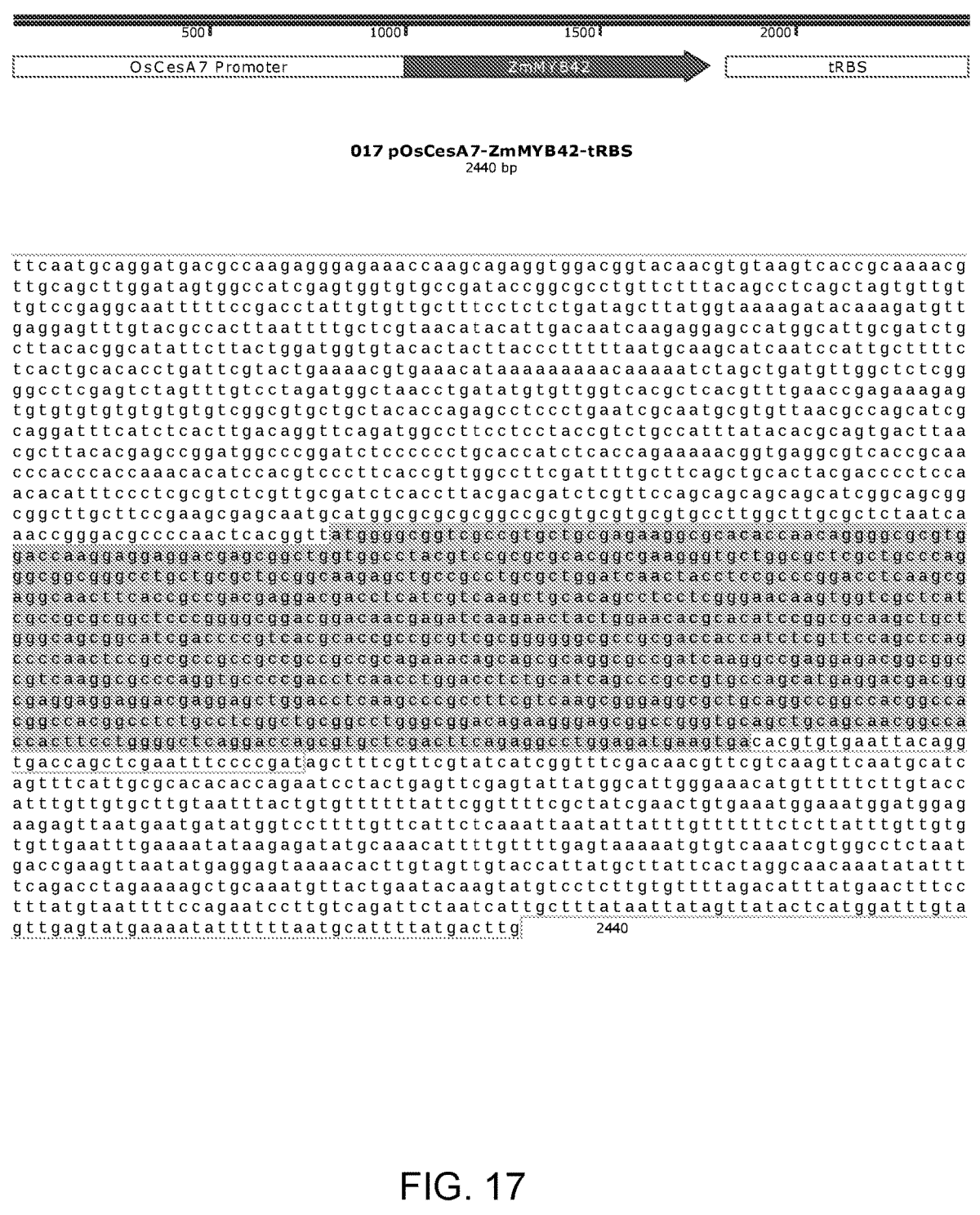

017 pOsCesA7-ZmMYB42-tRBS
2440 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttacccttttaatgcaagcatcaatccattgctttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctccccccctgcaccatctcaccagaaaaacggtgaggcgtcaccgcaa
cccacccaccaaacacatccacgtcccttcaccgttggccttcgatttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggcggtcgccgtgctgcgagaaggcgcacaccaacaggggcgcgtg
gaccaaggaggaggacgagcggctggtggcctacgtccgcgcgcacggcgaagggtgctggcgctcgctgcccag
ggcggcgggcctgctgcgctgcggcaagagctgccgcctgcgctggatcaactacctccgcccggacctcaagcg
aggcaacttcaccgccgacgaggacgacctcatcgtcaagctgcacagcctcctcgggaacaagtggtcgctcat
cgccgcgcggctcccggggcggacggacaacgagatcaagaactactggaacacgcacatccggcgcaagctgct
gggcagcggcatcgaccccgtcacgcaccgccgcgtcgcgggggcgccgcgaccaccatctcgttccagcccag
ccccaactccgccgccgccgccgccgccgcagaaacagcagcgcaggcgccgatcaaggccgaggagacggcggc
cgtcaaggcgcccaggtgccccgacctcaacctggacctctgcatcagcccgccgtgccagcatgaggacgacgg
cgaggaggaggacgaggagctggacctcaagcccgccttcgtcaagcgggaggcgctgcaggccggccacggcca
cggccacggcctctgcctcggctgcggcctgggcggacagaagggagcggccgggtgcagctgcagcaacggcca
ccacttcctggggctcaggaccagcgtgctcgacttcagaggcctggagatgaagtgacacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgtttttcttgtacc
atttgttgtgcttgtaatttactgtgtttttattcggttttcgctatcgaactgtgaaatggaaatggatggag
aagagttaatgaatgatatggtcctttgttcattctcaaattaatattatttgtttttctcttatttgttgtg
tgttgaatttgaaaatataagagatatgcaaacatttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatagttatactcatggatttgta
gttgagtatgaaaatatttttaatgcattttatgacttg
```
2440

FIG. 17

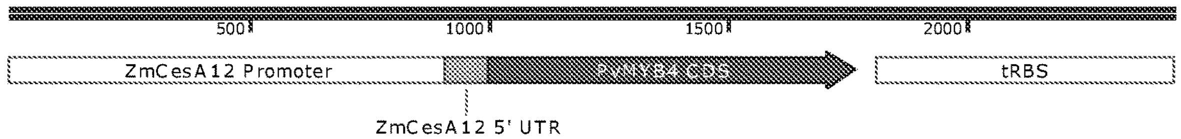

018 pZmCesA12-PvMYB4-tRBS
2428 bp

```
aggcggggccggaggagggcaccagagaggctgctcaggagagagaaataatagaatatgtggtatagagtaaac
atgagtgcggatgattgtggtatagagtaaagaatttgctgactaggacagaatattctttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcgggggctcgaccgaccg
acccaacgcctccatctccaccgcgcgcaccaaatcgcactcccgtccgccccgccgatcgaacagccaccgctc
acctctcccacccgccaaaaacctccggcctcctctcatattcatatagctagcccctgccacaaggtagagcgt
cgctcacacctgcgtcgccctgcctcgcaatcgcgaatctgtcgagcacctgaggggtcggaggccgagagctag
cctagcacgccggcctccgcgcgcgatggggcgatcgccgtgctgcgagaaggcgcacacgaacaagggcgcctg
gaccaaggaggaggacgaccgcctcgttgcctacatccgggcgcacggcgaggggtgctggcgctccctccccaa
ggccgcgggcctgctgcgctgcggcaagagctgccgcctgcgctggatcaactacctccgcccggacctcaagcg
cggcaacttcaccgccgacgaggacgacctcatcgtcaagctccacagcctcctcggcaacaagtggtcgctcat
cgccgcgcgcctccccggccgcaccgacaacgagatcaagaactactggaacacgcacatcaagcgcaagctcct
cagccgcggcatcgaccccgtcacacaccgccccatcgccgacgcagccagaaacgtcaccatctccttccagcc
cgacgcgccgtcgcagcagcagctcagcgacgacgccgaggcgccgccgccgccgccgccgcagcagcagcagca
gctcaagccgccgcccaggtgccccgacctcaatctcgacctctgcatcagcccgccctgccacaaggaagaaga
ggaccaggagctcgtcaagcccgccgccgtcaagcgcgagatgctgcaggccggccacggcactctaggactctg
cttcggctgcagcctgggcctccagaagggcgccgccgggtgcacctgcagcagcaacagccacttcctggggct
cagggtcggcatgctcctcgacttcagaggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgtttttcttgtaccatttgttgtgct
tgtaatttactgtgtttttttattcggttttcgctatcgaactgtgaaatggaaatggatggagaagagttaatga
atgatatggtccttttgttcattctcaaattaatattatttgtttttttctcttatttgttgtgtgttgaatttga
aaatataagagatatgcaaacatttgttttgagtaaaaatgtgtcaaatcgtggcctctaatgaccgaagttaa
tatgaggagtaaaacacttgtagttgtaccattatgcttattcactaggcaacaaatatatttcagacctagaa
aagctgcaaatgttactgaatacaagtatgtcctcttgtgttttagacatttatgaactttcctttatgtaattt
tccagaatccttgtcagattctaatcattgctttataattatagttatactcatggatttgtagttgagtatgaa
aatatttttaatgcattttatgacttg
```
2428

FIG. 18

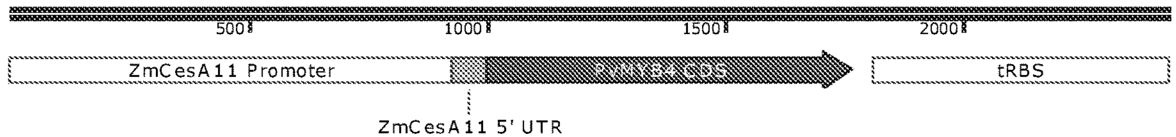

019 pZmCesA11-PvMYB4-tRBS

2428 bp atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatattttagcacaccgattttt
atatcatactgatgtttatcgttttgtatctatatttatatttgttttataataatattagatatttatttcgt
caatagaatattaatgttatgatgatactttactatattgattttacatatgatagtgatgttactccttccgta
tctatatttatattagttttatctcctggcaacacggtcacaacagaagagaagtttttcagaccgattccag
gatcgatttttttttatatctgggctaagacatcaggtagagattgtttaacctttgcggctttccgcactgac
ggacccacccccaccgcatcaacggaacctaccaaccacccccgtgctccgacccccatctgcccgtcttccag
gttacgccccgcgcggccgcgcgcgcggaagctgtatcaccccacccgtcgacgtcgtcttcgcttcgaaacccc
gcaaaaccccgcggaaaaaacccacctgctgcacgcacgcacccccctccctctccctccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctcccattctctcacacccaacacccagctatcacaccctgatccccgaggccg
cgcgtcggggtgaggaggaggggccatggggcgatcgccgtgctgcgagaaggcgcacacgaacaagggcgcctg
gaccaaggaggaggacgaccgcctcgttgcctacatccgggcgcacggcgaggggtgctggcgctccctccccaa
ggccgcgggcctgctgcgctgcggcaagagctgccgcctgcgctggatcaactacctccgcccggacctcaagcg
cggcaacttcaccgccgacgaggacgacctcatcgtcaagctccacagcctcctcggcaacaagtggtcgctcat
cgccgcgcgcctccccggccgcaccgacaacgagatcaagaactactggaacacgcacatcaagcgcaagctcct
cagccgcggcatcgaccccgtcacacaccgccccatcgccgacgcagccagaaacgtcaccatctccttccagcc
cgacgcgccgtcgcagcagcagctcagcgacgacgccgaggcgccgccgccgccgccgcagcagcagcagca
gctcaagccgccgcccaggtgccccgacctcaatctcgacctctgcatcagcccgccctgccacaaggaagaaga
ggaccaggagctcgtcaagcccgccgccgtcaagcgcgagatgctgcaggccggccacggcactctaggactctg
cttcggctgcagcctgggcctccagaagggcgccgccgggtgcacctgcagcagcaacagccacttcctggggct
cagggtcggcatgctcctcgacttcagaggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgtttttcttgtaccatttgttgtgct
tgtaatttactgtgtttttttattcggttttcgctatcgaactgtgaaatggaaatggatggagaagagttaatga
atgatatggtcctttttgttcattctcaaattaatattatttgtttttttctcttatttgttgtgtgttgaatttga
aaatataagagatatgcaaacattttgttttgagtaaaaatgtgtcaaatcgtggcctctaatgaccgaagttaa
tatgaggagtaaaacacttgtagttgtaccattatgcttattcactaggcaacaaatatatttcagacctagaa
aagctgcaaatgttactgaatacaagtatgtcctcttgtgttttagacatttatgaactttcctttatgtaattt
tccagaatccttgtcagattctaatcattgctttataattatagttatactcatggatttgtagttgagtatgaa
aatatttttttaatgcattttatgacttg 2428

FIG. 19

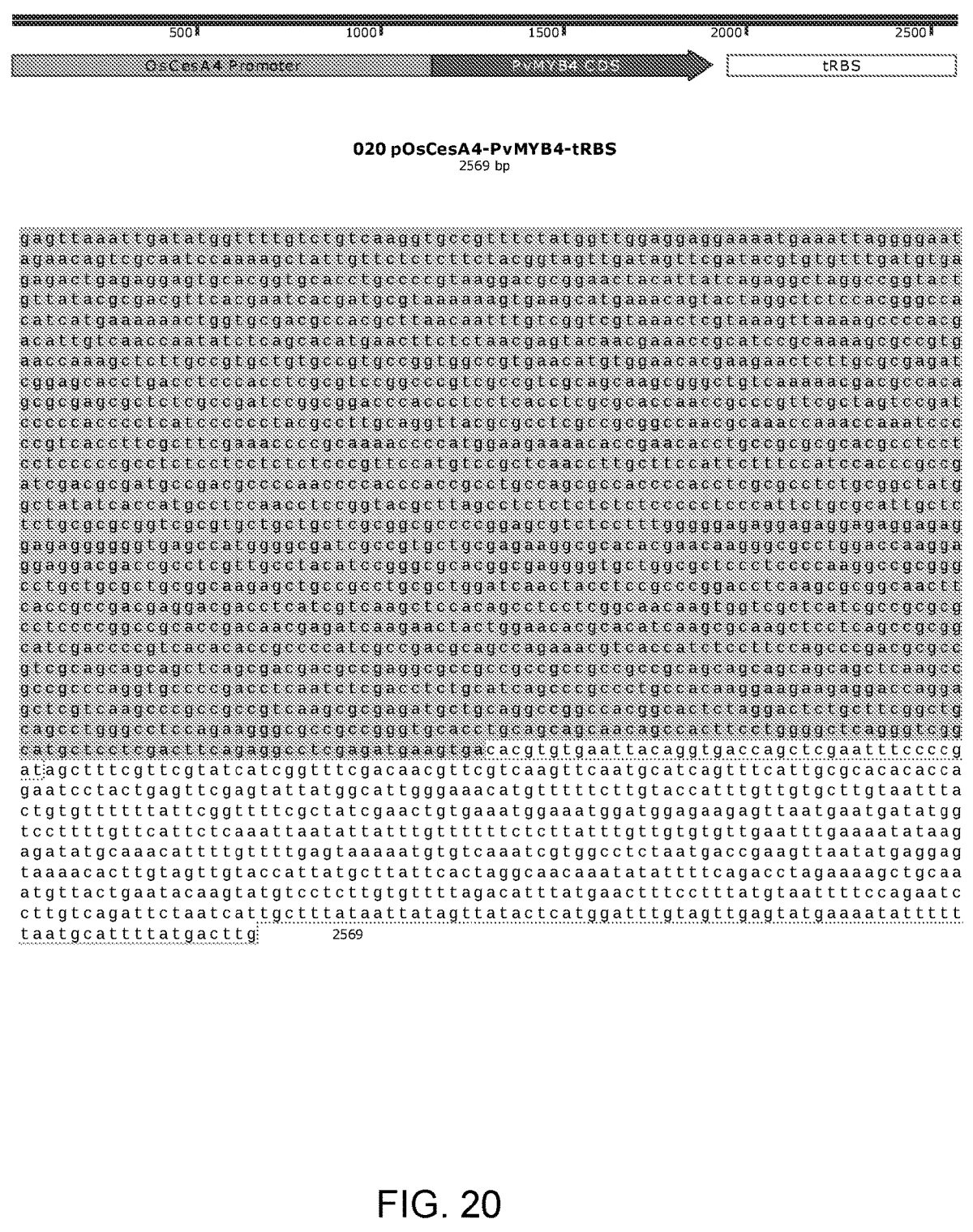

020 pOsCesA4-PvMYB4-tRBS
2569 bp gagttaaattgatatggttttgtctgtcaaggtgccgtttctatggttggaggaggaaaatgaaattaggggaat
agaacagtcgcaatccaaaagctattgttctctcttctacggtagttgatagttcgatacgtgtgtttgatgtga
gagactgagaggagtgcacggtgcacctgccccgtaaggacgcggaactacattatcagaggctaggccggtact
gttatacgcgacgttcacgaatcacgatgcgtaaaaaagtgaagcatgaaacagtactaggctctccacgggcca
catcatgaaaaaactggtgcgacgccacgcttaacaatttgtcggtcgtaaactcgtaaagttaaaagccccacg
acattgtcaaccaatatctcagcacatgaacttctctaacgagtacaacgaaaccgcatccgcaaaagcgccgtg
aaccaaagctcttgccgtgctgtgccgtgccggtggccgtgaacatgtggaacacgaagaactcttgcgcgagat
cggagcacctgacctcccacctcgcgtccggcccgtcgccgtcgcagcaagcgggctgtcaaaaacgacgccaca
gcgcgagcgctctcgccgatccggcggacccaccctcctcacctcgcgcaccaaccgcccgttcgctagtccgat
cccccacccctcatccccccctacgccttgcaggttacgcgcctcgccgcggccaacgcaaaccaaaccaaatccc
ccgtcaccttcgcttcgaaaccccgcaaaaccccatggaagaaaacaccgaacacctgccgcgcgcacgcctcct
cctcccccgcctctcctcctctctcccgttccatgtccgctcaaccttgcttccattctttccatccacccgccg
atcgacgcgatgccgacgccccaaccccacccaccgcctgccagcgccaccccacctcgcgcctctgcggctatg
gctatatcaccatgcctccaacctccggtacgcttagcctctctctctctccccctcccattctgcgcattgctc
tctgcgcgcggtcgcgtgctgctgctcgcggcgccccggagcgtctcctttgggggagaggagaggagaggagag
gagagggggtgagccatggggcgatcgccgtgctgcgagaaggcgcacacgaacaagggcgcctggaccaagga
ggaggacgaccgcctcgttgcctacatccgggcgcacggcgagggtgctggcgctccctccccaaggccgcggg
cctgctgcgctgcggcaagagctgccgcctgcgctggatcaactacctccgcccggacctcaagcgcggcaactt
caccgccgacgaggacgacctcatcgtcaagctccacagcctcctcggcaacaagtggtcgctcatcgccgcgcg
cctccccggccgcaccgacaacgagatcaagaactactggaacacgcacatcaagcgcaagctcctcagccgcgg
catcgaccccgtcacacaccgccccatcgccgacgcagccagaaacgtcaccatctccttccagcccgacgcgcc
gtcgcagcagcagctcagcgacgacgccgaggcgccgccgccgccgccgccgcagcagcagcagcagctcaagcc
gccgcccaggtgccccgacctcaatctcgacctctgcatcagcccgccctgccacaaggaagaagaggaccagga
gctcgtcaagcccgccgccgtcaagcgcgagatgctgcaggccggccacggcactctaggactctgcttcggctg
cagcctgggcctccagaagggcgccgccgggtgcacctgcagcagcaacagccacttcctggggctcagggtcgg
catgctcctcgacttcagaggcctcgagatgaagtgacacgtgtgaattacaggtgaccagctcgaatttccccg
atagctttcgttcgtatcatcggtttcgacaacgttcgtcaagttcaatgcatcagtttcattgcgcacacacca
gaatcctactgagttcgagtattatggcattgggaaacatgtttttcttgtaccatttgttgtgcttgtaattta
ctgtgtttttattcggttttcgctatcgaactgtgaaatggaaatggatggagaagagttaatgaatgatatgg
tccttttgttcattctcaaattaatattatttgtttttctcttatttgttgtgtgttgaatttgaaaatataag
agatatgcaaacattttgttttgagtaaaaatgtgtcaaatcgtggcctctaatgaccgaagttaatatgaggag
taaaacacttgtagttgtaccattatgcttattcactaggcaacaaatatattttcagacctagaaaagctgcaa
atgttactgaatacaagtatgtcctcttgtgttttagacatttatgaactttcctttatgtaattttccagaatc
cttgtcagattctaatcattgctttataattatagttatactcatggatttgtagttgagtatgaaaatatttttt
taatgcattttatgacttg 2569

FIG. 20

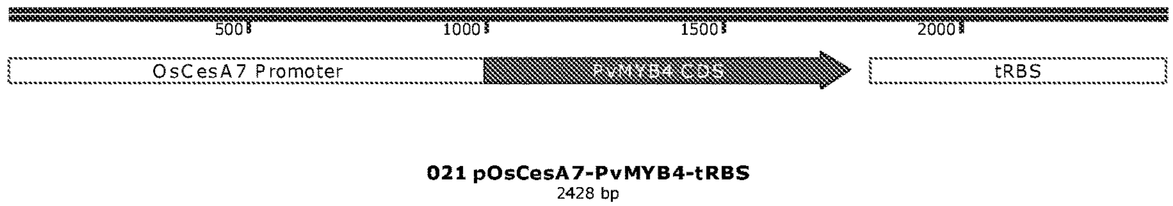

021 pOsCesA7-PvMYB4-tRBS
2428 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttacccttttaatgcaagcatcaatccattgcttttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctccccccctgcaccatctcaccagaaaaacggtgaggcgtcaccgcaa
cccacccaccaaacacatccacgtcccttcaccgttggccttcgattttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggcgatcgccgtgctgcgagaaggcgcacacgaacaagggcgcctg
gaccaaggaggaggacgaccgcctcgttgcctacatccgggcgcacggcgaggggtgctggcgctccctccccaa
ggccgcgggcctgctgcgctgcggcaagagctgccgcctgcgctggatcaactacctccgcccggacctcaagcg
cggcaacttcaccgccgacgaggacgacctcatcgtcaagctccacagcctcctcggcaacaagtggtcgctcat
cgccgcgcgcctccccggccgcaccgacaacgagatcaagaactactggaacacgcacatcaagcgcaagctcct
cagccgcggcatcgaccccgtcacacaccgccccatcgccgacgcagccagaaacgtcaccatctccttccagcc
cgacgcgccgtcgcagcagcagctcagcgacgacgccgaggcgccgccgccgccgccgcagcagcagcagca
gctcaagccgccgcccaggtgccccgacctcaatctcgacctctgcatcagcccgccctgccacaaggaagaaga
ggaccaggagctcgtcaagcccgccgccgtcaagcgcgagatgctgcaggccggccacggcactctaggactctg
cttcggctgcagcctgggcctccagaagggcgccgccgggtgcacctgcagcagcaacagccacttcctggggct
cagggtcggcatgctcctcgacttcagaggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgtttttcttgtaccatttgttgtgct
tgtaatttactgtgtttttttattcggttttcgctatcgaactgtgaaatggaaatggatggagaagagttaatga
atgatatggtcctttgttcattctcaaattaatattatttgtttttctcttatttgttgtgtgttgaatttga
aaatataagagatatgcaaacattttgttttgagtaaaaatgtgtcaaatcgtggcctctaatgaccgaagttaa
tatgaggagtaaaacacttgtagttgtaccattatgcttattcactaggcaacaaatatattttcagacctagaa
aagctgcaaatgttactgaatacaagtatgtcctcttgtgttttagacatttatgaactttcctttatgtaattt
tccagaatccttgtcagattctaatcattgctttataattatagttatactcatggatttgtagttgagtatgaa
aatatttttttaatgcattttatgacttg
```

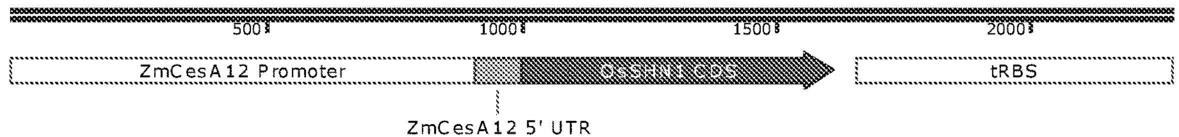

022 pZmCesA12-OsSHN1-tRBS
2275 bp aggcggggccggaggagggcaccagagaggctgctcaggagagagaaataatagaatatgtggtatagagtaaac
atgagtgcggatgattgtggtatagagtaaagaattttgctgactaggacagaatattctttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcgggggctcgaccgaccg
acccaacgcctccatctccaccgcgcgcaccaaatcgcactcccgtccgccccgccgatcgaacagccaccgctc
acctctcccacccgccaaaaacctccggcctcctctcatattcatatagctagcccctgccacaaggtagagcgt
cgctcacacctgcgtcgccctgcctcgcaatcgcgaatctgtcgagcacctgaggggtcggaggccgagagctag
cctagcacgccggcctccgcgcgcgatggtacagccaaagaagaagtttcgtggagtcaggcagcggcactgggg
ctcctgggtctctgagatcagacacccccctccttaaaaggagggtgtggctgggcacctttgagacggccgagga
ggctgcgcgagcctacgatgaggctgctgtgctgatgagtggccgcaacgccaagaccaacttccccgtgcagag
gaactccaccggtgatctcgccacggccgcagaccaggacgcccgtagcaatggcggtagcaggaactcctccgc
gggcaacctgtcacagattctcagtgctaagctccgcaagtgctgcaaggcgccatctccgtccttaacctgcct
ccgcctcgaccccgagaagtcccacattggcgtgtggcaaaagcgcgcaggggcccgtgctgactccaactgggt
gatgacggtggagctcaacaaagaggtagaaccaactgaacctgcagctcagcccacatcaacagcaacagcttc
gcaagtgacaatggatgatgaggaaaagattgcgctgcaaatgatcgaggagttgctgagcaggagcagtccagc
ttcaccctcacatggagagggagagggtagctttgtcatctgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgtttttcttgtaccatttgttgtgcttgt
aatttactgtgtttttattcggttttcgctatcgaactgtgaaatggaaatggatggagaagagttaatgaatg
atatggtcctttttgttcattctcaaattaatattatttgtttttttctcttatttgttgtgtgttgaatttgaaaa
tataagagatatgcaaacatttgttttgagtaaaaatgtgtcaaatcgtggcctctaatgaccgaagttaatat
gaggagtaaaacacttgtagttgtaccattatgcttattcactaggcaacaaatatattttcagacctagaaaag
ctgcaaatgttactgaatacaagtatgtcctcttgtgttttagacatttatgaactttcctttatgtaatttcc
agaatccttgtcagattctaatcattgctttataattatagttatactcatggatttgtagttgagtatgaaaat
atttttaatgcattttatgacttg 2275

FIG. 22

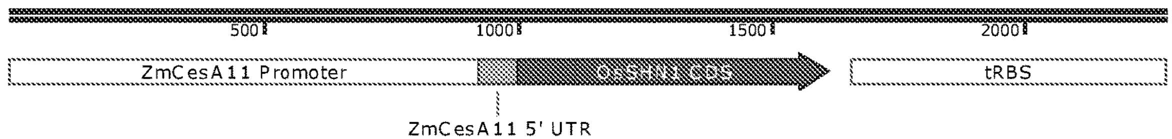

023 pZmCesA11-OsSHN1-tRBS
2275 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatttatatcgtcaatagaatattagtgttacggtgatattttagcacaccgattttttt
atatcatactgatgtttatcgttttgtatctatatttatatttgttttataataatattagatatttatttcgt
caatagaatattaatgttatgatgatactttactatattgattttacatatgatagtgatgttactccttccgta
tctatatttatattagttttatctcctggcaacacggtcacaacagaagagaagttttcagaccgattccag
gatcgatttttttttatatctgggctaagacatcaggtagagattgtttaacctttgcggctttccgcactgac
ggacccacccccaccgcatcaacggaacctaccaaccacccccgtgctccgacccccatctgcccgtcttccag
gttacgccccgcgcggccgcgcgcgcggaagctgtatcaccccacccgtcgacgtcgtcttcgcttcgaaacccc
gcaaaaccccgcggaaaaaacccacctgctgcacgcacgcaccccctccctctccctccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctcccattctctcacacccaacacccagctatcacaccctgatccccgaggccg
cgcgtcggggtgaggaggaggggccatggtacagccaaagaagaagtttcgtggagtcaggcagcggcactgggg
ctcctgggtctctgagatcagacacccccctccttaaaaggagggtgtggctgggcacctttgagacggccgagga
ggctgcgcgagcctacgatgaggctgctgtgctgatgagtggccgcaacgccaagaccaacttccccgtgcagag
gaactccaccggtgatctcgccacggccgcagaccaggacgcccgtagcaatggcggtagcaggaactcctccgc
gggcaacctgtcacagattctcagtgctaagctccgcaagtgctgcaaggcgccatctccgtccttaacctgcct
ccgcctcgaccccgagaagtcccacattggcgtgtggcaaaagcgcgcaggggcccgtgctgactccaactgggt
gatgacggtggagctcaacaaagaggtagaaccaactgaacctgcagctcagcccacatcaacagcaacagcttc
gcaagtgacaatggatgatgaggaaaagattgcgctgcaaatgatcgaggagttgctgagcaggagcagtccagc
ttcaccctcacatggagagggagagggtagctttgtcatctgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgtttttcttgtaccatttgttgtgcttgt
aatttactgtgtttttttattcggttttcgctatcgaactgtgaaatggaaatggatggagaagagttaatgaatg
atatggtcctttttgttcattctcaaattaatattatttgtttttttctcttatttgttgtgtgttgaatttgaaaa
tataagagatatgcaaacatttttgttttgagtaaaaatgtgtcaaatcgtggcctctaatgaccgaagttaatat
gaggagtaaaacacttgtagttgtaccattatgcttattcactaggcaacaaatatattttcagacctagaaaag
ctgcaaatgttactgaatacaagtatgtcctcttgtgtttttagacatttatgaactttcctttatgtaattttcc
agaatccttgtcagattctaatcattgctttataattatagttatactcatggatttgtagttgagtatgaaaat
atttttttaatgcattttatgacttg 2275
```

FIG. 23

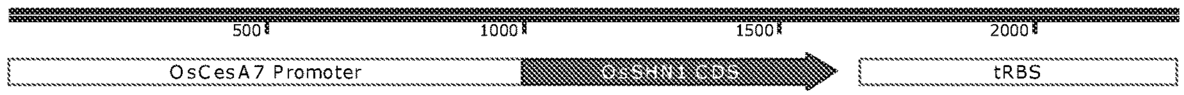

025 pOsCesA7-OsSHN1-tRBS
2275 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttacccttttaatgcaagcatcaatccattgcttttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctccccctgcaccatctcaccagaaaaacggtgaggcgtcaccgcaa
cccacccaccaaacacatccacgtcccttcaccgttggccttcgattttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggtacagccaaagaagaagtttcgtggagtcaggcagcggcactgggg
ctcctgggtctctgagatcagacaccccctccttaaaaggagggtgtggctgggcacctttgagacggccgagga
ggctgcgcgagcctacgatgaggctgctgtgctgatgagtggccgcaacgccaagaccaacttccccgtgcagag
gaactccaccggtgatctcgccacggccgcagaccaggacgcccgtagcaatggcggtagcaggaactcctccgc
gggcaacctgtcacagattctcagtgctaagctccgcaagtgctgcaaggcgccatctccgtccttaacctgcct
ccgcctcgaccccgagaagtcccacattggcgtgtggcaaaagcgcgcaggggcccgtgctgactccaactgggt
gatgacggtggagctcaacaaagaggtagaaccaactgaacctgcagctcagcccacatcaacagcaacagcttc
gcaagtgacaatggatgatgaggaaaagattgcgctgcaaatgatcgaggagttgctgagcaggagcagtccagc
ttcaccctcacatggagagggagagggtagctttgtcatctgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgtttttcttgtaccatttgttgtgcttgt
aatttactgtgtttttattcggttttcgctatcgaactgtgaaatggaaatggatggagaagagttaatgaatg
atatggtccttttgttcattctcaaattaatattatttgtttttctcttatttgttgtgtgttgaatttgaaaa
tataagagatatgcaaacatttgttttgagtaaaaatgtgtcaaatcgtggcctctaatgaccgaagttaatat
gaggagtaaaacacttgtagttgtaccattatgcttattcactaggcaacaaatatatttcagacctagaaaag
ctgcaaatgttactgaatacaagtatgtcctcttgtgttttagacatttatgaactttcctttatgtaatttcc
agaatccttgtcagattctaatcattgctttataattatagttatactcatggatttgtagttgagtatgaaaat
atttttaatgcatttatgacttg 2275
```

FIG. 25

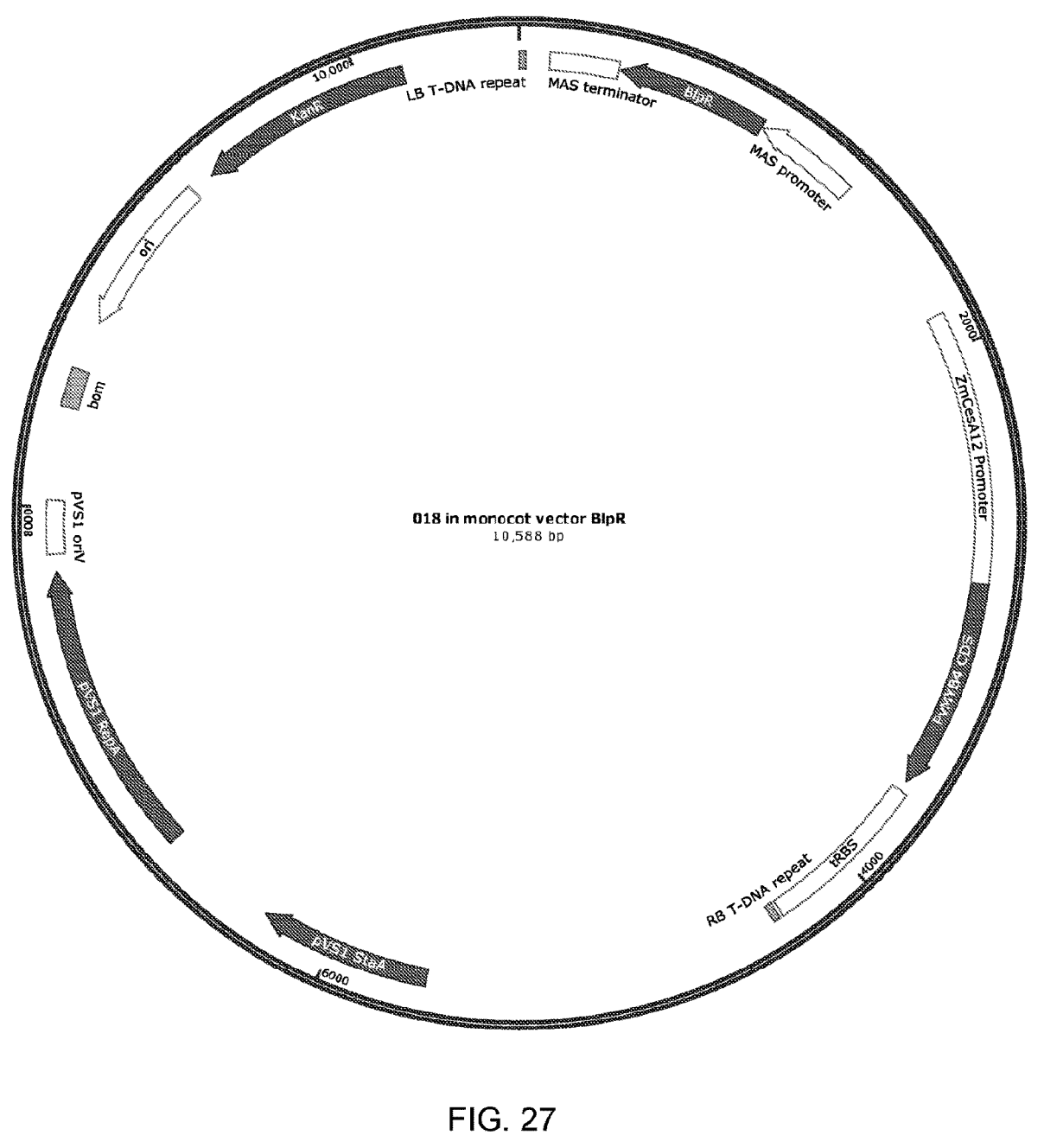

10,000
LB T-DNA repeat
MAS terminator
BlpR
KanR
MAS promoter
ori
2000
bom
ZmCesA12 Promoter
pVS1 oriV
8000
018 in monocot vector BlpR
10,588 bp
pVS1 RepA
tRBS
RB T-DNA repeat
4000
pVS1 StaA
6000

FIG. 27

COMPOSITIONS AND METHODS FOR INCREASING PLANT GROWTH AND IMPROVING MULTIPLE YIELD-RELATED TRAITS

CROSS-REFERENCE TO RELATED APPLICATION

This application is the U.S. national phase of PCT Application No. PCT/US2019/015688 filed on Jan. 29, 2019, which claims the benefit of U.S. Provisional Patent Application Ser. No. 62/623,279, filed Jan. 29, 2018, the disclosures of which are incorporated in their entirety by reference herein.

STATEMENT REGARDING FEDERALLY SPONSORED RESEARCH OR DEVELOPMENT

This invention was made with government support under Award Number 2016-33610-25368 awarded by the U.S. Department of Agriculture, Award Number NNX17CKO4P awarded by the National Aeronautics and Space Administration, and Award Number DE-SC0011309 awarded by the U.S. Department of Energy. The government has certain rights in this invention.

SEQUENCE LISTING

The text file 57798_0101_ST25 of size 170 KB created Jul. 29, 2020, filed herewith, is hereby incorporated by reference.

FIELD OF THE INVENTION

The present invention relates to genetic constructs and transgenic plants with vascular xylem tissue-targeting overexpression of transcription factors (TFs) involved in vascular xylem cell development, as well as their methods of use for enhancing plant growth and yield.

BACKGROUND OF THE INVENTION

Yield is commonly defined as the measurable economic value of agricultural product from a crop. This may be defined in terms of quantity or quality, or a combination of both. Yield is directly dependent on several factors, for example, the number and size of the organs, plant architecture (i.e. number of tillers or branches), seed production, nutrient content, assimilation of metabolic precursors, root development, nutrient uptake, stress tolerance, and early vigor. Optimizing the above-mentioned factors may, therefore, contribute to increasing crop and horticultural yield. Depending on the end use, the modification of certain yield traits may be favored over others. For example, for applications such as forage or wood production, or as a biofuel resource, an increase in the vegetative parts of a plant may be desirable, and for applications such as flour, starch, or oil production, an increase in seed parameters may be particularly desirable. Such plant growth and/or yield-related traits may be improved by enhancing vascular tissue meristematic activity.

In higher plants, vascular tissues are important for transporting water and nutrients throughout the plant and providing physical support for upright growth. Primary constituents of the vascular tissues, xylem and phloem, are derived from the meristematic vascular procambium and cambium (Esau, Plant Anatomy (1965); Esau, Anatomy of Seed Plants (1977)). Xylem cells are particularly important for developing secondary cell walls that form the largest part of plant lignocellulosic biomass that consists of cellulose, hemicellulose, and lignin. Histochemical studies have indicated that lignification of the secondary cell wall generally occurs after the initial deposition of the cellulosic and hemicellulosic components and that it is initiated in a spatially distinct manner, beginning with the lignification of the middle lamella. Comparative studies of the patterns of secondary cell wall deposition in xylem cells in many different vascular plants have shown that the patterning of secondary cell wall deposition in these cells is a highly conserved process across species (Esau, Plant Anatomy (1965); Meylan and Butterfield, *Three-Dimensional Structure of Wood* (1972)).

Traditional molecular biology approaches using mutant analysis have identified a series of enzymes involved in the formation and accumulation of secondary cell wall mass (Turner and Somerville, "Collapsed Xylem Phenotype of *Arabidopsis* Identifies Mutants Deficient in Cellulose Deposition in the Secondary Cell Wall," *Plant Cell* 9(5):689-701 (1997); Brown et al., "Identification of Novel Genes in *Arabidopsis* Involved in Secondary Cell Wall Formation Using Expression Profiling and Reverse Genetics," *Plant Cell* 17(8):2281-95 (2005); Oikawa et al., "An Integrative Approach to the Identification of *Arabidopsis* and Rice Genes Involved in Xylan and Secondary Wall Development," *PLoS ONE* 5(11):e15481 (2010); Hirano et al., "Survey of Genes Involved in Rice Secondary Cell Wall Formation Through a Co-Expression Network," *Plant Cell Physiol.* 54(1):1803-21 (2013); Hao and Mohnen, "A Review of Xylan and Lignin Biosynthesis: Foundation for Studying *Arabidopsis* Irregular Xylem Mutants with Pleiotropic Phenotypes," *Crit. Rev. Biochem. Mol. Biol.* 49(3): 212-41 (2014)). Namely, irregular xylem (irx) mutants, which show collapsed xylem vessels in *Arabidopsis*, and brittle culm (bc) mutants, which show two-fold decrease in breaking strength compared with wild-type in rice, implicate these genes in secondary cell wall formation. The genes identified from the mutant screening were IRX1: AT4G18780 (AtCesA8), IRX2: AT5G49720 (AtKOR1), IRX3: AT5G17420 (AtCesA7), IRX4: AT1G15950 (AtCCR1), IRX5: AT5G44030 (AtCesA4), IRX6: AT5G15630 (AtCOBL4), IRX7: AT2G28110 (AtFRA8), IRX8: AT5G54690 (AtGAUT12), IRX9: AT2G37090 (glycosyltransferases family 43), IRX10: AT1G27440 (AtGUT1), IRX11: AT1G62990 (AtKNAT7), IRX12: AT2G38080 (AtLAC4), IRX13: At5G03170 (AtFLA11), IRX14: AT4G36890 (glycosyltransferases family 43), IRX15: AT3G50220 (DUF579), BC1: 0s03g0416200 (OsCOBL5), BC2: (rice COBRA-like proteins), BC3: 0s02g0738900 (OsDRP2B), BC6: 0s09g0422500 (OsCESA9), BC7: Os01g0750300 (OsCESA4), BC10: 0s05g0170000 (DUF266), BC11: Os01g0750300 (CESA4), BC12: Os09g0114500 (OsKIN4A), BC14: 0s02g0614100 (OsNST1), and BC15: 0s09g0494200 (OsCTL1), which mainly consist of gene members coding endomembrane enzyme/protein for the cellulose and hemicellulose deposition and/or lignification. Integrated analysis of the series of mutants and co-expression gene datasets, in particular, revealed that distinct subgroups of CesA genes and proteins involved in cellulose biosynthesis in secondary cell walls are also conserved across plant species. For example, the products of three gene sets, such as the AtCesA4 (IRX5), AtCesA7 (IRX3), and AtCesA8 (IRX1) genes in *Arabidopsis*, the OsCesA4 (BC7), OsCesA7, and OsCesA9 (BC6) genes in rice, and the ZmCesA10, ZmCesA11, and ZmCesA12 genes in maize, appear to function non-redundantly to catalyze cellulose biosynthesis in secondary cell walls. Xylan is the most abundant hemicellulose found in the secondary cell walls of plants and is thought to function as the major cellulose cross-linking component in secondary cell walls. Several Golgi-localized glycosyltransferases, including protein members from glycosyltransferases family 43 (i.e. the above-mentioned IRX9 and IRX14), have been involved in the biosynthesis of the xylose sugar backbone in developing xylem cells. Many other orthologous genes co-expressed with the cellulose synthase and xylan synthase genes in vascular xylem tissues are found in both dicot and monocot species, which implies common biological functions (Oikawa et al., "An Integrative Approach to the Identification of *Arabidopsis* and Rice Genes Involved in Xylan and Secondary Wall Development," *PLoS ONE* 5(11):e15481 (2010)).

Since the expression amount of genes coding endomembrane enzyme/protein for the secondary cell wall cellulose/xylan deposition is specific and enormous in the vascular xylem tissues, their upstream sequence regions, namely promoters and 5'-UTR sequences, would be useful to overexpress heterogonous genes within the xylem tissues (Oikawa et al., "Golgi-Localized Enzyme Complexes for Plant Cell Wall Biosynthesis," *Trends Plant Sci.* 18:49-58, (2013); Oikawa et al., "An Integrative Approach to the Identification of *Arabidopsis* and Rice Genes Involved in Xylan and Secondary Wall Development," *PLoS ONE* 5(11):e15481 (2010)). As an example of the applications, the transgenic rice plants that expressed a sucrose synthase gene, OsSUS3, driven by the AtCesA8 (the above-mentioned IRX1) promoter maintained a normal growth with slightly increased biomass yields, and also reduced cellulose crystallinity and increased wall thickness, therefore leading to large improvements of both biomass saccharification and lodging (Fan et al., "AtCesA8-driven OsSUS3 Expression Leads to Largely Enhanced Biomass Saccharification and Lodging Resistance by Distinctively Altering Lignocellulose Features in Rice," *Biotechnol. Biofuels* 10:221 (2017)). Another recent example of the successful tailoring of biomass properties is tissue-specific overexpression of master TF (Logue and Scheller, "Spatially Modified Gene Expression in Plants," PCT Publication No. WO 2012/103555; Yang et al., "Engineering Secondary Cell Wall Deposition in Plants," *Plant Biotechnol. J.* 11(3):325-35 (2013)). Tissue-specific overexpression of TF operably linked to a heterologous promoter that induces expression of a gene that is a downstream target of the TF enabled a positive feedback manner that regulates the amplified production of the secondary cell wall production in woody tissue. To accomplish this, a tissue-specific promoter sequence such as an IRX1, IRX3, IRX5, IRX8, IRX9, IRX14, IRX7, and IRX10 promoter was linked in with NAC-MYB TFs such as NST1, NST2, SND1/NST3, SND2, SND3, MYB103, MYB85, MYB46, MYB83, MYB58, or MYB63. This strategy is, however, limited to the accumulation of specific secondary cell wall compounds such as cellulose, xylan, and lignin in xylem and fiber tissues. Overall yield and/or yield-related traits have yet to be improved since the protocol uses the series of TFs only involved in secondary cell wall development, not in the upstream process such as vascular xylem cell differentiation and/or cell development.

R2R3-MYB subfamily 4 and ERF/AP2 subfamily B-6 have been well known as TFs that modulate secondary metabolites, increase wax content, and enhance biotic/abiotic stress tolerances. For the function of R2R3-MYB subfamily 4 and its biotechnology applications, see: Tak et al., "Overexpression of MusaMYB31, a R2R3 type MYB Transcription Factor Gene Indicate its Role as a Negative Regulator of Lignin Biosynthesis in Banana," *PLoS ONE* 12(2): e0172695 (2017); Agarwal et al., "MYB31/MYB42 Syntelogs Exhibit Divergent Regulation of Phenylpropanoid Genes in Maize, Sorghum and Rice," *Sci. Rep.* 6:28502 (2016); Poovaiah et al., "Sugarcane Transgenics Expression MYB Transcription Factors Show Improved Glucose Release," *Biotechnol Biofuels* 9:143 (2016); Zhou et al., "Changing a Conserved Amino Acid in R2R3-MYB Transcription Repressors Results in Cytoplasmic Accumulation and Abolishes Their Repressive Activity in *Arabidopsis,*" *Plant J.* 84(2):395-403 (2015); Martin and Butelli, "Methods for Increasing the Anthocyanin Content of Citrus Fruit," *U.S. Patent* Publication 20140007287; Rouster et al., "Production of Plants Having Improved Water-Deficit Tolerance," *U.S. Patent* Publication 20130298282; Handakumbura and Hazen, "Transcriptional Regulation of Grass Secondary Cell Wall Biosynthesis: Playing Catch-Up With *Arabidopsis Thaliana*," Front. *Plant Sci.* 3:74 (2012); Guan et al., "Methods of Modifying Lignin Biosynthesis and Improving Digestability," *U.S. Patent* Publication 20120272406; Shen et al., "Compositions and Methods for Improved Plant Feedstock," *U.S. Patent* Publication 20120322122; Shen et al., "Functional Characterization of the Switchgrass (*Panicum virgatum*) R2R3-MYB Transcription Factor PvMYB4 for Improvement of Lignocellulosic Feedstocks," New Phytol. 193:121-36 (2012); Wang and Dixon, "On-Off Switches for Secondary Cell Wall Biosynthesis," *Mol. Plant.* 5(2):297-303 (2012); Bedon et al., "Subgroup 4 R2R3-MYBs in Conifer Trees: Gene Family Expansion and Contribution to the Isoprenoid—and Flavonoid—Oriented Responses," *Journal of Experimental Botany* 61(14):3847-3864 (2010); Fornalé et al., "ZmMYB31 Directly Represses Maize Lignin Genes and Redirects the Phenylpropanoid Metabolic Flux," *Plant J.* 64(4):633-44 (2010); Sonbol et al., "The Maize ZmMYB42 Represses the Phenylpropanoid Pathway and Affects the Cell Wall Structure, Composition and Degradability in *Arabidopsis Thaliana,*" *Plant Mol. Biol.* 70:283-96 (2009); Legay et al., "Molecular Characterization of EgMYB1, a Putative Transcriptional Repressor of the Lignin Biosynthetic Pathway," *Plant Sci.* 173:542-9 (2007); Fornalé et al., "Down-Regulation of the Maize and *Arabidopsis thaliana* Caffeic Acid O-methyl-transferase Genes by Two New Maize R2R3-MYB Transcription Factors," *Plant Mol. Biol.* 62(6):809-23 (2006); Coraggio et al., "Use of the Myb4 Transcriptional Factor From Rice to Increase the Production of Secondary Metabolites by Transformed Plants," PCT Publication No. WO 2005/080580; Preston et al., "AtMYB32 is Required for Normal Pollen Development in *Arabidopsis thaliana,*" *Plant J.* 40(6):979-95 (2004). For the function of ERF/AP2 subfamily B-6 and its biotechnology applications, see Xu et al., "Overexpression of the Transcription Factors GmSHN1 and GmSHN9 Differentially Regulates Wax and Cutin Biosynthesis, Alters Cuticle Properties, and Changes Leaf Phenotypes in *Arabidopsis,*" *Int. J. Mol. Sci.* 17(4):E587 (2016); Djemal and Khoudi, "Isolation and Molecular Characterization of a Novel WIN/SHN1 Ethylene-Responsive Transcription Factor TdSHN1 From Durum Wheat (*Triticum turgidum* L. subsp. durum) *Protoplasma* 252(6):1461-73 (2015); Al-Abdallat et al., "Over-Expression of SISHN1 Gene Improves Drought Tolerance by Increasing Cuticular Wax Accumulation in Tomato," *Int. J. Mol. Sci.* 15(11):19499-515 (2014); Sela et al., "Overexpression of AtSHN1/WIN1 provokes Unique Defense Responses," *PLoS One* 8(7):e70146 (2013); Loque and Scheller, "Spatially Modified Gene Expression in Plants," PCT Publication No. WO 2012/103555; Wang et al., "An Ethylene Response Factor OsWR1 Responsive to Drought Stress Transcriptionally Activate Wax Synthesis Related Genes and Increases Wax Production in Rice," *Plant Mol Biol.* 78(3):275-88 (2012); Shi et al., "SHINE Transcription Factors Act Redundantly to Pattern the Archetypal Surface of *Arabidopsis* Flower Organs," *PLoS Genet.* 7(5): e1001388 (2011); Kannangara et al., "The Transcription Factor WIN1/SHN1 Regulates Cutin Biosynthesis in *Arabidopsis thaliana,*" *Plant Cell* 19(4):1278-94 (2007); Aharoni et al., "The SHINE Clade of Transcription Factors and Their Use," PCT Publication WO 2005/120215; Aharoni et al., "The SHINE Glade of AP2 Domain Transcription Factors Activates Wax Biosynthesis, Alters Cuticle Properties, and Confers Drought Tolerance When Overexpressed in *Arabidopsis,*" *Plant Cell* 16(9):2463-80 (2004). Recent overexpression studies by traditional constitutive promoters demonstrated that a series of orthologous TFs from the R2R3-MYB subfamily 4 and ERF/AP2 subfamily B-6 are also potential regulators of the secondary cell wall NAC-MYB TFs (Hussey et al., "Navigating the Transcriptional Roadmap Regulating Plant Secondary Cell Wall Deposition," *Front. Plant Sci.* 4:325 (2013); Yang and Wang, "Molecular Mechanisms for Vascular Development and Secondary Cell wall Formation," *Front. Plant Sci.* 7:356 (2016); Ambavaram et al., "Coordinated Activation of Cellulose and Repression of Lignin Biosynthesis Pathways in Rice," *Plant Physiol.* 155(2):916-31 (2011); Legay et al., "EgMYB1, an R2R3 MYB Transcription Factor from *Eucalyptus* Negatively Regulates Secondary Cell Wall Formation in *Arabidopsis* and Poplar," New Phytol. 188(3):774-86 (2010)).

Although gene expression of *Arabidopsis* R2R3-MYB subfamily 4, MYB4, MYB7, and MYB32 are positively regulated by secondary wall MYB TF, MYB46, they are also shown to be involved in fine-tuning the upstream transcriptional regulation of developing vascular xylem cells. Overexpression of two maize homologs from the R2R3-MYB subfamily 4, namely ZmMYB31 and ZmMYB42, in *Arabidopsis* results in down-regulation of the lignin pathway and a patchy secondary cell wall deposition phenotype in fiber cells, which supports a repressive role for these proteins. In addition, there is molecular evidence showing that MYB4, MYB7, and MYB32 repress not only their own promoters but also the promoter of the secondary cell wall NAC master TF SND1/NST3 that regulates MYB46. Such negative regulations suggest that R2R3-MYB subfamily 4 may fine-tune the expressions and activities of secondary wall NAC-MYB-based transcriptional regulatory network for vascular xylem and fiber cells development.

The secondary cell wall master regulators in the endothecium of anthers include NST2, which is co-expressed with the SHN/WIN genes from ERF/AP2 subfamily B-6 and also with WRKY DNA-Binding Protein 12 (Wang et al., "Mutation of WRKY Transcription Factors Initiates Pith Secondary Wall Formation and Increases Stem Biomass in Dicotyledonous Plants," *Proc. Natl. Acad. Sci. U.S.A* 107(51): 22338-43 (2010); Yang et al., "PtrWRKY19, a Novel WRKY Transcription Factor, Contributes to the Regulation of Pith Secondary Wall Formation in *Populus trichocarpa,*" *Sci. Rep.* 6:18643 (2016)) that are believed to be upstream transcriptional regulators. The OsSHN1 gene, a homolog of *Arabidopsis* AtSHN2 in rice, is also tightly co-expressed with TFs and biosynthetic genes associated with the formation of the secondary cell wall in xylem and fiber cells. Although both AtSHN2 and OsSHN1 genes are suggested to regulate wax and lipid biosynthesis, they can also (a) enhance cellulose synthase genes expression; and (b) suppress lignin biosynthetic gene expression when they are overexpressed in rice. Additional molecular evidence shows that AtSHN2 can bind the promoters of secondary cell wall NAC-MYB TFs in rice, indicating an upstream mechanism of transcriptional regulation by SHN gene family in monocots.

The expression modulation of the TFs for the fundamental studies, however, has been controlled by constitutive promoters, which often show detrimental effects as yield drag. The previously noted vascular xylem tissue-targeting overexpression with the above-mentioned promoters has not been applied to the TFs that can potentially act before the secondary wall NAC-MYB TFs.

The present invention seeks to cure these deficiencies through the combination of promoters which preferably target vascular xylem tissue and a series of DNA transcription factors (TFs) involved in the transcriptional regulation of developing vascular xylem cells to enhance multiple yield-related traits in plants.

SUMMARY OF THE INVENTION

A first aspect of the present invention is directed to a nucleic acid construct that includes a polynucleotide encoding a transcription factor polypeptide and a heterologous, tissue-specific promoter operably linked to the polynucleotide encoding the transcription factor polypeptide, wherein the promoter specifically directs expression of the transcription factor polypeptide in vascular xylem tissue of a plant.

A second aspect of the present invention is directed to an expression vector that includes a nucleic acid construct of the present invention.

A third aspect of the present invention is directed to a recombinant host cell that includes a nucleic acid construct according to the first aspect of the invention or a recombinant expression vector according to the second aspect of the invention. In certain embodiments, the recombinant host cells are bacterial cells or plant cells.

A fourth aspect of the present invention is directed to a transgenic plant or transgenic plant seed that includes a nucleic acid construct according to the first aspect of the invention or a recombinant host cell according to the third aspect of the invention.

A fifth aspect of the present invention is directed to a plant having (i.e., including) a transgene that includes a heterologous, tissue-specific promoter operably linked to a polynucleotide encoding a transcription factor involved in vascular xylem cell development, wherein the promoter specifically directs expression of the transcription factor in vascular xylem tissue of the plant.

A sixth aspect of the present invention is directed to a rootstock, cutting, or seed obtained from a transgenic plant according to the fourth aspect of the invention or a plant according to the fifth aspect of the invention.

A seventh aspect of the invention is directed to a method of enhancing plant growth or yield by providing a transgenic plant or transgenic plant seed that is transformed with a nucleic acid construct according to the first aspect of the invention (which includes a transgenic plant or transgenic plant seed according to the fourth aspect of the invention). In one embodiment, the transgenic plant is provided, and then grown under conditions effective to permit the nucleic acid construct to express the transcription factor polypeptide in vascular xylem tissue of the transgenic plant, and thereby enhance plant growth or yield. In another embodiment, the transgenic plant seed is provided, planted in a growth medium, and a transgenic plant is then propagated from the transgenic plant seed to permit the nucleic acid construct to express the transcription factor polypeptide in vascular xylem tissue of the transgenic plant, and thereby enhance plant growth or yield.

An eighth aspect of the invention is directed to a method of enhancing plant growth or yield by providing a rootstock, cutting, or seed according to the sixth aspect of the invention, which rootstock, cutting, or seed is planted in a growth medium, and a transgenic plant is then propagated from the rootstock, cutting, or seed to permit the nucleic acid construct (or transgene) to express the transcription factor polypeptide in vascular xylem tissue of the transgenic plant, and thereby enhance plant growth or yield.

A ninth aspect of the invention is directed to a method of enhancing plant growth or yield by providing a plant according to the fifth aspect of the invention, and growing the plant under conditions effective to permit the transgene to express the transcription factor polypeptide in vascular xylem tissue of the transgenic plant, and thereby enhance plant growth or yield.

A tenth aspect of the present invention is directed to a method of planting, cultivating, or harvesting a part or all of a plant according to the first aspect of the invention or fifth aspect of the invention.

An eleventh aspect of the present invention is direct to a method of making a plant according to the fourth aspect of the invention or a plant according to the fifth aspect of the present invention. The method includes introducing a nucleic acid construct or transgene of the invention into a plant cell and propagating the plant from the plant cell.

A twelfth aspect of the present invention is directed to a method of enhancing degradability of plant biomass by providing a transgenic plant or transgenic plant seed that is transformed with a nucleic acid construct according to the first aspect of the invention (which includes a transgenic plant or transgenic plant seed according to the fourth aspect of the invention). In one embodiment, the transgenic plant is provided, and then grown under conditions effective to permit the nucleic acid construct to express the transcription factor polypeptide in vascular xylem tissue of the transgenic plant, and thereby enhance degradability of plant biomass. In another embodiment, the transgenic plant seed is provided, planted in a growth medium, and a transgenic plant is then propagated from the transgenic plant seed to permit the nucleic acid construct to express the transcription factor polypeptide in vascular xylem tissue of the transgenic plant, and thereby enhance degradability of plant biomass.

An thirteenth aspect of the invention is directed to a method of enhancing degradability of plant biomass by providing a rootstock, cutting, or seed according to the sixth aspect of the invention, which rootstock, cutting, or seed is planted in a growth medium, and a transgenic plant is then propagated from the rootstock, cutting, or seed to permit the nucleic acid construct (or transgene) to express the transcription factor polypeptide in vascular xylem tissue of the transgenic plant, and thereby enhance degradability of plant biomass.

A fourteenth aspect of the invention is directed to a method of enhancing degradability of plant biomass by providing a plant according to the fifth aspect of the invention, and growing the plant under conditions effective to permit the transgene to express the transcription factor polypeptide in vascular xylem tissue of the transgenic plant, and thereby enhance degradability of plant biomass.

The minimal cis-genic combination of (i) a promoter sequence that preferably targets vascular xylem tissues, and (ii) a TF polypeptides from an R2R3-MYB subfamily 4 or ERF/AP2 subfamily B-6 is unique. The accompanying Examples surprisingly demonstrate that multiple yield-related traits could be introduced into plant cells by the vascular xylem tissue-targeting overexpression of the TFs that are believed (a) to be upstream regulators of secondary cell wall NAC master TFs (i.e., SND1/NST3, NST1, NST2, VND6, VND7), and (b) to be involved in the vascular xylem cell development. The tissue-targeting manner of the TF overexpression also enables reduced lignin in only the vascular xylem tissue and maintains lignin in other tissue cells that are vital to the structural supports of the plant. This invention generated significantly improved crops with a combination of three beneficial traits: (1) accelerated root growth, (2) increased seeds/grains and vegetative biomass yields, and (3) enhanced degradability of inedible/lignocellulosic biomass. These traits may contribute to enhancing U.S. agricultural production, self-sustainability, the economy, food security, and bioenergy. The invention has wide applicability across plant species, including both monocots and dicots.

BRIEF DESCRIPTION OF THE DRAWINGS

FIG. 1 illustrates the map and nucleotide sequence for construct No. 001, pAtCTL2-AtMYB32-tRBS (SEQ ID NO:57), which includes the promoter and 5' UTR from AtCTL2, the open reading frame of AtMYB32, and the 3' RBS transcription terminator.

FIG. 2 illustrates the map and nucleotide sequence for construct No. 002, pAtLAC4-AtMYB32-tRBS (SEQ ID NO:58), which includes the promoter from AtLAC4, the open reading frame of AtMYB32, and the 3' RBS transcription terminator.

FIG. 3 illustrates the map and nucleotide sequence for construct No. 003, pAtCesA4-AtMYB32-tRBS (SEQ ID NO:59), which includes the promoter from AtCesA4, the open reading frame of AtMYB32, and the 3' RBS transcription terminator.

FIG. 4 illustrates the map and nucleotide sequence for construct No. 004, pAtCesA8-AtMYB32-tRBS (SEQ ID NO:60), which includes the promoter and 5' UTR from AtCesA8, the open reading frame of AtMYB32, and the 3' RBS transcription terminator.

FIG. 5 illustrates the map and nucleotide sequence for construct No. 005, pAtFLA11-AtMYB32-tRBS (SEQ ID NO:61), which includes the promoter and 5' UTR from AtFLA11, the open reading frame of AtMYB32, and the 3' RBS transcription terminator.

FIG. 6 illustrates the map and nucleotide sequence for construct No. 006, pAtCesA7-AtMYB32-tRBS (SEQ ID NO:62), which includes the promoter and 5' UTR from AtCesA7, the open reading frame of AtMYB32, and the 3' RBS transcription terminator.

FIG. 7 illustrates the map and nucleotide sequence for construct No. 007, pAtIRX9-AtMYB32-tRBS (SEQ ID NO:63), which includes the promoter and 5' UTR from AtIRX9, the open reading frame of AtMYB32, and the 3' RBS transcription terminator.

FIG. 8 illustrates the map and nucleotide sequence for construct No. 008, pAtCesA4-AtMYB4-tRBS (SEQ ID NO:64), which includes the promoter from AtCesA4, the open reading frame of AtMYB4, and the 3' RBS transcription terminator.

FIG. 9 illustrates the map and nucleotide sequence for construct No. 009, pAtCesA8-AtMYB4-tRBS (SEQ ID NO:65), which includes the promoter and 5' UTR from AtCesA8, the open reading frame of AtMYB4, and the 3' RBS transcription terminator.

FIG. 10 illustrates the map and nucleotide sequence for construct No. 010, pZmCesA12-ZmMYB31-tRBS (SEQ ID NO:66), which includes the promoter from ZmCesAl2, the open reading frame of ZmMYB31, and the 3' RBS transcription terminator.

FIG. 11 illustrates the map and nucleotide sequence for construct No. 011, pZmCesA11-ZmMYB31-tRBS (SEQ ID NO:67), which includes the promoter from ZmCesA11, the open reading frame of ZmMYB31, and the 3' RBS transcription terminator.

FIG. 12 illustrates the map and nucleotide sequence for construct No. 012, pOsCesA4-ZmMYB31-tRBS (SEQ ID NO:68), which includes the promoter from OsCesA4, the open reading frame of ZmMYB31, and the 3' RBS transcription terminator.

FIG. 13 illustrates the map and nucleotide sequence for construct No. 013, pOsCesA7-ZmMYB31-tRBS (SEQ ID NO:69), which includes the promoter from OsCesA7, the open reading frame of ZmMYB31, and the 3' RBS transcription terminator.

FIG. 14 illustrates the map and nucleotide sequence for construct No. 014, pZmCesA12-ZmMYB42-tRBS (SEQ ID NO:70), which includes the promoter from ZmCesAl2, the open reading frame of ZmMYB42, and the 3' RBS transcription terminator.

FIG. 15 illustrates the map and nucleotide sequence for construct No. 015, pZmCesA11-ZmMYB42-tRBS (SEQ ID NO:71), which includes the promoter from ZmCesA11, the open reading frame of ZmMYB42, and the 3' RBS transcription terminator.

FIG. 16 illustrates the map and nucleotide sequence for construct No. 016, pOsCesA4-ZmMYB42-tRBS (SEQ ID NO:72), which includes the promoter from OsCesA4, the open reading frame of ZmMYB42, and the 3' RBS transcription terminator.

FIG. 17 illustrates the map and nucleotide sequence for construct No. 017, pOsCesA7-ZmMYB42-tRBS (SEQ ID NO:73), which includes the promoter from OsCesA7, the open reading frame of ZmMYB42, and the 3' RBS transcription terminator.

FIG. 18 illustrates the map and nucleotide sequence for construct No. 018, pZmCesA12-PvMYB4-tRBS (SEQ ID NO:74), which includes the promoter from ZmCesAl2, the open reading frame of PvMYB4, and the 3' RBS transcription terminator.

FIG. 19 illustrates the map and nucleotide sequence for construct No. 019, pZmCesA11-PvMYB4-tRBS (SEQ ID NO:75), which includes the promoter from ZmCesA11, the open reading frame of PvMYB4, and the 3' RBS transcription terminator.

FIG. 20 illustrates the map and nucleotide sequence for construct No. 020, pOsCesA4-PvMYB4-tRBS (SEQ ID NO:76), which includes the promoter from OsCesA4, the open reading frame of PvMYB4, and the 3' RBS transcription terminator.

FIG. 21 illustrates the map and nucleotide sequence for construct No. 021, pOsCesA7-PvMYB4-tRBS (SEQ ID NO:77), which includes the promoter from OsCesA7, the open reading frame of PvMYB4, and the 3' RBS transcription terminator.

FIG. 22 illustrates the map and nucleotide sequence for construct No. 022, pZmCesA12-OsSHN1-tRBS (SEQ ID NO:78), which includes the promoter from ZmCesAl2, the open reading frame of OsSHN1, and the 3' RBS transcription terminator.

FIG. 23 illustrates the map and nucleotide sequence for construct No. 023, pZmCesA11-OsSHN1-tRBS (SEQ ID NO:79), which includes the promoter from ZmCesA11, the open reading frame of OsSHN1, and the 3' RBS transcription terminator.

FIG. 25 illustrates the map and nucleotide sequence for construct No. 025, pOsCesA7-OsSHN1-tRBS (SEQ ID NO:81), which includes the promoter from OsCesA7, the open reading frame of OsSHN1, and the 3' RBS transcription terminator.

FIG. 27 is a map of an exemplary plasmid operable in monocots, which includes construct 018 shown in FIG. 18. Similar monocot-functional plasmids containing construct Nos. 010-017 and 019-025 were also prepared.

DETAILED DESCRIPTION OF THE INVENTION

Figure 24:
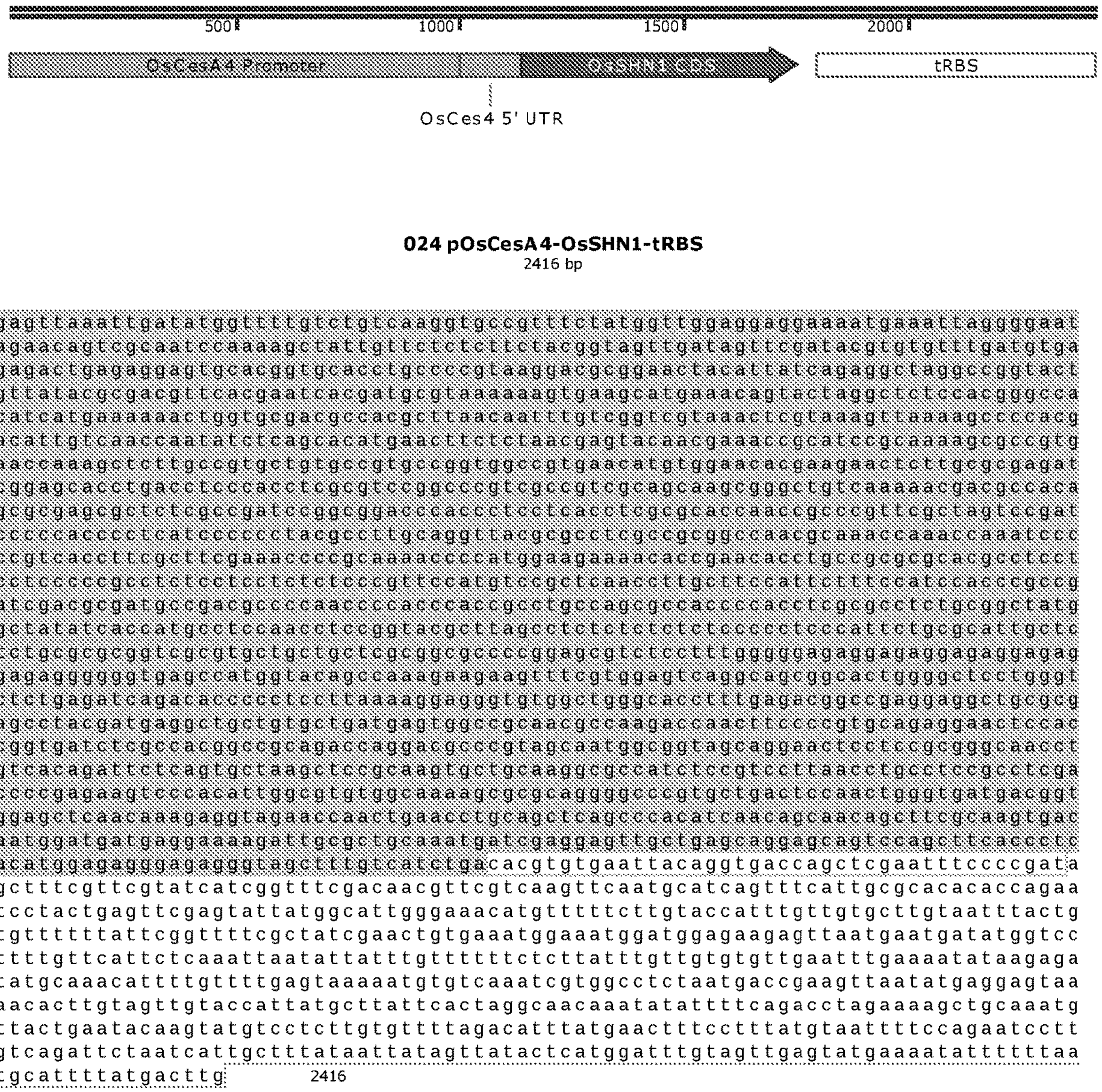
FIG. 24 illustrates the map and nucleotide sequence for construct No. 024, pOsCesA4-OsSHN1-tRBS (SEQ ID NO:80), which includes the promoter from OsCesA4, the open reading frame of OsSHN1, and the 3' RBS transcription terminator.

The present invention is directed to recombinant nucleic acid constructs and transgenes as well as expression vectors and host cells useful for generating transgenic plants that preferentially express the transgenes in vascular xylem tissue of the plant. Transgenic plant parts are also encompassed by the present invention, as are various methods for making the transgenic plants and plant parts. Also encompassed by the present invention are methods that utilize the transgenic plants or plant parts, including methods for enhancing plant growth, enhancing plant yield, modifying plant lignin content, promoting earlier reproductive maturation, and enhancing degradability of plant biomass. These recombinant materials and their use in practicing the various methods are described below.

One aspect of the present invention is directed to a nucleic acid construct that includes a polynucleotide encoding a transcription factor ("TF") polypeptide and a heterologous, tissue-specific promoter operably linked to the polynucleotide encoding the TF polypeptide, wherein the promoter specifically directs expression of the TF polypeptide in vascular xylem tissue of a plant.

According to one embodiment, the nucleic acid construct takes the form of a transgene that includes a heterologous, tissue-specific promoter operably linked to a polynucleotide encoding the TF polypeptide involved in vascular xylem cell development, and a 3' transcription termination sequence that is operably linked to the polynucleotide encoding the TF, wherein the promoter specifically directs expression of the TF in vascular xylem tissue of the plant.

Thus, this invention involves the formation and use of synthetic oligonucleotides or nucleotide sequences. A synthetic sequence is one that is initially produced or reproduced in a laboratory setting. The structure of the synthetic sequence is altered or different from that found in the sequence that is directly isolated from its natural setting. A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety). "Operably linked" is intended to mean a functional linkage between two or more elements.

In these and other aspects of the invention, the TF polypeptide encoded by the nucleic acid construct, or transgene, is one that modulates expression of at least one gene, and possibly a series of genes (i.e., two or more), involved with cell wall and secondary metabolite biosynthetic pathways. Transcription factors are proteins that are involved in the process of transcribing DNA into RNA. Transcription factors have DNA-binding domains that allow them to bind to specific DNA sequences (e.g., promoter sequences, enhancer sequences, and silencers). In certain embodiment of the present invention, the TF polypeptide is a polypeptide that can act as an upstream transcriptional regulator to secondary wall master TFs as an upstream transcriptional regulator.

Suitable classes of TF polypeptides include, without limitation, an R2R3-MYB subfamily 4 TF polypeptide, an ERF/AP2 subfamily B-6 TF polypeptide, and combinations thereof (i.e., when co-expressed). Both R2R3-MYB subfamily 4 TFs and ERF/AP2 subfamily B-6 TFs are widely conserved among both monocots and dicots, and therefore it is contemplated that any of a variety of TFs from these classes can be utilized.

Non-limiting examples of both the R2R3-MYB subfamily 4 TF polypeptide and an ERF/AP2 subfamily B-6 TF polypeptide are provided in the examples, and include those listed below.

ERF/AP2 subfamily B-6 Transcription Factors: *Arabidopsis* AtSHN3 (SEQ ID NOS:1,37); *Arabidopsis* AtSHN1/WIN1 (SEQ ID NOS: 2,38); *Arabidopsis* AtSHN2 (SEQ ID NOS: 3,39); rice OsSHN1 (OsEREB19) (SEQ ID NOS: 7,43); rice OsSHN2 (OsEREB114) (SEQ ID NOS: 8,44); sorghum SbEREB63 (SEQ ID NOS: 13,49); sorghum SbEREB150 (SEQ ID NOS: 14,50); and maize ZmEREB46 (SEQ ID NOS: 17,53).

R2R3-MYB Subfamily 4 Transcription Factors: *Arabidopsis* AtMYB32 (SEQ ID NOS: 4,40); *Arabidopsis* AtMYB4 (SEQ ID NOS: 5,41); *Arabidopsis* MYB7 (SEQ ID NOS: 6,42); rice OsMYB108-L (SEQ ID NOS: 9,45); rice OsMYB108 (SEQ ID NOS: 10,46); poplar PdMYB221 (SEQ ID NOS: 11,47); poplar PdMYB156 (SEQ ID NOS: 12,48); sorghum SbMYB86 (SEQ ID NOS: 15,51); sorghum SbMYB23 (SEQ ID NOS: 16,52); maize ZmMYB42 (SEQ ID NOS: 18,54); maize ZmMYB31 (SEQ ID NOS: 19,55); and switchgrass PvMYB4 (SEQ ID NOS: 20,56).

As will be appreciated by persons of skill in the art, polynucleotides encoding homologous TFs can be isolated from other monocots and dicots. Such homologous TFs can be substantially similar to one another at the protein level, and polynucleotides encoding those TFs can be substantially identical at the nucleic acid level. "Substantially identical," as used in the context of two nucleic acids or polypeptides, refers to a sequence that has at least 60% sequence identity with a reference sequence. Alternatively, percent identity can be any integer from 60% to 100% inclusive. In some embodiments, this identity is at least: 60%, 65%, 70%, 75%, 80%, 85%, 90%, 91%, 92%, 93%, 94%, 95%, 96%, 97%, 98%, or 99% compared to a reference sequence using the programs described herein; preferably BLAST using standard parameters, as described below. Embodiments of the present invention provide for nucleic acids encoding polypeptides that are substantially identical to any of the provided TFs sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. The BLAST algorithm also performs a statistical analysis of the similarity between two sequences. One measure of similarity provided by the BLAST algorithm is the smallest sum probability, which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$ (0.00001), and most preferably less than about $10^{-10}$ (0.0000000001).

The polynucleotides encoding such TFs can also be used to isolate corresponding sequences from other plants. In this manner, methods such as PCR and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities, and which hybridize under stringent conditions to the sequences disclosed herein, or to variants or fragments thereof, are encompassed by the present invention.

Variant sequences may also be identified by analysis of existing databases of sequenced genomes. In this manner, corresponding TF or enhancer sequences can be identified and used in the methods of the invention.

As noted above, the nucleic acid construct, or transgene, or the present invention includes tissue-specific promoters that specifically direct expression of the TF polypeptide in vascular xylem tissue of a plant, fiber tissues of a plant, or both.

A promoter is a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene, in this case the nucleic acid construct, or transgene, that includes a coding sequence for a TF of the type described above. A plant promoter is a promoter capable of initiating transcription in plant cells. Whereas a constitutive promoter is one that is capable of initiating transcription in nearly all tissue types, a tissue-specific promoter initiates transcription in one or a few particular tissue types, and a cell type-specific promoter initiates transcription only in one or a few particular cell types. As used herein, "tissue-specific" does not preclude the promoter from causing initiation of transcription in multiple different types of plant tissues. Rather, the term "tissue-specific" is intended to connote that the promoter causes preferential expression in one or more, but not all, plant tissues. In preferred embodiments, the tissue-specific promoter induces a high level of expression in the one or more plant tissues or, alternatively, where the tissue-specific promoter induces a high level of expression in the one or more plant tissues, the expression level is preferably elevated in vascular xylem and fiber tissues.

Expression levels of a TF can be increased (e.g., by up-regulation or overexpression) relative to the expression level of TF in a wild-type or control plant. With respect to the promoters of the present invention, "specifically directs expression in vascular xylem and fiber tissues" or "vascular xylem tissue-targeting expression" means that the promoter causes expression of a TF of the present invention that is at least 3-fold (e.g., 5-fold, 10-fold, 20-fold, 50-fold, etc.) greater in at least a portion of the vascular xylem tissue of a plant compared to other cell types (e.g., compared to epidermal or mesophyll cells). Vascular xylem tissues of a plant include plant procambium/cambium, xylem, and fiber cell types. In some embodiments, specific expression in plant vascular xylem tissues can be limited to a portion of the vasculature, e.g., above ground (aerial), below ground (roots), cambium cells only, xylem cells only, or both cambium and xylem cells. Further, in certain embodiment of the present invention, the tissue-specific promoter directs expression of the TF polypeptide in aerial parts of the plant, in roots of the plant, or in both the aerial parts and the roots of the plant.

The tissue-specific promoter directs expression of the TF polypeptide involved in developmental process of vascular xylem tissue cells that occurs before secondary wall thickening progresses with polysaccharide deposition and lignification.

The expression level of the TF may be measured, for example, by assaying for the level of the TF in the plant. Measurement of TF levels can be carried out directly using any of a variety of protein assays (e.g., by Western Blot) or indirectly by measuring the level of RNA transcripts (e.g., by northern blot).

Classes of suitable tissue-specific promoter include gene promoters for secondary cell wall development, an endomembrane protein gene promoter, or a secondary wall cellulose synthase (CesA) promoter. Exemplary tissue-specific promoters that induce elevated expression in vascular xylem and/or fiber tissues include, without limitation, *Arabidopsis* AtCTL2 promoter (SEQ ID NO:21); *Arabidopsis* AtLAC4 promoter (SEQ ID NO:22); *Arabidopsis* AtCesA4 promoter (SEQ ID NO:23); *Arabidopsis* AtCesA8 promoter (SEQ ID NO:24); *Arabidopsis* AtFLA11 promoter (SEQ ID NO:25); *Arabidopsis* AtCesA7 promoter (SEQ ID NO:26); *Arabidopsis* AtIRX9 promoter (SEQ ID NO:27); rice OsFLA9 promoter (SEQ ID NO:28); rice OsCTL1 promoter (SEQ ID NO:29); rice OsCesA4 promoter (SEQ ID NO:30); rice OcCesA7 promoter (SEQ ID NO:31); rice OsLac10 promoter (SEQ ID NO:32); rice OsGT43J promoter (SEQ ID NO:33); maize ZmCesA10 promoter (SEQ ID NO:34); maize ZmCesAl2 promoter (SEQ ID NO:35); maize ZmCesA11 promoter (SEQ ID NO:36).

As will be appreciated by persons of skill in the art, promoters from homologous genes can be isolated from other monocots and dicots. Such homologous promoters can be substantially identical at the nucleic acid level as defined above.

Alternative tissue-specific promoters that induce elevated expression in vascular xylem and/or fiber tissues can be identified by examining native protein expression levels in the specified plant tissues over the course of development. See Oikawa et al., "An Integrative Approach to the Identification of *Arabidopsis* and Rice Genes Involved in Xylan and Secondary Wall Development," *PLoS ONE* 5(11): e15481 (2010), which is hereby incorporated by reference in its entirety.

As noted above, the nucleic acid construct, or transgenes, of the invention include 5' and 3' regulatory sequences operably linked to a TF polynucleotide.

As noted above, the nucleic acid construct, or transgene, also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants, and any suitable 3' regulatory region can be used in accordance with the present invention.

Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety); and the pea Ribulose-1,5-Bisphosphate carboxylase/oxygenase Small subunit E9 ("RBS" or "E9") 3' regulatory region (Coruzzi et al., "Tissue-specific and light-regulated expression of a pea nuclear gene encoding the small subunit of ribulose-1,5-bisphosphate carboxylase," *EMBO J.* 3(8):1671-1679 (1984), which is hereby incorporated by reference in its entirety). Virtually any 3' regulatory region known to be operable in plants would be suitable for use in conjunction with the present invention.

Further aspects of the present invention include expression vectors including the nucleic acid constructs, or transgenes, described herein, as well as host cells, transgenic plants (plant cells and plant seeds produced from such transgenic plants), and transgenic plant seeds or plant parts transformed with the nucleic acid constructs described herein.

The nucleotide sequences used in the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK+/− or KS+/−(see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation.

The DNA sequences are cloned into the vector using standard cloning procedures in the art, as described by Sambrook et al., *Molecular Cloning: A Laboratory Manual, Second* Edition, Cold Spring Harbor, N.Y.:Cold Spring Harbor Press (1989), and Ausubel et al., *Current Protocols in Molecular Biology*, New York, N.Y: John Wiley & Sons (1989), which are hereby incorporated by reference in their entirety.

In preparing a nucleic acid construct for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soil-borne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat? Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Mol. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

The different components described above can be ligated together to produce the expression systems which contain the nucleic acid constructs used in the present invention, using well known molecular cloning techniques as described in Sambrook et al., *Molecular Cloning: A Laboratory Manual*, Second Edition Cold Spring Harbor, N.Y.: Cold Spring Harbor Press (1989), and Ausubel et al. *Current Protocols in Molecular Biology*, New York, N.Y: John Wiley & Sons (1989), which are hereby incorporated by reference in their entirety.

Once the nucleic acid construct has been prepared, it is ready to be incorporated into a host cell. Basically, this method is carried out by transforming a host cell with the nucleic acid construct under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Spring Harbor Laboratory, Cold Spring Harbor, N.Y. (1989), which is hereby incorporated by reference in its entirety. Suitable host cells are plant cells. Suitable host cells also include bacterial cells. Methods of transformation may result in transient or stable expression of the nucleic acid under control of the promoter. Stable transformation is intended to mean that the nucleotide construct introduced into a plant integrates into the genome of the plant and is capable of being inherited by the progeny thereof. Transient transformation is intended to mean that the nucleotide construct introduced into a plant is not stably integrated into the genome of the plant, but is maintained in the plant cell for a sufficient period of time to allow for the expression of the introduced genes. Preferably, the nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," Biotechnology and Genetic Engineering Reviews 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," Biotechnology and Genetic Engineering Reviews 15:79-119 (1998), which is hereby incorporated by reference in its entirety). The precise method of transformation is not critical to the practice of the present invention. Any method that results in efficient transformation of the host cell of choice is appropriate for practicing the present invention.

Yet a further method for introduction is by use of known techniques for genome editing or alteration. Such techniques for targeted genomic insertion involve, for example, inducing a double stranded DNA break precisely at one or more targeted genetic loci followed by integration of a chosen transgene or nucleic acid molecule (or construct) during repair. Such techniques or systems include, for example, zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7): 397-405 (2013), each of which is hereby incorporated by reference in its entirety).

In certain embodiments, transformation described herein is carried out by microinjection, *Agrobacterium*-mediated transformation, direct gene transfer, ballistic particle acceleration, whisker method transformation, vacuum infiltration, biolistic transformation, electroporation, micro-injection, polyethylene-mediated transformation, or laser-beam transformation.

After transformation, the transformed plant cells must be regenerated. Plant regeneration from cultured protoplasts is described in Evans et al., *Handbook of Plant Cell Cultures*, Vol. 1, New York, New York: MacMillan Publishing Co. (1983); Vasil, ed., *Cell Culture and Somatic Cell Genetics of Plants*, Vol. I (1984) and Vol. III (1986), Orlando: Acad. Press; and Fitch et al., "Somatic Embryogenesis and Plant Regeneration from Immature Zygotic Embryos of *Papaya* (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., "Vectors Containing a Prokaryotic Dihydrofolate Reductase Gene Transform *Drosophila* Cells to Methotrexate-resistance," *EMBO* 12:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, New York: Cold Spring Harbor Press (1989), which is hereby incorporated by reference in its entirety).

After a transgene containing a nucleic acid construct is stably incorporated in transgenic plants, the transgene can be transferred to other plants by sexual crossing. Any of a number of standard breeding techniques can be used, depending upon the species to be crossed. Once transgenic plants of this type are produced, the plants themselves can be transplanted to a suitable growth medium and cultivated in accordance with conventional procedure so that the nucleic acid construct is present in the resulting plants. Alternatively, transgenic seeds are recovered from the transgenic plants. These seeds can then be planted in a suitable growth medium and cultivated using conventional procedures to produce transgenic plants.

In these embodiments, suitable growth medium includes soil, soil-less particulate medium, or a liquid growth medium. Conditions for cultivating and harvesting may different depending on the type of growth medium and location, e.g., field, greenhouse, hydroponic environment, etc.

During subsequent growth and cultivation of the transgenic plants of the invention, it is also contemplated that individual plants may be selected based on their exhibiting one or more of the following properties: faster vegetative growth including that which leads to early maturation, increased biomass yields, enhanced root development, increased seed/grain production, improved nutrient contents in biomass, increased release of glucose saccharides, increased release of xylose saccharides, reduced lignin composition, and any combinations thereof.

The present invention may be used for transformation of any plant species, including, but not limited to, monocots and dicots. Examples of plant species of interest include, but are not limited to, the genus *Abies, Acacia, Acer, Aegilops, Aesculus, Agave, Ailanthus, Alnus, Amborella, Amelanchier, Arabidopsis, Arbutus, Arctostaphylos, Artemisia, Asiminia, Asparagus, Atriplex, Atropa, Aucuba, Avena, Berberis, Betula, Brachypodium, Brassica, Buddleia, Buxus, Calocedrus, Calotropis, Camellia, Camptotheca, Campsis, Cannabis, Capsicum, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, C/stus, Citrus, Citrullus, Cladrastis, Clematis, Coleogynia, Cornus, Corylus, Cotinus, Cotoneaster, Cowania, Crataegus, Crataegus, Cucumis, Cupressus, Cytisus, Daphne, Daucus, Deutzia, Diospyros, Dioscorea, Elaeagnus, Ephedra, Erythranthe, Escallonia, Eucalyptus, Euonymus, Eutrema, Fagus, Forsythia, Fragaria, Fraxinus, Gaultheria, Gelsemium, Genlisea, Ginkgo, Gleditsia, Glycine, Grevillea, Gymnocladus, Gossypium, Hamamelis, Hebe, Helianthus, Heliamphora, Hibiscus, Heterocallis, Hordeum, Hydrangea, Hyoscyamus, Hypericum, Lactuca, Linum, Lolium, Lycopersicon, Ilex, Ipomea, Juglans, Juniperus, Kalmia, Kerria, Koelreuteria, Lagerstroemia, Larix, Larrea, Libocedrus, Ligustrum, Liquidambar, Liriodendron, Lonicera, Lotus, Madura, Magnolia, Mahonia, Malus, Manihot, Majorana, Medicago, Menispermum, Morus, Myrica, Nicotiana, Nyssa, Oryza, Osmanthus, Ostrya, Oxydendron, Panicum, Pannesetum, Parthenocissus, Papaver, Persea, Phaseolus, Philadelphus, Photinia, Physocarpus, Picea, Pisum, Pinus, Pittosporum, Platanus, Populus, Podophyllum, Prosopis, Prunus, Pseudotsuga, Ptelea, Purshia, Pyrus, Quercus, Raphanus, Rhamnus, Rhaphiolepis, Rhododendron, Rhus, Ribes, Ricinus, Robinia, Rosa, Rubus, Salix, Sambucus, Sassafras, Sequoia, Secale, Setaria, Senecio, Shepherdia, Smilax, Sinapis, Solanum, Sophora, Sorbus, Sorghum, Spiraea, Staphylea, Stevia, Stewartia, Symphoricarpos, Syringa, Taxodium, Taxus, Theobroma, Thuja, Tilia, Triticum, Trigonella, Tsuga, Ulmus, Umbellularia, Vaccinium, Viburnum, Vitis, Vigna, Zanthoxylum, Zea*, or *Zelkova.*

Further aspects of the invention relates to the planting, cultivating, or harvesting a part or all of a transgenic plant of the present invention.

In addition to transgenic plants, the present invention also relates to transgenic plant parts including plant seeds, rootstock, and cuttings removed from the transgenic plant (including both woody and herbaceous cuttings). In certain embodiments, the plant, plant seed, rootstock, or cutting is (or is from) a monocot, including but not limited to those identified above. In other embodiments, the plant, plant seed, rootstock, or cutting is (or is from) a dicot, including but not limited to those identified above.

The present invention is also directed to one or more methods of enhancing plant growth or plant yield. As used herein, "yield" is defined as the measurement of the amount of a crop that was harvested per unit of land area. Crop yield is the measurement often used for grains or cereals and is typically measured as the amount of plant harvested per unit area for a given time, i.e., metric tons per hectare or kilograms per hectare. Crop yield can also refer to the actual seed or biomass produced or generated by the plant. Thus, an "enhanced yield" refers to an increase in yield relative to a non-transgenic control plant. As used herein, "enhanced plant growth" encompasses a number of aspects including, without limitation, faster vegetative growth including that which leads to early maturation, increased biomass yields, enhanced root development, increased seed/grain production, improved nutrient contents in biomass, and any combinations thereof.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; or (d) the subject plant or plant cell itself, under conditions in which the gene of interest is not expressed. A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

According to one embodiment, this method is carried out by providing a transgenic plant transformed with a nucleic acid construct of the present invention and growing the plant under conditions effective to permit the nucleic acid construct to express the TF polypeptide in vascular xylem tissue of the transgenic plant, and thereby enhance plant growth or yield.

According to a second embodiment, this method is carried out by providing a transgenic plant seed transformed with a nucleic acid construct of the present invention, planting the transgenic plant seed in a growth medium, and propagating a transgenic plant from the transgenic plant seed to permit the nucleic acid construct to express the TF polypeptide in vascular xylem tissue of the transgenic plant, and thereby enhance plant growth or yield.

According to a third embodiment, this method is carried out by providing a rootstock, cutting, or seed from a transgenic plant of the present invention, introducing the rootstock, cutting, or seed into a growth medium; and propagating a transgenic plant from the rootstock, cutting, or seed to permit the nucleic acid construct to express the TF polypeptide in vascular xylem tissue of the transgenic plant, and thereby enhance plant growth or yield.

According to a fourth embodiment, this method is carried out by providing a plant comprising a transgene that includes a heterologous, tissue-specific promoter operably linked to a polynucleotide encoding a TF involved in vascular xylem cell development, wherein the promoter specifically directs expression of the TF in vascular xylem tissue of the plant, and growing the plant under conditions effective to permit the transgene to express the TF polypeptide in vascular xylem tissue of the transgenic plant, and thereby enhance plant growth or yield.

According to a fifth embodiment, this method is carried out by providing a rootstock, cutting, or seed obtained from a plant comprising a transgene that includes a heterologous, tissue-specific promoter operably linked to a polynucleotide encoding a TF involved in vascular xylem cell development, wherein the promoter specifically directs expression of the TF in vascular xylem tissue of the plant, introducing the rootstock, cutting, or seed into a growth medium, and propagating a plant from the rootstock, cutting, or seed to permit the transgene to express the TF polypeptide in vascular xylem tissue of the transgenic plant, and thereby enhance plant growth or yield.

The present invention is also directed to one or more methods of enhancing degradability of plant biomass. As used herein, enhanced degradability of plant biomass refers to the rate of biomass degradation when otherwise exposed to similar environmental conditions, using comparable amounts of plant biomass, as compared to the biomass of a control plant. Enhanced degradability may refer to any one or more of: (i) increased release of glucose saccharides, (ii) increased release of xylose saccharides, (iii) reduced lignin composition, and any combinations thereof.

According to one embodiment, this method is carried out by providing a transgenic plant of the present invention and growing the plant under conditions effective to permit the nucleic acid construct to express the TF polypeptide in vascular xylem tissue of the transgenic plant, and thereby enhance degradability of plant biomass.

According to a second embodiment, this method is carried out by providing a transgenic plant seed of the present invention, planting the transgenic plant seed in a growth medium, and propagating a transgenic plant from the transgenic plant seed to permit the nucleic acid construct to express the TF polypeptide in vascular xylem tissue of the transgenic plant, and thereby enhance degradability of plant biomass.

According to a third embodiment, this method is carried out by providing a rootstock, cutting, or seed of the present invention, introducing the rootstock, cutting, or seed into a growth medium, and propagating a transgenic plant from the rootstock, cutting, or seed to permit the nucleic acid construct to express the TF polypeptide in vascular xylem tissue of the transgenic plant, and thereby enhance degradability of plant biomass.

According to a fourth embodiment, this method is carried out by providing a plant of the present invention and growing the plant under conditions effective to permit the transgene to express the TF polypeptide in vascular xylem tissue of the transgenic plant, and thereby enhance degradability of plant biomass.

According to a fifth embodiment, this method is carried out by providing a rootstock, cutting, or seed of the present invention, introducing the rootstock, cutting, or seed into a growth medium, and propagating a plant from the rootstock, cutting, or seed to permit the transgene to express the TF polypeptide in vascular xylem tissue of the transgenic plant, and thereby enhance degradability of plant biomass.

EXAMPLES

The examples below are intended to exemplify the practice of embodiments of the disclosure but are by no means intended to limit the scope thereof.

Example 1—Gene Combinations of a Promoter and a TF

A series of simple gene cassettes comprising TFs driven by promoters active in the target tissues were generated (see Tables 1 and 2). The promoters in Table 2 were selected based on their expression profile corresponding to the development of xylem tissue (Oikawa et al., "An Integrative Approach to the Identification of *Arabidopsis* and Rice Genes Involved in Xylan and Secondary Wall Development," *PLoS ONE* 5(11):e15481 (2010), which is hereby incorporated by reference in its entirety).

TABLE 1

Examples of Transcription Factors for Gene Combination

| Referenced expression database[1] | Expression[2] | Gene name | SEQ ID NO AA | SEQ ID NO NT | TF family | Species | Gene ID |
|---|---|---|---|---|---|---|---|
| Arabidopsis root transcripts | 291.76 | AtSHN3 | 1 | 37 | ERF/AP2 subfamily B-6 | Arabidopsis | At5g25390 |
| Arabidopsis root transcripts | 611.33 | AtSHN1/WIN1 | 2 | 38 | ERF/AP2 subfamily B-6 | Arabidopsis | At1g15360 |
| Arabidopsis root transcripts | N/A | AtSHN2 | 3 | 39 | ERF/AP2 subfamily B-6 | Arabidopsis | At5g11190 |
| Arabidopsis root transcripts | 448.22 | AtMYB32 | 4 | 40 | R2R3-MYB Subfamily 4 | Arabidopsis | At4g34990 |
| Arabidopsis root transcripts | 2052.79 | AtMYB4 | 5 | 41 | R2R3-MYB Subfamily 4 | Arabidopsis | At4g38620 |
| Arabidopsis root transcripts | 2630.65 | MYB7 | 6 | 42 | R2R3-MYB Subfamily 4 | Arabidopsis | At2g16720 |
| Rice mas transcripts | N/A | OsSHN1 (OsEREB19) | 7 | 43 | ERF/AP2 subfamily B-6 | Rice | LOC_Os02g10760/ Os02g0202000 |
| Rice mas transcripts | 5636.25 | OsSHN2 (OsEREB114) | 8 | 44 | ERF/AP2 subfamily B-6 | Rice | LOC_Os06g40150/ Os06g0604000 |
| Rice mas transcripts | N/A | OsMYB108-L | 9 | 45 | R2R3-MYB Subfamily 4 | Rice | Os08g0549000 |
| Rice mas transcripts | 3694.68 | OsMYB108 | 10 | 46 | R2R3-MYB Subfamily 4 | Rice | LOC_Os09g36730/ Os09g0538400 |
| Poplar development transcripts | 206.76 | PdMYB221 | 11 | 47 | R2R3-MYB Subfamily 4 | Poplar | POPTR_0004s18020 |
| Poplar development transcripts | 3436.2 | PdMYB156 | 12 | 48 | R2R3-MYB Subfamily 4 | Poplar | POPTR_0009s13640 |
| N/A | N/A | SbEREB63 | 13 | 49 | ERF/AP2 subfamily B-6 | Sorghum | Sb04g006970 |
| N/A | N/A | SbEREB150 | 14 | 50 | ERF/AP2 subfamily B-6 | Sorghum | Sb10g023600 |
| N/A | N/A | SbMYB86 | 15 | 51 | R2R3-MYB Subfamily 4 | Sorghum | Sb07g024890 |
| N/A | N/A | SbMYB23 | 16 | 52 | R2R3-MYB Subfamily 4 | Sorghum | Sb02g031190 |
| Maize leaf gradient transcripts | 23.74 | ZmEREB46 | 17 | 53 | ERF/AP2 subfamily B-6 | Maize | GRMZM2G085678 |
| Maize leaf gradient transcripts | 12.97 | ZmMYB42 | 18 | 54 | R2R3-MYB Subfamily 4 | Maize | GRMZM2G419239 |
| Maize leaf gradient transcripts | 64.76 | ZmMYB31 | 19 | 55 | R2R3-MYB Subfamily 4 | Maize | GRMZM2G050305 |
| N/A | N/A | PvMYB4 | 20 | 56 | R2R3-MYB Subfamily 4 | Switchgrass | Pavir.J16675.1 |

[1]The Bio-Analytic Resource for Plant Biology, available online at http://bar.utoronto.ca/ and described in Toufighi et al, "The Botany Array Resource: e-Northerns, Expression Angling, and Promoter Analyses," *The Plant Journal* 43: 153-63 (2005), each of which is hereby incorporated by reference in its entirety.
[2]Relative gene expression value in vascular tissues or xylem-related organ.

The sequences referenced in Table 1 are set forth below.

```
                                                          SEQ ID NO: 1
Met Val His Ser Lys Lys Phe Arg Gly Val Arg Gln Arg Gln Trp Gly

Ser Trp Val Ser Glu Ile Arg His Pro Leu Leu Lys Arg Arg Val Trp

Leu Gly Thr Phe Asp Thr Ala Glu Thr Ala Ala Arg Ala Tyr Asp Gln

Ala Ala Val Leu Met Asn Gly Gln Ser Ala Lys Thr Asn Phe Pro Val

Ile Lys Ser Asn Gly Ser Asn Ser Leu Glu Ile Asn Ser Ala Leu Arg

Ser Pro Lys Ser Leu Ser Glu Leu Leu Asn Ala Lys Leu Arg Lys Asn

Cys Lys Asp Gln Thr Pro Tyr Leu Thr Cys Leu Arg Leu Asp Asn Asp

Ser Ser His Ile Gly Val Trp Gln Lys Arg Ala Gly Ser Lys Thr Ser

Pro Asn Trp Val Lys Leu Val Glu Leu Gly Asp Lys Val Asn Ala Arg
```

-continued

Pro Gly Gly Asp Ile Glu Thr Asn Lys Met Lys Val Arg Asn Glu Asp

Val Gln Glu Asp Asp Gln Met Ala Met Gln Met Ile Glu Glu Leu Leu

Asn Trp Thr Cys Pro Gly Ser Gly Ser Ile Ala Gln Val

SEQ ID NO: 2

Met Val Gln Thr Lys Lys Phe Arg Gly Val Arg Gln Arg His Trp Gly

Ser Trp Val Ala Glu Ile Arg His Pro Leu Leu Lys Arg Arg Ile Trp

Leu Gly Thr Phe Glu Thr Ala Glu Glu Ala Ala Arg Ala Tyr Asp Glu

Ala Ala Val Leu Met Ser Gly Arg Asn Ala Lys Thr Asn Phe Pro Leu

Asn Asn Asn Asn Thr Gly Glu Thr Ser Glu Gly Lys Thr Asp Ile Ser

Ala Ser Ser Thr Met Ser Ser Ser Thr Ser Ser Ser Ser Leu Ser Ser

Ile Leu Ser Ala Lys Leu Arg Lys Cys Cys Lys Ser Pro Ser Pro Ser

Leu Thr Cys Leu Arg Leu Asp Thr Ala Ser Ser His Ile Gly Val Trp

Gln Lys Arg Ala Gly Ser Lys Ser Asp Ser Ser Trp Val Met Thr Val

Glu Leu Gly Pro Ala Ser Ser Ser Gln Glu Thr Thr Ser Lys Ala Ser

Gln Asp Ala Ile Leu Ala Pro Thr Thr Glu Val Glu Ile Gly Gly Ser

Arg Glu Glu Val Leu Asp Glu Glu Glu Lys Val Ala Leu Gln Met Ile

Glu Glu Leu Leu Asn Thr Asn

SEQ ID NO: 3

Met Val His Ser Arg Lys Phe Arg Gly Val Arg Gln Arg Gln Trp Gly

Ser Trp Val Ser Glu Ile Arg His Pro Leu Leu Lys Arg Arg Val Trp

Leu Gly Thr Phe Glu Thr Ala Glu Ala Ala Ala Arg Ala Tyr Asp Gln

Ala Ala Leu Leu Met Asn Gly Gln Asn Ala Lys Thr Asn Phe Pro Val

Val Lys Ser Glu Glu Gly Ser Asp His Val Lys Asp Val Asn Ser Pro

Leu Met Ser Pro Lys Ser Leu Ser Glu Leu Leu Asn Ala Lys Leu Arg

Lys Ser Cys Lys Asp Leu Thr Pro Ser Leu Thr Cys Leu Arg Leu Asp

Thr Asp Ser Ser His Ile Gly Val Trp Gln Lys Arg Ala Gly Ser Lys

Thr Ser Pro Thr Trp Val Met Arg Leu Glu Leu Gly Asn Val Val Asn

Glu Ser Ala Val Asp Leu Gly Leu Thr Thr Met Asn Lys Gln Asn Val

Glu Lys Glu Glu Glu Glu Glu Glu Ala Ile Ile Ser Asp Glu Asp Gln

Leu Ala Met Glu Met Ile Glu Glu Leu Leu Asn Trp Ser

SEQ ID NO: 4

Met Gly Arg Ser Pro Cys Cys Glu Lys Asp His Thr Asn Lys Gly Ala

Trp Thr Lys Glu Glu Asp Asp Lys Leu Ile Ser Tyr Ile Lys Ala His

Gly Glu Gly Cys Trp Arg Ser Leu Pro Arg Ser Ala Gly Leu Gln Arg

Cys Gly Lys Ser Cys Arg Leu Arg Trp Ile Asn Tyr Leu Arg Pro Asp

Leu Lys Arg Gly Asn Phe Thr Leu Glu Glu Asp Asp Leu Ile Ile Lys

Leu His Ser Leu Leu Gly Asn Lys Trp Ser Leu Ile Ala Thr Arg Leu

Pro Gly Arg Thr Asp Asn Glu Ile Lys Asn Tyr Trp Asn Thr His Val

Lys Arg Lys Leu Leu Arg Lys Gly Ile Asp Pro Ala Thr His Arg Pro

Ile Asn Glu Thr Lys Thr Ser Gln Asp Ser Ser Asp Ser Ser Lys Thr

Glu Asp Pro Leu Val Lys Ile Leu Ser Phe Gly Pro Gln Leu Glu Lys

Ile Ala Asn Phe Gly Asp Glu Arg Ile Gln Lys Arg Val Glu Tyr Ser

-continued

Val Val Glu Glu Arg Cys Leu Asp Leu Asn Leu Glu Leu Arg Ile Ser

Pro Pro Trp Gln Asp Lys Leu His Asp Glu Arg Asn Leu Arg Phe Gly

Arg Val Lys Tyr Arg Cys Ser Ala Cys Arg Phe Gly Phe Gly Asn Gly

Lys Glu Cys Ser Cys Asn Asn Val Lys Cys Gln Thr Glu Asp Ser Ser

Ser Ser Ser Tyr Ser Ser Thr Asp Ile Ser Ser Ser Ile Gly Tyr Asp

Phe Leu Gly Leu Asn Asn Thr Arg Val Leu Asp Phe Ser Thr Leu Glu

Met Lys

SEQ ID NO: 5

Met Gly Arg Ser Pro Cys Cys Glu Lys Ala His Thr Asn Lys Gly Ala

Trp Thr Lys Glu Glu Asp Glu Arg Leu Val Ala Tyr Ile Lys Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile LYs Asn Tyr Trp Asn Thr His Ile

Arg Arg Lys Leu Ile Asn Arg Gly Ile Asp Pro Thr Ser His Arg Pro

Ile Gln Glu Ser Ser Ala Ser Gln Asp Ser Lys Pro Thr Gln Leu Glu

Pro Val Thr Ser Asn Thr Ile Asn Ile Ser Phe Thr Ser Ala Pro Lys

Val Glu Thr Phe His Glu Ser Ile PSer he Pro Gly Lys Ser Glu Lys

Ile Ser Met Leu Thr Phe Lys Glu Glu Lys Asp Glu Cys Pro Val Gln

Glu Lys Phe Pro Asp Leu Asn Leu Glu Leu Arg Ile Ser Leu Pro Asp

Asp Val Asp Arg Leu Gln Gly His Gly Lys Ser Thr Thr Pro Arg Cys

Phe Lys Cys Ser Leu Gly Met Ile Asn Gly Met Glu Cys Arg Cys Gly

Arg Met Arg Cys Asp Val Val Gly Gly Ser Ser Lys Gly Ser Asp Met

Ser Asn Gly Phe Asp Phe Leu Gly Leu Ala Lys Lys Glu Thr Thr Ser

Leu Leu Gly Phe Arg Ser Leu Glu Met Lys

SEQ ID NO: 6

Met Gly Arg Ser Pro Cys Cys Glu Lys Glu His Met Asn Lys Gly Ala

Trp Thr Lys Glu Glu Asp Glu Arg Leu Val Ser Tyr Ile Lys Ser His

Gly Glu Gly Cys Trp Arg Ser Leu Pro Arg Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr His Asp Glu Asp Glu Leu Ile Ile Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Lys Arg Lys Leu Leu Ser Lys Gly Ile Asp Pro Ala Thr His Arg Gly

Ile Asn Glu Ala Lys Ile Ser Asp Leu Lys Lys Thr Lys Asp Gln Ile

Val Lys Asp Val Ser Phe Val Thr Lys Phe Glu Glu Thr Asp Lys Ser

Gly Asp Gln Lys Gln Asn Lys Tyr Ile Arg Asn Gly Leu Val Cys Lys

Glu Glu Arg Val Val Val Glu Glu Lys Ile Gly Pro Asp Leu Asn Leu

Glu Leu Arg Ile Ser Pro Pro Trp Gln Asn Gln Arg Glu Ile Ser Thr

Cys Thr Ala Ser Arg Phe Tyr Met Glu Asn Asp Met Glu Cys Ser Ser

-continued

Glu Thr Val Lys Cys Gln Thr Glu Asn Ser Ser Ser Ile Ser Tyr Ser

Ser Ile Asp Ile Ser Ser Ser Asn Val Gly Tyr Asp Phe Leu Gly Leu

Lys Thr Arg Ile Leu Asp Phe Arg Ser Leu Glu Met Lys

SEQ ID NO: 7

Met Gly Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Ile Leu Met Ser Gly Arg Asn Ala Lys Thr Asn Phe Pro

Val Ala Arg Asn Ala Thr Gly Glu Leu Thr Pro Ala Ala Ala Val Ala

Gly Arg Asp Gly Arg Val Gly Gly Gly Ser Gly Ser Ser Ser Ser Met

Thr Ala Asn Gly Gly Gly Asn Ser Leu Ser Gln Ile Leu Ser Ala Lys

Leu Arg Lys Cys Cys Lys Thr Pro Ser Pro Ser Leu Thr Cys Leu Arg

Leu Asp Pro Glu Lys Ser His Ile Gly Val Trp Gln Lys Arg Ala Gly

Ala Arg Ala Asp Ser Ser Trp Val Met Thr Val Glu Leu Asn Lys Asp

Thr Ala Val Ser Ser Ala Ala The Val Ala Ala Ala Thr Ala Val Ser

Ser Ser Asp Gln Pro Thr Pro Ser Asp Ser Thr Val Thr Thr Thr Ser

Thr Ser Thr Thr Gly Ser Pro Ser Pro Pro Pro Pro Ala Met Asp Asp

Glu Glu Arg Ile Ala Leu Gln Met Ile Glu Glu Leu Leu Gly Arg Ser

Gly Pro Gly Ser Pro Ser His Gly Leu Leu His Gly Gly Glu Gly Ser

Leu Val Ile

SEQ ID NO: 8

Met Gly Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Ile Leu Met Ser Gly Arg Asn Ala Lys Thr Asn Phe Pro

Val Ala Arg Asn Ala Thr Gly Glu Leu Thr Pro Ala Ala Ala Val Ala

Gly Arg Asp Gly Arg Val Gly Gly Gly Ser Gly Ser Ser Ser Ser Met

Thr Ala Asn Gly Gly Gly Asn Ser Leu Ser Gln Ile Leu Ser Ala Lys

Leu Arg Lys Cys Cys Lys Thr Pro Ser Pro Ser Leu Thr Cys Leu Arg

Leu Asp Pro Glu Lys Ser His Ile Gly Val Trp Gln Lys Arg Ala Gly

Ala Arg Ala Asp Ser Ser Trp Val Met Thr Val Glu Leu Asn Lys Asp

Thr Ala Val Ser Ser Ala Ala Thr Val Ala Ala Ala Thr Ala Val Ser

Ser Ser Asp Gln Pro Thr Pro Ser Asp Ser Thr Val Thr Thr Thr Ser

Thr Ser Thr Thr Gly Ser Pro Ser Pro Pro Pro Pro Ala Met Asp Asp

Glu Glu Arg Ile Ala Leu Gln Met Ile Glu Glu Leu Leu Gly Arg Ser

Gly Pro Gly Ser Pro Ser His Gly Leu Leu His Gly Gly Glu Gly Ser

Leu Val Ile

SEQ ID NO: 9

Met Gly Arg Ser Pro Cys Cys Glu Lys Glu His Thr Asn Lys Gly Ala

Trp Thr Lys Glu Glu Asp Glu Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

-continued

Leu Lys Arg Gly Asn Phe Thr Ala Asp Glu Asp Asp Leu Ile Ile Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Arg Arg Lys Leu Leu Gly Arg Gly Ile Asp Pro Val Thr His Arg Pro

Val Asn Ala Ala Ala Ala Thr Ile Ser Phe His Pro Gln Pro Pro Pro

Thr Thr Lys Glu Glu Gln Leu Ile Leu Ser Lys Pro Pro Lys Cys Pro

Asp Leu Asn Leu Asp Leu Cys Ile Ser Pro Pro Ser Cys Gln Glu Glu

Asp Asp Asp Tyr Glu Ala Lys Pro Ala Met Ile Val Arg Ala Pro Glu

Leu Gln Arg Arg Arg Gly Gly Leu Cys Phe Gly Cys Ser Leu Gly Leu

Gln Lys Glu Cys Lys Cys Ser Gly Gly Gly Ala Gly Ala Gly Ala Gly

Asn Asn Phe Leu Gly Leu Arg Ala Gly Met Leu Asp Phe Arg Ser Leu

Pro Met Lys

SEQ ID NO: 10

Met Gly Arg Ser Pro Cys Cys Glu Lys Ala His Thr Asn Lys Gly Ala

Trp Thr Lys Glu Glu Asp Asp Arg Leu Ile Ala Tyr Ile Lys Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Ser Arg Gly Ile Asp Pro Val Thr His Arg Pro

Ile Asn Asp Ser Ala Ser Asn Ile Thr Ile Ser Phe Glu Ala Ala Ala

Ala Ala Ala Arg Asp Asp Lys Ala Ala Val Phe Arg Arg Glu Asp His

Pro His Gln Pro Lys Ala Val Thr Val Ala Gln Glu Gln Gln Ala Ala

Ala Asp Trp Gly His Gly Lys Pro Leu Lys Cys Pro Asp Leu Asn Leu

Asp Leu Cys Ile Ser Leu Pro Ser Gln Glu Glu Pro Met Met Met Lys

Pro Val Lys Arg Glu Thr Gly Val Cys Phe Ser Cys Ser Leu Gly Leu

Pro Lys Ser Thr Asp Cys Lys Cys Ser Ser Phe Leu Gly Leu Arg Thr

Ala Met Leu Asp Phe Arg Ser Leu Glu Met Lys

SEQ ID NO: 11

Met Gly Arg Ser Pro Cys Cys Glu Lys Ala His Thr Asn Lys Gly Ala

Trp Thr Lys Glu Glu Asp Asp Arg Leu Ile Ala Tyr Ile Arg Thr His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Asn Arg Gly Ile Asp Pro Ala Thr His Arg Pro

Leu Asn Glu Pro Ala Gln Glu Ala Ser Thr Thr Ile Ser Phe Ser Thr

Thr Thr Ser Val Lys Glu Glu Ser Leu Ser Ser Val Lys Glu Glu Ser

Asn Lys Glu Lys Ile Ile Ser Ala Ala Ala Phe Ile Cys Lys Glu Glu

Lys Thr Pro Val Gln Glu Arg Cys Pro Asp Leu Asn Leu Glu Leu Arg

-continued

Ile Ser Leu Pro Cys Gln Asn Gln Pro Asp Arg His Gln Ala Phe Lys

Thr Gly Gly Ser Thr Ser Leu Cys Phe Ala Cys Ser Leu Gly Leu Gln

Asn Ser Lys Asp Cys Ser Cys Ser Val Ile Val Gly Thr Ile Gly Ser

Ser Ser Ser Ala Gly Ser Lys Thr Gly Tyr Asp Phe Leu Gly Met Lys

Ser Gly Val Leu Asp Tyr Arg Gly Leu Glu Met Lys

SEQ ID NO: 12

Met Gly Arg Ser Pro Cys Cys Glu Lys Ala His Thr Asn Lys Gly Ala

Trp Thr Lys Glu Glu Asp Asp Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Ala Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Asn Arg Gly Ile Asp Pro Ala Thr His Arg Pro

Leu Asn Glu Pro Ala Val Gln Glu Ala Thr Thr Thr Ile Ser Phe Thr

Thr Thr Thr Thr Ser Val Leu Glu Glu Glu Ser Leu Gly Ser Ile Ile

Lys Glu Glu Asn Lys Glu Lys Ile Ile Ser Ala Thr Ala Phe Val Cys

Lys Glu Glu Lys Thr Gln Val Gln Glu Arg Cys Pro Asp Leu Asn Leu

Glu Leu Gly Ile Ser Leu Pro Ser Gln Asn Gln Pro Asp His His Gln

Pro Phe Lys Thr Gly Gly Ser Arg Ser Leu Cys Phe Ala Cys Ser Leu

Gly Leu Gln Asn Ser Lys Asp Cys Ser Cys Asn Val Ile Val Ser Thr

Val Gly Ser Ser Gly Ser Thr Ser Thr Lys Thr Gly Tyr Asp Phe Leu

Gly Met Lys Ser Gly Val Leu Asp Tyr Arg Ser Leu Glu Met Lys

SEQ ID NO: 13

Met Pro Thr Pro Thr Pro Thr Pro Thr Pro Thr Cys Gly Asp Gly Ser

Leu Ala Gly Phe Ala Leu Leu Leu Arg Gly Glu Lys Arg Val Ala Asn

Gly Ala Arg Gly Gly Arg Gly Ile Gly Gly Glu Arg Ala Lys Ile Ile

Arg Arg Arg His Ala Glu Lys Thr His Gly Arg Arg Glu Arg Gly Gly

His Arg Arg Ser His Arg Leu Ala Tyr Pro Leu Trp Val Leu Asp Ile

Arg Ser Pro Asn Gly Ile Met Leu Gly Ile Phe Arg Gly Ala Ala Leu

Trp Leu Trp Thr Leu Ala Trp His Met

SEQ ID NO: 14

Met Val Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Val Leu Met Ser Gly Arg Asn Ala Lys Thr Asn Phe Pro

Val Pro Arg Thr Ala Thr Gly Glu Leu Ala Pro Val Pro Ala Ala Arg

Asp Ala Arg Gly Gly Gly Gly Ser Ser Ser Ala Ala Ala Ala Pro Gly

Gly Gly Thr Ser Asn Leu Ser Gln Ile Leu Ser Ala Lys Leu Arg Lys

Cys Cys Lys Thr Pro Ser Pro Ser Leu Thr Cys Leu Arg Leu Asp Pro

Glu Lys Ser His Ile Gly Val Trp Gln Lys Arg Ala Gly Ala Arg Ala

Asp Ser Ser Trp Val Met Thr Val Gln Leu Asn Lys Asp Val Pro Pro

-continued

Pro Ala Ser Ser Ser Gly Glu Glu Pro Val Pro Ser Asp Gly Gly Ala

Ala Ala Thr Thr Pro Thr Ser Thr Ser Thr Ser Ser Thr Val Thr Thr

Thr Gly Ser Pro Pro Pro Ala Met Met Met Asp Asp Glu Glu Arg Ile

Ala Leu Gln Met Ile Glu Glu Leu Leu Gly Ser Ser His Ser His Gly

Met Phe Gln Gly Ala Ala Gly Ser Ile Val Ile

SEQ ID NO: 15

Met Gly Arg Ser Pro Cys Cys Glu Lys Ala His Thr Asn Lys Gly Ala

Trp Thr Lys Glu Glu Asp Asp Arg Leu Val Ala Tyr Ile Arg Ala His

Gly Glu Gly Cys Trp Arg Ser Leu Pro Lys Ala Ala Gly Leu Met Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Ile Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Arg Arg Lys Leu Leu Gly Arg Gly Ile Asp Pro Val Thr His Arg Pro

Ile Ala Asp Ala Gly Ala Gly Thr Val Thr Thr Ile Ser Phe Gln Pro

Asn Lys Pro Asn Ala Ala Val Ala Ala Gln Ala Pro Gln His Gln Pro

Ile Lys Ala Val Ala Thr Ala Val Val Lys Val Pro Arg Cys Pro Asp

Leu Asn Leu Asp Leu Cys Ile Ser Pro Pro Cys Gln Gln Lys Glu Asp

Glu Glu Leu Asp Leu Lys Pro Ala Val Val Val Lys Arg Glu Val Leu

Gln Ala Gly His Gly Gly Ser Leu Cys Phe Gly Cys Ser Leu Gly Ile

Gln Lys Gly Ala Pro Gly Cys Ser Cys Ser Ser Ser Asn Ser His His

Arg Phe Leu Gly Leu Arg Ser Gly Met Leu Asp Phe Arg Gly Leu Glu

Met Lys

SEQ ID NO: 16

Met Gly Arg Ser Pro Cys Cys Glu Lys Ala His Thr Asn Lys Gly Ala

Trp Thr Lys Glu Glu Asp Asp Arg Leu Val Ala Tyr Ile Lys Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Ser Arg Gly Ile Asp Pro Val Thr His Arg Pro

Ile Asn Glu His Thr Ser Asn Ile Thr Ile Ser Phe Glu Ala Ala Ala

Ala Ala Arg Asp Arg Glu Glu Asn Lys Gly Ala Val Phe Arg Leu Glu

Glu His Asn Lys Ala Thr Ala Ala Ala Ala Ala Ala Ile Gly Arg Asp

His His Gln Asn His His Pro Ala Gly Asp Trp Gly Gln Gly Lys Pro

Leu Lys Cys Pro Asp Leu Asn Leu Asp Leu Cys Ile Ser Pro Pro Ala

Ala Pro Cys Gln Glu Glu Lys Ala Met Val Thr Met Lys Pro Val Lys

Arg Glu Ala Gly Leu Cys Phe Ser Cys Ser Leu Gly Leu Pro Lys Ser

Ala Asp Cys Lys Cys Ser Asn Phe Leu Gly Leu Arg Thr Ala Met Leu

Asp Phe Arg Ser Leu Glu Met Lys

-continued

SEQ ID NO: 17

Met Thr Glu Asn Leu His Ser Arg Lys Met Val Gln Pro Lys Lys Phe

Arg Gly Val Arg Gln Arg His Trp Gly Ser Trp Val Ser Glu Ile Arg

His Pro Leu Leu Lys Arg Arg Val Trp Leu Gly Thr Phe Glu Thr Ala

Glu Glu Ala Ala Arg Ala Tyr Asp Glu Ala Ala Val Leu Met Ser Gly

Arg Asn Ala Lys Thr Asn Phe Pro Ile Gln Arg Ser Ser Thr Gly Glu

Pro Thr Pro Ala Ala Gly Arg Asp Ala Arg Ser Asn Phe Ser Ser Gly

Ser Ser Thr Thr Asn Leu Ser Gln Ile Leu Ser Ala Lys Leu Arg Lys

Cys Cys Lys Ala Pro Ser Pro Ser Leu Thr Cys Leu Arg Leu Asp Pro

Glu Lys Ser His Ile Gly Val Trp Gln Lys Arg Ala Gly Ala Arg Ala

Asp Ser Asn Trp Val Met Thr Val Glu Leu Asn Lys Asp Ala Ala Ser

Thr Asp Ala Ala Ser Gln Ser Thr Ser Ala Thr Thr Ala Pro Pro Ala

Thr Pro Met Asp Glu Glu Glu Arg Ile Ala Leu Gln Met Ile Glu Glu

Leu Leu Ser Ser Ser Ser Pro Ala Ser Pro Ser Asn Gly Asp Asp Gln

Gly Arg Phe Ile Ile

SEQ ID NO: 18

Met Gly Arg Ser Pro Cys Cys Glu Lys Ala His Thr Asn Arg Gly Ala

Trp Thr Lys Glu Glu Asp Glu Arg Leu Val Ala Tyr Val Arg Ala His

Gly Glu Gly Cys Trp Arg Ser Leu Pro Arg Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Val Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Arg Arg Lys Leu Leu Gly Ser Gly Ile Asp Pro Val Thr His Arg Arg

Val Ala Gly Gly Ala Ala Thr Thr Ile Ser Phe Gln Pro Ser Pro Asn

Thr Ala Val Ala Ala Ala Ala Glu Thr Ala Ala Gln Ala Pro Ile Lys

Ala Glu Glu Thr Ala Ala Val Lys Ala Pro Arg Cys Pro Asp Leu Asn

Leu Asp Leu Cys Ile Ser Pro Pro Cys Gln His Glu Asp Asp Gly Glu

Glu Glu Glu Glu Glu Leu Asp Leu Ile Lys Pro Ala Val Val Lys Arg

Glu Ala Leu Gln Ala Gly His Gly His Gly His Gly Leu Cys Leu Gly

Cys Gly Leu Gly Gly Gln Lys Gly Ala Ala Gly Cys Ser Cys Ser Asn

Gly His His Phe Leu Gly Leu Arg Thr Ser Val Leu Asp Phe Arg Gly

Leu

SEQ ID NO: 19

Met Gly Arg Ser Pro Cys Cys Glu Lys Ala His Thr Asn Lys Gly Ala

Trp Thr Lys Glu Glu Asp Glu Arg Leu Val Ala His Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Val Lys

Leu His Ser Val Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Ser Arg Gly Ile Asp Pro Val Thr His Arg Pro

-continued

Val Thr Glu His His Ala Ser Asn Ile Thr Ile Ser Phe Glu Thr Glu

Val Ala Ala Ala Ala Arg Asp Asp Lys Lys Gly Ala Val Phe Arg Leu

Glu Glu Glu Glu Glu Arg Asn Lys Ala Thr Met Val Val Gly Arg Asp

Arg Gln Ser Gln Ser Gln Ser His Ser His Pro Ala Gly Glu Trp Gly

Gln Gly Lys Arg Pro Leu Lys Cys Pro Asp Leu Asn Leu Asp Leu Cys

Ile Ser Pro Pro Cys Gln Glu Glu Glu Glu Met Glu Glu Ala Ala Met

Arg Val Arg Pro Ala Val Lys Arg Glu Ala Gly Leu Cys Phe Gly Cys

Ser Leu Gly Leu Pro Arg Thr Ala Asp Cys Lys Cys Ser Ser Ser Ser

Phe Leu Gly Leu Arg Thr Ala Met Leu Asp Phe Arg Ser Leu Glu Met

Lys

SEQ ID NO: 20

Met Gly Arg Ser Pro Cys Cys Glu Lys Ala His Thr Asn Lys Gly Ala

Trp Thr Lys Glu Glu Asp Asp Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Val Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Lys Arg Lys Leu Leu Ser Arg Gly Ile Asp Pro Val Thr His Arg Pro

Ile Ala Asp Ala Ala Arg Asn Val Thr Ile Ser Phe Gln Pro Asp Ala

Pro Ser Gln Gln Gln Leu Ser Asp Asp Ala Glu Ala Pro Pro Pro Pro

Pro Pro Gln Gln Gln Gln Gln Leu Lys Pro Pro Pro Arg Cys Pro Asp

Leu Asn Leu Asp Leu Cys Ile Ser Pro Pro Cys His Lys Glu Glu Glu

Asp Gln Glu Leu Val Lys Pro Ala Ala Val Lys Arg Glu Met Leu Gln

Ala Gly His Gly Thr Leu Gly Leu Cys Phe Gly Cys Ser Leu Gly Leu

Gln Lys Gly Ala Ala Gly Cys Thr Cys Ser Ser Asn Ser His Phe Leu

Gly Leu Arg Val Gly Met Leu Leu Asp Phe Arg Gly Leu Glu Met Lys

SEQ ID NO: 37 atg gta cat tcg aag aag ttc cga ggt gtc cgc cag cgt cag tgg ggt tct tgg gtt tct gag att cgt cat cct ctc ttg aag aga aga gtg tgg cta gga aca ttc gac acg gcg gaa aca gcg gct aga gcc tac gac caa gcc gcg gtt cta atg aac ggc cag agc gcg aag act aac ttc ccc gtc atc aaa tcg aac ggt tca aat tcc ttg gag att aac tct gcg tta agg tct ccc aaa tca tta tcg gaa cta ttg aac gct aag cta agg aag aac tgt aaa gac cag aca ccg tat ctg acg tgt ctc cgc ctc gac aac gac agc tca cac atc ggc gtc tgg cag aaa cgc gcc ggg tca aaa acg agt cca aac tgg gtc aag ctt gtt gaa cta ggt gac aaa gtt aac gca cgt ccc ggt ggt gat att gag act aat aag atg aag gta cga aac gaa gac gtt cag gaa gat gat caa atg gcg atg cag atg atc gag gag ttg ctt aac tgg acc tgt cct gga tct gga tcc att gca cag gtc taa -continued

SEQ ID NO: 38 atg gta cag acg aag aag ttc aga ggt gtc agg caa cgc cat tgg ggt tct tgg gtc gct gag att cgt cat cct ctc ttg aaa cgg agg att tgg cta ggg acg ttc gag acc gca gag gag gca gca aga gca tac gac gag gcc gcc gtt tta atg agc ggc cgc aac gcc aaa acc aac ttt ccc ctc aac aac aac aac acc gga gaa act tcc gag ggc aaa acc gat att tca gct tcg tcc aca atg tca tcc tca aca tca tct tca tcg ctc tct tcc atc ctc agc gcc aaa ctg agg aaa tgc tgc aag tct cct tcc cca tcc ctc acc tgc ctc cgt ctt gac aca gcc agc tcc cat atc ggc gtc tgg cag aaa cgg gcc ggt tca aag tct gac tcc agc tgg gtc atg acg gtg gag cta ggt ccc gca agc tcc tcc caa gag act act agt aaa gct tca caa gac gct att ctt gct ccg acc act gaa gtt gaa att ggt ggc agc aga gaa gaa gta ttg gat gag gaa gaa aag gtt gct ttg caa atg ata gag gag ctt ctc aat aca aac taa

SEQ ID NO: 39 atg gta cat tcg agg aag ttc cga ggt gtc cgc cag cga caa tgg ggt tct tgg gtc tct gag att cgc cat cct cta ttg aag aga aga gtg tgg ctt gga act ttc gaa acg gca gaa gcg gct gca aga gca tac gac caa gcg gct ctt cta atg aac ggc caa aac gct aag acc aat ttc cct gtc gta aaa tca gag gaa ggc tcc gat cac gtt aaa gat gtt aac tct ccg ttg atg tca cca aag tca tta tct gag ctt ttg aac gct aag cta agg aag agc tgc aaa gac cta acg cct tct ttg acg tgt ctc cgt ctt gat act gac agt tcc cac att gga gtt tgg cag aaa cgg gcc ggg tcg aaa aca agt ccg act tgg gtc atg cgc ctc gaa ctt ggg aac gta gtc aac gaa agt gcg gtt gac tta ggg ttg act acg atg aac aaa caa aac gtt gag aaa gaa gaa gaa gaa gaa gaa gct att att agt gat gag gat cag tta gct atg gag atg atc gag gag ttg ctg aat tgg agt tga

SEQ ID NO: 40 atg gga agg tct cct tgc tgt gag aaa gac cac aca aac aaa gga gct tgg act aag gaa gaa gac gat aag ctc atc tct tac atc aaa gct cac ggt gaa ggt tgt tgg cgt tct ctt cct aga tcc gcc ggt ctt caa cgt tgc gga aaa agc tgt cgt ctc cga tgg att aac tat ctc cga cct gat ctc aag agg ggt aac ttc acc ctc gaa gaa gat gat ctc atc atc aaa cta cat agc ctt ctc ggt aac aag tgg tct ctt att gcg acg aga tta cca gga aga aca gat aac gag att aag aat tac tgg aac aca cat gtt aag agg aag cta tta aga aaa ggg att gat ccg gcg act cat cga cct atc aac gag acc aaa act tct caa gat tcg tct gat tct agt aaa aca gag gac cct ctt gtc aag att ctc tct ttt ggt cct cag ctg gag aaa ata gca aat ttc ggg gac gag aga att caa aag aga gtt gag tac tca gtt gtt gaa gaa aga tgt ctg gac ttg aat ctt gag ctt agg atc agt cca cca tgg caa gac aag ctc cat gat gag agg aac cta agg ttt ggg aga gtg aag tat agg tgc agt gcg tgc cgt ttt gga ttc ggg aac ggc -continued aag gag tgt agc tgt aat aat gtg aaa tgt caa aca gag gac agt agt agc agc agt tat tct tca acc gac att agt agt agc att ggt tat gac ttc ttg ggt cta aac aac act agg gtt ttg gat ttt agc act ttg gaa atg aaa tga

SEQ ID NO: 41 atg gga agg tca ccg tgc tgt gag aaa gct cac aca aac aaa gga gca tgg acg aaa gaa gag gac gag agg ctc gtc gcc tac att aaa gct cat gga gaa ggc tgc tgg aga tct ctc ccc aaa gcc gcc gga ctt ctt cgc tgt ggc aag agc tgc cgt ctc cgg tgg atc aac tat ctc cgg cct gac ctt aag cgt gga aac ttc acc gag gaa gaa gac gaa ctc atc atc aag ctc cat agc ctt ctt ggc aac aaa tgg tcg ctt att gcc ggg aga tta ccg gga aga aca gat aac gag ata aag aac tat tgg aac acg cat ata cga aga aag ctt ata aac aga ggg att gat cca acg agt cat aga cca atc caa gaa tca tca gct tct caa gat tct aaa cct aca caa cta gaa cca gtt acg agt aat acc att aat atc tca ttc act tct gct cca aag gtc gaa acg ttc cat gaa agt ata agc ttt ccg gga aaa tca gag aaa atc tca atg ctt acg ttc aaa gaa gaa aaa gat gag tgc cca gtt caa gaa aag ttc cca gat ttg aat ctt gag ctc aga atc agt ctt cct gat gat gtt gat cgt ctt caa ggg cat gga aag tca aca acg cca cgt tgt ttc aag tgc agc tta ggg atg ata aac ggc atg gag tgc aga tgc gga aga atg aga tgc gat gta gtc gga ggt agc agc aag ggg agt gac atg agc aat gga ttt gat ttt tta ggg ttg gca aag aaa gag acc act tct ctt ttg ggc ttt cga agc ttg gag atg aaa taa

SEQ ID NO: 42 atg gga aga tct cct tgc tgc gag aaa gaa cac atg aac aaa ggt gct tgg act aaa gaa gaa gat gag aga cta gtc tct tac atc aag tct cac ggt gaa ggt tgt tgg cga tct ctt cct aga gcc gct ggt ctc ctt cgc tgc ggt aaa agc tgc cgt ctt cgg tgg att aac tat ctc cga cct gat ctc aaa aga gga aac ttt aca cat gat gaa gat gaa ctt atc atc aag ctt cat agc ctc cta ggc aac aag tgg tct ttg att gcg gcg aga tta cct gga aga aca gat aac gag atc aag aac tac tgg aac aca cat ata aag agg aag ctt ttg agc aaa ggg att gat cca gcc act cat aga ggg atc aac gag gca aaa att tct gat ttg aag aaa aca aag gac caa att gta aaa gat gtt tct ttt gtg aca aag ttt gag gaa aca gac aag tct ggg gac cag aag caa aat aag tat att cga aat ggg tta gtt tgc aaa gaa gag aga gtt gtt gtt gaa gaa aaa ata ggc cca gat ttg aat ctt gag ctt agg atc agt cca cca tgg caa aac cag aga gaa ata tct act tgc act gcg tcc cgt ttt tac atg gaa aac gac atg gag tgt agt agt gaa act gtg aaa tgt caa aca gag aat agt agc agc att agc tat tct tct att gat att agt agt agt aac gtt ggt tat gac ttc ttg ggt ttg aag aca aga att ttg gat ttt cga agc ttg gaa atg aaa taa -continued

SEQ ID NO: 43 atg gta cag cca aag aag aag ttt cgt gga gtc agg cag cgg cac tgg ggc tcc tgg gtc tct gag atc aga cac ccc ctc ctt aaa agg agg gtg tgg ctg ggc acc ttt gag acg gcc gag gag gct gcg cga gcc tac gat gag gct gct gtg ctg atg agt ggc cgc aac gcc aag acc aac ttc ccc gtg cag agg aac tcc acc ggt gat ctc gcc acg gcc gca gac cag gac gcc cgt agc aat ggc ggt agc agg aac tcc tcc gcg ggc aac ctg tca cag att ctc agt gct aag ctc cgc aag tgc tgc aag gcg cca tct ccg tcc tta acc tgc ctc cgc ctc gac ccc gag aag tcc cac att ggc gtg tgg caa aag cgc gca ggg gcc cgt gct gac tcc aac tgg gtg atg acg gtg gag ctc aac aaa gag gta gaa cca act gaa cct gca gct cag ccc aca tca aca gca aca gct tcg caa gtg aca atg gat gat gag gaa aag att gcg ctg caa atg atc gag gag ttg ctg agc agg agc agt cca gct tca ccc tca cat gga gag gga gag ggt agc ttt gtc atc tga

SEQ ID NO: 44 atg gga cag tcg aag aag aag ttc cgc gga gtc agg cag cgc cac tgg ggc tcc tgg gtc tcc gag atc agg cac cct ctc ctt aag agg agg gtg tgg ctg ggt acc ttt gag acg gcg gag gag gcg gcg cgg gcg tac gac gag gcc gcc atc ctg atg agc ggc cgc aac gcc aag acc aac ttc cca gtc gcg agg aac gcc acg ggg gag ctc aca ccg gcg gct gcg gtg gca ggg cgg gat ggc cgt gtc ggc ggc ggc agc ggc agc tcg tcc tca atg acg gcc aac ggc ggc ggg aac agc ctg tct cag atc ctc agc gcc aag ctc cgc aag tgc tgc aag acg ccg tcg ccg tcg ctc acc tgc ctc cgc ctt gac ccg gag aag tcc cac att ggc gtc tgg cag aag cgc gcc ggc gca cgc gct gac tcc agc tgg gtc atg acc gtc gag ctc aac aag gac acg gcc gtg tcg tcg gct gcg acg gtg gca gca gca aca gca gtg tcg tcc agc gac cag ccg act ccg agt gac agc aca gtc aca acg acg tcc acg tcc acc acg ggc tcg ccg tcg cca cca cct ccg gca atg gac gac gag gag agg atc gcg ctg cag atg atc gag gag ctg ctg ggc agg agc ggc ccg ggc tcg ccg tca cat ggg ctg ctg cac ggt ggt gaa ggt agc ctc gtc atc tga

SEQ ID NO: 45 atg ggg agg tcg ccg tgc tgc gag aag gag cac act aac aag ggc gcg tgg acc aag gag gag gac gag cgc ctc gtc gcc tac atc cgc gcc cac ggc gag ggc tgc tgg cgc tcg ctc ccc aag gcc gcc ggc ctc ctc cgc tgc ggc aag agc tgc cgc ctc cgc tgg atc aac tac ctc cgc ccc gac ctc aag cgc ggc aac ttc acc gcc gac gag gac gac ctc atc atc aag ctc cac agc ctc ctc ggc aac aag tgg tct ctg atc gcg gcg agg ctg ccg ggg agg acg gac aac gag atc aag aac tac tgg aac acg cac atc cgc cgg aag ctt ctc ggc agg ggg atc gac ccc gtc acg cac cgc ccc gtc aac gcc gcc gcc gcc acc atc tcc ttc cat ccc cag ccg ccg cca acg acg aag gag gag cag ctc ata ctc agc aag ccg ccc aag tgc ccc -continued gac ctc aac ctg gac ctc tgc atc agc ccg ccg tcg tgc cag gaa gaa gac gat gac tat gag gcg aag ccg gcg atg atc gtg agg gcg ccg gag ctg cag cgc cgc cgc ggc ggc ctc tgc ttc ggc tgc agc ctc ggc ctc cag aag gag tgc aag tgc agc ggc ggc ggc gcc ggc gcc ggc gcc ggc aac aac ttc ctc ggc ctc agg gct ggc atg ctc gac ttc aga agc ctc ccc atg aaa tga

SEQ ID NO: 46 atg ggg agg tca ccg tgc tgc gag aag gca cac acc aac aag gga gca tgg acc aag gag gaa gat gac cgg ctc att gcc tac atc aag gcg cac ggc gaa ggt tgc tgg cga tcg ctg ccc aag gcc gcc ggc ctc ctc cgc tgt ggc aag agc tgc cgc ctc cgg tgg atc aac tac ctc cgg cct gac ctc aag cgc ggc aac ttc acc gag gag gag gat gag ctg atc atc aag ctt cac agc ctt tta ggc aac aaa tgg tct ctg ata gcc ggg agg ttg cca gga aga acg gac aac gag atc aag aac tac tgg aac acg cac atc agg agg aag ctg ctg agc cgt ggc atc gac ccg gtg aca cac cgg ccg atc aac gac agc gcg tcc aac atc acc ata tca ttc gag gcg gcc gcg gcg gcg gcg agg gac gac aag gcc gcc gtg ttc cgg cga gag gac cat cct cat cag ccg aag gcg gtg aca gtg gca cag gag cag cag gca gcc gcc gat tgg ggc cat ggg aag cca ctc aag tgc cct gac ctc aat ctg gac ctc tgc atc agc ctc cct tcc caa gaa gag ccc atg atg atg aag ccg gtg aag agg gag acc ggc gtc tgc ttc agc tgc agc ctg ggg ctc ccc aag agc aca gac tgc aag tgc agc agc ttc ctg gga ctc agg aca gcc atg ctc gac ttc aga agc ttg gaa atg aaa tga

SEQ ID NO: 47 atg gga agg tct cct tgc tgt gaa aaa gct cat aca aac aaa ggc gca tgg act aag gaa gaa gat gat cgc ctt att gct tac att aga acc cac ggt gaa ggt tgc tgg cgt tca ctt cct aaa gct gct ggc ctt cta aga tgc ggc aag agc tgc aga ctt cgt tgg atc aac tat tta aga cct gac ctt aaa cgt ggc aat ttt act gaa gaa gaa gat gag ctc att atc aaa ctc cat agt ctc ctc ggc aac aaa tgg tca ctt ata gcc gga agg tta cca ggg aga aca gat aat gag ata aag aat tat tgg aac aca cat ata aga agg aag ctc ttg aat aga ggc ata gat cct gcg act cat agg cca ctc aat gaa cca gcc caa gaa gct tca aca aca ata tct ttc agc act act acc tca gtt aaa gaa gag tcg ttg agt tct gtt aaa gag gaa agt aat aag gag aag ata att agc gca gct gct ttt ata tgc aaa gaa gag aaa acc cca gtt caa gaa agg tgt cca gac ttg aat ctt gaa ctt aga att agc ctt cct tgc caa aac cag cct gat cgt cac cag gca ttc aaa act gga gga agt aca agt ctt tgt ttt gct tgc agc ttg ggg cta caa aac agc aag gac tgc agt tgc agt gtc att gtg ggt act att gga agc agc agt agt gct ggc tcc aaa act ggc tat gac ttc tta ggg atg aaa agt ggt gtg ttg gat tat aga ggt ttg gag atg aaa tga -continued

SEQ ID NO: 48 atg gga agg tct cct tgc tgt gaa aaa gcc cat aca aac aag ggt gcg
tgg acc aag gag gaa gac gat cgc ctt gtt gct tac att aga gct cac
ggt gaa ggt tgc tgg cgc tca ctt cct aaa gcc gct ggc ctt ctt aga
tgt ggc aag agt tgc aga ctt cgt tgg atc aac tat tta aga cct gac
ctt aaa cgt ggc aat ttc acc gaa gca gaa gat gag ctc att atc aaa
ctc cat agc ctc ctt gga aac aaa tgg tca ctc ata gct gga aga tta
cca ggg aga aca gat aat gag ata aag aat tat tgg aac aca cat ata
aga agg aag ctt ttg aac aga ggc ata gat ccc gca act cat agg cca
ctc aac gaa cca gca gta caa gaa gcc aca aca aca ata tct ttc acc
acg act act act tca gta ctt gaa gaa gag tct ctg ggt tct ata att
aaa gag gaa aat aaa gag aag ata att agc gca act gct ttc gta tgc
aaa gaa gag aaa acc caa gtt caa gaa agg tgt cca gac ttg aat ctc
gag ctt gga att agc ctt cct tcc caa aac cag cct gat cat cac cag
cca ttc aaa act gga gga agt aga agt ctt tgt ttt gct tgc agt ttg
ggg cta caa aac agc aag gat tgc agc tgc aat gtt att gtg agc act
gtt ggg agc agt ggc agc act agc aca aag act ggt tat gac ttc ttg
ggc atg aaa agt ggt gtt ttg gat tat aga agt tta gag atg aaa taa

SEQ ID NO: 49 atg aca gag aat ctc cac tcc aag aaa atg gta cag cca aag aag ttt
cgt gga gtc cgg cag cgc cac tgg ggt tcc tgg gtc tcc gag atc agg
cat ccc ctc ctt aag agg agg gtc tgg ctg ggc acc ttc gag acc gct
gag gag gca gcg aga gca tat gac gag gct gcc gtg ctg atg agc ggc
cgc aac gcc aag acc aac ttc ccg gtc caa agg agc agc aca ggg gag
cca acc cca gct gcg gga agg gac gct cac agc aac gcc ggc agc ggc
tcc tct acc gcc aac ctg tcc cag att ctc agt gcg aag ctc cgc aaa
tgc tgc aag gcg cca tcg ccc tcc ctg acc tgt ctc cgc ctt gac cct
gag aag tcc cac att ggt gtt tgg cag aag cgt gca gga gcc cgt gct
gac tcc aac tgg gtc atg acc gtg gag ctc aac aaa ggt gca gca tcc
act gat gct gca tca cag tcc aca tca gca aca act gct cca cca gcc
acc ccg atg gat gac gag gag agg atc gcc ctg caa atg atc gaa gag
ttg ctg agc agc agc agc cca gct tca ccc tcg cac gga gat gac caa
ggt cgc ttc atc atc tga

SEQ ID NO: 50 atg gtg caa tca aag aag aag ttc cgc ggc gtc agg cag cgc cac tgg
ggc tcc tgg gtc tcc gag atc agg cac ccg ctg ctt aag agg agg gtg
tgg ctg ggc acc ttc gag acg gca gag gag gcg gcg cgg gcg tac gac
gag gcc gcc gtc ctc atg agc ggc cgc aac gcc aag acc aac ttc ccc
gtc cca agg acc gcc acc ggg gag ctg gcc ccc gtg ccg gcc gcg cgg
gac gca cgt ggc ggc ggc ggc tcg tcc tcc gcg gca gca gcg ccc ggc
ggc ggc acc agc aac ctg tcg cag atc ctc agc gcc aag ctc cgc aag
tgc tgc aag acg ccg tcg ccg tcg ctc acc tgc ctc cgc ctc gac ccg -continued gag aag tcc cac att ggc gtc tgg cag aag cgc gcg ggc gcg cgc gcc gac tcc agc tgg gtc atg acc gtc cag ctc aac aag gac gtg ccg ccg ccg gcg tcc tcc tcc ggc gag gag ccg gtg ccc agc gac gga ggc gca gcg gcc acc acg ccc acg tcc act tcc acg tcg tcc acg gtc acg acg acc ggc tcg cct cca cct gcg atg atg atg gac gac gag gag agg att gcg ctg cag atg atc gag gag ctg ctg ggc agc tcg cac tca cat ggg atg ttc cag ggt gca gcg ggc agc atc gtc atc tga

SEQ ID NO: 51 atg ggg cgg tcg ccg tgc tgc gag aag gcg cac acg aac aag ggc gcg tgg acc aag gag gag gac gac cgc ctg gtg gcg tac atc cgc gcg cac ggc gaa ggg tgc tgg cgg tcg ctg ccc aag gcg gcc gga ctg atg cgc tgc ggc aag agc tgc cgc ctc cgc tgg atc aac tac ctc cgc ccc gac ctc aag cgc ggc aac ttc acc gcc gac gag gac gac ctc atc atc aag ctg cac agc ctc ctc ggc aac aag tgg tcg ctc atc gcc gcg cgg ctc ccg ggg cgg acg gac aac gag atc aag aac tac tgg aac acg cac atc cgg cgg aag ctg ctt ggc agg ggc atc gac ccc gtc acg cac cgc ccc atc gcc gac gcc ggc gcc ggc acc gtc acc acc atc tcg ttc cag ccc aac aaa ccc aac gcc gcc gtc gca gcg cag gcg cca caa cat cag ccg atc aag gcg gtg gcg acg gcc gtc gtt aag gtg ccc agg tgc ccc gac ctc aac ctc gat ctc tgc atc agc ccg ccg tgc caa cag aag gaa gac gag gag ctg gac ctc aag ccc gcc gtc gtc gtc aag cgg gag gtg ctg cag gcc ggc cat ggc ggc agc ctc tgc ttc ggc tgc agc ctg ggc atc caa aaa gga gcc ccc ggg tgc agc tgc agc agc agc aac agc cac cac cgc ttc ttg ggg ctc cgg tcc ggc atg ctc gac ttc aga ggc ctc gag atg aag tga

SEQ ID NO: 52 atg ggg agg tcg ccg tgc tgc gag aag gcg cac acc aac aag ggc gcg tgg acc aag gag gag gac gac cgc ctc gtg gcg tac atc aag gcg cac ggc gag ggt tgc tgg cgc tcg ctg ccc aag gcc gcc ggc ctc ctg cgc tgc ggc aag agc tgc cgc ctc cgg tgg atc aac tac ctc cgc ccc gac ctc aag cgc ggc aac ttc acg gaa gag gag gac gag ctc atc atc aag ctc cac agc ctc ctc ggc aac aaa tgg tcc ctg atc gct gga agg ctg ccg gga agg acg gac aac gag atc aag aac tac tgg aac acg cac atc cgg agg aag ctg ctg agc agg ggg atc gac ccg gtg aca cac cgc ccc atc aac gag cac acg tcc aac ata acc atc tcg ttc gag gcg gcg gcg gcc gcg cgt gac cgt gag gag aat aag ggc gcc gtg ttc cgg ctg gag gag cac aac aag gcg acg gcg gcg gcg gcc gcc gcg atc ggc cgc gat cat cat cag aac cac cac ccc gcc ggc gac tgg ggc cag ggg aag ccg ctc aag tgc ccc gac ctc aac ctg gac ctc tgc atc agc ccg ccg gcg gcg ccg tgc cag gag gag aag gcc atg gtg acg atg aag ccc gtg aag cgg gag gcc ggg ctc tgc ttc agc tgc agc ctg ggc ctc ccc aag agc -continued gcc gac tgc aag tgc agc aac ttc ctc gga ctc agg acc gcc atg ctc gac ttc aga agc ctc gag atg aaa tga

SEQ ID NO: 53 atg aca gag aat ctc cac tcc agg aaa atg gta cag cca aag aag ttt cgt gga gtc cgg cag cgc cac tgg ggc tcc tgg gtc tct gag atc agg cat ccc ctc ctt aag agg agg gtc tgg ctg ggt acc ttt gag acg gct gag gag gca gcg aga gca tat gat gag gct gct gtg ctg atg agc gga cgc aac gcc aag acc aac ttc cca atc caa aga agc agc aca ggg gag cct acc cca gct gcg gga agg gac gcc cgc agc aac ttc agc agc ggc tcc tct acc acc aac ctg tcc cag att ctc agt gcg aag ctc cgc aaa tgc tgc aag gcg cca tca ccg tcc ctg acc tgt ctc cgc ctt gac cct gag aag tcc cac att ggt gtt tgg cag aag cgt gca gga gcc cgt gct gac tcc aac tgg gtc atg aca gtg gag ctc aac aaa gat gca gca tcc act gat gct gca tca cag tcc aca tca gca aca act gct cca cca gcc acg ccg atg gat gag gag gag agg atc gca ctg caa atg atc gaa gag ttg ctg agc agc agc agc cca gct tca ccc tca aac gga gat gac caa ggt cgc ttc atc atc tga

SEQ ID NO: 54 atg ggg cgg tcg ccg tgc tgc gag aag gcg cac acc aac agg ggc gcg tgg acc aag gag gag gac gag cgg ctg gtg gcc tac gtc cgc gcg cac ggc gaa ggg tgc tgg cgc tcg ctg ccc agg gcg gcg ggc ctg ctg cgc tgc ggc aag agc tgc cgc ctg cgc tgg atc aac tac ctc cgc ccg gac ctc aag cga ggc aac ttc acc gcc gac gag gac gac ctc atc gtc aag ctg cac agc ctc ctc ggg aac aag tgg tcg ctc atc gcc gcg cgg ctc ccg ggg cgg acg gac aac gag atc aag aac tac tgg aac acg cac atc cgg cgc aag ctg ctg ggc agc ggc atc gac ccc gtc acg cac cgc cgc gtc gcg ggg ggc gcc gcg acc acc atc tcg ttc cag ccc agc ccc aac tcc gcc gcc gcc gcc gcc gcc gca gaa aca gca gcg cag gcg ccg atc aag gcc gag gag acg gcg gcc gtc aag gcg ccc agg tgc ccc gac ctc aac ctg gac ctc tgc atc agc ccg ccg tgc cag cat gag gac gac ggc gag gag gag gac gag gag ctg gac ctc aag ccc gcc ttc gtc aag cgg gag gcg ctg cag gcc ggc cac ggc cac ggc cac ggc ctc tgc ctc ggc tgc ggc ctg ggc gga cag aag gga gcg gcc ggg tgc agc tgc agc aac ggc cac cac ttc ctg ggg ctc agg acc agc gtg ctc gac ttc aga ggc ctg gag atg aag tga

SEQ ID NO: 55 atg ggg agg tcg ccg tgc tgc gag aag gcg cac acc aac aag ggc gcg tgg acc aag gag gag gac gag cgc ctg gtc gcg cac atc agg gcg cac ggc gag ggg tgc tgg cgc tcg ctg ccc aag gcc gcc ggc ctc ctg cgc tgc ggc aag agc tgc cgc ctc cgc tgg atc aac tac ctc cgc ccc gac ctc aag cgc ggc aac ttc acg gag gaa gag gac gag ctc atc gtc aag ctg cac agc gtc ctc ggc aac aag tgg tcc ctg atc gcc gga agg ctg -continued ccc ggc agg acg gac aac gag atc aag aac tac tgg aac acg cac atc cgg agg aag ctg ctg agc agg ggg atc gac ccg gtg acg cac cgc ccg gtc acg gag cac cac gcg tcc aac atc acc ata tcg ttc gag acg gaa gtg gcc gcc gct gcc cgt gat gat aag aag ggc gcc gtc ttc cgg ttg gag gac gag gag gag gag gag cgc aac aag gcg acg atg gtc gtc ggc cgc gac cgg cag agc cag agc cac agc cac agc cac ccc gcc ggc gag tgg ggc cag ggg aag agg ccg ctc aag tgc ccc gac ctc aac ctg gac ctc tgc atc agc ccg ccg tgc cag gag gag gag gag atg gag gag gct gcg atg aga gtg aga ccg gcg gtg aag cgg gag gcc ggg ctc tgc ttc ggc tgc agc ctg ggg ctc ccc agg acc gcg gac tgc aag tgc agc agc agc agc ttc ctc ggg ctc agg acc gcc atg ctc gac ttc aga agc ctc gag atg aaa tga

SEQ ID NO: 56 atg ggg cga tcg ccg tgc tgc gag aag gcg cac acg aac aag ggc gcc tgg acc aag gag gag gac gac cgc ctc gtt gcc tac atc cgg gcg cac ggc gag ggg tgc tgg cgc tcc ctc ccc aag gcc gcg ggc ctg ctg cgc tgc ggc aag agc tgc cgc ctg cgc tgg atc aac tac ctc cgc ccg gac ctc aag cgc ggc aac ttc acc gcc gac gag gac gac ctc atc gtc aag ctc cac agc ctc ctc ggc aac aag tgg tcg ctc atc gcc gcg cgc ctc ccc ggc cgc acc gac aac gag atc aag aac tac tgg aac acg cac atc aag cgc aag ctc ctc agc cgc ggc atc gac ccc gtc aca cac cgc ccc atc gcc gac gca gcc aga aac gtc acc atc tcc ttc cag ccc gac gcg ccg tcg cag cag cag ctc agc gac gac gcc gag gcg ccg ccg ccg ccg ccg ccg cag cag cag cag cag ctc aag ccg ccg ccc agg tgc ccc gac ctc aat ctc gac ctc tgc atc agc ccg ccc tgc cac aag gaa gaa gag gac cag gag ctc gtc aag ccc gcc gcc gtc aag cgc gag atg ctg cag gcc ggc cac ggc act cta gga ctc tgc ttc ggc tgc agc ctg ggc ctc cag aag ggc gcc gcc ggg tgc acc tgc agc agc aac agc cac ttc ctg ggg ctc agg gtc ggc atg ctc ctc gac ttc aga ggc ctc gag atg aag tga

TABLE 2

| Examples of Vascular Xylem Tissue Targeting Promoters for Gene Combination | | | | | | | |
|---|---|---|---|---|---|---|---|
| Referenced expression database[1] | Expression[2] | Gene name | SEQ ID NO: | Sequence Feature and Location | Protein family (Pfam) | Species | Gene ID |
| Arabidopsis root transcripts | 14279.9 | AtCTL2 | 21 | promoter (1) . . . (1000); 5'UTR (1001) . . . (1014) | PF00182 | Arabidopsis | AT3G16920 |
| Arabidopsis root transcripts | 11468.5 | AtLAC4 | 22 | promoter (1) . . . (1000); 5'UTR (1001) . . . (1296) | PF00394 | Arabidopsis | AT2G38080 |
| Arabidopsis root transcripts | 9693.64 | AtCesA4 | 23 | promoter (1) . . . (1000) | PF03552 | Arabidopsis | AT5G44030 |

TABLE 2-continued

Examples of Vascular Xylem Tissue Targeting Promoters for Gene Combination

| Referenced expression database[1] | Expression[2] | Gene name | SEQ ID NO: | Sequence Feature and Location | Protein family (Pfam) | Species | Gene ID |
|---|---|---|---|---|---|---|---|
| Arabidopsis root transcripts | 9591.84 | AtCesA8 | 24 | promoter (1) . . . (1000); 5'UTR (1001) . . . (1167) | PF03552 | Arabidopsis | AT4G18780 |
| Arabidopsis root transcripts | 8423.1 | AtFLA11 | 25 | promoter (1) . . . (1000); 5'UTR (1001) . . . (1019) | PF02469 | Arabidopsis | AT5G03170 |
| Arabidopsis root transcripts | 6779.81 | AtCesA7 | 26 | promoter (1) . . . (1000); 5'UTR (1001) . . . (1093) | PF03552 | Arabidopsis | AT5G17420 |
| Arabidopsis root transcripts | 6471.5 | AtIRX9 | 27 | promoter (1) . . . (1000); 5'UTR (1001) . . . (1146) | PF03360 | Arabidopsis | AT2G37090 |
| Rice mas transcripts | 15061.86 | OsFLA9 | 28 | promoter (1) . . . (948); 5'UTR (949) . . . (1000) | PF02469 | Rice | LOC_Os05g07060/ Os05g0163300 |
| Rice mas transcripts | 10893.78 | OsCTL1 | 29 | promoter (1) . . . (677); 5'UTR (678) . . . (1000) | PF00182 | Rice | LOC_Os09g32080/ Os09g0494200 |
| Rice mas transcripts | 8754.03 | OsCesA4 | 30 | promoter (1) . . . (1000); 5'UTR (1001) . . . (1141) | PF03552 | Rice | LOC_Os01g54620/ Os01g0750300 |
| Rice mas transcripts | 7977.04 | OcCesA7 | 31 | promoter (1) . . . (1000) | PF03552 | Rice | LOC_Os10g32980/ Os10g0467800 |
| Rice mas transcripts | 7972.41 | OsLac10 | 32 | promoter (1) . . . (845); 5'UTR (895) . . . (1000) | PF00394 | Rice | LOC_Os03g16610/ Os03g0273200 |
| Rice mas transcripts | 7099.66 | OsGT43J | 33 | promoter (1) . . . (1000); 5'UTR (1001) . . . (1247) | PF03360 | Rice | LOC_Os06g47340/ Os06g0687900 |
| Maize leaf gradient transcripts | 446.24 | ZmCesA10 | 34 | promoter (1) . . . (977); 5'UTR (978) . . . (1000) | PF03552 | Maize | GRMZM2G445905 |
| Maize leaf gradient transcripts | 123.92 | ZmCesA12 | 35 | promoter (1) . . . (909); 5'UTR (910) . . . (1000) | PF03552 | Maize | GRMZM2G142898 |
| Maize leaf gradient transcripts | 44.89 | ZmCesA11 | 36 | promoter (1) . . . (926); 5'UTR (927) . . . (1000) | PF03552 | Maize | GRMZM2G037413 |

[1]The Bio-Analytic Resource for Plant Biology, available online at http://bar.utoronto.ca/ and described in Toufighi et al, "The Botany Array Resource: e-Northerns, Expression Angling, and Promoter Analyses," *The Plant Journal* 43: 153-63 (2005), each of which is hereby incorporated by reference in its entirety.
[2]Relative gene expression value in vascular tissues or xylem-related organ.

The sequences referenced in Table 2 are set forth below.

SEQ ID NO: 21

```
acgtacctcg tgtccaccgg tgactctatc cccggcgtta gaagtgatga tagtctcgtt

cccaagggaa atcagccttc gaattggaat tgatccctcc ggacattttg tgccgttcgt

gtgccagact tgccatccat ataatgcatc ttcttctttt tttcccgcag atggcatgtc

cgttggtctt tcctgtatca tttatttaca aaagaaaaat aaattaaaca tttattaagt

tccccccgta aaaaaaaaat atatatatat atatatatat aacacatgca tcataattgg

tatgtccgta ggtgtttcct tatcataact gaaccattgg taaactatcg gttccgttaa

agcataagac tagaaaaggc tcggtgcgac tcgctaccac gtttctaaag attttattta
```

-continued gcaaattaac cccaatatat attttgctat gagggtctaa acaaactggt atatgagcca tttacttacc acttattagt tccaagtatt tattttttgg gttaattaat gtttaaatta ttggttgaca aaaaatataa aaataatggt taagttattg aaatgacttg agcaatctga tgcaactgcg gataacatga actcattcga agtgacgtcc caaatatttg attctttgtt tttattcctt tttgtcaagg tcaagattgg ccaaacattt tcaatatcta aatatattga cattcatagc ctggaaaaga aaaaatatat ggttaaatta gttccaaagt attctagcag caacaaaacc gctccaataa acgatttcca atttctatct caaacttgtt tcccaatcat tagttataat ccgtccccta aaccaaaaaa aaatctaatt gtaaaggtgt tgcaatagat taaccatttt tattttattt tggtaaaata gattaaccat tttgttagaa aaatgaagtt taaaacattt acagttctac gtgtacatgc ttcgaccaat atgcttcgac caat

SEQ ID NO: 22 atacatgtca tgattttata attatgtata tataaatact aattgatgta tgaagtacgt agataatgtt acgatctatt aatctattta cattaacttt taattagtgt tgagtaggga aaattaacat ataaaccttt agcagttggt tgtattatta aaaataattt gaacttaaaa tccaccttcg aaaagataaa tcaaacaagt ataaaaaatg ctataaatcc agaatattta cctaaggttt ttattcttct acttaataat gtaagataaa accggcacaa tacttgttac gtatgcatgg taggtaccgc aattgtgtaa gcaaatcggc acaatactaa ggttacatat actaactaaa taaaacaatc tgatttcagt gacaccgtat atctaacctt tattcaaatc caagggaaca tgacttgact tcttctgttg gaactaactc gatccctcaa ccatctccag ggatagaaga gttagtaaaa tcaaacttga agtgaggaag taagcagttt aacgactcca tatgactaca gttatataca aagttgggca caaagtacaa gtactaaata ctcaaagtca gataataatt ttaataagta caaactatat atatgcagta caattattga gtatatataa acgagactgg tgatttgggg cattgtccac cagggtgtta tatcccaatt gaaatttgaa aatttaagtg tgtgagtgtt acgacaaaaa aaagtgtgtg aattgtaggc gcggtgaaaa ggtaaattaa gattggaact agaaaaatag ttgaatatcc tttactaaaa gttgtcaatt ccggttttag taaaaaaaaa ttttaaaata gaaattttat ccaaaagact tcaaacacac atattcgcat atataacata agatatcatt ttttgtaaac agttaaaaag aaaaacacat gttttttttt ttaatttaga aaaaaacatg ttattataca aaacagagtt ttgcccactt ttaatatgtt atgaaaagaa aaatgatttt cttgggtttg gtcagagaga ttggttgtgg taagaatggg aatcttaatt acaaagaatt ggattttggg tcgacctacc acctaaaacg acgtcgcctc catctctggt ttccaaatct ctttctcctc tccctttata agcttgcgtt ggccagtcgc tcatctcgaa aacagagaga aaaagactaa aaacacagtt taagaagaag gagagataga gagagaagag aaagatagag agggag

SEQ ID NO: 23 aactagaaca cttcagataa attttgtcgt tctgttgact tcatttattc tctaaacaca aagaactata gaccataatc gaaataaaaa ccctaaaaac caaatttatc tatttaaaac aaacattagc tatttgagtt tcttttaggt aagttattta aggttttgga gactttaaga tgttttcagc atttatggtt gtgtcattaa tttgtttagt ttagtaaaga aagaaaagat agtaattaaa gagttggttg tgaaatcata tttaaaacat taataggtat ttatgtctaa tttggggaca aaatagtgga attctttatc atatctagct agttcttatc gagtttgaac tcgggttatg attatgttac atgcattggt ccatataaat ctatgagcaa tcaatataat -continued tcgagcattt tggtataaca taatgagcca agtataacaa aagtatcaaa cctatgcagg ggagaagatg atgaaaagaa gagtgtgagc caatacaaag cagatttgag gacatggctt acaagtcttg ggtacagagt ttggggagtg atgggtgcac aatggaacag cttctctggt tgtccagttc ccaagagaac cttcaagctc cctaactcca tctactatgt cgcctgatta aatcttattt actaacaaaa caataagatc agagtttcat tctgattctt gagtcttttt tttctctctc cctcttttca tttctggttt atataaccaa ttcaaatgct tatgatccat gcatgaacca tgatcatctt tgtgtttttt tttccttctg tattaccatt ttgggccttt gtgaaattga ttttgggctt ttgttatata atctcctctt tctctttctc tacctgattg gattcaagaa catagccaga tttggtaaag tttataagat acaaaatatt aagtaagact aaagtagaaa tacataataa cttgaaagct actctaagtt

SEQ ID NO: 24 tacatcagtt tcatcatcta tcttgtttct tatagaagct cacaatcttc ttcctggtcg agtttagaaa tgtcagagag agttgtttcc acagagacgt agaaacccat aactttagta ttcttcaacc cttacaactt atctgagcaa aatcagaagg tcgaatttga tggatggttt tgctgtattt ggtcaacggt tttatttgag acagtagacc agaggaaact cagatgtgat gatgcaaaga ctgaattggt taagagtgta gattgatttg ttctaacatt gcaaatgtag agtagaatta tgcaaaaaac gttaatgaac agagaagtga ttaagcagaa acaaaattag agaagtgata ttatatctca aaatttattt ttggtacagc taaagctcaa attgttatag agattagaga tattaaacca aatgacgagt gttttcttta gtagtaaacg gtgaaaattc tcttctgaca aagacaatta aaattttagg tttaagactt taatatttgt cacaaattgt catttaccta aataaaaaaa aaactaaata tttttttttag atacatatgt gtcttataat tttaactata aattttaatt ttatgtctta aataattgtt tacactataa atttaaatat tttaatgcta aaattaattt gattcaaaaa agtgatttta attcttattt ttcttataga aagttggtga ttgaaaagat ttacttaaaa attataacaa cttcaatggt gaataacccg acccgaataa accggatata acaacttcaa tgttagcttg atatagaaag tacggtgacg cttaggaggc aagcaagcta gtatctgccg ctggttagag acaaagaaca tgtgtcactc ctctcaacta aaactttcct tcactttccc gcaaaatcat ttcaaaaaag ctccaaattt agcttaccca tcagctttct cagaaaacca gtgaaagaaa cttctcaact tccgattttt cacaatccac caaacttttt ttaataactt tttttcctct tattacaaaa cctccactct catggcttct caaacttgtt atccatccaa atctcaatcc ctaattaggg ttcatttctc tgtttctcca aacaggggaa ttcgaag

SEQ ID NO: 25 tcttcttgca tcaatgatat caacaacaat gggtaataaa gaagctactt cgaaattata tattttttcg tattctatat tgatcatcag tcttaagtgg tttggtttgt tgcagtgaag aagaactatg tatggatcta cgccaccgtt cagttcggtt ttgtggtcct tttcgctcag cttttctaca gagttgtaag atttgatgta atgtcacaga gaaaccttac tttgttgtca cagagaaacc ttactttgtt gaagagtttt tgattcctca cactctctct cattaacttg tgtgtaggtg aagcagccgg taatgtgcat tgtcttagcc actatgatcg gatttggact caccatgacc ggcacaacag ctattaacga gtatttgaaa tggaggagaa gcaattccca cctgccagaa gagccagcaa gtactcaggt ggtttgacag cagcgtagat cttttgagtg aagctagagt ccctaaaggg ttggatcggt tttcaattaa ccggtcggga ttcggttttc ggtttagctt taatcgactt gtctaggttg agatcagatt tggttttcaa tacttccaag -continued

```
tcttttttttt tttgccaact aaaatataag gaatgatgat aggcacacac atgacacata

aaatcataat gaacagtagt atgattagca atccatattt cttggataac acttcttcac

agctttttttg acaggtcact ataacacctt tttcagttca tttttcattt tcaatcctca

cccacccaaa ctctcccttc aaagcaatgt ctctcctctc tctttctcaa ttcaaacaaa

ctttattaaa cctaaaagaa acatttccaa tctctaatga cttagttgat agaatctcat

ttagttacct agtaataatc ttcacactag taagagaatc ctactcttca ccaaactaca

tctctctcta tataacaaac cccaaaacat ctcaacatac acacacaaca actacaaca
```

SEQ ID NO: 26

```
tgcgaacagt ttgattctgt ttttcttttt cctttttttg ggtaattttc ttataacttt

tttcatagtt tcgattattt ggataaaatt ttcagattga ggatcatttt atttatttat

tagtgtagtc taatttagtt gtataactat aaaattgttg tttgtttccg aatcataagt

tttttttttt tttggttttg tattgatagg tgcaagagac tcaaaattct ggtttcgatg

ttaacagaat tcaagtagct gcccacttga ttcgatttgt tttgtatttg gaaacaacca

tggctggtca aggcccagcc cgttgtgctt ctgaacctgc ctagtcccat ggactagatc

tttatccgca gactccaaaa gaaaaaggat tggcgcagag gaattgtcat ggaaacagaa

tgaacaagaa agggtgaaga agatcaaagg catatatgat ctttacattc tctttagctt

atgtatgcag aaaattcacc taattaagga cagggaacgt aacttggctt gcactcctct

caccaaacct tacccccctaa ctaattttaa ttcaaaatta ctagtatttt ggccgatcac

tttatataat aagataccag atttattata tttacgaatt atcagcatgc atatactgta

tatagttttt tttttgttaa agggtaaaat aataggatcc ttttgaataa aatgaacata

tataattagt ataatgaaaa cagaaggaaa tgagattagg acagtaagta aaatgagaga

gacctgcaaa ggataaaaaa gagaagctta aggaaaccgc gacgatgaaa gaaagacatg

tcatcagctg atggatgtga gtgatgagtt tgttgcagtt gtgtagaaat ttttactaaa

acagttgttt ttacaaaaaa gaaataatat aaaacgaaag cttagcttga aggcaatgga

gactctacaa caaactatgt accatacaga gagagaaact aaaagctttt cacacataaa

aaccaaactt attcgtctct cattgatcac cgttttgttc tctcaagatc gctgctaatc

tccggccgtc cct
```

SEQ ID NO: 27

```
tctctaattg tcaagtatct tagtctagag ttaattactt aaatactaaa aggctgtcga

caaaatcaag cttgaatctc cttgtggtat cttcaactct tcgttgtctg cttacgagtg

gtttactcag taattatcta taatatgtta tttttttttcc ctcatctttt agttgttgtt

tcattacatt gaaaagcttg taatgtcttt atatggtata tatggatctt atgagtgagg

caagatccat gatgtttttg atcttagaat gtatatgatg atcttagaat gtatttgacc

gcccacaaat tattgttcat tgggattata tctctagtcc aactccaagc aatcgaaatg

ggtcctgctt ttaagaacaa cagtatatgt ttaagaataa taactttata tattctcgat

tttaagatct tttgacaaaa cctccttttc gttaggagcg tactaatttc caagtgtttg

attagtgggg tctccgtaaa tttatttaga gtttctatct atttattaat agctcaatta

attaatctat actgtatcta aacatcaatt tatatattta ctcttgagac caaaactgtc

aatttataac attggatagt ttcttaattc ttattatata tttttcaaac acttttcaag

actaatctcc acattaggta ctctctctag agataaaaat atttatcaaa aacattttta

tttatttatt aagtagtaga taaactactg tggcaaaatc gtaaatgtct aaatgctgat
```

-continued gaattttttt tgctgctcca atctggttta gtgctccata tacatccacg gccaaaatga atctatggcg gcattaagat tcattagtaa gcaacgatta tattaatata attgttttta gcaatgattt tccgtaattt cccaaatatg tttcagttaa tgtgttccaa tcccaacaac tggttgttgc aaaagaccac caacgcaagc aatcatcaaa catcaaaata atcttacctt agcgaacaaa caataactac acaattctca taaagctctt atatatcact aacttcacac attttgtttt ccacaaaaat aaaaacggaa ctcactcaag aaaccttctt ccttgaagag agggtt

SEQ ID NO: 28 tacagggtct caagccagga tgacctcctt tgaaacgtac gagtggtaaa acagtacgaa gaacatcaaa ttttcatgag aattttcata ggagacaggt taagagagaa cttcaagaga ttggacctta tgttaacttc ttctagagat tggaccttat gttaactttc ttctataaaa tattagtgaa gtgaggaaac ttctaaaaca attatatgga gtgatgaaaa aaattatttg gtcagacggt aactatgagt actccataat ccgtataaga taataacatg gtaattctat taggcgttcg ccaacgaagc cccaagcagc cacccaaggt agctaggcgg tgcctttgtc cgtgtatcaa aaatctccat gcacgggagc cattccaaat aaaattttga agctccaagt ttttgttccg aaggatcaaa tagaaaaatt atccgtagaa attgaatcct aacaaaaatt ccccacaatt cctctaatta aaacgaggcc gaagcggctt cctgatcgga cggctggaag gccatacatg tcctggcatt aattatcact caccttagat tattacagct cggagctaga aagccctgca agttgcaatt aatggtgagt atgatctgat ctgcagcgaa atgatctatc gatgtcccta gttaagcagt cattgtgtcc cttacccacc taaatccacg agtgtcagag ctaagcgcga tcccgatcct taaaccccaa ccccactctc ttgctgctcc atcaagcaac caaccccaat ccacacacca tacataatta catactacca gctaattaat tactaataat gacttaatat tccatcatct cccagctcag ttatcacttc ttgatcacac cccctaccat tgattaacct cttccatctc actctacacg cctatataat tagcctaatg atctcacttt gcaaagcatc tcattgcact aaactgctca ctgcatttgc

SEQ ID NO: 29 actcgattcc attagattat tcacaaaccc atgtgaaccg tgactgtcag tcaggtgagg aaacagatat tccaaaaatc atattctttc cttttgtatt aaccaaattc acacaaaggt gatatttaaa actgacgaag atgaaaatta agttgacgca cgtaaaatga aaaagctatc ggcatatgat taattaaatt taattattac aaacttgata aatgaatata tttgatattt taaggcaact tctatataaa actttttat atgaagagga ctgctacaaa acgggatccc gttgcaacgg gataaggcat attaactatt ctcttgcatg agtatcacag atatcaggcc ctaagtatca taggtaccag gtaacaggta tcacaggtat cgggtaccat acagctcgta ccacaacagg tatcaggtac tatctcataa aaggtaacgt gataccgttg tctaggtttt ctgttatatg aaacatattg tagtttaaaa aacgtgccaa cgaaaataga gataaaaatc tgaatcttga tgagaaaatc atgcccaaat ttcaccctaa aacagtcaat ttcccgcgaa aaaaagcaaa aaaaaaaaaa ctccagacag ttgttaaaag gggaaaaaaa aagacagaat gctcagccgt cgagacacac acaacggcaa cgtcttacca gctcggagct ctctcgcttg ctgcctcttc tcttcttcct cccgccaccg acaccacctc caccagcagc ttcgccttcg ccgcgtcggc atctgcagtt gccacttcgc tttcttccac tccctcctcc tcctcgctta -continued cctcacactc ctccccccca atttcatccc ccacccacca ccagatcccc caccacctgc cgcattctcc cccccaagat ccagatcgcc ggtcaccccc acgaactcgc tcgagatcca gagagagaga gagaggcagt ttcttggttg attttcgagg

SEQ ID NO: 30 gagttaaatt gatatggttt tgtctgtcaa ggtgccgttt ctatggttgg aggaggaaaa tgaaattagg ggaatagaac agtcgcaatc caaaagctat tgttctctct tctacggtag ttgatagttc gatacgtgtg tttgatgtga gagactgaga ggagtgcacg gtgcacctgc cccgtaagga cgcggaacta cattatcaga ggctaggccg gtactgttat acgcgacgtt cacgaatcac gatgcgtaaa aaagtgaagc atgaaacagt actaggctct ccacgggcca catcatgaaa aaactggtgc gacgccacgc ttaacaattt gtcggtcgta aactcgtaaa gttaaaagcc ccacgacatt gtcaaccaat atctcagcac atgaacttct ctaacgagta caacgaaacc gcatccgcaa aagcgccgtg aaccaaagct cttgccgtgc tgtgccgtgc cggtggccgt gaacatgtgg aacacgaaga actcttgcgc gagatcggag cacctgacct cccacctcgc gtccggcccg tcgccgtcgc agcaagcggg ctgtcaaaaa cgacgccaca gcgcgagcgc tctcgccgat ccggcggacc caccctcctc acctcgcgca ccaaccgccc gttcgctagt ccgatccccc acccctcatc cccccctacgc cttgcaggtt acgcgcctcg ccgcggccaa cgcaaaccaa accaaatccc ccgtcacctt cgcttcgaaa ccccgcaaaa ccccatggaa gaaaacaccg aacacctgcc gcgcgcacgc ctcctcctcc cccgcctctc ctcctctctc ccgttccatg tccgctcaac cttgcttcca ttctttccat ccacccgccg atcgacgcga tgccgacgcc ccaaccccac ccaccgcctg ccagcgccac ccccacctcgc gcctctgcgg ctatggctat atcaccatgc ctccaacctc cggtacgctt agcctctctc tctctccccc tcccattctg cgcattgctc tctgcgcgcg gtcgcgtgct gctgctcgcg gcgccccgga gcgtctcctt tgggggagag gagaggagag gagaggagag gggggtgagc c

SEQ ID NO: 31 ttcaatgcag gatgacgcca agagggagaa accaagcaga ggtggacggt acaacgtgta agtcaccgca aaacgttgca gcttggatag tggccatcga gtggtgtgcc gataccggcg cctgttcttt acagcctcag ctagtgttgt tgtccgaggc aatttttccg acctattgtg ttgctttcct ctctgatagc ttatggtaaa agatacaaag atgttgagga gtttgtacgc cacttaattt tgctcgtaac atacattgac aatcaagagg agccatggca ttgcgatctg cttacacggc atattcttac tggatggtgt acactactta cccttttttaa tgcaagcatc aatccattgc ttttctcact gcacacctga ttcgtactga aaacgtgaaa cataaaaaaa aacaaaaatc tagctgatgt tggctctcgg ggcctcgagt ctagtttgtc ctagatggct aacctgatat gtgttggtca cgctcacgtt tgaaccgaga aagagtgtgt gtgtgtgtgt gtcggcgtgc tgctacacca gagcctccct gaatcgcaat gcgtgttaac gccagcatcg caggatttca tctcacttga caggttcaga tggccttcct cctaccgtct gccatttata cacgcagtga cttaacgctt acacgagccg gatggcccgg atctcccccc tgcaccatct caccagaaaa acggtgaggc gtcaccgcaa cccacccacc aaacacatcc acgtcccttc accgttggcc ttcgattttg cttcagctgc actacgaccc ctccaacaca tttccctcgc -continued gtctcgttgc gatctcacct tacgacgatc tcgttccagc agcagcagca tcggcagcgg
cggcttgctt ccgaagcgag caatgcatgg cgcgcgcggc cgcgtgcgtg cgtgccttgg
cttgcgctct aatcaaaccg ggacgcccca actcacggtt

SEQ ID NO: 32 acaacccctg ttgcaccaaa cttgcttttt taagttttaa ctgaaattag gatagcaaag
agagtacttt aggcttcatg ctacgagctg cctacgacca tagacaggct taatcttgtc
ttatagttgt atcttgttga tcattaggtg cctaactgcc tacataggca taatgcatcc
tttcatctga tctttgtcac tgaccccatg tacagagtcc tataagttgc aatgttctaa
tccttgtttc gtcagtcatt tcgtacacat ggatgaaagt ctggggttta accaccgatg
cgatccaatc ttctcctaca gtcgatgata aggaaatcgt aacaaagaat gtgaattttt
ttgacgctac aaagaatgtg aatgatctga ccagtctatc tttcaccgaa ctgaagcata
tactctgaat gtctaagatc atacttagac tgaactatat actctgaata tctaaagatc
tcatacattc atacttacgc tgcaggttgc aaattctagt cattattaca ctcgagacct
aaattatgat tagtggggtg tactccgata gaacagttta cagttcagaa ctcaaaagct
acgaatgaat tcatgacaaa aggcgacaag tgatacgtat tcgagaataa atgtgtgaac
aaaggccgtc tcaaaaaaaa aaaagaaaaa aaaaaagaga atccctttgc ctgcactcta
aaacccagcc cgacccaact ctttgtacat gaccagcaaa agcaccgtct gctgcgactt
tttttctctt gtgcaatcta ttgtcgggaa aaaagagagg agaattatca tatcatcacc
taataaattg caaccaccag aggtactgtc ctctctatat aactctttct cgggcatttt
gctggcactt gcctgttcta gtatctatag ctagctaact gttactgtac ctcctcccat
atatcatctt catatttttg cagatcgata agcgagaaaa

SEQ ID NO: 33 catactttac cttgttgtat aactgcatgc ataagaatct gagagccatt gctcaattct
tttcaacgaa gatgtgaact gttggaaggc aatgtaaaac gggaagcgct gtatgaaaga
atatgacgca catcgtcttt tgttttttaa gaattgagta tatattcgtt gtggggaaca
gcctgatgat gggccccggg aattaacgct cgagcaacgt tggaccattc tgacatcgcg
tttcctgatt agcacaatgt ttcgttttat ttggaaattg aattgaatgt ttctactgtt
attaattgca gacagtacac caaacgacca aatctatctg caaacaatta accaagacca
actggagaat ttacagatga atcactgtgt tacacctgta aactgtggct cctttgagaa
ttgagttaca acaagagttt ggagatgaac ttgtagttca tctatatcat cttaattaaa
caataatatt tattcaggaa tgcagttcag agactgctta acacacacac acacaaaaaa
aaaacctaaa cctgaggctt gtactggaac aaggtcatta gcaaggtgtc ctctagactc
ccggaccgac actacccttg gaagtcaaac gcagctggca caaacaaacg gagcctcggt
gacgccggta aaccgcacca atcattgtta aaccaaaaaa cgtgaacaac aaaccaaaaa
gaaactaaaa aaccgctaaa aagacgcaaa agagagagaa aaaaaatgaa agaagaaaag
aaacgacgcg gactcgctga cgacccgcgg cccggtccaa cccaaccccc accgcctctc
tcgccgaccc cgtccactcc gccgaattcc cccccaaacc caaacccaac gcgacctcac
ctcacccgca cgacgacggc acgacgcgac gcgttgcccg agctgacggc ttgacgacgc
ctccgtcccc gtccggcacc aacccatccc aacccaacgc tccccttttc cactgaccaa
ttgatagccc aacctcacct ctcctctcct cctcccccct cctctcctcc tcgcctccgc
accagcagtt tcgtgcaccg cacttcaccc acctacctcc cccaacctcc ccatcaaaaa -continued ctagtagtag cagtatccac ccatccacgc acgcgaccga gcgcgatcga ttcgaggcgg cggcggcgga ggaggaggag ggggagtaga tccggcgggc ggcagcg

SEQ ID NO: 34 tttgtgctga gatcggcacc agctttcatt taatacagcc tcagcttacc tgaggcaatt ttcgcacctg ttatgatgtt gttttgctct cagataggtt tatgtagcac aagaaagata tgttggagac gttgacgatt ttgtatgcaa ctaaatttct atcttaatat gccccgattc aacagcaccc agtcgagtca ttgcgttctg gagattcttg cagcgcattt ccatgtttaa gaccttatta tgaaatgtct ggcattcgtg gatccactga gcttctttct gcgaatgtgc catatcgtgg cattggccga agcaaccaaa catttgttgc ccttttgtgt cggtgtttta taaagtacct caatgacgat acagcctcag ggcgcttcct gcttttgcac ttattcggag ttcaggcgag ttaacgaagt tcagacggtt ctgaagagag gccgtgttgt gttttgtcgg cgtggtatcg cgcaagcaca tgtgtctttg gtaagatggt ctggatggct gtcctaccac ctgccattta tacacacact gacttcaccg tcacactggc acgacatgag ctcgccatcc taccagaaac gctgagacgt caccggcaac cacccctctc gctcgctctg gcctctgctc ctgatttgat ttggacagaa aactgggcag ggcagggcgc gctcagcacg tttgcttcgg aaacactgcg agtgtgcgac acatttcccg gcttgatctc gaagcgagcc ctgatgtgtt tgtcatgcac ctgcctgcct tggcttgtgc tctaatcaac gccggactcc ccaactcacg gttggtgcgg gacgccaccc cgccacctta ccgcccgcct cggcgcctca ccagtcacca cacctcgcgc ctgccatcag ctatatcacc gtggccactt ccgtgtccct tcacggatac ctcaccccca cagcccccgg tcgatcgctc ggcaatcggc

SEQ ID NO: 35 aggcggggcc ggaggagggc accagagagg ctgctcagga gagagaaata atagaatatg tggtatagag taaacatgag tgcggatgat tgtggtatag agtaaagaat tttgctgact aggacagaat attcttttta gggtagaaat ttagagtact atgagtgcgg atagcctaag gaccacttta aatttgacac aatattgaaa tttgaatggt tttaacattt gaaggctgaa aaccaaaata ctttgtagct aagtgttgga aacccgactc ggccaataag tcgacagacc gtaaaataag gtcaatctaa actttatgat aaatattctt gtttgatagc aatagcattg caggaccagg acccaaggga agagaagatg ccaaatccca tcgaggctaa agcaaaaacg atccaattta tgagcaaacc cacactgaag tttcaaaatt gttttctgaa aaaaaagtaa ccagcaagtt aaaaaatgag atggcgggaa agccaagtct cggttggtcg aggggttggt tggggcgcag cctgacaagt gacaacggca gcaggatagt agcatcaggc gcaagccagc gcaggcggca gcgcgaggat ttcgcttcac ttagcggcaa cggagacgct gcacccaacc aacacgagct ccccctcacc cgctgcgacg cgcgcgtccc acgagcggaa gccccccgcg ccgacgcgag cgcgggggct cgaccgaccg acccaacgcc tccatctcca ccgcgcgcac caaatcgcac tcccgtccgc cccgccgatc gaacagccac cgctcacctc tcccacccgc caaaaacctc cggcctcctc tcatattcat atagctagcc cctgccacaa ggtagagcgt cgctcacacc tgcgtcgccc tgcctcgcaa tcgcgaatct gtcgagcacc tgaggggtcg gaggccgaga gctagcctag cacgccggcc tccgcgcgcg

SEQ ID NO: 36 atactgaaca ttatgttgca taacatgtag ataaggacac gaaaacatag aaagtttctc agttatattt acccatcaac atgaaataaa aaacaacaaa gatgtcatag tgatgtttgt ttcaacttac caagggtgac catgtcgtat ttataataat attatatatt tatatcgtca -continued

```
atagaatatt agtgttacgg tgatatttta gcacaccgat tttttatatc atactgatgt

ttatcgtttt gtatctatat tttatatttg ttttataata atattagata tttatttcgt

caatagaata ttaatgttat gatgatactt tactatattg attttacata tgatagtgat

gttactcctt ccgtatctat attttatatt agtttttatc tcctggcaac acggtcacaa

cagaagagaa gtttttcaga ccgattccag gatcgatttt ttttttatat ctgggctaag

acatcaggta gagattgttt aacctttgcg gctttccgca ctgacggacc cacccccacc

gcatcaacgg aacctaccaa ccacccccgt gctccgaccc cccatctgcc cgtcttccag

gttacgcccc gcgcggccgc gcgcgcggaa gctgtatcac cccacccgtc gacgtcgtct

tcgcttcgaa accccgcaaa accccgcgga aaaaacccac ctgctgcacg cacgcacccc

ctccctctcc ctccccatgg cgcctcccct cacccaactc tttgcttcca ttctttccat

ccacccgcca atgcgacgcc gacgccgcaa ctccacccac cgcctgccag cgccacctca

ccgcaccgct tccatcaccc cgcgatcatg ggctaccgct atatcaccac gcctccaacc

tccggcacgc ttagcctctc tctcccattc tctcacaccc aacacccagc tatcacaccc

tgatccccga ggccgcgcgt cggggtgagg aggaggggcc
```

Twenty-five independent plasmids suitable for *Agrobacterium*-mediated plant transformation were generated (see Table 3). Nine (9) combinations (construct 001 to construct 009 shown in Table 3) and one vector control were integrated into a dicot binary vector for alfalfa, canola, and other dicot transformation, and sixteen (16) combinations (construct 010 to construct 025 shown in Table 3) and one vector were generated into a monocot binary vector for sorghum, switchgrass, and other monocot transformation.

TABLE 3

List of Constructs

| | | Promoter and 5'UTR | | | Coding sequence | | | |
|---|---|---|---|---|---|---|---|---|
| Construct number | SEQ ID NO: | Gene name | SEQ ID NO: | Gene ID | Gene name | SEQ ID NO: AA | SEQ ID NO: NT | Gene ID |
| 001 | 57 | AtCTL2 | 21 | AT3G16920 | AtMYB32 | 4 | 40 | At4g34990 |
| 002 | 58 | AtLAC4 | 22 | AT2G38080 | AtMYB32 | 4 | 40 | At4g34990 |
| 003 | 59 | AtCesA4 | 23 | AT5G44030 | AtMYB32 | 4 | 40 | At4g34990 |
| 004 | 60 | AtCesA8 | 24 | AT4G18780 | AtMYB32 | 4 | 40 | At4g34990 |
| 005 | 61 | AtFLA11 | 25 | AT5G03170 | AtMYB32 | 4 | 40 | At4g34990 |
| 006 | 62 | AtCesA7 | 26 | AT5G17420 | AtMYB32 | 4 | 40 | At4g34990 |
| 007 | 63 | AtIRX9 | 29 | AT2G37090 | AtMYB32 | 4 | 40 | At4g34990 |
| 008 | 64 | AtCesA4 | 23 | AT5G44030 | AtMYB4 | 5 | 41 | At4g38620 |
| 009 | 65 | AtCesA8 | 24 | AT4G18780 | AtMYB4 | 5 | 41 | At4g38620 |
| 010 | 66 | ZmCesA12 | 35 | GRMZM2G142898 | ZmMYB31 | 19 | 55 | GRMZM2G050305 |
| 011 | 67 | ZmCesA11 | 36 | GRMZM2G037413 | ZmMYB31 | 19 | 55 | GRMZM2G050305 |
| 012 | 68 | OsCesA4 | 30 | LOC_Os01g54620/ Os01g0750300 | ZmMYB31 | 19 | 55 | GRMZM2G050305 |
| 013 | 69 | OcCesA7 | 31 | LOC_Os10g32980/ Os10g0467800 | ZmMYB31 | 19 | 55 | GRMZM2G050305 |
| 014 | 70 | ZmCesA12 | 35 | GRMZM2G142898 | ZmMYB42 | 19 | 55 | GRMZM2G419239 |
| 015 | 71 | ZmCesA11 | 36 | GRMZM2G037413 | ZmMYB42 | 19 | 55 | GRMZM2G419239 |
| 016 | 72 | OsCesA4 | 30 | LOC_Os01g54620/ Os01g0750300 | ZmMYB42 | 19 | 55 | GRMZM2G419239 |
| 017 | 73 | OcCesA7 | 31 | LOC_Os10g32980/ Os10g0467800 | ZmMYB42 | 19 | 55 | GRMZM2G419239 |
| 018 | 74 | ZmCesA12 | 35 | GRMZM2G142898 | PvMYB4 | 20 | 56 | Pavir.J16675 |
| 019 | 75 | ZmCesA11 | 36 | GRMZM2G037413 | PvMYB4 | 20 | 56 | Pavir.J16675 |
| 020 | 76 | OsCesA4 | 30 | LOC_Os01g54620/ Os01g0750300 | PvMYB4 | 20 | 56 | Pavir.J16675 |
| 021 | 77 | OcCesA7 | 31 | LOC_Os10g32980/ Os10g0467800 | PvMYB4 | 20 | 56 | Pavir.J16675 |
| 022 | 78 | ZmCesA12 | 35 | GRMZM2G142898 | OsSHN1 | 7 | 43 | LOC_Os06g40150/ Os06g0604000 |

TABLE 3-continued

List of Constructs

| | Promoter and 5'UTR | | | | Coding sequence | | | |
|---|---|---|---|---|---|---|---|---|
| Construct number | SEQ ID NO: | Gene name | SEQ ID NO: | Gene ID | Gene name | SEQ ID NO: AA | SEQ ID NO: NT | Gene ID |
| 023 | 79 | ZmCesA11 | 36 | GRMZM2G037413 | OsSHN1 | 7 | 43 | LOC_Os06g40150/ Os06g0604000 |
| 024 | 80 | OsCesA4 | 30 | LOC_Os01g54620/ Os01g0750300 | OsSHN1 | 7 | 43 | LOC_Os06g40150/ Os06g0604000 |
| 025 | 81 | OcCesA7 | 31 | LOC_Os10g32980/ Os10g0467800 | OsSHN1 | 7 | 43 | LOC_Os06g40150/ Os06g0604000 |

Figure 26:
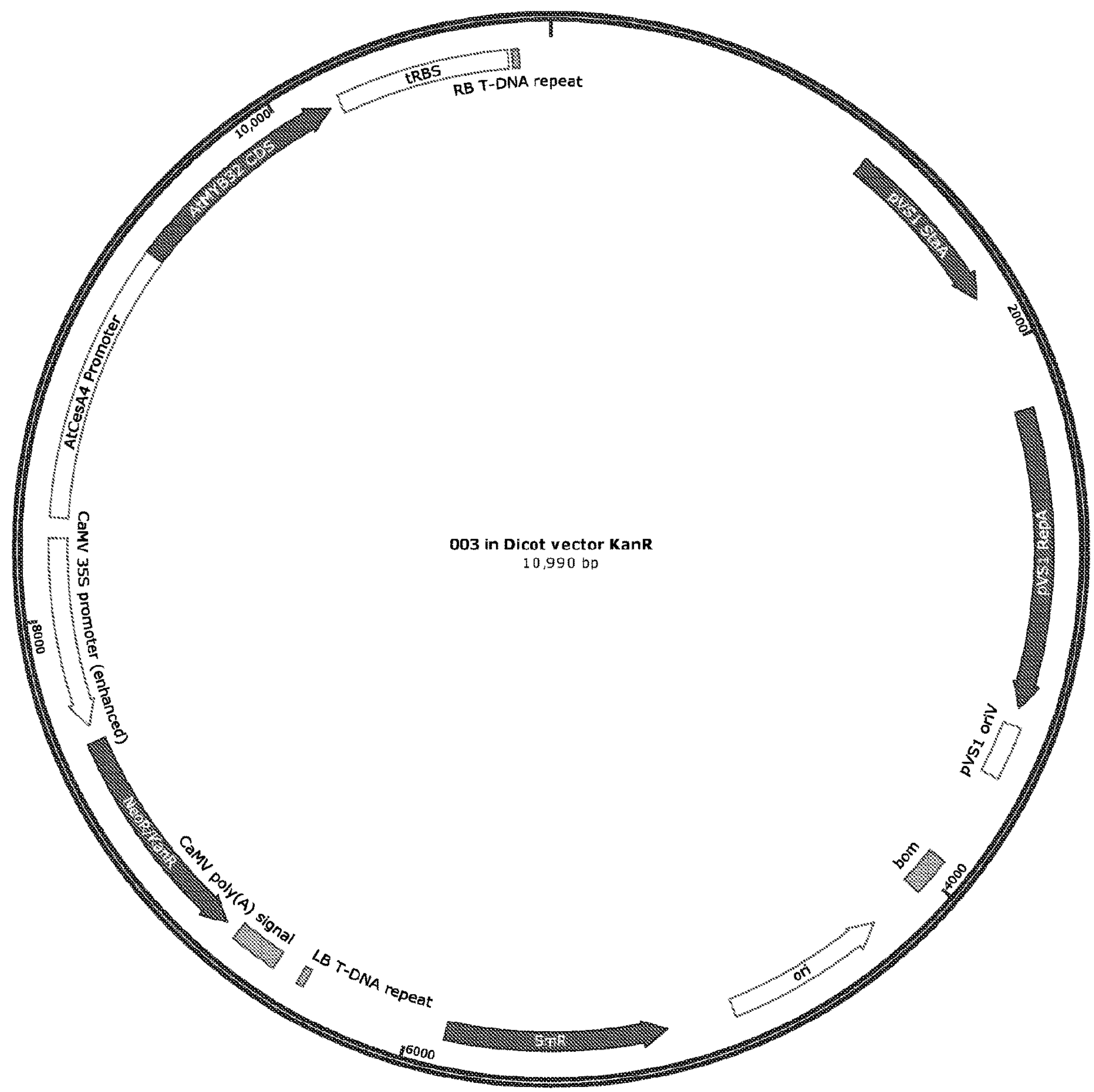
FIG. 26 is a map of an exemplary plasmid operable in dicots, which includes construct No. 003 shown in FIG. 3. Similar dicot-functional plasmids containing construct Nos. 001, 002 and 004-009 were also prepared.

A similar approach was used for preparation of each of the constructs and plasmids. Briefly, approximately 1.0 kb of genome sequences upstream of the respective AtCTL2 (AT3G16920), AtLAC4 (AT2G38080), AtCesA4 (AT5G44030), AtCesA8 (AT4G18780), AtFLA11 (AT5G03170), AtCesA7 (AT5G17420), and AtIRX9 (AT2G37090) start codons were amplified by PCR from *Arabidopsis thaliana* genomic DNA; and the nucleotide sequences from start codon to stop codon of transcription factor AtMYB32 (At4g34990) and AtMYB4 (At4g38620) coding region were amplified by PCR from *Arabidopsis thaliana* cDNA derived from reverse transcription reaction using stem tissue RNA. The two nucleotide sequences (promoter and coding regions) were then combined with RBS terminator region into a commonly used binary vector plasmid (including Kanamycin selection marker) through Gibson cloning (Gibson et al., "Enzymatic Assembly of DNA Molecules up to Several Hundred Kilobases," *Nature Methods* 6(5):343-345 (2009), which is hereby incorporated by reference in its entirety). The result was assembly of constructs 001-009: pAtCTL2-AtMYB32-tRBS (FIG. 1), pAtLAC4-AtMYB32-tRBS (FIG. 2), pAtCesA4-AtMYB32-tRBS (FIG. 3), pAtCesA8-AtMYB32-tRBS (FIG. 4), pAtFLA11-AtMYB32-tRBS (FIG. 5), pAtCesA7-AtMYB32-tRBS (FIG. 6), pAtIRX9-AtMYB32-tRBS (FIG. 7), pAtCesA4-AtMYB4-tRBS (FIG. 8), and pAtCesA8-AtMYB4-tRBS (FIG. 9), respectively. A representative plasmid map for construct 003 is shown in FIG. 26. Similar dicot-functional plasmids containing constructs 001, 002 and 004-009 were also prepared.

Using this same approach, approximately 1.0 kb of genome sequences upstream of the respective ZmCesAl2 (GRMZM2G142898) ZmCesA11 (GRMZM2G037413), OsCesA4 (LOC_Os01g54620), and OcCesA7 (LOC_Os10g32980) start codons were amplified by PCR from corn and rice genomic DNA; and the nucleotide sequences from start codon to stop codon of transcription factors ZmMYB31 (GRMZM2G050305), ZmMYB42 (GRMZM2G419239), PvMYB4 (Pavir.J16675), and OsSHN1 (LOC 0s06g40150) were amplified by PCR from corn, rice, and switchgrass cDNA derived from reverse transcription reaction using stem tissue RNA. The two nucleotide sequences (promoter and coding regions) were then combined with RBS terminator region into a commonly used binary vector plasmid (including Kanamycin selection marker) through Gibson cloning (Gibson et al., "Enzymatic Assembly of DNA Molecules up to Several Hundred Kilobases," *Nature Methods* 6(5):343-345 (2009), which is hereby incorporated by reference in its entirety). The result was assembly of constructs 010-025: pZmCesA12-ZmMYB31-tRBS (FIG. 10), pZmCesA11-ZmMYB31-tRBS (FIG. 11), pOsCesA4-ZmMYB31-tRBS (FIG. 12), pOsCesA7-ZmMYB31-tRBS (FIG. 13), pZmCesA12-ZmMYB42-tRBS (FIG. 14), pZmCesA11-ZmMYB42-tRBS (FIG. 15), pOsCesA4-ZmMYB42-tRBS (FIG. 16), pOsCesA7-ZmMYB42-tRBS (FIG. 17), pZmCesA12-PvMYB4-tRBS (FIG. 18), pZmCesA11-PvMYB4-tRBS (FIG. 19), pOsCesA4-PvMYB4-tRBS (FIG. 20), pOsCesA7-PvMYB4-tRBS (FIG. 21), pZmCesA12-OsSHN1-tRBS (FIG. 22), pZmCesA11-OsSHN1-tRBS (FIG. 23), pOsCesA4-OsSHN1-tRBS (FIG. 24), and pOsCesA7-OsSHN1-tRBS (FIG. 25). A representative plasmid map for construct 018 is shown in FIG. 27. Similar monocot-functional plasmids containing constructs 010-017 and 019-025 were also prepared.

Empty vectors corresponding to those shown in FIGS. 26 and 27, but lacking the constructs 001-025, were used as controls in the following molecular biology analysis and phenotypic analysis described in the following Examples.

Example 2—Introduction of Construct Nos. 003 and 008 into Alfalfa (*Medicago sativa* L. cv Regen S)

The vectors containing construct Nos. 003 and 008, along with the control vector, were used to generate transgenic alfalfa (*Medicago sativa* L. cv Regen 5) using tissue culture and the *Agrobacterium*-mediated transformation method. After selection of primary transgenic plants using kanamycin, multiple events were obtained from the regeneration medium, cloned and propagated vegetatively, and transferred to soil after roots were developed. Introduction of the transgene cassette in the genome of the regenerated plants was confirmed by PCR using genomic DNA extracted from leaves.

Figure 28:
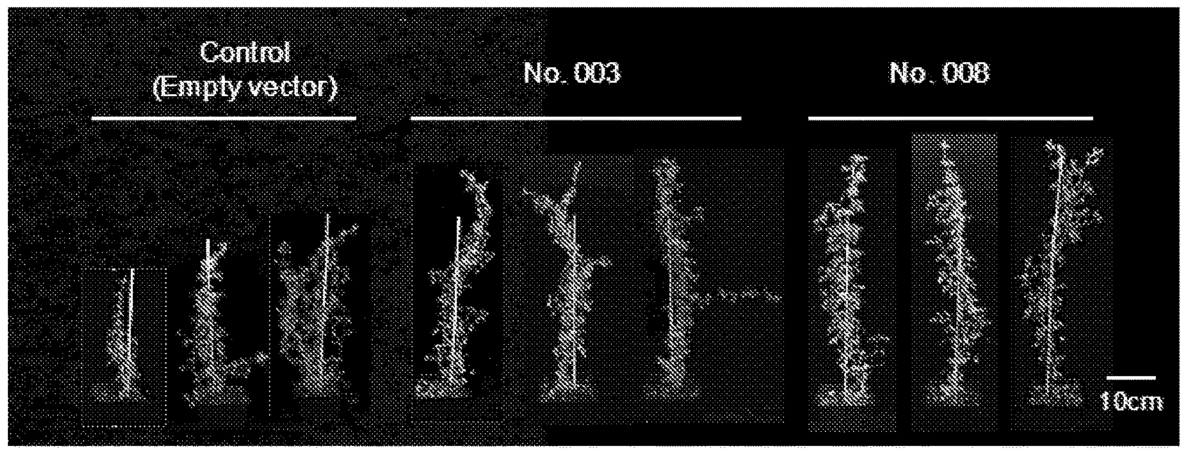
FIG. 28 is an image of representative control (empty vector) and vector-transformed alfalfa (*Medicago sativa* L. cv Regen 5) using construct No. 003 (center) and construct 008 (right). The height difference between the control and transgenic plants is evident.

The experimentally confirmed and propagated plants were grown in individual pots inside growth chambers with 18/6-hour light/dark cycles. Table 4 shows biomass yield and stem internode length at approximately 250 days after propagation along with similar data for the control alfalfa plant with the construct. Engineered alfalfa shows approximately 15-18% longer internodes and 58-63% increased yields compared to the control plant. Representative images of control and inventive vector-transformed alfalfa plants are shown in FIG. 28.

TABLE 4

| Biomass yield and stem length in alfalfa plants | | | | |
|---|---|---|---|---|
| | | | Biomass yield (g) | |
| Construct | Events (n) | Stem length | Fresh weight | Dry weight |
| Control | 8 (17) | 57.56 ± 5.42 | 11.42 ± 2.99 | 2.20 ± 0.51 |
| No. 008 | 8 (21) | 66.47 ± 7.77*** | 17.74 ± 5.80*** | 3.49 ± 1.10*** |
| No. 003 | 7 (16) | 68.37 ± 6.28*** | 17.47 ± 3.95*** | 3.60 ± 0.73*** |

***$p < 0.001$

RNA was extracted from the leaves and stems in the engineered alfalfa lines for quantitative RT-PCR. Results show that the expression level of the target TF was similar to that of the native UbiQ gene. Moreover, transcript levels of the target TF were approximately 50 times higher in stem-enriched tissues compared to leaves, which highlights the tissue-preferential expression pattern enabled by the promoter used to drive expression of the TF. During the course of propagation, engineered alfalfa No. 003 also showed better development not only in stems but also significantly in roots. Table 5 shows regeneration efficiency and root length of alfalfa control and engineered No. 003 at 13 days after initiation of the regeneration step using sectioned internodes.

The construct No. 003 and No. 008 alfalfa lines also showed a reduction of insoluble lignin and ash content (Table 6) and changes in lignin monomeric composition (Table 7), which indicate the inventive constructs also enhance biomass degradability through reduced lignin composition. Moreover, 12% and 16% less insoluble lignin content and 20% and 38% less ash content were observed in the No. 003 and No. 008 alfalfa lines, respectively, compared to control lines.

TABLE 5

| Regeneration efficiency of new roots from sectioned stems | | | | |
|---|---|---|---|---|
| Construct | Prepared stem fragments (n) | Number of rooted stems | Rooting efficiency (%) | Regenerated root length (mm) |
| Control | 59 | 10 | 16.95 | 1.91 ± 2.47 (Max: 19.0) |
| No. 003 | 62 | 24 | 38.71 | 8.25** ± 5.90 (Max: 29.0) |

**$p < 0.01$

TABLE 6

| Ash and insoluble lignin content in cell wall biomass | | | |
|---|---|---|---|
| Construct | Events (n) | Insoluble lignin (%) | Ash (%) |
| Control | 8 (8) | 12.96 ± 1.94 | 0.26 ± 0.09 |
| No. 008 | 11 (11) | 10.93* ± 0.86 | 0.16 ± 0.04 |
| No. 003 | 10 (10) | 11.45* ± 0.57 | 0.21* ± 0.04 |

*$p < 0.05$

TABLE 7

| Lignin monomeric composition in cell wall biomass | | | | |
|---|---|---|---|---|
| Construct (events) | H unit (%) | G unit (%) | S unit (%) | S/G ratio |
| Control (3) | 1.77 ± 0.74 | 63.58 ± 1.24 | 34.65 ± 0.50 | 0.55 ± 0.02 |
| No. 008 (3) | 1.48 ± 0.34 | 48.39 ± 1.47 | 50.13 ± 1.76 | 1.04** ± 0.07 |
| No. 003 (3) | 1.48 ± 0.39 | 51.08 ± 3.28 | 46.99 ± 3.08 | 0.93* ± 0.11 |

**$p < 0.01$,
*$p < 0.05$

Table 8 summarizes the composition of saccharide released from cell wall fraction in the control lines and construct No. 003 and No. 008 lines. After a mild thermo-chemical treatment, glucose, xylose, and arabinose saccharides from constructs No. 003 and No. 008 biomass cell wall fraction were released two to three times more efficiently than the control lines.

TABLE 8

| Composition of saccharide released from cell wall biomass | | | |
|---|---|---|---|
| Construct (events) | Glucose (%) | Xylose (%) | Arabinose (%) |
| Control (11) | 4.71 ± 2.46 | 8.01 ± 3.32 | 1.56 ± 0.18 |
| No. 008 (11) | 14.14** ± 3.79 | 15.78** ± 3.57 | 1.82** ± 0.18 |
| No. 003 (11) | 14.11** ± 4.05 | 15.84** ± 3.48 | 1.98*** ± 0.23 |

***p < 0.001,
**p < 0.01

Example 3—Introduction of Construct No. 004 into Canola (*Brassica napus* L. cv Westar)

The vector containing construct No. 004 and the control vector were used to generate transgenic canola (*Brassica napus* L. cv Westar) using tissue culture and the *Agrobacterium*-mediated transformation method. After selection of primary transgenic plants using kanamycin, multiple events were obtained on the regeneration agar plates and transferred to soil after vegetative tissue and roots were developed and cloned by vegetative propagation.

Figure 29:
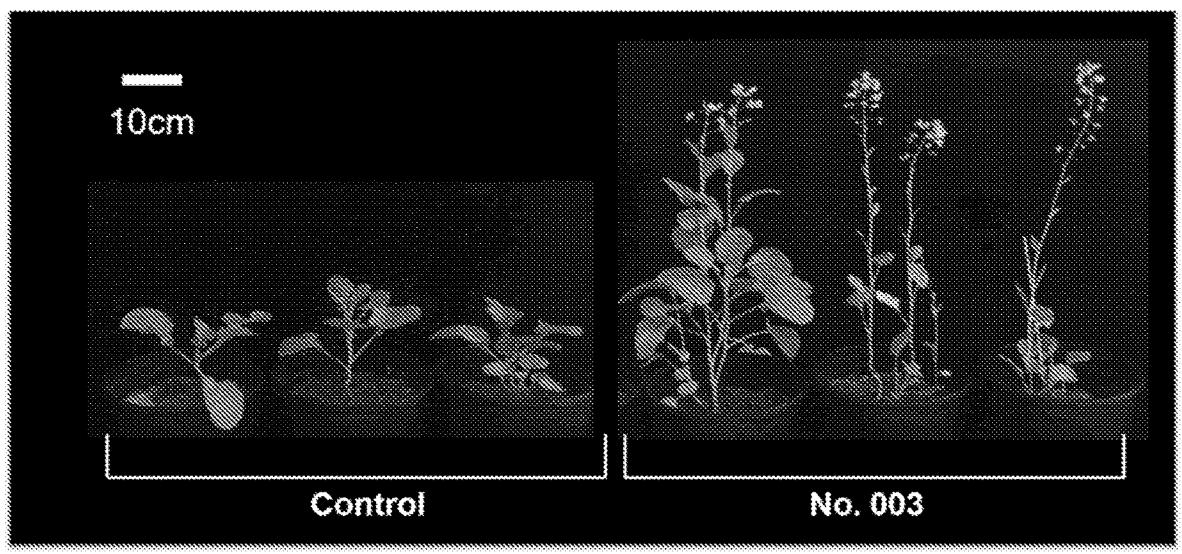
FIG. 29 is an image of representative control (empty vector) and vector-transformed canola (*Brassica napus* L. cv Westar) using construct No. 004. The height difference between the control and transgenic plants is evident.

Table 9 summarizes the measured heights of five (5) transformed control canola lines compared to the four (4) No. 004 lines. The height of the plants transformed with the inventive method is approximately two times taller than the height of the control plants at 130 days after regeneration. These results indicate the inventive constructs enhance stem internode development and may increase biomass yield. Representative images of control and inventive vector-transformed canola plants are shown in FIG. 29.

TABLE 9

| Plant height over 30-day period after regeneration | | | | | |
|---|---|---|---|---|---|
| | | Days after regeneration | | | |
| Construct | Events (n) | 100 | 110 | 120 | 130 |
| Control | 5 (5) | 18.58 ± 1.78 | 19.52 ± 1.82 | 20.38 ± 1.70 | 2.26 ± 1.75 |
| No. 004 | 4 (4) | 18.90 ± 0.70 | 22.35* ± 1.43 | 27.48** ± 3.23 | 46.45*** ± 4.18 |

***p < 0.001,
**p < 0.01,
*p < 0.05

The measured number of branches and flowers for five (5) control lines compared to the four (4) lines engineered with inventive constructs are shown in Table 10. Among the examined lines at day 150 after regeneration, two control lines and three No. 004 lines possessed grain pods, although grain in mature pods was observed in only No. 004 lines as shown in Table 11. All of the results indicate the inventive constructs enhance vegetative growth, root redevelopment as well as reproductive tissue development, and may increase overall yields.

TABLE 10

| Numbers of Branch and Flower at 130 and 140 days after regeneration (DAR) | | | | | |
|---|---|---|---|---|---|
| | | Number of Branch | | Number of Flower | |
| Construct | Events (n) | 130 DAR | 140 DAR | 130 DAR | 140 DAR |
| Control | 5 (5) | 1.00 ± 0.00 | 1.40 ± 0.48 | 0.00 ± 0.00 | 0.00 ± 0.00 |
| No. 004 | 4 (4) | 4.00** ± 1.00 | 4.00* ± 1.00 | 12.00** ± 4.50 | 41.50*** ± 8.75 |

***p < 0.001,
**p < 0.01,
*p < 0.05

TABLE 11

| Number of seed pods and seeds at 150 days after regeneration | | | | |
|---|---|---|---|---|
| Construct | Number of plant with grain pods | Number of grain pods per event | Diameter of pods (cm) | Number of grain per pod |
| Control | 2 (2) | 5.50 ± 1.50 | 1.60 ± 0.10 | 0.00 ± 0.00 |
| No. 004 | 3 (3) | 25.67** ± 15.6 | 3.17** ± 1.38 | 6.67** ± 4.44 |

**p < 0.01

Example 4—Introduction of Construct No. 018 into Sorghum (*Sorghum bicolor* P898012)

The vector containing construct No. 018 and the control vector were used to generate transgenic sorghum (*Sorghum bicolor* P898012) using tissue culture and the *Agrobacterium*-mediated transformation method. After selection of primary transgenic plants using glufosinate, multiple lines were obtained on the regeneration agar plates and transferred to soil after vegetative issue and roots were developed and cloned by vegetative propagation. Introduction of the transgene cassette was confirmed by PCR using genomic DNA extracted from the regenerated plant's leaves as the template.

Figure 30:
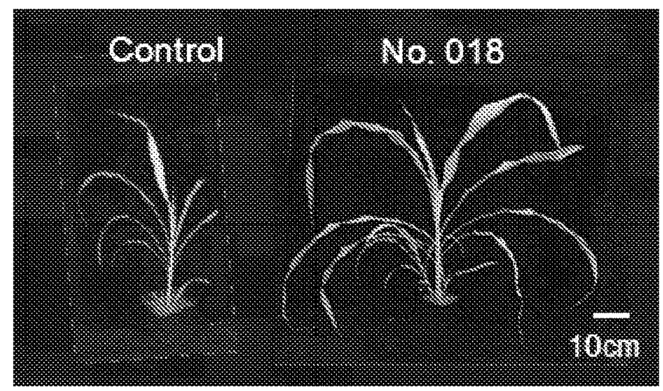
FIG. 30 is an image of representative control (empty vector) and vector-transformed sorghum (*Sorghum bicolor* P898012) using construct No. 018. The height difference between the control and transgenic plant is evident.

The experimentally confirmed and propagated plants were grown in individual pots inside the greenhouse with 18/6-hour light/dark cycles. Table 12 shows biomass yield, number of branches and plant height at approximately 250 days after propagation, along with similar data for sorghum control lines. The engineered sorghum lines showed approximately 80% more dry weight than the control lines, probably due to enhanced branching specific to the engineered lines. The obtained grain number and weight data, summarized in Table 13, indicate improved grain production. Representative images of control and inventive vector-transformed sorghum plants are shown in FIG. 30.

TABLE 12

Biomass yield and related-morphology data from engineered sorghum

| Construct | Events n) | Plant height (cm) | Number of branches | Biomass yield (Dry weight: g) |
|---|---|---|---|---|
| Control | 8 (8) | 128.81 ± 15.98 | 0.00 ± 0.00 | 100.94 ± 25.14 |
| No. 018 | 8 (8) | 134.29 ± 16.41 | 6.57*** ± 1.63 | 183.29*** ± 14.17 |

***p < 0.001

TABLE 13

Grains from engineered sorghum

| Construct | Events (n) | Number of grains | Average grain weight (mg) |
|---|---|---|---|
| Control (8) | 8 (8) | 975 ± 84 | 40 |
| No. 018 (8) | 8 (8) | 4082* ± 526 | 40 |

*p < 0.05

Example 5—Introduction of Construct No. 018 into Switchgrass (*Panicum virgatum* Alamo)

The vector containing construct No. 018 and the empty vector control were used to generate transgenic switchgrass (*Panicum virgatum* Alamo) using tissue culture and the *Agrobacterium*-mediated transformation method. After selection of primary transgenic plants using hygromycin, multiple events were obtained on the regeneration agar plates and transferred to soil after vegetative tissue and roots were developed and cloned by vegetative propagation. Introduction of the transgene cassette was confirmed by PCR using genomic DNA extracted from the regenerated plant's leaves as the template.

The experimentally confirmed and propagated plants were grown in individual pots with 18/6 hours light/dark cycles at a green house facility. RNA was extracted from the engineered switchgrass leaves and stems for quantitative RT-PCR. The analysis confirmed the target TF genes are mainly expressed in the stem rather than the leaves, suggesting that the tissue-preferred expression was enabled by the used cellulose synthase gene promoters.

Figure 31:
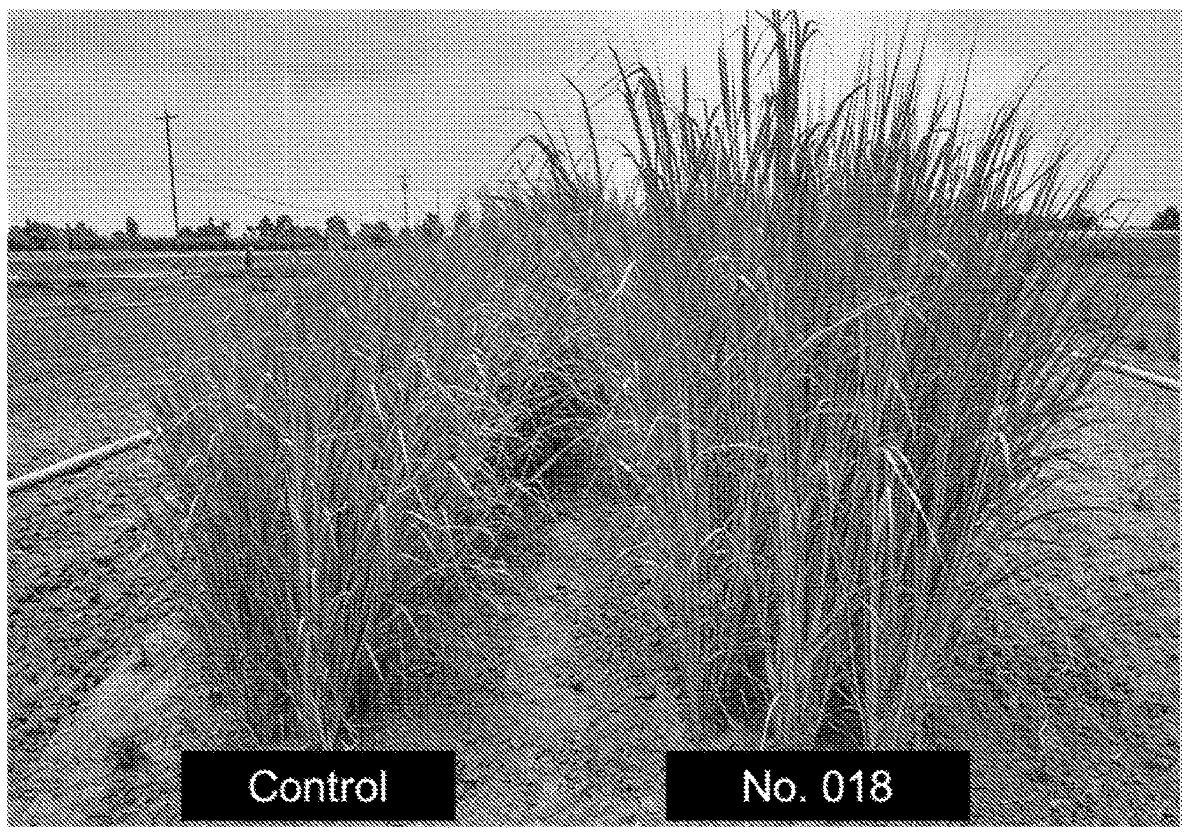
FIG. 31 is an image of representative control (empty vector) and vector-transformed switchgrass (*Panicum virgatum* Alamo) using construct No. 018. The height difference between the control and transgenic plants is evident.

During the course of transgenic plant generation, the engineered switchgrass with the gene cassette tended to show better differentiation and vegetative development. Table 14 compares plant height and number of tillers at 40 days after ratooning. In comparison to the control lines, approximately double the growth and 2-3× times more tillers were observed in the engineered lines. Representative images of control and inventive vector-transformed switchgrass plants are shown in FIG. 31.

TABLE 14

Plant height and number of tillers (40 days after ratooning)

| Construct | Event (n) | Plant height (cm) | Number of tillers |
|---|---|---|---|
| Control | 3 (3) | 83.00 ± 9.42 | 6.00 ± 2.83 |
| No. 010 | 5 (5) | 159.00** ± 18.14 | 22.80** ± 9.66 |
| No. 012 | 8 (8) | 178.00*** ± 10.09 | 32.88*** ± 8.33 |
| No. 013 | 5 (5) | 161.60*** ± 4.63 | 25.20** ± 10.72 |
| No. 020 | 7 (7) | 139.71** ± 23.14 | 24.00** ± 7.80 |
| No. 022 | 8 (8) | 164.13** ± 15.81 | 16.38** ± 4.47 |

***p < 0.001,
**p < 0.01

The switchgrass engineered by MYB TFs showed not only faster growth but also approximately 10-20% less insoluble lignin content (see Table 15: Constructs No. 010, No. 012, No. 013, and No. 020). Plants engineered by ERF TFs, however, maintained a similar amount of insoluble lignin (see Table 15: Construct No. 022), suggesting that the R2R3-MYB subfamily 4 and ERF/AP2 subfamily B-6 contribute to faster growth through distinguished mechanisms.

TABLE 15

Insoluble lignin content in upper and lower stem biomass

| Construct | Event (n) | Insoluble lignin content (%) | |
|---|---|---|---|
| | | Upper stem biomass | Lower stem biomass |
| WT | 6 | 17.46 ± 0.59 | 21.13 ± 0.46 |
| Control | 3 (11) | 17.06 ± 0.41 | 20.00 ± 0.90 |
| No. 010 | 5 (5) | 15.92** ± 0.32 | 18.62** ± 0.54 |
| No. 012 | 5 (5) | 15.95** ± 0.92 | 18.33** ± 0.90 |
| No. 013 | 4 (4) | 15.15** ± 0.25 | 17.44** ± 0.34 |
| No. 020 | 4 (4) | 15.51** ± 0.41 | 16.96** ± 0.16 |
| No. 022 | 7 (7) | 17.59 ± 1.47 | 21.18 ± 0.85 |

**p < 0.01

Faster development in the reproductive phase was also observed in the engineered lines. Mature seeds produced after the completion of reproductive development were harvested and quantitatively analyzed (Table 16). Among engineered lines, construct No. 012, No. 013, and No. 018 switchgrass produced large quantities of seeds, approximately 6-7× more seeds than the control lines.

TABLE 16

Number of mature seeds produced

| Construct | Event (n) | Number of seeds produced |
|---|---|---|
| Control | 11 (11) | 165.4 ± 39.9 |
| No. 012 | 12 (12) | 915.3** ± 153.7 |
| No. 013 | 5 (5) | 1012.0** ± 153.2 |
| No. 018 | 7 (7) | 1109.0* ± 451.4 |

**$p < 0.01$,
*$p < 0.05$

Germinating efficiency from the obtained Ti seeds was examined by using a 96 well format system. Two containers that included pre-soaked sponges with 96 well halls were prepared for seed planting and used for the gemination process in dark conditions at 25° C. Time-course observation of the germinated seedlings confirmed that the seeds from construct No. 012 and No. 018 switchgrass enhance not only the gemination rate but also seedling development (seedling length) in comparison to the control lines (Table 17).

TABLE 17

Time course of T1 seedling length (cm)

| | Days after seed planting | | | | | | |
|---|---|---|---|---|---|---|---|
| Construct | 0 | 8 | 10 | 13 | 16 | 20 | 23 |
| Control Container 1 | 0.00 ± 0.00 | 0.19 ± 0.48 | 0.49 ± 0.84 | 1.35 ± 1.14 | 1.42 ± 1.17 | 1.75 ± 1.20 | 3.31 ± 1.78 |
| Control Container 2 | 0.00 ± 0.00 | 0.00 ± 0.00 | 0.29 ± 0.51 | 1.13 ± 1.32 | 1.45 ± 1.37 | 2.06 ± 1.50 | 3.76 ± 2.49 |
| No. 012 Container 1 | 0.00 ± 0.00 | 2.22** ± 1.92 | 3.57** ± 2.36 | 4.40** ± 2.61 | 4.61** ± 2.70 | 4.92** ± 2.56 | 5.48** ± 2.43 |
| No. 012 Container 2 | 0.00 ± 0.00 | 2.22** ± 1.57 | 3.25** ± 1.85 | 4.03** ± 1.34 | 4.19** ± 1.22 | 4.78** ± 0.99 | 5.74** ± 0.96 |
| No. 018 Container 1 | 0.00 ± 0.00 | 1.77** ± 1.72 | 2.20** ± 2.32 | 3.10** ± 2.35 | 3.80** ± 2.52 | 4.77** ± 2.48 | 6.35** ± 2.94 |
| No. 018 Container 2 | 0.00 ± 0.00 | 2.07** ± 1.97 | 2.61** ± 2.59 | 3.37** ± 2.63 | 4.16** ± 2.82 | 5.06** ± 2.67 | 6.50** ± 2.54 |

**$p < 0.01$

Growth and morphology of the engineered lines were also examined in a field environment. Switchgrass plantlets were grown under greenhouse conditions and transplanted to field plots with a total of 1,000 square feet. A total of 30 plantlets was distributed to each plot, and a total of 120 plantlets were planted per construct. Table 18 shows biomass data for constructs No. 012 and No. 018 switchgrass that yielded approximately 35% more than wild-type and control lines.

TABLE 18

Biomass yield (total dry weight) from the field test

| Construct | n per plot | Number of plots | Biomass yield (kg) from one plot |
|---|---|---|---|
| WT | 30 | 4 | 8.82 ± 1.04 |
| Control | 30 | 4 | 8.44 ± 1.09 |
| No. 012 | 30 | 4 | 12.14** ± 1.29 |
| No. 018 | 30 | 4 | 12.96** ± 1.21 |

**$p < 0.01$

Construct No. 012 and No. 018 plants grown in field conditions also showed cell wall characteristics similar to those observed in laboratory-grown plants. As shown in Table 19, the constructs had 10% less insoluble lignin content and higher S/G unit composition ratios in comparison to wild-type switchgrass, suggesting the engineered switchgrass could be useful as potential forage with better digestibility and/or as less recalcitrant feedstock for a cost-effective biorefinery process.

TABLE 19

| Lignin characteristics from the field test. | | | | |
|---|---|---|---|---|
| Construct | Insoluble lignin (%) | G unit (%) | S (%) | S/G ratio |
| WT | 22.74 ± 1.94 | 75.01 ± 0.05 | 24.99 ± 0.47 | 0.33 ± 0.0008 |
| No. 012 | 20.48** ± 1.58 | 69.47** ± 0.70 | 30.53** ± 0.53 | 0.44** ± 0.01 |
| No. 018 | 20.90** ± 0.78 | 65.49** ± 0.53 | 34.51** ± 0.54 | 0.53** ± 0.01 |

**p < 0.01

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A transgenic switchgrass (Panicum virgatum) plant having at least 3% i) increased plant height and number of tillers; and ii) lower insoluble lignin content as compared with a non-transgenic switchgrass plant of the same variety, wherein the transgenic switchgrass plant comprises a transgene that includes a heterologous, plant tissue-specific promoter selected from the group consisting of SEQ ID NO: 35, 30 or 31, operably linked to a polynucleotide encoding a transcription factor polypeptide of SEQ ID NO: 19.

2. The transgenic switchgrass plant according to claim 1, wherein the transgene is stably integrated into the genome of the switchgrass plant.

3. The transgenic switchgrass plant according to claim 1, wherein the transgene is present on a plasmid.

4. The transgenic switchgrass plant according to claim 1, wherein the heterologous, plant tissue-specific promoter is selected from the group consisting of SEQ ID NO: 30 or 31, and wherein the transgenic switchgrass plant further comprises at least 3% increased seed production as compared with a non-transgenic switchgrass plant of the same variety.

5. The transgenic switchgrass plant according to claim 4, wherein the transgene is stably integrated into the genome of the switchgrass plant.

6. The transgenic switchgrass plant according to claim 4, wherein the transgene is present on a plasmid.

7. The transgenic switchgrass plant according to claim 1, wherein the heterologous, plant tissue-specific promoter is SEQ ID NO: 30, and wherein the transgenic switchgrass plant further comprises at least 3% i) increased seed production; ii) increased germination and seedling development; and iii) increased biomass yield, as compared with a non-transgenic switchgrass plant of the same variety.

8. The transgenic switchgrass plant according to claim 7, wherein the transgene is stably integrated into the genome of the switchgrass plant.

9. The transgenic switchgrass plant according to claim 7, wherein the transgene is present on a plasmid.

* * * * *

SEQUENCE LISTING

```
<160> NUMBER OF SEQ ID NOS: 81

<210> SEQ ID NO 1
<211> LENGTH: 189
<212> TYPE: PRT
<213> ORGANISM: Arabidopsis Thaliana
<220> FEATURE:
<221> NAME/KEY: PEPTIDE
<222> LOCATION: (1)..(189)

<400> SEQUENCE: 1

Met Val His Ser Lys Lys Phe Arg Gly Val Arg Gln Arg Gln Trp Gly
1               5                   10                  15

Ser Trp Val Ser Glu Ile Arg His Pro Leu Leu Lys Arg Arg Val Trp
            20                  25                  30

Leu Gly Thr Phe Asp Thr Ala Glu Thr Ala Ala Arg Ala Tyr Asp Gln
        35                  40                  45

Ala Ala Val Leu Met Asn Gly Gln Ser Ala Lys Thr Asn Phe Pro Val
    50                  55                  60

Ile Lys Ser Asn Gly Ser Asn Ser Leu Glu Ile Asn Ser Ala Leu Arg
65                  70                  75                  80

Ser Pro Lys Ser Leu Ser Glu Leu Leu Asn Ala Lys Leu Arg Lys Asn
                85                  90                  95

Cys Lys Asp Gln Thr Pro Tyr Leu Thr Cys Leu Arg Leu Asp Asn Asp
            100                 105                 110

Ser Ser His Ile Gly Val Trp Gln Lys Arg Ala Gly Ser Lys Thr Ser
        115                 120                 125

Pro Asn Trp Val Lys Leu Val Glu Leu Gly Asp Lys Val Asn Ala Arg
    130                 135                 140

Pro Gly Gly Asp Ile Glu Thr Asn Lys Met Lys Val Arg Asn Glu Asp
145                 150                 155                 160

Val Gln Glu Asp Asp Gln Met Ala Met Gln Met Ile Glu Glu Leu Leu
                165                 170                 175

Asn Trp Thr Cys Pro Gly Ser Gly Ser Ile Ala Gln Val
            180                 185


<210> SEQ ID NO 2
<211> LENGTH: 199
<212> TYPE: PRT
<213> ORGANISM: Arabidopsis Thaliana
```

```
<400> SEQUENCE: 2

Met Val Gln Thr Lys Lys Phe Arg Gly Val Arg Gln Arg His Trp Gly
1               5                   10                  15

Ser Trp Val Ala Glu Ile Arg His Pro Leu Leu Lys Arg Arg Ile Trp
            20                  25                  30

Leu Gly Thr Phe Glu Thr Ala Glu Glu Ala Ala Arg Ala Tyr Asp Glu
        35                  40                  45

Ala Ala Val Leu Met Ser Gly Arg Asn Ala Lys Thr Asn Phe Pro Leu
    50                  55                  60

Asn Asn Asn Asn Thr Gly Glu Thr Ser Glu Gly Lys Thr Asp Ile Ser
65                  70                  75                  80

Ala Ser Ser Thr Met Ser Ser Ser Thr Ser Ser Ser Ser Leu Ser Ser
                85                  90                  95

Ile Leu Ser Ala Lys Leu Arg Lys Cys Cys Lys Ser Pro Ser Pro Ser
            100                 105                 110

Leu Thr Cys Leu Arg Leu Asp Thr Ala Ser Ser His Ile Gly Val Trp
        115                 120                 125

Gln Lys Arg Ala Gly Ser Lys Ser Asp Ser Ser Trp Val Met Thr Val
    130                 135                 140

Glu Leu Gly Pro Ala Ser Ser Ser Gln Glu Thr Thr Ser Lys Ala Ser
145                 150                 155                 160

Gln Asp Ala Ile Leu Ala Pro Thr Thr Glu Val Glu Ile Gly Gly Ser
                165                 170                 175

Arg Glu Glu Val Leu Asp Glu Glu Glu Lys Val Ala Leu Gln Met Ile
            180                 185                 190

Glu Glu Leu Leu Asn Thr Asn
        195


<210> SEQ ID NO 3
<211> LENGTH: 189
<212> TYPE: PRT
<213> ORGANISM: Arabidopsis Thaliana
<220> FEATURE:
<221> NAME/KEY: PEPTIDE
<222> LOCATION: (1)..(189)

<400> SEQUENCE: 3

Met Val His Ser Arg Lys Phe Arg Gly Val Arg Gln Arg Gln Trp Gly
1               5                   10                  15

Ser Trp Val Ser Glu Ile Arg His Pro Leu Leu Lys Arg Arg Val Trp
            20                  25                  30

Leu Gly Thr Phe Glu Thr Ala Glu Ala Ala Ala Arg Ala Tyr Asp Gln
        35                  40                  45

Ala Ala Leu Leu Met Asn Gly Gln Asn Ala Lys Thr Asn Phe Pro Val
    50                  55                  60

Val Lys Ser Glu Glu Gly Ser Asp His Val Lys Asp Val Asn Ser Pro
65                  70                  75                  80

Leu Met Ser Pro Lys Ser Leu Ser Glu Leu Leu Asn Ala Lys Leu Arg
                85                  90                  95

Lys Ser Cys Lys Asp Leu Thr Pro Ser Leu Thr Cys Leu Arg Leu Asp
            100                 105                 110

Thr Asp Ser Ser His Ile Gly Val Trp Gln Lys Arg Ala Gly Ser Lys
        115                 120                 125

Thr Ser Pro Thr Trp Val Met Arg Leu Glu Leu Gly Asn Val Val Asn
    130                 135                 140
```

```
Glu Ser Ala Val Asp Leu Gly Leu Thr Thr Met Asn Lys Gln Asn Val
145                 150                 155                 160

Glu Lys Glu Glu Glu Glu Glu Glu Ala Ile Ile Ser Asp Glu Asp Gln
                165                 170                 175

Leu Ala Met Glu Met Ile Glu Glu Leu Leu Asn Trp Ser
            180                 185


<210> SEQ ID NO 4
<211> LENGTH: 274
<212> TYPE: PRT
<213> ORGANISM: Arabidopsis Thaliana
<220> FEATURE:
<221> NAME/KEY: PEPTIDE
<222> LOCATION: (1)..(274)

<400> SEQUENCE: 4

Met Gly Arg Ser Pro Cys Cys Glu Lys Asp His Thr Asn Lys Gly Ala
1               5                   10                  15

Trp Thr Lys Glu Glu Asp Asp Lys Leu Ile Ser Tyr Ile Lys Ala His
            20                  25                  30

Gly Glu Gly Cys Trp Arg Ser Leu Pro Arg Ser Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Leu Glu Glu Asp Asp Leu Ile Ile Lys
65                  70                  75                  80

Leu His Ser Leu Leu Gly Asn Lys Trp Ser Leu Ile Ala Thr Arg Leu
                85                  90                  95

Pro Gly Arg Thr Asp Asn Glu Ile Lys Asn Tyr Trp Asn Thr His Val
            100                 105                 110

Lys Arg Lys Leu Leu Arg Lys Gly Ile Asp Pro Ala Thr His Arg Pro
        115                 120                 125

Ile Asn Glu Thr Lys Thr Ser Gln Asp Ser Ser Asp Ser Ser Lys Thr
    130                 135                 140

Glu Asp Pro Leu Val Lys Ile Leu Ser Phe Gly Pro Gln Leu Glu Lys
145                 150                 155                 160

Ile Ala Asn Phe Gly Asp Glu Arg Ile Gln Lys Arg Val Glu Tyr Ser
                165                 170                 175

Val Val Glu Glu Arg Cys Leu Asp Leu Asn Leu Glu Leu Arg Ile Ser
            180                 185                 190

Pro Pro Trp Gln Asp Lys Leu His Asp Glu Arg Asn Leu Arg Phe Gly
        195                 200                 205

Arg Val Lys Tyr Arg Cys Ser Ala Cys Arg Phe Gly Phe Gly Asn Gly
    210                 215                 220

Lys Glu Cys Ser Cys Asn Asn Val Lys Cys Gln Thr Glu Asp Ser Ser
225                 230                 235                 240

Ser Ser Ser Tyr Ser Ser Thr Asp Ile Ser Ser Ser Ile Gly Tyr Asp
                245                 250                 255

Phe Leu Gly Leu Asn Asn Thr Arg Val Leu Asp Phe Ser Thr Leu Glu
            260                 265                 270

Met Lys


<210> SEQ ID NO 5
<211> LENGTH: 282
<212> TYPE: PRT
<213> ORGANISM: Arabidopsis Thaliana
<220> FEATURE:
```

<221> NAME/KEY: PEPTIDE
<222> LOCATION: (1)..(282)

<400> SEQUENCE: 5

```
Met Gly Arg Ser Pro Cys Cys Glu Lys Ala His Thr Asn Lys Gly Ala
1               5                   10                  15

Trp Thr Lys Glu Glu Asp Glu Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Ile Asn Arg Gly Ile Asp Pro Thr Ser His Arg Pro
        115                 120                 125

Ile Gln Glu Ser Ser Ala Ser Gln Asp Ser Lys Pro Thr Gln Leu Glu
    130                 135                 140

Pro Val Thr Ser Asn Thr Ile Asn Ile Ser Phe Thr Ser Ala Pro Lys
145                 150                 155                 160

Val Glu Thr Phe His Glu Ser Ile Ser Phe Pro Gly Lys Ser Glu Lys
                165                 170                 175

Ile Ser Met Leu Thr Phe Lys Glu Glu Lys Asp Glu Cys Pro Val Gln
            180                 185                 190

Glu Lys Phe Pro Asp Leu Asn Leu Glu Leu Arg Ile Ser Leu Pro Asp
        195                 200                 205

Asp Val Asp Arg Leu Gln Gly His Gly Lys Ser Thr Thr Pro Arg Cys
    210                 215                 220

Phe Lys Cys Ser Leu Gly Met Ile Asn Gly Met Glu Cys Arg Cys Gly
225                 230                 235                 240

Arg Met Arg Cys Asp Val Val Gly Gly Ser Ser Lys Gly Ser Asp Met
                245                 250                 255

Ser Asn Gly Phe Asp Phe Leu Gly Leu Ala Lys Lys Glu Thr Thr Ser
            260                 265                 270

Leu Leu Gly Phe Arg Ser Leu Glu Met Lys
        275                 280
```

<210> SEQ ID NO 6
<211> LENGTH: 269
<212> TYPE: PRT
<213> ORGANISM: Arabidopsis Thaliana
<220> FEATURE:
<221> NAME/KEY: PEPTIDE
<222> LOCATION: (1)..(269)

<400> SEQUENCE: 6

```
Met Gly Arg Ser Pro Cys Cys Glu Lys Glu His Met Asn Lys Gly Ala
1               5                   10                  15

Trp Thr Lys Glu Glu Asp Glu Arg Leu Val Ser Tyr Ile Lys Ser His
            20                  25                  30

Gly Glu Gly Cys Trp Arg Ser Leu Pro Arg Ala Ala Gly Leu Leu Arg
        35                  40                  45
```

```
Cys Gly Lys Ser Cys Arg Leu Arg Trp Ile Asn Tyr Leu Arg Pro Asp
    50                  55                  60

Leu Lys Arg Gly Asn Phe Thr His Asp Glu Asp Glu Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Lys Gly Ile Asp Pro Ala Thr His Arg Gly
        115                 120                 125

Ile Asn Glu Ala Lys Ile Ser Asp Leu Lys Lys Thr Lys Asp Gln Ile
    130                 135                 140

Val Lys Asp Val Ser Phe Val Thr Lys Phe Glu Glu Thr Asp Lys Ser
145                 150                 155                 160

Gly Asp Gln Lys Gln Asn Lys Tyr Ile Arg Asn Gly Leu Val Cys Lys
                165                 170                 175

Glu Glu Arg Val Val Val Glu Glu Lys Ile Gly Pro Asp Leu Asn Leu
            180                 185                 190

Glu Leu Arg Ile Ser Pro Pro Trp Gln Asn Gln Arg Glu Ile Ser Thr
        195                 200                 205

Cys Thr Ala Ser Arg Phe Tyr Met Glu Asn Asp Met Glu Cys Ser Ser
    210                 215                 220

Glu Thr Val Lys Cys Gln Thr Glu Asn Ser Ser Ser Ile Ser Tyr Ser
225                 230                 235                 240

Ser Ile Asp Ile Ser Ser Ser Asn Val Gly Tyr Asp Phe Leu Gly Leu
                245                 250                 255

Lys Thr Arg Ile Leu Asp Phe Arg Ser Leu Glu Met Lys
            260                 265


<210> SEQ ID NO 7
<211> LENGTH: 243
<212> TYPE: PRT
<213> ORGANISM: Oryza sativa
<220> FEATURE:
<221> NAME/KEY: PEPTIDE
<222> LOCATION: (1)..(243)

<400> SEQUENCE: 7

Met Gly Gln Ser Lys Lys Lys Phe Arg Gly Val Arg Gln Arg His Trp
1               5                   10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
        35                  40                  45

Glu Ala Ala Ile Leu Met Ser Gly Arg Asn Ala Lys Thr Asn Phe Pro
    50                  55                  60

Val Ala Arg Asn Ala Thr Gly Glu Leu Thr Pro Ala Ala Ala Val Ala
65                  70                  75                  80

Gly Arg Asp Gly Arg Val Gly Gly Gly Ser Gly Ser Ser Ser Ser Met
                85                  90                  95

Thr Ala Asn Gly Gly Gly Asn Ser Leu Ser Gln Ile Leu Ser Ala Lys
            100                 105                 110

Leu Arg Lys Cys Cys Lys Thr Pro Ser Pro Ser Leu Thr Cys Leu Arg
        115                 120                 125

Leu Asp Pro Glu Lys Ser His Ile Gly Val Trp Gln Lys Arg Ala Gly
    130                 135                 140
```

```
Ala Arg Ala Asp Ser Ser Trp Val Met Thr Val Glu Leu Asn Lys Asp
145                 150                 155                 160

Thr Ala Val Ser Ser Ala Ala Thr Val Ala Ala Ala Thr Ala Val Ser
                165                 170                 175

Ser Ser Asp Gln Pro Thr Pro Ser Asp Ser Thr Val Thr Thr Thr Ser
            180                 185                 190

Thr Ser Thr Thr Gly Ser Pro Ser Pro Pro Pro Pro Ala Met Asp Asp
        195                 200                 205

Glu Glu Arg Ile Ala Leu Gln Met Ile Glu Glu Leu Leu Gly Arg Ser
    210                 215                 220

Gly Pro Gly Ser Pro Ser His Gly Leu Leu His Gly Gly Glu Gly Ser
225                 230                 235                 240

Leu Val Ile


<210> SEQ ID NO 8
<211> LENGTH: 243
<212> TYPE: PRT
<213> ORGANISM: Oryza sativa
<220> FEATURE:
<221> NAME/KEY: PEPTIDE
<222> LOCATION: (1)..(243)

<400> SEQUENCE: 8

Met Gly Gln Ser Lys Lys Lys Phe Arg Gly Val Arg Gln Arg His Trp
1               5                   10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
        35                  40                  45

Glu Ala Ala Ile Leu Met Ser Gly Arg Asn Ala Lys Thr Asn Phe Pro
    50                  55                  60

Val Ala Arg Asn Ala Thr Gly Glu Leu Thr Pro Ala Ala Ala Val Ala
65                  70                  75                  80

Gly Arg Asp Gly Arg Val Gly Gly Gly Ser Gly Ser Ser Ser Ser Met
                85                  90                  95

Thr Ala Asn Gly Gly Gly Asn Ser Leu Ser Gln Ile Leu Ser Ala Lys
            100                 105                 110

Leu Arg Lys Cys Cys Lys Thr Pro Ser Pro Ser Leu Thr Cys Leu Arg
        115                 120                 125

Leu Asp Pro Glu Lys Ser His Ile Gly Val Trp Gln Lys Arg Ala Gly
    130                 135                 140

Ala Arg Ala Asp Ser Ser Trp Val Met Thr Val Glu Leu Asn Lys Asp
145                 150                 155                 160

Thr Ala Val Ser Ser Ala Ala Thr Val Ala Ala Ala Thr Ala Val Ser
                165                 170                 175

Ser Ser Asp Gln Pro Thr Pro Ser Asp Ser Thr Val Thr Thr Thr Ser
            180                 185                 190

Thr Ser Thr Thr Gly Ser Pro Ser Pro Pro Pro Pro Ala Met Asp Asp
        195                 200                 205

Glu Glu Arg Ile Ala Leu Gln Met Ile Glu Glu Leu Leu Gly Arg Ser
    210                 215                 220

Gly Pro Gly Ser Pro Ser His Gly Leu Leu His Gly Gly Glu Gly Ser
225                 230                 235                 240

Leu Val Ile
```

<210> SEQ ID NO 9
<211> LENGTH: 243
<212> TYPE: PRT
<213> ORGANISM: Oryza sativa
<220> FEATURE:
<221> NAME/KEY: PEPTIDE
<222> LOCATION: (1)..(243)

<400> SEQUENCE: 9

```
Met Gly Arg Ser Pro Cys Cys Glu Lys Glu His Thr Asn Lys Gly Ala
1               5                   10                  15

Trp Thr Lys Glu Glu Asp Glu Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Val Asn Ala Ala Ala Ala Thr Ile Ser Phe His Pro Gln Pro Pro Pro
    130                 135                 140

Thr Thr Lys Glu Glu Gln Leu Ile Leu Ser Lys Pro Pro Lys Cys Pro
145                 150                 155                 160

Asp Leu Asn Leu Asp Leu Cys Ile Ser Pro Pro Ser Cys Gln Glu Glu
                165                 170                 175

Asp Asp Asp Tyr Glu Ala Lys Pro Ala Met Ile Val Arg Ala Pro Glu
            180                 185                 190

Leu Gln Arg Arg Arg Gly Gly Leu Cys Phe Gly Cys Ser Leu Gly Leu
        195                 200                 205

Gln Lys Glu Cys Lys Cys Ser Gly Gly Gly Ala Gly Ala Gly Ala Gly
    210                 215                 220

Asn Asn Phe Leu Gly Leu Arg Ala Gly Met Leu Asp Phe Arg Ser Leu
225                 230                 235                 240

Pro Met Lys
```

<210> SEQ ID NO 10
<211> LENGTH: 251
<212> TYPE: PRT
<213> ORGANISM: Oryza sativa
<220> FEATURE:
<221> NAME/KEY: PEPTIDE
<222> LOCATION: (1)..(251)

<400> SEQUENCE: 10

```
Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
```

```
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Asp Ser Ala Ser Asn Ile Thr Ile Ser Phe Glu Ala Ala Ala
    130                 135                 140

Ala Ala Ala Arg Asp Asp Lys Ala Ala Val Phe Arg Arg Glu Asp His
145                 150                 155                 160

Pro His Gln Pro Lys Ala Val Thr Val Ala Gln Glu Gln Gln Ala Ala
                165                 170                 175

Ala Asp Trp Gly His Gly Lys Pro Leu Lys Cys Pro Asp Leu Asn Leu
            180                 185                 190

Asp Leu Cys Ile Ser Leu Pro Ser Gln Glu Glu Pro Met Met Met Lys
        195                 200                 205

Pro Val Lys Arg Glu Thr Gly Val Cys Phe Ser Cys Ser Leu Gly Leu
    210                 215                 220

Pro Lys Ser Thr Asp Cys Lys Cys Ser Ser Phe Leu Gly Leu Arg Thr
225                 230                 235                 240

Ala Met Leu Asp Phe Arg Ser Leu Glu Met Lys
                245                 250


<210> SEQ ID NO 11
<211> LENGTH: 268
<212> TYPE: PRT
<213> ORGANISM: Populus trichocarpa
<220> FEATURE:
<221> NAME/KEY: PEPTIDE
<222> LOCATION: (1)..(268)

<400> SEQUENCE: 11

Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Thr His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Pro Ala Gln Glu Ala Ser Thr Thr Ile Ser Phe Ser Thr
    130                 135                 140

Thr Thr Ser Val Lys Glu Glu Ser Leu Ser Ser Val Lys Glu Glu Ser
145                 150                 155                 160
```

```
Asn Lys Glu Lys Ile Ile Ser Ala Ala Ala Phe Ile Cys Lys Glu Glu
                165                 170                 175

Lys Thr Pro Val Gln Glu Arg Cys Pro Asp Leu Asn Leu Glu Leu Arg
            180                 185                 190

Ile Ser Leu Pro Cys Gln Asn Gln Pro Asp Arg His Gln Ala Phe Lys
        195                 200                 205

Thr Gly Gly Ser Thr Ser Leu Cys Phe Ala Cys Ser Leu Gly Leu Gln
    210                 215                 220

Asn Ser Lys Asp Cys Ser Cys Ser Val Ile Val Gly Thr Ile Gly Ser
225                 230                 235                 240

Ser Ser Ser Ala Gly Ser Lys Thr Gly Tyr Asp Phe Leu Gly Met Lys
                245                 250                 255

Ser Gly Val Leu Asp Tyr Arg Gly Leu Glu Met Lys
            260                 265


<210> SEQ ID NO 12
<211> LENGTH: 271
<212> TYPE: PRT
<213> ORGANISM: Populus trichocarpa
<220> FEATURE:
<221> NAME/KEY: PEPTIDE
<222> LOCATION: (1)..(271)

<400> SEQUENCE: 12

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Ala Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Pro Ala Val Gln Glu Ala Thr Thr Thr Ile Ser Phe Thr
    130                 135                 140

Thr Thr Thr Thr Ser Val Leu Glu Glu Glu Ser Leu Gly Ser Ile Ile
145                 150                 155                 160

Lys Glu Glu Asn Lys Glu Lys Ile Ile Ser Ala Thr Ala Phe Val Cys
                165                 170                 175

Lys Glu Glu Lys Thr Gln Val Gln Glu Arg Cys Pro Asp Leu Asn Leu
            180                 185                 190

Glu Leu Gly Ile Ser Leu Pro Ser Gln Asn Gln Pro Asp His His Gln
        195                 200                 205

Pro Phe Lys Thr Gly Gly Ser Arg Ser Leu Cys Phe Ala Cys Ser Leu
    210                 215                 220

Gly Leu Gln Asn Ser Lys Asp Cys Ser Cys Asn Val Ile Val Ser Thr
225                 230                 235                 240

Val Gly Ser Ser Gly Ser Thr Ser Thr Lys Thr Gly Tyr Asp Phe Leu
                245                 250                 255
```

```
Gly Met Lys Ser Gly Val Leu Asp Tyr Arg Ser Leu Glu Met Lys
            260                 265                 270


<210> SEQ ID NO 13
<211> LENGTH: 105
<212> TYPE: PRT
<213> ORGANISM: Sorghum bicolor
<220> FEATURE:
<221> NAME/KEY: PEPTIDE
<222> LOCATION: (1)..(105)

<400> SEQUENCE: 13

Met Pro Thr Pro Thr Pro Thr Pro Thr Pro Thr Cys Gly Asp Gly Ser
1               5                   10                  15

Leu Ala Gly Phe Ala Leu Leu Leu Arg Gly Glu Lys Arg Val Ala Asn
            20                  25                  30

Gly Ala Arg Gly Gly Arg Gly Ile Gly Gly Glu Arg Ala Lys Ile Ile
        35                  40                  45

Arg Arg Arg His Ala Glu Lys Thr His Gly Arg Arg Glu Arg Gly Gly
    50                  55                  60

His Arg Arg Ser His Arg Leu Ala Tyr Pro Leu Trp Val Leu Asp Ile
65                  70                  75                  80

Arg Ser Pro Asn Gly Ile Met Leu Gly Ile Phe Arg Gly Ala Ala Leu
                85                  90                  95

Trp Leu Trp Thr Leu Ala Trp His Met
            100                 105


<210> SEQ ID NO 14
<211> LENGTH: 235
<212> TYPE: PRT
<213> ORGANISM: Sorghum bicolor
<220> FEATURE:
<221> NAME/KEY: PEPTIDE
<222> LOCATION: (1)..(235)

<400> SEQUENCE: 14

Met Val Gln Ser Lys Lys Lys Phe Arg Gly Val Arg Gln Arg His Trp
1               5                   10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
        35                  40                  45

Glu Ala Ala Val Leu Met Ser Gly Arg Asn Ala Lys Thr Asn Phe Pro
    50                  55                  60

Val Pro Arg Thr Ala Thr Gly Glu Leu Ala Pro Val Pro Ala Ala Arg
65                  70                  75                  80

Asp Ala Arg Gly Gly Gly Gly Ser Ser Ser Ala Ala Ala Ala Pro Gly
                85                  90                  95

Gly Gly Thr Ser Asn Leu Ser Gln Ile Leu Ser Ala Lys Leu Arg Lys
            100                 105                 110

Cys Cys Lys Thr Pro Ser Pro Ser Leu Thr Cys Leu Arg Leu Asp Pro
        115                 120                 125

Glu Lys Ser His Ile Gly Val Trp Gln Lys Arg Ala Gly Ala Arg Ala
    130                 135                 140

Asp Ser Ser Trp Val Met Thr Val Gln Leu Asn Lys Asp Val Pro Pro
145                 150                 155                 160

Pro Ala Ser Ser Ser Gly Glu Glu Pro Val Pro Ser Asp Gly Gly Ala
                165                 170                 175
```

```
Ala Ala Thr Thr Pro Thr Ser Thr Ser Thr Ser Ser Thr Val Thr Thr
            180                 185                 190

Thr Gly Ser Pro Pro Pro Ala Met Met Met Asp Asp Glu Glu Arg Ile
        195                 200                 205

Ala Leu Gln Met Ile Glu Glu Leu Leu Gly Ser Ser His Ser His Gly
    210                 215                 220

Met Phe Gln Gly Ala Ala Gly Ser Ile Val Ile
225                 230                 235


<210> SEQ ID NO 15
<211> LENGTH: 258
<212> TYPE: PRT
<213> ORGANISM: Sorghum bicolor
<220> FEATURE:
<221> NAME/KEY: PEPTIDE
<222> LOCATION: (1)..(258)

<400> SEQUENCE: 15

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Met Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Ile Ala Asp Ala Gly Ala Gly Thr Val Thr Thr Ile Ser Phe Gln Pro
    130                 135                 140

Asn Lys Pro Asn Ala Ala Val Ala Ala Gln Ala Pro Gln His Gln Pro
145                 150                 155                 160

Ile Lys Ala Val Ala Thr Ala Val Val Lys Val Pro Arg Cys Pro Asp
                165                 170                 175

Leu Asn Leu Asp Leu Cys Ile Ser Pro Pro Cys Gln Gln Lys Glu Asp
            180                 185                 190

Glu Glu Leu Asp Leu Lys Pro Ala Val Val Val Lys Arg Glu Val Leu
        195                 200                 205

Gln Ala Gly His Gly Gly Ser Leu Cys Phe Gly Cys Ser Leu Gly Ile
    210                 215                 220

Gln Lys Gly Ala Pro Gly Cys Ser Cys Ser Ser Ser Asn Ser His His
225                 230                 235                 240

Arg Phe Leu Gly Leu Arg Ser Gly Met Leu Asp Phe Arg Gly Leu Glu
                245                 250                 255

Met Lys


<210> SEQ ID NO 16
<211> LENGTH: 264
<212> TYPE: PRT
<213> ORGANISM: Sorghum bicolor
```

```
<220> FEATURE:
<221> NAME/KEY: PEPTIDE
<222> LOCATION: (1)..(264)

<400> SEQUENCE: 16

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Glu His Thr Ser Asn Ile Thr Ile Ser Phe Glu Ala Ala Ala
    130                 135                 140

Ala Ala Arg Asp Arg Glu Glu Asn Lys Gly Ala Val Phe Arg Leu Glu
145                 150                 155                 160

Glu His Asn Lys Ala Thr Ala Ala Ala Ala Ala Ala Ile Gly Arg Asp
                165                 170                 175

His His Gln Asn His His Pro Ala Gly Asp Trp Gly Gln Gly Lys Pro
            180                 185                 190

Leu Lys Cys Pro Asp Leu Asn Leu Asp Leu Cys Ile Ser Pro Pro Ala
        195                 200                 205

Ala Pro Cys Gln Glu Glu Lys Ala Met Val Thr Met Lys Pro Val Lys
    210                 215                 220

Arg Glu Ala Gly Leu Cys Phe Ser Cys Ser Leu Gly Leu Pro Lys Ser
225                 230                 235                 240

Ala Asp Cys Lys Cys Ser Asn Phe Leu Gly Leu Arg Thr Ala Met Leu
                245                 250                 255

Asp Phe Arg Ser Leu Glu Met Lys
            260


<210> SEQ ID NO 17
<211> LENGTH: 213
<212> TYPE: PRT
<213> ORGANISM: Zea mays
<220> FEATURE:
<221> NAME/KEY: PEPTIDE
<222> LOCATION: (1)..(213)

<400> SEQUENCE: 17

Met Thr Glu Asn Leu His Ser Arg Lys Met Val Gln Pro Lys Lys Phe
1               5                   10                  15

Arg Gly Val Arg Gln Arg His Trp Gly Ser Trp Val Ser Glu Ile Arg
            20                  25                  30

His Pro Leu Leu Lys Arg Arg Val Trp Leu Gly Thr Phe Glu Thr Ala
        35                  40                  45

Glu Glu Ala Ala Arg Ala Tyr Asp Glu Ala Ala Val Leu Met Ser Gly
    50                  55                  60
```

```
Arg Asn Ala Lys Thr Asn Phe Pro Ile Gln Arg Ser Ser Thr Gly Glu
65                  70                  75                  80

Pro Thr Pro Ala Ala Gly Arg Asp Ala Arg Ser Asn Phe Ser Ser Gly
                85                  90                  95

Ser Ser Thr Thr Asn Leu Ser Gln Ile Leu Ser Ala Lys Leu Arg Lys
            100                 105                 110

Cys Cys Lys Ala Pro Ser Pro Ser Leu Thr Cys Leu Arg Leu Asp Pro
        115                 120                 125

Glu Lys Ser His Ile Gly Val Trp Gln Lys Arg Ala Gly Ala Arg Ala
    130                 135                 140

Asp Ser Asn Trp Val Met Thr Val Glu Leu Asn Lys Asp Ala Ala Ser
145                 150                 155                 160

Thr Asp Ala Ala Ser Gln Ser Thr Ser Ala Thr Thr Ala Pro Pro Ala
                165                 170                 175

Thr Pro Met Asp Glu Glu Glu Arg Ile Ala Leu Gln Met Ile Glu Glu
            180                 185                 190

Leu Leu Ser Ser Ser Ser Pro Ala Ser Pro Ser Asn Gly Asp Asp Gln
        195                 200                 205

Gly Arg Phe Ile Ile
    210


<210> SEQ ID NO 18
<211> LENGTH: 257
<212> TYPE: PRT
<213> ORGANISM: Zea mays
<220> FEATURE:
<221> NAME/KEY: PEPTIDE
<222> LOCATION: (1)..(257)

<400> SEQUENCE: 18

Met Gly Arg Ser Pro Cys Cys Glu Lys Ala His Thr Asn Arg Gly Ala
1               5                   10                  15

Trp Thr Lys Glu Glu Asp Glu Arg Leu Val Ala Tyr Val Arg Ala His
            20                  25                  30

Gly Glu Gly Cys Trp Arg Ser Leu Pro Arg Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Ser Gly Ile Asp Pro Val Thr His Arg Arg
        115                 120                 125

Val Ala Gly Gly Ala Ala Thr Thr Ile Ser Phe Gln Pro Ser Pro Asn
    130                 135                 140

Thr Ala Val Ala Ala Ala Ala Glu Thr Ala Ala Gln Ala Pro Ile Lys
145                 150                 155                 160

Ala Glu Glu Thr Ala Ala Val Lys Ala Pro Arg Cys Pro Asp Leu Asn
                165                 170                 175

Leu Asp Leu Cys Ile Ser Pro Pro Cys Gln His Glu Asp Asp Gly Glu
            180                 185                 190

Glu Glu Glu Glu Glu Leu Asp Leu Ile Lys Pro Ala Val Val Lys Arg
```

```
        195                 200                 205

Glu Ala Leu Gln Ala Gly His Gly His Gly His Gly Leu Cys Leu Gly
    210                 215                 220

Cys Gly Leu Gly Gly Gln Lys Gly Ala Ala Gly Cys Ser Cys Ser Asn
225                 230                 235                 240

Gly His His Phe Leu Gly Leu Arg Thr Ser Val Leu Asp Phe Arg Gly
                245                 250                 255

Leu


<210> SEQ ID NO 19
<211> LENGTH: 273
<212> TYPE: PRT
<213> ORGANISM: Zea mays
<220> FEATURE:
<221> NAME/KEY: PEPTIDE
<222> LOCATION: (1)..(273)

<400> SEQUENCE: 19

Met Gly Arg Ser Pro Cys Cys Glu Lys Ala His Thr Asn Lys Gly Ala
1               5                   10                  15

Trp Thr Lys Glu Glu Asp Glu Arg Leu Val Ala His Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Val Lys
65                  70                  75                  80

Leu His Ser Val Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Val Thr Glu His His Ala Ser Asn Ile Thr Ile Ser Phe Glu Thr Glu
    130                 135                 140

Val Ala Ala Ala Ala Arg Asp Asp Lys Lys Gly Ala Val Phe Arg Leu
145                 150                 155                 160

Glu Glu Glu Glu Glu Arg Asn Lys Ala Thr Met Val Val Gly Arg Asp
                165                 170                 175

Arg Gln Ser Gln Ser Gln Ser His Ser His Pro Ala Gly Glu Trp Gly
            180                 185                 190

Gln Gly Lys Arg Pro Leu Lys Cys Pro Asp Leu Asn Leu Asp Leu Cys
        195                 200                 205

Ile Ser Pro Pro Cys Gln Glu Glu Glu Glu Met Glu Glu Ala Ala Met
    210                 215                 220

Arg Val Arg Pro Ala Val Lys Arg Glu Ala Gly Leu Cys Phe Gly Cys
225                 230                 235                 240

Ser Leu Gly Leu Pro Arg Thr Ala Asp Cys Lys Cys Ser Ser Ser Ser
                245                 250                 255

Phe Leu Gly Leu Arg Thr Ala Met Leu Asp Phe Arg Ser Leu Glu Met
            260                 265                 270

Lys


<210> SEQ ID NO 20
```

<211> LENGTH: 256
<212> TYPE: PRT
<213> ORGANISM: Panicum virgatum
<220> FEATURE:
<221> NAME/KEY: PEPTIDE
<222> LOCATION: (1)..(256)

<400> SEQUENCE: 20

```
Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Arg Gly Ile Asp Pro Val Thr His Arg Pro
        115                 120                 125

Ile Ala Asp Ala Ala Arg Asn Val Thr Ile Ser Phe Gln Pro Asp Ala
    130                 135                 140

Pro Ser Gln Gln Gln Leu Ser Asp Asp Ala Glu Ala Pro Pro Pro Pro
145                 150                 155                 160

Pro Pro Gln Gln Gln Gln Gln Leu Lys Pro Pro Pro Arg Cys Pro Asp
                165                 170                 175

Leu Asn Leu Asp Leu Cys Ile Ser Pro Pro Cys His Lys Glu Glu Glu
            180                 185                 190

Asp Gln Glu Leu Val Lys Pro Ala Ala Val Lys Arg Glu Met Leu Gln
        195                 200                 205

Ala Gly His Gly Thr Leu Gly Leu Cys Phe Gly Cys Ser Leu Gly Leu
    210                 215                 220

Gln Lys Gly Ala Ala Gly Cys Thr Cys Ser Ser Asn Ser His Phe Leu
225                 230                 235                 240

Gly Leu Arg Val Gly Met Leu Leu Asp Phe Arg Gly Leu Glu Met Lys
                245                 250                 255
```

<210> SEQ ID NO 21
<211> LENGTH: 1014
<212> TYPE: DNA
<213> ORGANISM: Arabidopsis thaliana
<220> FEATURE:
<221> NAME/KEY: promoter
<222> LOCATION: (1)..(1000)
<220> FEATURE:
<221> NAME/KEY: 5'UTR
<222> LOCATION: (1001)..(1014)

<400> SEQUENCE: 21

```
acgtacctcg tgtccaccgg tgactctatc cccggcgtta gaagtgatga tagtctcgtt      60

cccaagggaa atcagccttc gaattggaat tgatccctcc ggacattttg tgccgttcgt     120

gtgccagact tgccatccat ataatgcatc ttcttctttt tttcccgcag atggcatgtc     180

cgttggtctt tcctgtatca tttatttaca aaagaaaaat aaattaaaca tttattaagt     240
```

```
tccccccgta aaaaaaaaat atatatatat atatatatat aacacatgca tcataattgg    300

tatgtccgta ggtgtttcct tatcataact gaaccattgg taaactatcg gttccgttaa    360

agcataagac tagaaaaggc tcggtgcgac tcgctaccac gtttctaaag attttattta    420

gcaaattaac cccaatatat attttgctat gagggtctaa acaaactggt atatgagcca    480

tttacttacc acttattagt tccaagtatt tattttttgg gttaattaat gtttaaatta    540

ttggttgaca aaaaatataa aaataatggt taagttattg aaatgacttg agcaatctga    600

tgcaactgcg gataacatga actcattcga agtgacgtcc caaatatttg attctttgtt    660

tttattcctt tttgtcaagg tcaagattgg ccaaacattt tcaatatcta aatatattga    720

cattcatagc ctggaaaaga aaaaatatat ggttaaatta gttccaaagt attctagcag    780

caacaaaacc gctccaataa acgatttcca atttctatct caaacttgtt tcccaatcat    840

tagttataat ccgtccccta aaccaaaaaa aaatctaatt gtaaaggtgt tgcaatagat    900

taaccatttt tattttattt tggtaaaata gattaaccat tttgttagaa aaatgaagtt    960

taaaacattt acagttctac gtgtacatgc ttcgaccaat atgcttcgac caat         1014
```

<210> SEQ ID NO 22
<211> LENGTH: 1296
<212> TYPE: DNA
<213> ORGANISM: Arabidopsis thaliana
<220> FEATURE:
<221> NAME/KEY: promoter
<222> LOCATION: (1)..(1000)
<220> FEATURE:
<221> NAME/KEY: 5'UTR
<222> LOCATION: (1000)..(1296)

<400> SEQUENCE: 22

```
atacatgtca tgattttata attatgtata tataaatact aattgatgta tgaagtacgt     60

agataatgtt acgatctatt aatctattta cattaacttt taattagtgt tgagtaggga    120

aaattaacat ataaaccttt agcagttggt tgtattatta aaaataattt gaacttaaaa    180

tccaccttcg aaaagataaa tcaaacaagt ataaaaaatg ctataaatcc agaatattta    240

cctaaggttt ttattcttct acttaataat gtaagataaa accggcacaa tacttgttac    300

gtatgcatgg taggtaccgc aattgtgtaa gcaaatcggc acaatactaa ggttacatat    360

actaactaaa taaaacaatc tgatttcagt gacaccgtat atctaacctt tattcaaatc    420

caagggaaca tgacttgact tcttctgttg gaactaactc gatccctcaa ccatctccag    480

ggatagaaga gttagtaaaa tcaaacttga agtgaggaag taagcagttt aacgactcca    540

tatgactaca gttatataca aagttgggca caaagtacaa gtactaaata ctcaaagtca    600

gataataatt ttaataagta caaactatat atatgcagta caattattga gtatatataa    660

acgagactgg tgatttgggg cattgtccac cagggtgtta tatcccaatt gaaatttgaa    720

aatttaagtg tgtgagtgtt acgacaaaaa aaagtgtgtg aattgtaggc gcggtgaaaa    780

ggtaaattaa gattggaact agaaaaatag ttgaatatcc tttactaaaa gttgtcaatt    840

ccggttttag taaaaaaaaa ttttaaaata gaaattttat ccaaaagact tcaaacacac    900

atattcgcat atataacata agatatcatt ttttgtaaac agttaaaaag aaaaacacat    960

gttttttttt ttaatttaga aaaaaacatg ttattataca aaacagagtt ttgcccactt   1020

ttaatatgtt atgaaaagaa aaatgatttt cttgggtttg gtcagagaga ttggttgtgg   1080

taagaatggg aatcttaatt acaaagaatt ggattttggg tcgacctacc acctaaaacg   1140

acgtcgcctc catctctggt ttccaaatct ctttctcctc tccctttata agcttgcgtt   1200
```

ggccagtcgc tcatctcgaa aacagagaga aaaagactaa aaacacagtt taagaagaag 1260
gagagataga gagagaagag aaagatagag agggag 1296

<210> SEQ ID NO 23
<211> LENGTH: 1000
<212> TYPE: DNA
<213> ORGANISM: Arabidopsis thaliana
<220> FEATURE:
<221> NAME/KEY: promoter
<222> LOCATION: (1)..(1000)

<400> SEQUENCE: 23
aactagaaca cttcagataa attttgtcgt tctgttgact tcatttattc tctaaacaca 60
aagaactata gaccataatc gaaataaaaa ccctaaaaac caaatttatc tatttaaaac 120
aaacattagc tatttgagtt tcttttaggt aagttattta aggttttgga gactttaaga 180
tgttttcagc atttatggtt gtgtcattaa tttgtttagt ttagtaaaga aagaaaagat 240
agtaattaaa gagttggttg tgaaatcata tttaaaacat taataggtat ttatgtctaa 300
tttggggaca aaatagtgga attctttatc atatctagct agttcttatc gagtttgaac 360
tcgggttatg attatgttac atgcattggt ccatataaat ctatgagcaa tcaatataat 420
tcgagcattt tggtataaca taatgagcca agtataacaa aagtatcaaa cctatgcagg 480
ggagaagatg atgaaaagaa gagtgtgagc caatacaaag cagatttgag gacatggctt 540
acaagtcttg ggtacagagt ttggggagtg atgggtgcac aatggaacag cttctctggt 600
tgtccagttc ccaagagaac cttcaagctc cctaactcca tctactatgt cgcctgatta 660
aatcttattt actaacaaaa caataagatc agagtttcat tctgattctt gagtcttttt 720
tttctctctc cctcttttca tttctggttt atataaccaa ttcaaatgct tatgatccat 780
gcatgaacca tgatcatctt tgtgtttttt tttccttctg tattaccatt ttgggccttt 840
gtgaaattga ttttgggctt ttgttatata atctcctctt tctctttctc tacctgattg 900
gattcaagaa catagccaga tttggtaaag tttataagat acaaaatatt aagtaagact 960
aaagtagaaa tacataataa cttgaaagct actctaagtt 1000

<210> SEQ ID NO 24
<211> LENGTH: 1167
<212> TYPE: DNA
<213> ORGANISM: Arabidopsis thaliana
<220> FEATURE:
<221> NAME/KEY: promoter
<222> LOCATION: (1)..(1000)
<220> FEATURE:
<221> NAME/KEY: 5'UTR
<222> LOCATION: (1000)..(1167)

<400> SEQUENCE: 24
tacatcagtt tcatcatcta tcttgtttct tatagaagct cacaatcttc ttcctggtcg 60
agtttagaaa tgtcagagag agttgtttcc acagagacgt agaaacccat aactttagta 120
ttcttcaacc cttacaactt atctgagcaa aatcagaagg tcgaatttga tggatggttt 180
tgctgtattt ggtcaacggt tttatttgag acagtagacc agaggaaact cagatgtgat 240
gatgcaaaga ctgaattggt taagagtgta gattgatttg ttctaacatt gcaaatgtag 300
agtagaatta tgcaaaaaac gttaatgaac agagaagtga ttaagcagaa acaaaattag 360
agaagtgata ttatatctca aaatttattt ttggtacagc taaagctcaa attgttatag 420
agattagaga tattaaacca aatgacgagt gttttcttta gtagtaaacg gtgaaaattc 480

```
tcttctgaca aagacaatta aaattttagg tttaagactt taatatttgt cacaaattgt    540

catttaccta aataaaaaaa aaactaaata tttttttag atacatatgt gtcttataat    600

tttaactata aattttaatt ttatgtctta aataattgtt tacactataa atttaaatat    660

tttaatgcta aaattaattt gattcaaaaa agtgatttta attcttattt ttcttataga    720

aagttggtga ttgaaaagat ttacttaaaa attataacaa cttcaatggt gaataacccg    780

acccgaataa accggatata acaacttcaa tgttagcttg atatagaaag tacggtgacg    840

cttaggaggc aagcaagcta gtatctgccg ctggttagag acaaagaaca tgtgtcactc    900

ctctcaacta aaactttcct tcactttccc gcaaaatcat ttcaaaaaag ctccaaattt    960

agcttaccca tcagctttct cagaaaacca gtgaaagaaa cttctcaact tccgattttt   1020

cacaatccac caaacttttt ttaataactt tttttcctct tattacaaaa cctccactct   1080

catggcttct caaacttgtt atccatccaa atctcaatcc ctaattaggg ttcatttctc   1140

tgtttctcca aacaggggaa ttcgaag                                       1167
```

```
<210> SEQ ID NO 25
<211> LENGTH: 1019
<212> TYPE: DNA
<213> ORGANISM: Arabidopsis thaliana
<220> FEATURE:
<221> NAME/KEY: promoter
<222> LOCATION: (1)..(1000)
<220> FEATURE:
<221> NAME/KEY: 5'UTR
<222> LOCATION: (1000)..(1019)

<400> SEQUENCE: 25

tcttcttgca tcaatgatat caacaacaat gggtaataaa gaagctactt cgaaattata     60

tattttttcg tattctatat tgatcatcag tcttaagtgg tttggtttgt tgcagtgaag    120

aagaactatg tatggatcta cgccaccgtt cagttcggtt ttgtggtcct tttcgctcag    180

cttttctaca gagttgtaag atttgatgta atgtcacaga gaaaccttac tttgttgtca    240

cagagaaacc ttactttgtt gaagagtttt tgattcctca cactctctct cattaacttg    300

tgtgtaggtg aagcagccgg taatgtgcat tgtcttagcc actatgatcg gatttggact    360

caccatgacc ggcacaacag ctattaacga gtatttgaaa tggaggagaa gcaattccca    420

cctgccagaa gagccagcaa gtactcaggt ggtttgacag cagcgtagat cttttgagtg    480

aagctagagt ccctaaaggg ttggatcggt tttcaattaa ccggtcggga ttcggttttc    540

ggtttagctt taatcgactt gtctaggttg agatcagatt tggttttcaa tacttccaag    600

tctttttttt tttgccaact aaaatataag gaatgatgat aggcacacac atgacacata    660

aaatcataat gaacagtagt atgattagca atccatattt cttggataac acttcttcac    720

agcttttttg acaggtcact ataacacctt tttcagttca tttttcattt tcaatcctca    780

cccacccaaa ctctcccttc aaagcaatgt ctctcctctc tctttctcaa ttcaaacaaa    840

ctttattaaa cctaaaagaa acatttccaa tctctaatga cttagttgat agaatctcat    900

ttagttacct agtaataatc ttcacactag taagagaatc ctactcttca ccaaactaca    960

tctctctcta tataacaaac cccaaaacat ctcaacatac acacacaaca actacaaca   1019
```

```
<210> SEQ ID NO 26
<211> LENGTH: 1093
<212> TYPE: DNA
<213> ORGANISM: Arabidopsis thaliana
<220> FEATURE:
```

<221> NAME/KEY: promoter
<222> LOCATION: (1)..(1000)
<220> FEATURE:
<221> NAME/KEY: 5'UTR
<222> LOCATION: (1000)..(1093)

<400> SEQUENCE: 26

```
tgcgaacagt ttgattctgt ttttcttttt ccttttttttg ggtaattttc ttataacttt      60
tttcatagtt tcgattattt ggataaaatt ttcagattga ggatcatttt atttatttat     120
tagtgtagtc taatttagtt gtataactat aaaattgttg tttgtttccg aatcataagt     180
ttttttttt tttggttttg tattgatagg tgcaagagac tcaaaattct ggtttcgatg      240
ttaacagaat tcaagtagct gcccacttga ttcgatttgt tttgtatttg gaaacaacca     300
tggctggtca aggcccagcc cgttgtgctt ctgaacctgc ctagtcccat ggactagatc     360
tttatccgca gactccaaaa gaaaaaggat tggcgcagag gaattgtcat ggaaacagaa     420
tgaacaagaa agggtgaaga agatcaaagg catatatgat ctttacattc tctttagctt     480
atgtatgcag aaaattcacc taattaagga cagggaacgt aacttggctt gcactcctct     540
caccaaacct taccccctaa ctaattttaa ttcaaaatta ctagtatttt ggccgatcac     600
tttatataat aagataccag atttattata tttacgaatt atcagcatgc atatactgta     660
tatagttttt tttttgttaa agggtaaaat aataggatcc ttttgaataa aatgaacata     720
tataattagt ataatgaaaa cagaaggaaa tgagattagg acagtaagta aaatgagaga     780
gacctgcaaa ggataaaaaa gagaagctta aggaaaccgc gacgatgaaa gaaagacatg     840
tcatcagctg atggatgtga gtgatgagtt tgttgcagtt gtgtagaaat ttttactaaa     900
acagttgttt ttacaaaaaa gaaataatat aaaacgaaag cttagcttga aggcaatgga     960
gactctacaa caaactatgt accatacaga gagagaaact aaaagctttt cacacataaa    1020
aaccaaactt attcgtctct cattgatcac cgttttgttc tctcaagatc gctgctaatc    1080
tccggccgtc cct                                                       1093
```

<210> SEQ ID NO 27
<211> LENGTH: 1146
<212> TYPE: DNA
<213> ORGANISM: Arabidopsis thaliana

<400> SEQUENCE: 27

```
tctctaattg tcaagtatct tagtctagag ttaattactt aaatactaaa aggctgtcga      60
caaaatcaag cttgaatctc cttgtggtat cttcaactct tcgttgtctg cttacgagtg     120
gtttactcag taattatcta taatatgtta tttttttcc ctcatctttt agttgttgtt     180
tcattacatt gaaaagcttg taatgtcttt atatggtata tatggatctt atgagtgagg     240
caagatccat gatgtttttg atcttagaat gtatatgatg atcttagaat gtatttgacc     300
gcccacaaat tattgttcat tgggattata tctctagtcc aactccaagc aatcgaaatg     360
ggtcctgctt ttaagaacaa cagtatatgt ttaagaataa taactttata tattctcgat     420
tttaagatct tttgacaaaa cctccttttc gttaggagcg tactaatttc caagtgtttg     480
attagtgggg tctccgtaaa tttatttaga gtttctatct atttattaat agctcaatta     540
attaatctat actgtatcta aacatcaatt tatatattta ctcttgagac caaaactgtc     600
aatttataac attggatagt ttcttaattc ttattatata tttttcaaac acttttcaag     660
actaatctcc acattaggta ctctctctag agataaaaat atttatcaaa aacattttta     720
tttatttatt aagtagtaga taaactactg tggcaaaatc gtaaatgtct aaatgctgat     780
```

gaattttttt tgctgctcca atctggttta gtgctccata tacatccacg gccaaaatga 840
atctatggcg gcattaagat tcattagtaa gcaacgatta tattaatata attgttttta 900
gcaatgattt tccgtaattt cccaaatatg tttcagttaa tgtgttccaa tcccaacaac 960
tggttgttgc aaaagaccac caacgcaagc aatcatcaaa catcaaaata atcttacctt 1020
agcgaacaaa caataactac acaattctca taaagctctt atatatcact aacttcacac 1080
attttgtttt ccacaaaaat aaaaacggaa ctcactcaag aaaccttctt ccttgaagag 1140
agggtt 1146

<210> SEQ ID NO 28
<211> LENGTH: 1000
<212> TYPE: DNA
<213> ORGANISM: Oryza sativa

<400> SEQUENCE: 28
tacagggtct caagccagga tgacctcctt tgaaacgtac gagtggtaaa acagtacgaa 60
gaacatcaaa ttttcatgag aattttcata ggagacaggt taagagagaa cttcaagaga 120
ttggacctta tgttaacttc ttctagagat tggaccttat gttaactttc ttctataaaa 180
tattagtgaa gtgaggaaac ttctaaaaca attatatgga gtgatgaaaa aaattatttg 240
gtcagacggt aactatgagt actccataat ccgtataaga taataacatg gtaattctat 300
taggcgttcg ccaacgaagc cccaagcagc cacccaaggt agctaggcgg tgcctttgtc 360
cgtgtatcaa aaatctccat gcacgggagc cattccaaat aaaattttga agctccaagt 420
ttttgttccg aaggatcaaa tagaaaaatt atccgtagaa attgaatcct aacaaaaatt 480
ccccacaatt cctctaatta aaacgaggcc gaagcggctt cctgatcgga cggctggaag 540
gccatacatg tcctggcatt aattatcact caccttagat tattacagct cggagctaga 600
aagccctgca agttgcaatt aatggtgagt atgatctgat ctgcagcgaa atgatctatc 660
gatgtcccta gttaagcagt cattgtgtcc cttacccacc taaatccacg agtgtcagag 720
ctaagcgcga tcccgatcct taaaccccaa ccccactctc ttgctgctcc atcaagcaac 780
caaccccaat ccacacacca tacataatta catactacca gctaattaat tactaataat 840
gacttaatat tccatcatct cccagctcag ttatcacttc ttgatcacac cccctaccat 900
tgattaacct cttccatctc actctacacg cctatataat tagcctaatg atctcacttt 960
gcaaagcatc tcattgcact aaactgctca ctgcatttgc 1000

<210> SEQ ID NO 29
<211> LENGTH: 1000
<212> TYPE: DNA
<213> ORGANISM: Oryza sativa

<400> SEQUENCE: 29
actcgattcc attagattat tcacaaaccc atgtgaaccg tgactgtcag tcaggtgagg 60
aaacagatat tccaaaaatc atattctttc cttttgtatt aaccaaattc acacaaaggt 120
gatatttaaa actgacgaag atgaaaatta agttgacgca cgtaaaatga aaaagctatc 180
ggcatatgat taattaaatt taattattac aaacttgata aatgaatata tttgatattt 240
taaggcaact tctatataaa actttttttat atgaagagga ctgctacaaa acgggatccc 300
gttgcaacgg gataaggcat attaactatt ctcttgcatg agtatcacag atatcaggcc 360
ctaagtatca taggtaccag gtaacaggta tcacaggtat cgggtaccat acagctcgta 420
ccacaacagg tatcaggtac tatctcataa aaggtaacgt gataccgttg tctaggtttt 480
ctgttatatg aaacatattg tagtttaaaa aacgtgccaa cgaaaataga gataaaaatc 540
tgaatcttga tgagaaaatc atgcccaaat ttcaccctaa aacagtcaat ttcccgcgaa 600
aaaaagcaaa aaaaaaaaaa ctccagacag ttgttaaaag gggaaaaaaa aagacagaat 660
gctcagccgt cgagacacac acaacggcaa cgtcttacca gctcggagct ctctcgcttg 720
ctgcctcttc tcttcttcct cccgccaccg acaccacctc caccagcagc ttcgccttcg 780
ccgcgtcggc atctgcagtt gccacttcgc tttcttccac tccctcctcc tcctcgctta 840
cctcacactc ctccccccca atttcatccc ccacccacca ccagatcccc caccacctgc 900
cgcattctcc cccccaagat ccagatcgcc ggtcaccccc acgaactcgc tcgagatcca 960
gagagagaga gagaggcagt ttcttggttg attttcgagg 1000

<210> SEQ ID NO 30
<211> LENGTH: 1141
<212> TYPE: DNA
<213> ORGANISM: Oryza sativa

<400> SEQUENCE: 30
gagttaaatt gatatggttt tgtctgtcaa ggtgccgttt ctatggttgg aggaggaaaa 60
tgaaattagg ggaatagaac agtcgcaatc caaaagctat tgttctctct tctacggtag 120
ttgatagttc gatacgtgtg tttgatgtga gagactgaga ggagtgcacg gtgcacctgc 180
cccgtaagga cgcggaacta cattatcaga ggctaggccg gtactgttat acgcgacgtt 240
cacgaatcac gatgcgtaaa aaagtgaagc atgaaacagt actaggctct ccacgggcca 300
catcatgaaa aaactggtgc gacgccacgc ttaacaattt gtcggtcgta aactcgtaaa 360
gttaaaagcc ccacgacatt gtcaaccaat atctcagcac atgaacttct ctaacgagta 420
caacgaaacc gcatccgcaa aagcgccgtg aaccaaagct cttgccgtgc tgtgccgtgc 480
cggtggccgt gaacatgtgg aacacgaaga actcttgcgc gagatcggag cacctgacct 540
cccacctcgc gtccggcccg tcgccgtcgc agcaagcggg ctgtcaaaaa cgacgccaca 600
gcgcgagcgc tctcgccgat ccggcggacc caccctcctc acctcgcgca ccaaccgccc 660
gttcgctagt ccgatccccc accccctcatc cccccctacgc cttgcaggtt acgcgcctcg 720
ccgcggccaa cgcaaaccaa accaaatccc ccgtcacctt cgcttcgaaa ccccgcaaaa 780
ccccatggaa gaaaacaccg aacacctgcc gcgcgcacgc ctcctcctcc cccgcctctc 840
ctcctctctc ccgttccatg tccgctcaac cttgcttcca ttctttccat ccacccgccg 900
atcgacgcga tgccgacgcc ccaaccccac ccaccgcctg ccagcgccac ccccacctcgc 960 gcctctgcgg ctatggctat atcaccatgc ctccaacctc cggtacgctt agcctctctc 1020
tctctccccc tcccattctg cgcattgctc tctgcgcgcg gtcgcgtgct gctgctcgcg 1080
gcgccccgga gcgtctcctt tgggggagag gagaggagag gagaggagag gggggtgagc 1140
c 1141

<210> SEQ ID NO 31
<211> LENGTH: 1000
<212> TYPE: DNA
<213> ORGANISM: Oryza sativa

<400> SEQUENCE: 31
ttcaatgcag gatgacgcca agagggagaa accaagcaga ggtggacggt acaacgtgta 60
agtcaccgca aaacgttgca gcttggatag tggccatcga gtggtgtgcc gataccggcg 120

```
cctgttcttt acagcctcag ctagtgttgt tgtccgaggc aatttttccg acctattgtg    180

ttgctttcct ctctgatagc ttatggtaaa agatacaaag atgttgagga gtttgtacgc    240

cacttaattt tgctcgtaac atacattgac aatcaagagg agccatggca ttgcgatctg    300

cttacacggc atattcttac tggatggtgt acactactta cccttttta tgcaagcatc     360

aatccattgc ttttctcact gcacacctga ttcgtactga aaacgtgaaa cataaaaaaa    420

aacaaaaatc tagctgatgt tggctctcgg ggcctcgagt ctagtttgtc ctagatggct    480

aacctgatat gtgttggtca cgctcacgtt tgaaccgaga aagagtgtgt gtgtgtgtgt    540

gtcggcgtgc tgctacacca gagcctccct gaatcgcaat gcgtgttaac gccagcatcg    600

caggatttca tctcacttga caggttcaga tggccttcct cctaccgtct gccatttata    660

cacgcagtga cttaacgctt acacgagccg gatggcccgg atctcccccc tgcaccatct    720

caccagaaaa acggtgaggc gtcaccgcaa cccacccacc aaacacatcc acgtcccttc    780

accgttggcc ttcgattttg cttcagctgc actacgaccc ctccaacaca tttccctcgc    840

gtctcgttgc gatctcacct tacgacgatc tcgttccagc agcagcagca tcggcagcgg    900

cggcttgctt ccgaagcgag caatgcatgg cgcgcgcggc cgcgtgcgtg cgtgccttgg    960

cttgcgctct aatcaaaccg ggacgcccca actcacggtt                          1000
```

<210> SEQ ID NO 32
<211> LENGTH: 1000
<212> TYPE: DNA
<213> ORGANISM: Oryza sativa

<400> SEQUENCE: 32

```
acaacccctg ttgcaccaaa cttgcttttt taagttttaa ctgaaattag gatagcaaag     60

agagtacttt aggcttcatg ctacgagctg cctacgacca tagacaggct taatcttgtc    120

ttatagttgt atcttgttga tcattaggtg cctaactgcc tacataggca taatgcatcc    180

tttcatctga tctttgtcac tgaccccatg tacagagtcc tataagttgc aatgttctaa    240

tccttgtttc gtcagtcatt tcgtacacat ggatgaaagt ctggggttta accaccgatg    300

cgatccaatc ttctcctaca gtcgatgata aggaaatcgt aacaaagaat gtgaattttt    360

ttgacgctac aaagaatgtg aatgatctga ccagtctatc tttcaccgaa ctgaagcata    420

tactctgaat gtctaagatc atacttagac tgaactatat actctgaata tctaaagatc    480

tcatacattc atacttacgc tgcaggttgc aaattctagt cattattaca ctcgagacct    540

aaattatgat tagtggggtg tactccgata gaacagttta cagttcagaa ctcaaaagct    600

acgaatgaat tcatgacaaa aggcgacaag tgatacgtat tcgagaataa atgtgtgaac    660

aaaggccgtc tcaaaaaaaa aaaagaaaaa aaaaaagaga atccctttgc ctgcactcta    720

aaacccagcc cgacccaact ctttgtacat gaccagcaaa agcaccgtct gctgcgactt    780

tttttctctt gtgcaatcta ttgtcgggaa aaaagagagg agaattatca tatcatcacc    840

taataaattg caaccaccag aggtactgtc ctctctatat aactctttct cgggcatttt    900

gctggcactt gcctgttcta gtatctatag ctagctaact gttactgtac ctcctcccat    960

atatcatctt catatttttg cagatcgata agcgagaaaa                         1000
```

<210> SEQ ID NO 33
<211> LENGTH: 1247
<212> TYPE: DNA
<213> ORGANISM: Oryza sativa

<400> SEQUENCE: 33

```
catactttac cttgttgtat aactgcatgc ataagaatct gagagccatt gctcaattct     60
tttcaacgaa gatgtgaact gttggaaggc aatgtaaaac gggaagcgct gtatgaaaga    120
atatgacgca catcgtcttt tgttttttaa gaattgagta tatattcgtt gtggggaaca    180
gcctgatgat gggccccggg aattaacgct cgagcaacgt tggaccattc tgacatcgcg    240
tttcctgatt agcacaatgt ttcgttttat ttggaaattg aattgaatgt ttctactgtt    300
attaattgca gacagtacac caaacgacca aatctatctg caaacaatta accaagacca    360
actggagaat ttacagatga atcactgtgt tacacctgta aactgtggct cctttgagaa    420
ttgagttaca acaagagttt ggagatgaac ttgtagttca tctatatcat cttaattaaa    480
caataatatt tattcaggaa tgcagttcag agactgctta acacacacac acacaaaaaa    540
aaaacctaaa cctgaggctt gtactggaac aaggtcatta gcaaggtgtc ctctagactc    600
ccggaccgac actacccttg gaagtcaaac gcagctggca caaacaaacg gagcctcggt    660
gacgccggta aaccgcacca atcattgtta aaccaaaaaa cgtgaacaac aaaccaaaaa    720
gaaactaaaa aaccgctaaa aagacgcaaa agagagagaa aaaaaatgaa agaagaaaag    780
aaacgacgcg gactcgctga cgacccgcgg cccggtccaa cccaaccccc accgcctctc    840
tcgccgaccc cgtccactcc gccgaattcc cccccaaacc caaacccaac gcgacctcac    900
ctcacccgca cgacgacggc acgacgcgac gcgttgcccg agctgacggc ttgacgacgc    960
ctccgtcccc gtccggcacc aacccatccc aacccaacgc tccccttttc cactgaccaa   1020
ttgatagccc aacctcacct ctcctctcct cctccccct cctctcctcc tcgcctccgc   1080
accagcagtt tcgtgcaccg cacttcaccc acctacctcc cccaacctcc ccatcaaaaa   1140
ctagtagtag cagtatccac ccatccacgc acgcgaccga gcgcgatcga ttcgaggcgg   1200
cggcggcgga ggaggaggag ggggagtaga tccggcgggc ggcagcg                 1247
```

<210> SEQ ID NO 34
<211> LENGTH: 1000
<212> TYPE: DNA
<213> ORGANISM: Zea mays

<400> SEQUENCE: 34

```
tttgtgctga gatcggcacc agctttcatt taatacagcc tcagcttacc tgaggcaatt     60
ttcgcacctg ttatgatgtt gttttgctct cagataggtt tatgtagcac aagaaagata    120
tgttggagac gttgacgatt ttgtatgcaa ctaaatttct atcttaatat gccccgattc    180
aacagcaccc agtcgagtca ttgcgttctg gagattcttg cagcgcattt ccatgtttaa    240
gaccttatta tgaaatgtct ggcattcgtg gatccactga gcttctttct gcgaatgtgc    300
catatcgtgg cattggccga agcaaccaaa catttgttgc ccttttgtgt cggtgtttta    360
taaagtacct caatgacgat acagcctcag ggcgcttcct gcttttgcac ttattcggag    420
ttcaggcgag ttaacgaagt tcagacggtt ctgaagagag gccgtgttgt gttttgtcgg    480
cgtggtatcg cgcaagcaca tgtgtctttg gtaagatggt ctggatggct gtcctaccac    540
ctgccattta tacacacact gacttcaccg tcacactggc acgacatgag ctcgccatcc    600
taccagaaac gctgagacgt caccggcaac cacccctctc gctcgctctg gcctctgctc    660
ctgatttgat ttggacagaa aactgggcag ggcagggcgc gctcagcacg tttgcttcgg    720
aaacactgcg agtgtgcgac acatttcccg gcttgatctc gaagcgagcc ctgatgtgtt    780
tgtcatgcac ctgcctgcct tggcttgtgc tctaatcaac gccggactcc ccaactcacg    840
```

```
gttggtgcgg gacgccaccc cgccacctta ccgcccgcct cggcgcctca ccagtcacca    900

cacctcgcgc ctgccatcag ctatatcacc gtggccactt ccgtgtccct tcacggatac    960

ctcaccccca cagcccccgg tcgatcgctc ggcaatcggc                         1000


<210> SEQ ID NO 35
<211> LENGTH: 1000
<212> TYPE: DNA
<213> ORGANISM: Zea mays

<400> SEQUENCE: 35

aggcggggcc ggaggagggc accagagagg ctgctcagga gagagaaata atagaatatg     60

tggtatagag taaacatgag tgcggatgat tgtggtatag agtaaagaat tttgctgact    120

aggacagaat attcttttta gggtagaaat ttagagtact atgagtgcgg atagcctaag    180

gaccacttta aatttgacac aatattgaaa tttgaatggt tttaacattt gaaggctgaa    240

aaccaaaata ctttgtagct aagtgttgga aacccgactc ggccaataag tcgacagacc    300

gtaaaataag gtcaatctaa actttatgat aaatattctt gtttgatagc aatagcattg    360

caggaccagg acccaaggga agagaagatg ccaaatccca tcgaggctaa agcaaaaacg    420

atccaattta tgagcaaacc cacactgaag tttcaaaatt gttttctgaa aaaaaagtaa    480

ccagcaagtt aaaaaatgag atggcgggaa agccaagtct cggttggtcg aggggttggt    540

tggggcgcag cctgacaagt gacaacggca gcaggatagt agcatcaggc gcaagccagc    600

gcaggcggca gcgcgaggat ttcgcttcac ttagcggcaa cggagacgct gcacccaacc    660

aacacgagct ccccctcacc cgctgcgacg cgcgcgtccc acgagcggaa gccccccgcg    720

ccgacgcgag cgcgggggct cgaccgaccg acccaacgcc tccatctcca ccgcgcgcac    780

caaatcgcac tcccgtccgc cccgccgatc gaacagccac cgctcacctc tcccacccgc    840

caaaaacctc cggcctcctc tcatattcat atagctagcc cctgccacaa ggtagagcgt    900

cgctcacacc tgcgtcgccc tgcctcgcaa tcgcgaatct gtcgagcacc tgaggggtcg    960

gaggccgaga gctagcctag cacgccggcc tccgcgcgcg                         1000


<210> SEQ ID NO 36
<211> LENGTH: 1000
<212> TYPE: DNA
<213> ORGANISM: Zea mays

<400> SEQUENCE: 36

catgtatata agtattcaat acataaatca gttctggtaa agagtgaatt aagttaatgg     60

acgtgctgaa aatggtttgg cttagtcttg ttgtgtttta tggaaaaatt gtgtaggtca    120

cgattacttc tcaatgcaat tgagaaaagt tttaattgca agccatttat ggttatttat    180

taaaaaaaca aggagtaaca cgtcattgtt caaggcgcca agctaccaca tcactatgat    240

tcaaagaacc acttcagatt ttactcaaga ttggaaattg aatggttttg atatttaagg    300

ttacttttta ccgaaaaata ttggaaacga tcagactgaa atcgacttga tctagaaatt    360

atgatagaat ctcttgtttc atagcgggtc cggtgggaag acaaaatgtg taatcccgtc    420

gatatgtgct ttctaaatgc taaaaacgat ccaatatacg acgtgtgctt tctagcctgt    480

ttgtttgtct ttaatctgta ctagtttcta tgtttttttt ctcattgaat tacagctaca    540

gtagtctaaa caacagcggg ctttaattcg aagcgaacaa cacctgctga gtaagcaaac    600

ccacgctgaa tagtttcaga aatgttttct ggatgaatag caaaattgta gtagcaacag    660
```

```
gatagacggc gggaaagcca agtctcggtt ggtccggccg tccggacgca gcctgacaag    720

ggcagcagca tagcaatagc atcaggcgca agccagcgca ggcggctttc gcttcactta    780

gcggcaacgg ggacgcagcg cccgcaccca accaacacga gctcctctcc tcacccgccg    840

cgacacgcgc gcggctccaa cgcctccatc tccatcgcgc gcaccaaatc gcactccgtc    900

cgccccgtcg atcgaacagc caccgctcac ctctctcacc cgccaaaacc tcctccccctg   960

gcctcctctc atactcatat agctgagcag cccctgccac                         1000
```

```
<210> SEQ ID NO 37
<211> LENGTH: 570
<212> TYPE: DNA
<213> ORGANISM: Arabidopsis thaliana

<400> SEQUENCE: 37

atggtacatt cgaagaagtt ccgaggtgtc cgccagcgtc agtggggttc ttgggtttct     60

gagattcgtc atcctctctt gaagagaaga gtgtggctag gaacattcga cacggcggaa    120

acagcggcta gagcctacga ccaagccgcg gttctaatga acggccagag cgcgaagact    180

aacttccccg tcatcaaatc gaacggttca aattccttgg agattaactc tgcgttaagg    240

tctcccaaat cattatcgga actattgaac gctaagctaa ggaagaactg taaagaccag    300

acaccgtatc tgacgtgtct ccgcctcgac aacgacagct cacacatcgg cgtctggcag    360

aaacgcgccg ggtcaaaaac gagtccaaac tgggtcaagc ttgttgaact aggtgacaaa    420

gttaacgcac gtcccggtgg tgatattgag actaataaga tgaaggtacg aaacgaagac    480

gttcaggaag atgatcaaat ggcgatgcag atgatcgagg agttgcttaa ctggacctgt    540

cctggatctg gatccattgc acaggtctaa                                     570
```

```
<210> SEQ ID NO 38
<211> LENGTH: 600
<212> TYPE: DNA
<213> ORGANISM: Arabidopsis thaliana

<400> SEQUENCE: 38

atggtacaga cgaagaagtt cagaggtgtc aggcaacgcc attggggttc ttgggtcgct     60

gagattcgtc atcctctctt gaaacggagg atttggctag ggacgttcga gaccgcagag    120

gaggcagcaa gagcatacga cgaggccgcc gttttaatga gcggccgcaa cgccaaaacc    180

aactttcccc tcaacaacaa caacaccgga gaaacttccg agggcaaaac cgatatttca    240

gcttcgtcca caatgtcatc ctcaacatca tcttcatcgc tctcttccat cctcagcgcc    300

aaactgagga aatgctgcaa gtctccttcc ccatccctca cctgcctccg tcttgacaca    360

gccagctccc atatcggcgt ctggcagaaa cgggccggtt caaagtctga ctccagctgg    420

gtcatgacgg tggagctagg tcccgcaagc tcctcccaag agactactag taaagcttca    480

caagacgcta ttcttgctcc gaccactgaa gttgaaattg gtggcagcag agaagaagta    540

ttggatgagg aagaaaaggt tgctttgcaa atgatagagg agcttctcaa tacaaactaa    600
```

```
<210> SEQ ID NO 39
<211> LENGTH: 570
<212> TYPE: DNA
<213> ORGANISM: Arabidopsis thaliana

<400> SEQUENCE: 39

atggtacatt cgaggaagtt ccgaggtgtc cgccagcgac aatggggttc ttgggtctct     60

gagattcgcc atcctctatt gaagagaaga gtgtggcttg gaactttcga aacggcagaa    120
```

```
gcggctgcaa gagcatacga ccaagcggct cttctaatga acggccaaaa cgctaagacc    180

aatttccctg tcgtaaaatc agaggaaggc tccgatcacg ttaaagatgt taactctccg    240

ttgatgtcac caaagtcatt atctgagctt ttgaacgcta agctaaggaa gagctgcaaa    300

gacctaacgc cttctttgac gtgtctccgt cttgatactg acagttccca cattggagtt    360

tggcagaaac gggccgggtc gaaaacaagt ccgacttggg tcatgcgcct cgaacttggg    420

aacgtagtca acgaaagtgc ggttgactta gggttgacta cgatgaacaa acaaaacgtt    480

gagaaagaag aagaagaaga agaagctatt attagtgatg aggatcagtt agctatggag    540

atgatcgagg agttgctgaa ttggagttga                                      570
```

<210> SEQ ID NO 40
<211> LENGTH: 825
<212> TYPE: DNA
<213> ORGANISM: Arabidopsis thaliana

<400> SEQUENCE: 40

```
atgggaaggt ctccttgctg tgagaaagac cacacaaaca aaggagcttg gactaaggaa     60

gaagacgata agctcatctc ttacatcaaa gctcacggtg aaggttgttg gcgttctctt    120

cctagatccg ccggtcttca acgttgcgga aaaagctgtc gtctccgatg gattaactat    180

ctccgacctg atctcaagag gggtaacttc accctcgaag aagatgatct catcatcaaa    240

ctacatagcc ttctcggtaa caagtggtct cttattgcga cgagattacc aggaagaaca    300

gataacgaga ttaagaatta ctggaacaca catgttaaga ggaagctatt aagaaaaggg    360

attgatccgg cgactcatcg acctatcaac gagaccaaaa cttctcaaga ttcgtctgat    420

tctagtaaaa cagaggaccc tcttgtcaag attctctctt ttggtcctca gctggagaaa    480

atagcaaatt tcggggacga gagaattcaa aagagagttg agtactcagt tgttgaagaa    540

agatgtctgg acttgaatct tgagcttagg atcagtccac catggcaaga caagctccat    600

gatgagagga acctaaggtt tgggagagtg aagtataggt gcagtgcgtg ccgttttgga    660

ttcgggaacg gcaaggagtg tagctgtaat aatgtgaaat gtcaaacaga ggacagtagt    720

agcagcagtt attcttcaac cgacattagt agtagcattg gttatgactt cttgggtcta    780

aacaacacta gggttttgga ttttagcact ttggaaatga aatga                     825
```

<210> SEQ ID NO 41
<211> LENGTH: 849
<212> TYPE: DNA
<213> ORGANISM: Arabidopsis thaliana

<400> SEQUENCE: 41

```
atgggaaggt caccgtgctg tgagaaagct cacacaaaca aaggagcatg gacgaaagaa     60

gaggacgaga ggctcgtcgc ctacattaaa gctcatggag aaggctgctg gagatctctc    120

cccaaagccg ccggacttct tcgctgtggc aagagctgcc gtctccggtg gatcaactat    180

ctccggcctg accttaagcg tggaaacttc accgaggaag aagacgaact catcatcaag    240

ctccatagcc ttcttggcaa caaatggtcg cttattgccg ggagattacc gggaagaaca    300

gataacgaga taaagaacta ttggaacacg catatacgaa gaaagcttat aaacagaggg    360

attgatccaa cgagtcatag accaatccaa gaatcatcag cttctcaaga ttctaaacct    420

acacaactag aaccagttac gagtaatacc attaatatct cattcacttc tgctccaaag    480

gtcgaaacgt tccatgaaag tataagcttt ccgggaaaat cagagaaaat ctcaatgctt    540
```

```
acgttcaaag aagaaaaaga tgagtgccca gttcaagaaa agttcccaga tttgaatctt    600

gagctcagaa tcagtcttcc tgatgatgtt gatcgtcttc aagggcatgg aaagtcaaca    660

acgccacgtt gtttcaagtg cagcttaggg atgataaacg gcatggagtg cagatgcgga    720

agaatgagat gcgatgtagt cggaggtagc agcaagggga gtgacatgag caatggattt    780

gattttttag ggttggcaaa gaaagagacc acttctcttt tgggctttcg aagcttggag    840

atgaaataa                                                            849
```

<210> SEQ ID NO 42
<211> LENGTH: 810
<212> TYPE: DNA
<213> ORGANISM: Arabidopsis thaliana

<400> SEQUENCE: 42

```
atgggaagat ctccttgctg cgagaaagaa cacatgaaca aaggtgcttg gactaaagaa     60

gaagatgaga gactagtctc ttacatcaag tctcacggtg aaggttgttg gcgatctctt    120

cctagagccg ctggtctcct tcgctgcggt aaaagctgcc gtcttcggtg gattaactat    180

ctccgacctg atctcaaaag aggaaacttt acacatgatg aagatgaact tatcatcaag    240

cttcatagcc tcctaggcaa caagtggtct ttgattgcgg cgagattacc tggaagaaca    300

gataacgaga tcaagaacta ctggaacaca catataaaga ggaagctttt gagcaaaggg    360

attgatccag ccactcatag agggatcaac gaggcaaaaa tttctgattt gaagaaaaca    420

aaggaccaaa ttgtaaaaga tgtttctttt gtgacaaagt ttgaggaaac agacaagtct    480

ggggaccaga agcaaaataa gtatattcga aatgggttag tttgcaaaga agagagagtt    540

gttgttgaag aaaaaatagg cccagatttg aatcttgagc ttaggatcag tccaccatgg    600

caaaaccaga gagaaatatc tacttgcact gcgtcccgtt tttacatgga aaacgacatg    660

gagtgtagta gtgaaactgt gaaatgtcaa acagagaata gtagcagcat tagctattct    720

tctattgata ttagtagtag taacgttggt tatgacttct tgggtttgaa gacaagaatt    780

ttggattttc gaagcttgga aatgaaataa                                     810
```

<210> SEQ ID NO 43
<211> LENGTH: 618
<212> TYPE: DNA
<213> ORGANISM: Oryza sativa

<400> SEQUENCE: 43

```
atggtacagc caaagaagaa gtttcgtgga gtcaggcagc ggcactgggg ctcctgggtc     60

tctgagatca gacacccccct ccttaaaagg agggtgtggc tgggcacctt tgagacggcc    120

gaggaggctg cgcgagccta cgatgaggct gctgtgctga tgagtggccg caacgccaag    180

accaacttcc ccgtgcagag gaactccacc ggtgatctcg ccacggccgc agaccaggac    240

gcccgtagca atggcggtag caggaactcc tccgcgggca acctgtcaca gattctcagt    300

gctaagctcc gcaagtgctg caaggcgcca tctccgtcct taacctgcct ccgcctcgac    360

cccgagaagt cccacattgg cgtgtggcaa aagcgcgcag gggcccgtgc tgactccaac    420

tgggtgatga cggtggagct caacaaagag gtagaaccaa ctgaacctgc agctcagccc    480

acatcaacag caacagcttc gcaagtgaca atggatgatg aggaaaagat tgcgctgcaa    540

atgatcgagg agttgctgag caggagcagt ccagcttcac cctcacatgg agagggagag    600

ggtagctttg tcatctga                                                  618
```

<210> SEQ ID NO 44
<211> LENGTH: 732
<212> TYPE: DNA
<213> ORGANISM: Oryza sativa

<400> SEQUENCE: 44
atgggacagt cgaagaagaa gttccgcgga gtcaggcagc gccactgggg ctcctgggtc 60
tccgagatca ggcaccctct ccttaagagg agggtgtggc tgggtacctt tgagacggcg 120
gaggaggcgg cgcgggcgta cgacgaggcc gccatcctga tgagcggccg caacgccaag 180
accaacttcc cagtcgcgag gaacgccacg ggggagctca caccggcggc tgcggtggca 240
gggcgggatg gccgtgtcgg cggcggcagc ggcagctcgt cctcaatgac ggccaacggc 300
ggcgggaaca gcctgtctca gatcctcagc gccaagctcc gcaagtgctg caagacgccg 360
tcgccgtcgc tcacctgcct ccgccttgac ccggagaagt cccacattgg cgtctggcag 420
aagcgcgccg gcgcacgcgc tgactccagc tgggtcatga ccgtcgagct caacaaggac 480
acggccgtgt cgtcggctgc gacggtggca gcagcaacag cagtgtcgtc cagcgaccag 540
ccgactccga gtgacagcac agtcacaacg acgtccacgt ccaccacggg ctcgccgtcg 600
ccaccacctc cggcaatgga cgacgaggag aggatcgcgc tgcagatgat cgaggagctg 660
ctgggcagga gcggcccggg ctcgccgtca catgggctgc tgcacggtgg tgaaggtagc 720
ctcgtcatct ga 732

<210> SEQ ID NO 45
<211> LENGTH: 732
<212> TYPE: DNA
<213> ORGANISM: Oryza sativa

<400> SEQUENCE: 45
atggggaggt cgccgtgctg cgagaaggag cacactaaca agggcgcgtg gaccaaggag 60
gaggacgagc gcctcgtcgc ctacatccgc gcccacggcg agggctgctg gcgctcgctc 120
cccaaggccg ccggcctcct ccgctgcggc aagagctgcc gcctccgctg gatcaactac 180
ctccgccccg acctcaagcg cggcaacttc accgccgacg aggacgacct catcatcaag 240
ctccacagcc tcctcggcaa caagtggtct ctgatcgcgg cgaggctgcc ggggaggacg 300
gacaacgaga tcaagaacta ctggaacacg cacatccgcc ggaagcttct cggcaggggg 360
atcgaccccg tcacgcaccg ccccgtcaac gccgccgccg ccaccatctc cttccatccc 420
cagccgccgc caacgacgaa ggaggagcag ctcatactca gcaagccgcc caagtgcccc 480
gacctcaacc tggacctctg catcagcccg ccgtcgtgcc aggaagaaga cgatgactat 540
gaggcgaagc cggcgatgat cgtgagggcg ccggagctgc agcgccgccg cggcggcctc 600
tgcttcggct gcagcctcgg cctccagaag gagtgcaagt gcagcggcgg cggcgccggc 660
gccggcgccg gcaacaactt cctcggcctc agggctggca tgctcgactt cagaagcctc 720
cccatgaaat ga 732

<210> SEQ ID NO 46
<211> LENGTH: 756
<212> TYPE: DNA
<213> ORGANISM: Oryza sativa

<400> SEQUENCE: 46
atggggaggt caccgtgctg cgagaaggca cacaccaaca agggagcatg gaccaaggag 60
gaagatgacc ggctcattgc ctacatcaag gcgcacggcg aaggttgctg gcgatcgctg 120

```
cccaaggccg ccggcctcct ccgctgtggc aagagctgcc gcctccggtg gatcaactac    180

ctccggcctg acctcaagcg cggcaacttc accgaggagg aggatgagct gatcatcaag    240

cttcacagcc ttttaggcaa caaatggtct ctgatagccg ggaggttgcc aggaagaacg    300

gacaacgaga tcaagaacta ctggaacacg cacatcagga ggaagctgct gagccgtggc    360

atcgacccgg tgacacaccg gccgatcaac gacagcgcgt ccaacatcac catatcattc    420

gaggcggccg cggcggcggc gagggacgac aaggccgccg tgttccggcg agaggaccat    480

cctcatcagc cgaaggcggt gacagtggca caggagcagc aggcagccgc cgattggggc    540

catgggaagc cactcaagtg ccctgacctc aatctggacc tctgcatcag cctcccttcc    600

caagaagagc ccatgatgat gaagccggtg aagagggaga ccggcgtctg cttcagctgc    660

agcctggggc tccccaagag cacagactgc aagtgcagca gcttcctggg actcaggaca    720

gccatgctcg acttcagaag cttggaaatg aaatga                              756
```

```
<210> SEQ ID NO 47
<211> LENGTH: 807
<212> TYPE: DNA
<213> ORGANISM: Populus trichocarpa

<400> SEQUENCE: 47

atgggaaggt ctccttgctg tgaaaaagct catacaaaca aaggcgcatg gactaaggaa     60

gaagatgatc gccttattgc ttacattaga acccacggtg aaggttgctg gcgttcactt    120

cctaaagctg ctggccttct aagatgcggc aagagctgca gacttcgttg gatcaactat    180

ttaagacctg accttaaacg tggcaatttt actgaagaag aagatgagct cattatcaaa    240

ctccatagtc tcctcggcaa caaatggtca cttatagccg gaaggttacc agggagaaca    300

gataatgaga taaagaatta ttggaacaca catataagaa ggaagctctt gaatagaggc    360

atagatcctg cgactcatag gccactcaat gaaccagccc aagaagcttc aacaacaata    420

tctttcagca ctactacctc agttaaagaa gagtcgttga gttctgttaa agaggaaagt    480

aataaggaga agataattag cgcagctgct tttatatgca aagaagagaa aaccccagtt    540

caagaaaggt gtccagactt gaatcttgaa cttagaatta gccttccttg ccaaaaccag    600

cctgatcgtc accaggcatt caaaactgga ggaagtacaa gtctttgttt tgcttgcagc    660

ttggggctac aaaacagcaa ggactgcagt tgcagtgtca ttgtgggtac tattggaagc    720

agcagtagtg ctggctccaa aactggctat gacttcttag ggatgaaaag tggtgtgttg    780

gattatagag gtttggagat gaaatga                                        807
```

```
<210> SEQ ID NO 48
<211> LENGTH: 816
<212> TYPE: DNA
<213> ORGANISM: Populus trichocarpa

<400> SEQUENCE: 48

atgggaaggt ctccttgctg tgaaaaagcc catacaaaca agggtgcgtg gaccaaggag     60

gaagacgatc gccttgttgc ttacattaga gctcacggtg aaggttgctg gcgctcactt    120

cctaaagccg ctggccttct tagatgtggc aagagttgca gacttcgttg gatcaactat    180

ttaagacctg accttaaacg tggcaatttc accgaagcag aagatgagct cattatcaaa    240

ctccatagcc tccttggaaa caaatggtca ctcatagctg gaagattacc agggagaaca    300

gataatgaga taaagaatta ttggaacaca catataagaa ggaagctttt gaacagaggc    360

atagatcccg caactcatag gccactcaac gaaccagcag tacaagaagc cacaacaaca    420
```

```
atatctttca ccacgactac tacttcagta cttgaagaag agtctctggg ttctataatt    480

aaagaggaaa ataaagagaa gataattagc gcaactgctt tcgtatgcaa agaagagaaa    540

acccaagttc aagaaaggtg tccagacttg aatctcgagc ttggaattag ccttccttcc    600

caaaaccagc ctgatcatca ccagccattc aaaactggag gaagtagaag tctttgtttt    660

gcttgcagtt tggggctaca aaacagcaag gattgcagct gcaatgttat tgtgagcact    720

gttgggagca gtggcagcac tagcacaaag actggttatg acttcttggg catgaaaagt    780

ggtgttttgg attatagaag tttagagatg aaataa                              816


<210> SEQ ID NO 49
<211> LENGTH: 642
<212> TYPE: DNA
<213> ORGANISM: Sorghum bicolor

<400> SEQUENCE: 49

atgacagaga atctccactc caagaaaatg gtacagccaa agaagtttcg tggagtccgg     60

cagcgccact ggggttcctg ggtctccgag atcaggcatc cctccttaa gaggagggtc    120

tggctgggca ccttcgagac cgctgaggag gcagcgagag catatgacga ggctgccgtg    180

ctgatgagcg gccgcaacgc caagaccaac ttcccggtcc aaaggagcag cacaggggag    240

ccaaccccag ctgcgggaag ggacgctcac agcaacgccg gcagcggctc ctctaccgcc    300

aacctgtccc agattctcag tgcgaagctc cgcaaatgct gcaaggcgcc atcgccctcc    360

ctgacctgtc tccgccttga ccctgagaag tcccacattg gtgtttggca gaagcgtgca    420

ggagcccgtg ctgactccaa ctgggtcatg accgtggagc tcaacaaagg tgcagcatcc    480

actgatgctg catcacagtc cacatcagca acaactgctc caccagccac cccgatggat    540

gacgaggaga ggatcgccct gcaaatgatc gaagagttgc tgagcagcag cagcccagct    600

tcaccctcgc acggagatga ccaaggtcgc ttcatcatct ga                       642


<210> SEQ ID NO 50
<211> LENGTH: 708
<212> TYPE: DNA
<213> ORGANISM: Sorghum bicolor

<400> SEQUENCE: 50

atggtgcaat caaagaagaa gttccgcggc gtcaggcagc gccactgggg ctcctgggtc     60

tccgagatca ggcacccgct gcttaagagg agggtgtggc tgggcacctt cgagacggca    120

gaggaggcgg cgcgggcgta cgacgaggcc gccgtcctca tgagcggccg caacgccaag    180

accaacttcc ccgtcccaag gaccgccacc ggggagctgg cccccgtgcc ggccgcgcgg    240

gacgcacgtg gcggcggcgg ctcgtcctcc gcggcagcag cgcccggcgg cggcaccagc    300

aacctgtcgc agatcctcag cgccaagctc cgcaagtgct gcaagacgcc gtcgccgtcg    360

ctcacctgcc tccgcctcga cccggagaag tcccacattg gcgtctggca gaagcgcgcg    420

ggcgcgcgcg ccgactccag ctgggtcatg accgtccagc tcaacaagga cgtgccgccg    480

ccggcgtcct cctccggcga ggagccggtg cccagcgacg gaggcgcagc ggccaccacg    540

cccacgtcca cttccacgtc gtccacggtc acgacgaccg gctcgcctcc acctgcgatg    600

atgatggacg acgaggagag gattgcgctg cagatgatcg aggagctgct gggcagctcg    660

cactcacatg ggatgttcca gggtgcagcg ggcagcatcg tcatctga                 708


<210> SEQ ID NO 51
```

<211> LENGTH: 777
<212> TYPE: DNA
<213> ORGANISM: Sorghum bicolor

<400> SEQUENCE: 51
atggggcggt cgccgtgctg cgagaaggcg cacacgaaca agggcgcgtg gaccaaggag 60
gaggacgacc gcctggtggc gtacatccgc gcgcacggcg aagggtgctg gcggtcgctg 120
cccaaggcgg ccggactgat gcgctgcggc aagagctgcc gcctccgctg gatcaactac 180
ctccgccccg acctcaagcg cggcaacttc accgccgacg aggacgacct catcatcaag 240
ctgcacagcc tcctcggcaa caagtggtcg ctcatcgccg cgcggctccc ggggcggacg 300
gacaacgaga tcaagaacta ctggaacacg cacatccggc ggaagctgct tggcaggggc 360
atcgaccccg tcacgcaccg ccccatcgcc gacgccggcg ccggcaccgt caccaccatc 420
tcgttccagc ccaacaaacc caacgccgcc gtcgcagcgc aggcgccaca acatcagccg 480
atcaaggcgg tggcgacggc cgtcgttaag gtgcccaggt gccccgacct caacctcgat 540
ctctgcatca gcccgccgtg ccaacagaag gaagacgagg agctggacct caagcccgcc 600
gtcgtcgtca agcgggaggt gctgcaggcc ggccatggcg gcagcctctg cttcggctgc 660
agcctgggca tccaaaaagg agcccccggg tgcagctgca gcagcagcaa cagccaccac 720
cgcttcttgg ggctccggtc cggcatgctc gacttcagag gcctcgagat gaagtga 777

<210> SEQ ID NO 52
<211> LENGTH: 795
<212> TYPE: DNA
<213> ORGANISM: Sorghum bicolor

<400> SEQUENCE: 52
atggggaggt cgccgtgctg cgagaaggcg cacaccaaca agggcgcgtg gaccaaggag 60
gaggacgacc gcctcgtggc gtacatcaag gcgcacggcg agggttgctg gcgctcgctg 120
cccaaggccg ccggcctcct gcgctgcggc aagagctgcc gcctccggtg gatcaactac 180
ctccgccccg acctcaagcg cggcaacttc acggaagagg aggacgagct catcatcaag 240
ctccacagcc tcctcggcaa caaatggtcc ctgatcgctg gaaggctgcc gggaaggacg 300
gacaacgaga tcaagaacta ctggaacacg cacatccgga ggaagctgct gagcaggggg 360
atcgacccgg tgacacaccg ccccatcaac gagcacacgt ccaacataac catctcgttc 420
gaggcggcgg cggccgcgcg tgaccgtgag gagaataagg gcgccgtgtt ccggctggag 480
gagcacaaca aggcgacggc ggcggcggcc gccgcgatcg gccgcgatca tcatcagaac 540
caccaccccg ccggcgactg gggccagggg aagccgctca agtgccccga cctcaacctg 600
gacctctgca tcagcccgcc ggcggcgccg tgccaggagg agaaggccat ggtgacgatg 660
aagcccgtga agcgggaggc cgggctctgc ttcagctgca gcctgggcct ccccaagagc 720
gccgactgca agtgcagcaa cttcctcgga ctcaggaccg ccatgctcga cttcagaagc 780
ctcgagatga aatga 795

<210> SEQ ID NO 53
<211> LENGTH: 642
<212> TYPE: DNA
<213> ORGANISM: Zea mays

<400> SEQUENCE: 53
atgacagaga atctccactc caggaaaatg gtacagccaa agaagtttcg tggagtccgg 60
cagcgccact ggggctcctg ggtctctgag atcaggcatc cctccttaa gaggagggtc 120

```
tggctgggta cctttgagac ggctgaggag gcagcgagag catatgatga ggctgctgtg    180

ctgatgagcg gacgcaacgc caagaccaac ttcccaatcc aaagaagcag cacaggggag    240

cctaccccag ctgcgggaag ggacgcccgc agcaacttca gcagcggctc ctctaccacc    300

aacctgtccc agattctcag tgcgaagctc cgcaaatgct gcaaggcgcc atcaccgtcc    360

ctgacctgtc tccgccttga ccctgagaag tcccacattg gtgtttggca gaagcgtgca    420

ggagcccgtg ctgactccaa ctgggtcatg acagtggagc tcaacaaaga tgcagcatcc    480

actgatgctg catcacagtc cacatcagca acaactgctc caccagccac gccgatggat    540

gaggaggaga ggatcgcact gcaaatgatc gaagagttgc tgagcagcag cagcccagct    600

tcaccctcaa acggagatga ccaaggtcgc ttcatcatct ga                        642
```

```
<210> SEQ ID NO 54
<211> LENGTH: 783
<212> TYPE: DNA
<213> ORGANISM: Zea mays

<400> SEQUENCE: 54

atggggcggt cgccgtgctg cgagaaggcg cacaccaaca ggggcgcgtg gaccaaggag     60

gaggacgagc ggctggtggc ctacgtccgc gcgcacggcg aagggtgctg gcgctcgctg    120

cccagggcgg cgggcctgct gcgctgcggc aagagctgcc gcctgcgctg gatcaactac    180

ctccgcccgg acctcaagcg aggcaacttc accgccgacg aggacgacct catcgtcaag    240

ctgcacagcc tcctcgggaa caagtggtcg ctcatcgccg cgcggctccc ggggcggacg    300

gacaacgaga tcaagaacta ctggaacacg cacatccggc gcaagctgct gggcagcggc    360

atcgaccccg tcacgcaccg ccgcgtcgcg gggggcgccg cgaccaccat ctcgttccag    420

cccagcccca actccgccgc cgccgccgcc gccgcagaaa cagcagcgca ggcgccgatc    480

aaggccgagg agacggcggc cgtcaaggcg cccaggtgcc ccgacctcaa cctggacctc    540

tgcatcagcc cgccgtgcca gcatgaggac gacggcgagg aggaggacga ggagctggac    600

ctcaagcccg ccttcgtcaa gcgggaggcg ctgcaggccg gccacggcca cggccacggc    660

ctctgcctcg gctgcggcct gggcggacag aagggagcgg ccgggtgcag ctgcagcaac    720

ggccaccact tcctggggct caggaccagc gtgctcgact tcagaggcct ggagatgaag    780

tga                                                                  783
```

```
<210> SEQ ID NO 55
<211> LENGTH: 828
<212> TYPE: DNA
<213> ORGANISM: Zea mays

<400> SEQUENCE: 55

atggggaggt cgccgtgctg cgagaaggcg cacaccaaca agggcgcgtg gaccaaggag     60

gaggacgagc gcctggtcgc gcacatcagg gcgcacggcg aggggtgctg gcgctcgctg    120

cccaaggccg ccggcctcct gcgctgcggc aagagctgcc gcctccgctg gatcaactac    180

ctccgccccg acctcaagcg cggcaacttc acggaggaag aggacgagct catcgtcaag    240

ctgcacagcg tcctcggcaa caagtggtcc ctgatcgccg gaaggctgcc cggcaggacg    300

gacaacgaga tcaagaacta ctggaacacg cacatccgga ggaagctgct gagcaggggg    360

atcgacccgg tgacgcaccg cccggtcacg gagcaccacg cgtccaacat caccatatcg    420

ttcgagacgg aagtggccgc cgctgcccgt gatgataaga agggcgccgt cttccggttg    480
```

```
gaggacgagg aggaggagga gcgcaacaag gcgacgatgg tcgtcggccg cgaccggcag    540

agccagagcc acagccacag ccaccccgcc ggcgagtggg gccaggggaa gaggccgctc    600

aagtgccccg acctcaacct ggacctctgc atcagcccgc cgtgccagga ggaggaggag    660

atggaggagg ctgcgatgag agtgagaccg gcggtgaagc gggaggccgg gctctgcttc    720

ggctgcagcc tggggctccc caggaccgcg gactgcaagt gcagcagcag cagcttcctc    780

gggctcagga ccgccatgct cgacttcaga agcctcgaga tgaaatga                 828
```

<210> SEQ ID NO 56
<211> LENGTH: 771
<212> TYPE: DNA
<213> ORGANISM: Panicum virgatum

<400> SEQUENCE: 56

```
atggggcgat cgccgtgctg cgagaaggcg cacacgaaca agggcgcctg gaccaaggag     60

gaggacgacc gcctcgttgc ctacatccgg gcgcacggcg aggggtgctg gcgctccctc    120

cccaaggccg cgggcctgct gcgctgcggc aagagctgcc gcctgcgctg gatcaactac    180

ctccgcccgg acctcaagcg cggcaacttc accgccgacg aggacgacct catcgtcaag    240

ctccacagcc tcctcggcaa caagtggtcg ctcatcgccg cgcgcctccc cggccgcacc    300

gacaacgaga tcaagaacta ctggaacacg cacatcaagc gcaagctcct cagccgcggc    360

atcgaccccg tcacacaccg ccccatcgcc gacgcagcca gaaacgtcac catctccttc    420

cagcccgacg cgccgtcgca gcagcagctc agcgacgacg ccgaggcgcc gccgccgccg    480

ccgccgcagc agcagcagca gctcaagccg ccgcccaggt gccccgacct caatctcgac    540

ctctgcatca gcccgccctg ccacaaggaa gaagaggacc aggagctcgt caagcccgcc    600

gccgtcaagc gcgagatgct gcaggccggc cacggcactc taggactctg cttcggctgc    660

agcctgggcc tccagaaggg cgccgccggg tgcacctgca gcagcaacag ccacttcctg    720

gggctcaggg tcggcatgct cctcgacttc agaggcctcg agatgaagtg a             771
```

<210> SEQ ID NO 57
<211> LENGTH: 2496
<212> TYPE: DNA
<213> ORGANISM: Artificial
<220> FEATURE:
<223> OTHER INFORMATION: Construct No. 001

<400> SEQUENCE: 57

```
acgtacctcg tgtccaccgg tgactctatc cccggcgtta gaagtgatga tagtctcgtt     60

cccaagggaa atcagccttc gaattggaat tgatccctcc ggacattttg tgccgttcgt    120

gtgccagact tgccatccat ataatgcatc ttcttctttt tttcccgcag atggcatgtc    180

cgttggtctt tcctgtatca tttatttaca aaagaaaaat aaattaaaca tttattaagt    240

tccccccgta aaaaaaaaat atatatatat atatatatat aacacatgca tcataattgg    300

tatgtccgta ggtgtttcct tatcataact gaaccattgg taaactatcg gttccgttaa    360

agcataagac tagaaaaggc tcggtgcgac tcgctaccac gtttctaaag attttattta    420

gcaaattaac cccaatatat attttgctat gagggtctaa acaaactggt atatgagcca    480

tttacttacc acttattagt tccaagtatt tattttttgg gttaattaat gtttaaatta    540

ttggttgaca aaaaatataa aaataatggt taagttattg aaatgacttg agcaatctga    600

tgcaactgcg gataacatga actcattcga agtgacgtcc caaatatttg attctttgtt    660

tttattcctt tttgtcaagg tcaagattgg ccaaacattt tcaatatcta aatatattga    720
```

```
cattcatagc ctggaaaaga aaaaatatat ggttaaatta gttccaaagt attctagcag    780

caacaaaacc gctccaataa acgatttcca atttctatct caaacttgtt tcccaatcat    840

tagttataat ccgtccccta aaccaaaaaa aaatctaatt gtaaaggtgt tgcaatagat    900

taaccatttt tatttttattt tggtaaaata gattaaccat tttgttagaa aaatgaagtt    960

taaaacattt acagttctac gtgtacatgc ttcgaccaat atgcttcgac caatatggca   1020

aggtctcctt gctgtgagaa agaccacaca aacaaaggag cttggactaa ggaagaagac   1080

gataagctca tctcttacat caaagctcac ggtgaaggtt gttggcgttc tcttcctaga   1140

tccgccggtc ttcaacgttg cggaaaaagc tgtcgtctcc gatggattaa ctatctccga   1200

cctgatctca agaggggtaa cttcaccctc gaagaagatg atctcatcat caaactacat   1260

agccttctcg gtaacaagtg gtctcttatt gcgacgagat taccaggaag aacagataac   1320

gagattaaga attactggaa cacacatgtt aagaggaagc tattaagaaa agggattgat   1380

ccggcgactc atcgacctat caacgagacc aaaacttctc aagattcgtc tgattctagt   1440

aaaacagagg accctcttgt caagattctc tcttttggtc ctcagctgga gaaaatagca   1500

aatttcgggg acgagagaat tcaaaagaga gttgagtact cagttgttga agaaagatgt   1560

ctggacttga atcttgagct taggatcagt ccaccatggc aagacaagct ccatgatgag   1620

aggaacctaa ggtttgggag agtgaagtat aggtgcagtg cgtgccgttt tggattcggg   1680

aacggcaagg agtgtagctg taataatgtg aaatgtcaaa cagaggacag tagtagcagc   1740

agttattctt caaccgacat tagtagtagc attggttatg acttcttggg tctaaacaac   1800

actagggttt tggattttag cactttggaa atgaaatgac acgtgtgaat tacaggtgac   1860

cagctcgaat ttccccgata gctttcgttc gtatcatcgg tttcgacaac gttcgtcaag   1920

ttcaatgcat cagtttcatt gcgcacacac cagaatccta ctgagttcga gtattatggc   1980

attgggaaac atgtttttct tgtaccattt gttgtgcttg taatttactg tgttttttat   2040

tcggttttcg ctatcgaact gtgaaatgga aatggatgga gaagagttaa tgaatgatat   2100

ggtccttttg ttcattctca aattaatatt atttgttttt tctcttattt gttgtgtgtt   2160

gaatttgaaa atataagaga tatgcaaaca ttttgttttg agtaaaaatg tgtcaaatcg   2220

tggcctctaa tgaccgaagt taatatgagg agtaaaacac ttgtagttgt accattatgc   2280

ttattcacta ggcaacaaat atattttcag acctagaaaa gctgcaaatg ttactgaata   2340

caagtatgtc ctcttgtgtt ttagacattt atgaactttc ctttatgtaa ttttccagaa   2400

tccttgtcag attctaatca ttgctttata attatagtta tactcatgga tttgtagttg   2460

agtatgaaaa tattttttaa tgcattttat gacttg                             2496
```

<210> SEQ ID NO 58
<211> LENGTH: 2778
<212> TYPE: DNA
<213> ORGANISM: Artificial
<220> FEATURE:
<223> OTHER INFORMATION: Construct No. 002

<400> SEQUENCE: 58

```
atacatgtca tgattttata attatgtata tataaatact aattgatgta tgaagtacgt     60

agataatgtt acgatctatt aatctattta cattaacttt taattagtgt tgagtaggga    120

aaattaacat ataaaccttt agcagttggt tgtattatta aaaataattt gaacttaaaa    180

tccaccttcg aaaagataaa tcaaacaagt ataaaaaatg ctataaatcc agaatattta    240
```

```
cctaaggttt ttattcttct acttaataat gtaagataaa accggcacaa tacttgttac    300

gtatgcatgg taggtaccgc aattgtgtaa gcaaatcggc acaatactaa ggttacatat    360

actaactaaa taaaacaatc tgatttcagt gacaccgtat atctaacctt tattcaaatc    420

caagggaaca tgacttgact tcttctgttg gaactaactc gatccctcaa ccatctccag    480

ggatagaaga gttagtaaaa tcaaacttga agtgaggaag taagcagttt aacgactcca    540

tatgactaca gttatataca aagttgggca caaagtacaa gtactaaata ctcaaagtca    600

gataataatt ttaataagta caaactatat atatgcagta caattattga gtatatataa    660

acgagactgg tgatttgggg cattgtccac cagggtgtta tatcccaatt gaaatttgaa    720

aatttaagtg tgtgagtgtt acgacaaaaa aaagtgtgtg aattgtaggc gcggtgaaaa    780

ggtaaattaa gattggaact agaaaaatag ttgaatatcc tttactaaaa gttgtcaatt    840

ccggttttag taaaaaaaaa ttttaaaata gaaattttat ccaaaagact tcaaacacac    900

atattcgcat atataacata agatatcatt ttttgtaaac agttaaaaag aaaaacacat    960

gttttttttt ttaatttaga aaaaaacatg ttattataca aaacagagtt ttgcccactt   1020

ttaatatgtt atgaaaagaa aaatgatttt cttgggtttg gtcagagaga ttggttgtgg   1080

taagaatggg aatcttaatt acaaagaatt ggattttggg tcgacctacc acctaaaacg   1140

acgtcgcctc catctctggt ttccaaatct ctttctcctc tccctttata agcttgcgtt   1200

ggccagtcgc tcatctcgaa aacagagaga aaaagactaa aaacacagtt taagaagaag   1260

gagagataga gagagaagag aaagatagag agggagatgg caaggtctcc ttgctgtgag   1320

aaagaccaca caaacaaagg agcttggact aaggaagaag acgataagct catctcttac   1380

atcaaagctc acggtgaagg ttgttggcgt tctcttccta gatccgccgg tcttcaacgt   1440

tgcggaaaaa gctgtcgtct ccgatggatt aactatctcc gacctgatct caagaggggt   1500

aacttcaccc tcgaagaaga tgatctcatc atcaaactac atagccttct cggtaacaag   1560

tggtctctta ttgcgacgag attaccagga agaacagata acgagattaa gaattactgg   1620

aacacacatg ttaagaggaa gctattaaga aaagggattg atccggcgac tcatcgacct   1680

atcaacgaga ccaaaacttc tcaagattcg tctgattcta gtaaaacaga ggaccctctt   1740

gtcaagattc tctcttttgg tcctcagctg gagaaaatag caaatttcgg ggacgagaga   1800

attcaaaaga gagttgagta ctcagttgtt gaagaaagat gtctggactt gaatcttgag   1860

cttaggatca gtccaccatg gcaagacaag ctccatgatg agaggaacct aaggtttggg   1920

agagtgaagt ataggtgcag tgcgtgccgt tttggattcg ggaacggcaa ggagtgtagc   1980

tgtaataatg tgaaatgtca aacagaggac agtagtagca gcagttattc ttcaaccgac   2040

attagtagta gcattggtta tgacttcttg ggtctaaaca acactagggt tttggatttt   2100

agcactttgg aaatgaaatg acacgtgtga attacaggtg accagctcga atttccccga   2160

tagctttcgt tcgtatcatc ggtttcgaca acgttcgtca agttcaatgc atcagtttca   2220

ttgcgcacac accagaatcc tactgagttc gagtattatg gcattgggaa acatgttttt   2280

cttgtaccat ttgttgtgct tgtaatttac tgtgtttttt attcggtttt cgctatcgaa   2340

ctgtgaaatg gaaatggatg gagaagagtt aatgaatgat atggtccttt tgttcattct   2400

caaattaata ttatttgttt tttctcttat ttgttgtgtg ttgaatttga aaatataaga   2460

gatatgcaaa cattttgttt tgagtaaaaa tgtgtcaaat cgtggcctct aatgaccgaa   2520

gttaatatga ggagtaaaac acttgtagtt gtaccattat gcttattcac taggcaacaa   2580

atatattttc agacctagaa aagctgcaaa tgttactgaa tacaagtatg tcctcttgtg   2640
```

ttttagacat ttatgaactt tcctttatgt aattttccag aatccttgtc agattctaat 2700
cattgcttta taattatagt tatactcatg gatttgtagt tgagtatgaa aatattttt 2760 aatgcatttt atgacttg 2778

<210> SEQ ID NO 59
<211> LENGTH: 2482
<212> TYPE: DNA
<213> ORGANISM: Artificial
<220> FEATURE:
<223> OTHER INFORMATION: Construct No. 003

<400> SEQUENCE: 59
aactagaaca cttcagataa attttgtcgt tctgttgact tcatttattc tctaaacaca 60
aagaactata gaccataatc gaaataaaaa ccctaaaaac caaatttatc tatttaaaac 120
aaacattagc tatttgagtt tcttttaggt aagttattta aggttttgga gactttaaga 180
tgttttcagc atttatggtt gtgtcattaa tttgtttagt ttagtaaaga aagaaaagat 240
agtaattaaa gagttggttg tgaaatcata tttaaaacat taataggtat ttatgtctaa 300
tttggggaca aaatagtgga attctttatc atatctagct agttcttatc gagtttgaac 360
tcgggttatg attatgttac atgcattggt ccatataaat ctatgagcaa tcaatataat 420
tcgagcattt tggtataaca taatgagcca agtataacaa aagtatcaaa cctatgcagg 480
ggagaagatg atgaaaagaa gagtgtgagc caatacaaag cagatttgag gacatggctt 540
acaagtcttg ggtacagagt ttggggagtg atgggtgcac aatggaacag cttctctggt 600
tgtccagttc ccaagagaac cttcaagctc cctaactcca tctactatgt cgcctgatta 660
aatcttattt actaacaaaa caataagatc agagtttcat tctgattctt gagtcttttt 720
tttctctctc cctcttttca tttctggttt atataaccaa ttcaaatgct tatgatccat 780
gcatgaacca tgatcatctt tgtgtttttt tttccttctg tattaccatt ttgggccttt 840
gtgaaattga ttttgggctt ttgttatata atctcctctt tctctttctc tacctgattg 900
gattcaagaa catagccaga tttggtaaag tttataagat acaaaatatt aagtaagact 960
aaagtagaaa tacataataa cttgaaagct actctaagtt atggcaaggt ctccttgctg 1020
tgagaaagac cacacaaaca aaggagcttg gactaaggaa gaagacgata agctcatctc 1080
ttacatcaaa gctcacggtg aaggttgttg gcgttctctt cctagatccg ccggtcttca 1140
acgttgcgga aaaagctgtc gtctccgatg gattaactat ctccgacctg atctcaagag 1200
gggtaacttc accctcgaag aagatgatct catcatcaaa ctacatagcc ttctcggtaa 1260
caagtggtct cttattgcga cgagattacc aggaagaaca gataacgaga ttaagaatta 1320
ctggaacaca catgttaaga ggaagctatt aagaaaaggg attgatccgg cgactcatcg 1380
acctatcaac gagaccaaaa cttctcaaga ttcgtctgat tctagtaaaa cagaggaccc 1440
tcttgtcaag attctctctt ttggtcctca gctggagaaa atagcaaatt tcggggacga 1500
gagaattcaa aagagagttg agtactcagt tgttgaagaa agatgtctgg acttgaatct 1560
tgagcttagg atcagtccac catggcaaga caagctccat gatgagagga acctaaggtt 1620
tgggagagtg aagtataggt gcagtgcgtg ccgttttgga ttcgggaacg gcaaggagtg 1680
tagctgtaat aatgtgaaat gtcaaacaga ggacagtagt agcagcagtt attcttcaac 1740
cgacattagt agtagcattg gttatgactt cttgggtcta aacaacacta gggttttgga 1800
ttttagcact ttggaaatga aatgacacgt gtgaattaca ggtgaccagc tcgaatttcc 1860

```
ccgatagctt tcgttcgtat catcggtttc gacaacgttc gtcaagttca atgcatcagt   1920
ttcattgcgc acacaccaga atcctactga gttcgagtat tatggcattg ggaaacatgt   1980
ttttcttgta ccatttgttg tgcttgtaat ttactgtgtt ttttattcgg ttttcgctat   2040
cgaactgtga aatggaaatg gatggagaag agttaatgaa tgatatggtc cttttgttca   2100
ttctcaaatt aatattattt gttttttctc ttatttgttg tgtgttgaat ttgaaaatat   2160
aagagatatg caaacatttt gttttgagta aaaatgtgtc aaatcgtggc ctctaatgac   2220
cgaagttaat atgaggagta aaacacttgt agttgtacca ttatgcttat tcactaggca   2280
acaaatatat tttcagacct agaaaagctg caaatgttac tgaatacaag tatgtcctct   2340
tgtgttttag acatttatga actttccttt atgtaatttt ccagaatcct tgtcagattc   2400
taatcattgc tttataatta tagttatact catggatttg tagttgagta tgaaaatatt   2460
ttttaatgca ttttatgact tg                                            2482
```

<210> SEQ ID NO 60
<211> LENGTH: 2546
<212> TYPE: DNA
<213> ORGANISM: Artificial
<220> FEATURE:
<223> OTHER INFORMATION: Construct No. 004

<400> SEQUENCE: 60

```
aacccataac tttagtattc ttcaaccctt acaacttatc tgagcaaaat cagaaggtcg     60
aatttgatgg atggttttgc tgtatttggt caacggtttt atttgagaca gtagaccaga    120
ggaaactcag atgtgatgat gcaaagactg aattggttaa gagtgtagat tgatttgttc    180
taacattgca aatgtagagt agaattatgc aaaaaacgtt aatgaacaga gaagtgatta    240
agcagaaaca aaattagaga agtgatatta tatctcaaaa tttatttttg gtacagctaa    300
agctcaaatt gttatagaga ttagagatat taaaccaaat gacgagtgtt ttctttagta    360
gtaaacggtg aaaattctct tctgacaaag acaattaaaa ttttaggttt aagactttaa    420
tatttgtcac aaattgtcat ttacctaaat aaaaaaaaaa ctaaatattt tttttagata    480
catatgtgtc ttataatttt aactataaat tttaatttta tgtcttaaat aattgtttac    540
actataaatt taaatatttt aatgctaaaa ttaatttgat tcaaaaaagt gattttaatt    600
cttatttttc ttatagaaag ttggtgattg aaaagattta cttaaaaatt ataacaactt    660
caatggtgaa taacccgacc cgaataaacc ggatataaca acttcaatgt tagcttgata    720
tagaaagtac ggtgacgctt aggaggcaag caagctagta tctgccgctg gttagagaca    780
aagaacatgt gtcactcctc tcaactaaaa ctttccttca ctttcccgca aaatcatttc    840
aaaaaagctc caaatttagc ttacccatca gctttctcag aaaaccagtg aaagaaactt    900
ctcaacttcc gatttttcac aatccaccaa acttttttta ataacttttt ttcctcttat    960
tacaaaacct ccactctcat ggcttctcaa acttgttatc catccaaatc tcaatcccta   1020
attagggttc atttctctgt ttctccaaac aggggaattc gaagatggca aggtctcctt   1080
gctgtgagaa agaccacaca aacaaaggag cttggactaa ggaagaagac gataagctca   1140
tctcttacat caaagctcac ggtgaaggtt gttggcgttc tcttcctaga tccgccggtc   1200
ttcaacgttg cggaaaaagc tgtcgtctcc gatggattaa ctatctccga cctgatctca   1260
agaggggtaa cttcaccctc gaagaagatg atctcatcat caaactacat agccttctcg   1320
gtaacaagtg gtctcttatt gcgacgagat taccaggaag aacagataac gagattaaga   1380
attactggaa cacacatgtt aagaggaagc tattaagaaa agggattgat ccggcgactc   1440
```

```
atcgacctat caacgagacc aaaacttctc aagattcgtc tgattctagt aaaacagagg   1500

accctcttgt caagattctc tcttttggtc ctcagctgga gaaaatagca aatttcgggg   1560

acgagagaat tcaaaagaga gttgagtact cagttgttga agaaagatgt ctggacttga   1620

atcttgagct taggatcagt ccaccatggc aagacaagct ccatgatgag aggaacctaa   1680

ggtttgggag agtgaagtat aggtgcagtg cgtgccgttt tggattcggg aacggcaagg   1740

agtgtagctg taataatgtg aaatgtcaaa cagaggacag tagtagcagc agttattctt   1800

caaccgacat tagtagtagc attggttatg acttcttggg tctaaacaac actagggttt   1860

tggattttag cactttggaa atgaaatgac acgtgtgaat tacaggtgac cagctcgaat   1920

ttccccgata gctttcgttc gtatcatcgg tttcgacaac gttcgtcaag ttcaatgcat   1980

cagtttcatt gcgcacacac cagaatccta ctgagttcga gtattatggc attgggaaac   2040

atgtttttct tgtaccattt gttgtgcttg taatttactg tgtttttat tcggttttcg   2100

ctatcgaact gtgaaatgga aatggatgga gaagagttaa tgaatgatat ggtccttttg   2160

ttcattctca aattaatatt atttgttttt tctcttattt gttgtgtgtt gaatttgaaa   2220

atataagaga tatgcaaaca ttttgttttg agtaaaaatg tgtcaaatcg tggcctctaa   2280

tgaccgaagt taatatgagg agtaaaacac ttgtagttgt accattatgc ttattcacta   2340

ggcaacaaat atattttcag acctagaaaa gctgcaaatg ttactgaata caagtatgtc   2400

ctcttgtgtt ttagacattt atgaactttc ctttatgtaa ttttccagaa tccttgtcag   2460

attctaatca ttgctttata attatagtta tactcatgga tttgtagttg agtatgaaaa   2520

tattttttaa tgcattttat gacttg                                        2546
```

```
<210> SEQ ID NO 61
<211> LENGTH: 2501
<212> TYPE: DNA
<213> ORGANISM: Artificial
<220> FEATURE:
<223> OTHER INFORMATION: Construct No. 005

<400> SEQUENCE: 61

tcttcttgca tcaatgatat caacaacaat gggtaataaa gaagctactt cgaaattata     60

tattttttcg tattctatat tgatcatcag tcttaagtgg tttggtttgt tgcagtgaag    120

aagaactatg tatggatcta cgccaccgtt cagttcggtt ttgtggtcct tttcgctcag    180

cttttctaca gagttgtaag atttgatgta atgtcacaga gaaaccttac tttgttgtca    240

cagagaaacc ttactttgtt gaagagtttt tgattcctca cactctctct cattaacttg    300

tgtgtaggtg aagcagccgg taatgtgcat tgtcttagcc actatgatcg gatttggact    360

caccatgacc ggcacaacag ctattaacga gtatttgaaa tggaggagaa gcaattccca    420

cctgccagaa gagccagcaa gtactcaggt ggtttgacag cagcgtagat cttttgagtg    480

aagctagagt ccctaaaggg ttggatcggt tttcaattaa ccggtcggga ttcggttttc    540

ggtttagctt taatcgactt gtctaggttg agatcagatt tggttttcaa tacttccaag    600

tctttttttt tttgccaact aaaatataag gaatgatgat aggcacacac atgacacata    660

aaatcataat gaacagtagt atgattagca atccatattt cttggataac acttcttcac    720

agctttttttg acaggtcact ataacacctt tttcagttca tttttcattt tcaatcctca    780

cccacccaaa ctctcccttc aaagcaatgt ctctcctctc tctttctcaa ttcaaacaaa    840

ctttattaaa cctaaaagaa acatttccaa tctctaatga cttagttgat agaatctcat    900
```

```
ttagttacct agtaataatc ttcacactag taagagaatc ctactcttca ccaaactaca     960

tctctctcta tataacaaac cccaaaacat ctcaacatac acacacaaca actacaacaa    1020

tggcaaggtc tccttgctgt gagaaagacc acacaaacaa aggagcttgg actaaggaag    1080

aagacgataa gctcatctct tacatcaaag ctcacggtga aggttgttgg cgttctcttc    1140

ctagatccgc cggtcttcaa cgttgcggaa aaagctgtcg tctccgatgg attaactatc    1200

tccgacctga tctcaagagg ggtaacttca ccctcgaaga agatgatctc atcatcaaac    1260

tacatagcct tctcggtaac aagtggtctc ttattgcgac gagattacca ggaagaacag    1320

ataacgagat taagaattac tggaacacac atgttaagag gaagctatta agaaaaggga    1380

ttgatccggc gactcatcga cctatcaacg agaccaaaac ttctcaagat tcgtctgatt    1440

ctagtaaaac agaggaccct cttgtcaaga ttctctcttt tggtcctcag ctggagaaaa    1500

tagcaaattt cggggacgag agaattcaaa agagagttga gtactcagtt gttgaagaaa    1560

gatgtctgga cttgaatctt gagcttagga tcagtccacc atggcaagac aagctccatg    1620

atgagaggaa cctaaggttt gggagagtga agtataggtg cagtgcgtgc cgttttggat    1680

tcgggaacgg caaggagtgt agctgtaata atgtgaaatg tcaaacagag gacagtagta    1740

gcagcagtta ttcttcaacc gacattagta gtagcattgg ttatgacttc ttgggtctaa    1800

acaacactag ggttttggat tttagcactt tggaaatgaa atgacacgtg tgaattacag    1860

gtgaccagct cgaatttccc cgatagcttt cgttcgtatc atcggtttcg acaacgttcg    1920

tcaagttcaa tgcatcagtt tcattgcgca cacaccagaa tcctactgag ttcgagtatt    1980

atggcattgg gaaacatgtt tttcttgtac catttgttgt gcttgtaatt tactgtgttt    2040

tttattcggt tttcgctatc gaactgtgaa atggaaatgg atggagaaga gttaatgaat    2100

gatatggtcc ttttgttcat tctcaaatta atattatttg ttttttctct tatttgttgt    2160

gtgttgaatt tgaaaatata agagatatgc aaacattttg ttttgagtaa aaatgtgtca    2220

aatcgtggcc tctaatgacc gaagttaata tgaggagtaa aacacttgta gttgtaccat    2280

tatgcttatt cactaggcaa caaatatatt ttcagaccta gaaaagctgc aaatgttact    2340

gaatacaagt atgtcctctt gtgttttaga catttatgaa ctttccttta tgtaattttc    2400

cagaatcctt gtcagattct aatcattgct ttataattat agttatactc atggatttgt    2460

agttgagtat gaaaatattt tttaatgcat tttatgactt g                        2501
```

<210> SEQ ID NO 62
<211> LENGTH: 2575
<212> TYPE: DNA
<213> ORGANISM: Artificial
<220> FEATURE:
<223> OTHER INFORMATION: Construct No. 006

<400> SEQUENCE: 62

```
tgcgaacagt ttgattctgt ttttcttttt ccttttttttg ggtaattttc ttataacttt      60

tttcatagtt tcgattattt ggataaaatt ttcagattga ggatcatttt atttatttat     120

tagtgtagtc taatttagtt gtataactat aaaattgttg tttgtttccg aatcataagt     180

ttttttttt tttggttttg tattgatagg tgcaagagac tcaaaattct ggtttcgatg     240

ttaacagaat tcaagtagct gcccacttga ttcgatttgt tttgtatttg gaaacaacca     300

tggctggtca aggcccagcc cgttgtgctt ctgaacctgc ctagtcccat ggactagatc     360

tttatccgca gactccaaaa gaaaaaggat tggcgcagag gaattgtcat ggaaacagaa     420

tgaacaagaa agggtgaaga agatcaaagg catatatgat ctttacattc tctttagctt     480
```

```
atgtatgcag aaaattcacc taattaagga cagggaacgt aacttggctt gcactcctct    540

caccaaacct tacccoctaa ctaattttaa ttcaaaatta ctagtatttt ggccgatcac    600

tttatataat aagataccag atttattata tttacgaatt atcagcatgc atatactgta    660

tatagttttt tttttgttaa agggtaaaat aataggatcc ttttgaataa aatgaacata    720

tataattagt ataatgaaaa cagaaggaaa tgagattagg acagtaagta aaatgagaga    780

gacctgcaaa ggataaaaaa gagaagctta aggaaaccgc gacgatgaaa gaaagacatg    840

tcatcagctg atggatgtga gtgatgagtt tgttgcagtt gtgtagaaat ttttactaaa    900

acagttgttt ttacaaaaaa gaaataatat aaaacgaaag cttagcttga aggcaatgga    960

gactctacaa caaactatgt accatacaga gagagaaact aaaagctttt cacacataaa   1020

aaccaaactt attcgtctct cattgatcac cgttttgttc tctcaagatc gctgctaatc   1080

tccggccgtc cctatggcaa ggtctccttg ctgtgagaaa gaccacacaa acaaaggagc   1140

ttggactaag gaagaagacg ataagctcat ctcttacatc aaagctcacg gtgaaggttg   1200

ttggcgttct cttcctagat ccgccggtct tcaacgttgc ggaaaaagct gtcgtctccg   1260

atggattaac tatctccgac ctgatctcaa gaggggtaac ttcaccctcg aagaagatga   1320

tctcatcatc aaactacata gccttctcgg taacaagtgg tctcttattg cgacgagatt   1380

accaggaaga acagataacg agattaagaa ttactggaac acacatgtta agaggaagct   1440

attaagaaaa gggattgatc cggcgactca tcgacctatc aacgagacca aaacttctca   1500

agattcgtct gattctagta aaacagagga ccctcttgtc aagattctct cttttggtcc   1560

tcagctggag aaaatagcaa atttcgggga cgagagaatt caaaagagag ttgagtactc   1620

agttgttgaa gaaagatgtc tggacttgaa tcttgagctt aggatcagtc caccatggca   1680

agacaagctc catgatgaga ggaacctaag gtttgggaga gtgaagtata ggtgcagtgc   1740

gtgccgtttt ggattcggga acggcaagga gtgtagctgt aataatgtga aatgtcaaac   1800

agaggacagt agtagcagca gttattcttc aaccgacatt agtagtagca ttggttatga   1860

cttcttgggt ctaaacaaca ctagggtttt ggattttagc actttggaaa tgaaatgaca   1920

cgtgtgaatt acaggtgacc agctcgaatt tccccgatag ctttcgttcg tatcatcggt   1980

ttcgacaacg ttcgtcaagt tcaatgcatc agtttcattg cgcacacacc agaatcctac   2040

tgagttcgag tattatggca ttgggaaaca tgtttttctt gtaccatttg ttgtgcttgt   2100

aatttactgt gtttttttatt cggttttcgc tatcgaactg tgaaatggaa atggatggag   2160

aagagttaat gaatgatatg gtccttttgt tcattctcaa attaatatta tttgtttttt   2220

ctcttatttg ttgtgtgttg aatttgaaaa tataagagat atgcaaacat tttgttttga   2280

gtaaaaatgt gtcaaatcgt ggcctctaat gaccgaagtt aatatgagga gtaaaacact   2340

tgtagttgta ccattatgct tattcactag gcaacaaata tattttcaga cctagaaaag   2400

ctgcaaatgt tactgaatac aagtatgtcc tcttgtgttt tagacattta tgaactttcc   2460

tttatgtaat tttccagaat ccttgtcaga ttctaatcat tgctttataa ttatagttat   2520

actcatggat ttgtagttga gtatgaaaat attttttaat gcattttatg acttg        2575
```

<210> SEQ ID NO 63
<211> LENGTH: 2628
<212> TYPE: DNA
<213> ORGANISM: Artificial
<220> FEATURE:
<223> OTHER INFORMATION: Construct No. 007

<400> SEQUENCE: 63

```
tctctaattg tcaagtatct tagtctagag ttaattactt aaatactaaa aggctgtcga     60
caaaatcaag cttgaatctc cttgtggtat cttcaactct tcgttgtctg cttacgagtg    120
gtttactcag taattatcta taatatgtta tttttttcc ctcatctttt agttgttgtt    180
tcattacatt gaaaagcttg taatgtcttt atatggtata tatggatctt atgagtgagg    240
caagatccat gatgttttg atcttagaat gtatatgatg atcttagaat gtatttgacc    300
gcccacaaat tattgttcat tgggattata tctctagtcc aactccaagc aatcgaaatg    360
ggtcctgctt ttaagaacaa cagtatatgt ttaagaataa taactttata tattctcgat    420
tttaagatct tttgacaaaa cctccttttc gttaggagcg tactaatttc caagtgtttg    480
attagtgggg tctccgtaaa tttatttaga gtttctatct atttattaat agctcaatta    540
attaatctat actgtatcta aacatcaatt tatatattta ctcttgagac caaaactgtc    600
aatttataac attggatagt ttcttaattc ttattatata tttttcaaac acttttcaag    660
actaatctcc acattaggta ctctctctag agataaaaat atttatcaaa aacattttta    720
tttatttatt aagtagtaga taaactactg tggcaaaatc gtaaatgtct aaatgctgat    780
gaattttttt tgctgctcca atctggttta gtgctccata tacatccacg gccaaaatga    840
atctatggcg gcattaagat tcattagtaa gcaacgatta tattaatata attgttttta    900
gcaatgattt tccgtaattt cccaaatatg tttcagttaa tgtgttccaa tcccaacaac    960
tggttgttgc aaaagaccac caacgcaagc aatcatcaaa catcaaaata atcttacctt   1020
agcgaacaaa caataactac acaattctca taaagctctt atatatcact aacttcacac   1080
attttgtttt ccacaaaaat aaaaacggaa ctcactcaag aaaccttctt ccttgaagag   1140
agggttatgg caaggtctcc ttgctgtgag aaagaccaca caaacaaagg agcttggact   1200
aaggaagaag acgataagct catctcttac atcaaagctc acggtgaagg ttgttggcgt   1260
tctcttccta gatccgccgg tcttcaacgt tgcggaaaaa gctgtcgtct ccgatggatt   1320
aactatctcc gacctgatct caagaggggt aacttcaccc tcgaagaaga tgatctcatc   1380
atcaaactac atagccttct cggtaacaag tggtctctta ttgcgacgag attaccagga   1440
agaacagata acgagattaa gaattactgg aacacacatg ttaagaggaa gctattaaga   1500
aaagggattg atccggcgac tcatcgacct atcaacgaga ccaaaacttc tcaagattcg   1560
tctgattcta gtaaaacaga ggaccctctt gtcaagattc tctcttttgg tcctcagctg   1620
gagaaaatag caaatttcgg ggacgagaga attcaaaaga gagttgagta ctcagttgtt   1680
gaagaaagat gtctggactt gaatcttgag cttaggatca gtccaccatg gcaagacaag   1740
ctccatgatg agaggaacct aaggtttggg agagtgaagt ataggtgcag tgcgtgccgt   1800
tttggattcg ggaacggcaa ggagtgtagc tgtaataatg tgaaatgtca aacagaggac   1860
agtagtagca gcagttattc ttcaaccgac attagtagta gcattggtta tgacttcttg   1920
ggtctaaaca acactagggt tttggatttt agcactttgg aaatgaaatg acacgtgtga   1980
attacaggtg accagctcga atttccccga tagctttcgt tcgtatcatc ggtttcgaca   2040
acgttcgtca agttcaatgc atcagtttca ttgcgcacac accagaatcc tactgagttc   2100
gagtattatg gcattgggaa acatgttttt cttgtaccat ttgttgtgct tgtaatttac   2160
tgtgtttttt attcggtttt cgctatcgaa ctgtgaaatg gaaatggatg gagaagagtt   2220
aatgaatgat atggtccttt tgttcattct caaattaata ttatttgttt tttctcttat   2280
ttgttgtgtg ttgaatttga aaatataaga gatatgcaaa cattttgttt tgagtaaaaa   2340
```

```
tgtgtcaaat cgtggcctct aatgaccgaa gttaatatga ggagtaaaac acttgtagtt   2400

gtaccattat gcttattcac taggcaacaa atatattttc agacctagaa aagctgcaaa   2460

tgttactgaa tacaagtatg tcctcttgtg ttttagacat ttatgaactt tcctttatgt   2520

aattttccag aatccttgtc agattctaat cattgcttta taattatagt tatactcatg   2580

gatttgtagt tgagtatgaa aatatttttt aatgcatttt atgacttg                2628
```

<210> SEQ ID NO 64
<211> LENGTH: 2506
<212> TYPE: DNA
<213> ORGANISM: Artificial
<220> FEATURE:
<223> OTHER INFORMATION: Construct No. 008

<400> SEQUENCE: 64

```
aactagaaca cttcagataa attttgtcgt tctgttgact tcatttattc tctaaacaca     60

aagaactata gaccataatc gaaataaaaa ccctaaaaac caaatttatc tatttaaaac    120

aaacattagc tatttgagtt tcttttaggt aagttattta aggttttgga gactttaaga    180

tgttttcagc atttatggtt gtgtcattaa tttgtttagt ttagtaaaga aagaaaagat    240

agtaattaaa gagttggttg tgaaatcata tttaaaacat taataggtat ttatgtctaa    300

tttggggaca aaatagtgga attctttatc atatctagct agttcttatc gagtttgaac    360

tcgggttatg attatgttac atgcattggt ccatataaat ctatgagcaa tcaatataat    420

tcgagcattt tggtataaca taatgagcca agtataacaa aagtatcaaa cctatgcagg    480

ggagaagatg atgaaaagaa gagtgtgagc caatacaaag cagatttgag gacatggctt    540

acaagtcttg ggtacagagt ttggggagtg atgggtgcac aatggaacag cttctctggt    600

tgtccagttc ccaagagaac cttcaagctc cctaactcca tctactatgt cgcctgatta    660

aatcttattt actaacaaaa caataagatc agagtttcat tctgattctt gagtcttttt    720

tttctctctc cctcttttca tttctggttt atataaccaa ttcaaatgct tatgatccat    780

gcatgaacca tgatcatctt tgtgtttttt tttccttctg tattaccatt ttgggccttt    840

gtgaaattga ttttgggctt ttgttatata atctcctctt tctctttctc tacctgattg    900

gattcaagaa catagccaga tttggtaaag tttataagat acaaaatatt aagtaagact    960

aaagtagaaa tacataataa cttgaaagct actctaagtt atgggaaggt caccgtgctg   1020

tgagaaagct cacacaaaca aaggagcatg gacgaaagaa gaggacgaga ggctcgtcgc   1080

ctacattaaa gctcatggag aaggctgctg gagatctctc cccaaagccg ccggacttct   1140

tcgctgtggc aagagctgcc gtctccggtg gatcaactat ctccggcctg accttaagcg   1200

tggaaacttc accgaggaag aagacgaact catcatcaag ctccatagcc ttcttggcaa   1260

caaatggtcg cttattgccg ggagattacc gggaagaaca gataacgaga taaagaacta   1320

ttggaacacg catatacgaa gaaagcttat aaacagaggg attgatccaa cgagtcatag   1380

accaatccaa gaatcatcag cttctcaaga ttctaaacct acacaactag aaccagttac   1440

gagtaatacc attaatatct cattcacttc tgctccaaag gtcgaaacgt tccatgaaag   1500

tataagcttt ccgggaaaat cagagaaaat ctcaatgctt acgttcaaag aagaaaaaga   1560

tgagtgccca gttcaagaaa agttcccaga tttgaatctt gagctcagaa tcagtcttcc   1620

tgatgatgtt gatcgtcttc aagggcatgg aaagtcaaca acgccacgtt gtttcaagtg   1680

cagcttaggg atgataaacg gcatggagtg cagatgcgga agaatgagat gcgatgtagt   1740
```

```
cggaggtagc agcaagggga gtgacatgag caatggattt gatttttttag ggttggcaaa   1800

gaaagagacc acttctcttt tgggctttcg aagcttggag atgaaataac acgtgtgaat   1860

tacaggtgac cagctcgaat ttccccgata gctttcgttc gtatcatcgg tttcgacaac   1920

gttcgtcaag ttcaatgcat cagtttcatt gcgcacacac cagaatccta ctgagttcga   1980

gtattatggc attgggaaac atgtttttct tgtaccattt gttgtgcttg taatttactg   2040

tgttttttat tcggttttcg ctatcgaact gtgaaatgga aatggatgga gaagagttaa   2100

tgaatgatat ggtccttttg ttcattctca aattaatatt atttgttttt tctcttattt   2160

gttgtgtgtt gaatttgaaa atataagaga tatgcaaaca ttttgttttg agtaaaaatg   2220

tgtcaaatcg tggcctctaa tgaccgaagt taatatgagg agtaaaacac ttgtagttgt   2280

accattatgc ttattcacta ggcaacaaat atattttcag acctagaaaa gctgcaaatg   2340

ttactgaata caagtatgtc ctcttgtgtt ttagacattt atgaactttc ctttatgtaa   2400

ttttccagaa tccttgtcag attctaatca ttgctttata attatagtta tactcatgga   2460

tttgtagttg agtatgaaaa tattttttaa tgcattttat gacttg                  2506
```

<210> SEQ ID NO 65
<211> LENGTH: 2570
<212> TYPE: DNA
<213> ORGANISM: Artificial
<220> FEATURE:
<223> OTHER INFORMATION: Construct No. 009

<400> SEQUENCE: 65

```
aacccataac tttagtattc ttcaaccctt acaacttatc tgagcaaaat cagaaggtcg     60

aatttgatgg atggttttgc tgtatttggt caacggtttt atttgagaca gtagaccaga    120

ggaaactcag atgtgatgat gcaaagactg aattggttaa gagtgtagat tgatttgttc    180

taacattgca aatgtagagt agaattatgc aaaaaacgtt aatgaacaga gaagtgatta    240

agcagaaaca aaattagaga agtgatatta tatctcaaaa tttatttttg gtacagctaa    300

agctcaaatt gttatagaga ttagagatat taaaccaaat gacgagtgtt ttctttagta    360

gtaaacggtg aaaattctct tctgacaaag acaattaaaa ttttaggttt aagactttaa    420

tatttgtcac aaattgtcat ttacctaaat aaaaaaaaaa ctaaatattt tttttagata    480

catatgtgtc ttataatttt aactataaat tttaatttta tgtcttaaat aattgtttac    540

actataaatt taaatatttt aatgctaaaa ttaatttgat tcaaaaaagt gattttaatt    600

cttatttttc ttatagaaag ttggtgattg aaaagattta cttaaaaatt ataacaactt    660

caatggtgaa taacccgacc cgaataaacc ggatataaca acttcaatgt tagcttgata    720

tagaaagtac ggtgacgctt aggaggcaag caagctagta tctgccgctg gttagagaca    780

aagaacatgt gtcactcctc tcaactaaaa ctttccttca ctttcccgca aaatcatttc    840

aaaaaagctc caaatttagc ttacccatca gctttctcag aaaaccagtg aaagaaactt    900

ctcaacttcc gatttttcac aatccaccaa acttttttta ataacttttt ttcctcttat    960

tacaaaacct ccactctcat ggcttctcaa acttgttatc catccaaatc tcaatcccta   1020

attagggttc atttctctgt ttctccaaac aggggaattc gaagatggga aggtcaccgt   1080

gctgtgagaa agctcacaca aacaaaggag catggacgaa agaagaggac gagaggctcg   1140

tcgcctacat taaagctcat ggagaaggct gctggagatc tctccccaaa gccgccggac   1200

ttcttcgctg tggcaagagc tgccgtctcc ggtggatcaa ctatctccgg cctgacctta   1260

agcgtggaaa cttcaccgag gaagaagacg aactcatcat caagctccat agccttcttg   1320
```

```
gcaacaaatg gtcgcttatt gccgggagat taccgggaag aacagataac gagataaaga   1380

actattggaa cacgcatata cgaagaaagc ttataaacag agggattgat ccaacgagtc   1440

atagaccaat ccaagaatca tcagcttctc aagattctaa acctacacaa ctagaaccag   1500

ttacgagtaa taccattaat atctcattca cttctgctcc aaaggtcgaa acgttccatg   1560

aaagtataag ctttccggga aaatcagaga aaatctcaat gcttacgttc aaagaagaaa   1620

aagatgagtg cccagttcaa gaaaagttcc cagatttgaa tcttgagctc agaatcagtc   1680

ttcctgatga tgttgatcgt cttcaagggc atggaaagtc aacaacgcca cgttgtttca   1740

agtgcagctt agggatgata aacggcatgg agtgcagatg cggaagaatg agatgcgatg   1800

tagtcggagg tagcagcaag gggagtgaca tgagcaatgg atttgatttt ttagggttgg   1860

caaagaaaga gaccacttct cttttgggct ttcgaagctt ggagatgaaa taacacgtgt   1920

gaattacagg tgaccagctc gaatttcccc gatagctttc gttcgtatca tcggtttcga   1980

caacgttcgt caagttcaat gcatcagttt cattgcgcac acaccagaat cctactgagt   2040

tcgagtatta tggcattggg aaacatgttt ttcttgtacc atttgttgtg cttgtaattt   2100

actgtgtttt ttattcggtt ttcgctatcg aactgtgaaa tggaaatgga tggagaagag   2160

ttaatgaatg atatggtcct tttgttcatt ctcaaattaa tattatttgt tttttctctt   2220

atttgttgtg tgttgaattt gaaaatataa gagatatgca aacattttgt tttgagtaaa   2280

aatgtgtcaa atcgtggcct ctaatgaccg aagttaatat gaggagtaaa acacttgtag   2340

ttgtaccatt atgcttattc actaggcaac aaatatattt tcagacctag aaaagctgca   2400

aatgttactg aatacaagta tgtcctcttg tgttttagac atttatgaac tttcctttat   2460

gtaattttcc agaatccttg tcagattcta atcattgctt tataattata gttatactca   2520

tggatttgta gttgagtatg aaaatatttt ttaatgcatt ttatgacttg              2570
```

<210> SEQ ID NO 66
<211> LENGTH: 2485
<212> TYPE: DNA
<213> ORGANISM: Artificial
<220> FEATURE:
<223> OTHER INFORMATION: Construct No. 010

<400> SEQUENCE: 66

```
aggcggggcc ggaggagggc accagagagg ctgctcagga gagagaaata atagaatatg     60

tggtatagag taaacatgag tgcggatgat tgtggtatag agtaaagaat tttgctgact    120

aggacagaat attcttttta gggtagaaat ttagagtact atgagtgcgg atagcctaag    180

gaccacttta aatttgacac aatattgaaa tttgaatggt tttaacattt gaaggctgaa    240

aaccaaaata ctttgtagct aagtgttgga aacccgactc ggccaataag tcgacagacc    300

gtaaaataag gtcaatctaa actttatgat aaatattctt gtttgatagc aatagcattg    360

caggaccagg acccaaggga agagaagatg ccaaatccca tcgaggctaa agcaaaaacg    420

atccaattta tgagcaaacc cacactgaag tttcaaaatt gttttctgaa aaaaaagtaa    480

ccagcaagtt aaaaaatgag atggcgggaa agccaagtct cggttggtcg aggggttggt    540

tggggcgcag cctgacaagt gacaacggca gcaggatagt agcatcaggc gcaagccagc    600

gcaggcggca gcgcgaggat ttcgcttcac ttagcggcaa cggagacgct gcacccaacc    660

aacacgagct ccccctcacc cgctgcgacg cgcgcgtccc acgagcggaa gccccccgcg    720

ccgacgcgag cgcgggggct cgaccgaccg acccaacgcc tccatctcca ccgcgcgcac    780
```

```
caaatcgcac tcccgtccgc cccgccgatc gaacagccac cgctcacctc tcccacccgc    840

caaaaacctc cggcctcctc tcatattcat atagctagcc cctgccacaa ggtagagcgt    900

cgctcacacc tgcgtcgccc tgcctcgcaa tcgcgaatct gtcgagcacc tgaggggtcg    960

gaggccgaga gctagcctag cacgccggcc tccgcgcgcg atggggaggt cgccgtgctg   1020

cgagaaggcg cacaccaaca agggcgcgtg gaccaaggag gaggacgagc gcctggtcgc   1080

gcacatcagg gcgcacggcg aggggtgctg gcgctcgctg cccaaggccg ccggcctcct   1140

gcgctgcggc aagagctgcc gcctccgctg gatcaactac ctccgccccg acctcaagcg   1200

cggcaacttc acggaggaag aggacgagct catcgtcaag ctgcacagcg tcctcggcaa   1260

caagtggtcc ctgatcgccg gaaggctgcc cggcaggacg gacaacgaga tcaagaacta   1320

ctggaacacg cacatccgga ggaagctgct gagcaggggg atcgacccgg tgacgcaccg   1380

cccggtcacg gagcaccacg cgtccaacat caccatatcg ttcgagacgg aagtggccgc   1440

cgctgcccgt gatgataaga agggcgccgt cttccggttg gaggacgagg aggaggagga   1500

gcgcaacaag gcgacgatgg tcgtcggccg cgaccggcag agccagagcc acagccacag   1560

ccaccccgcc ggcgagtggg gccaggggaa gaggccgctc aagtgccccg acctcaacct   1620

ggacctctgc atcagcccgc cgtgccagga ggaggaggag atggaggagg ctgcgatgag   1680

agtgagaccg gcggtgaagc gggaggccgg gctctgcttc ggctgcagcc tggggctccc   1740

caggaccgcg gactgcaagt gcagcagcag cagcttcctc gggctcagga ccgccatgct   1800

cgacttcaga agcctcgaga tgaaatgaca cgtgtgaatt acaggtgacc agctcgaatt   1860

tccccgatag ctttcgttcg tatcatcggt ttcgacaacg ttcgtcaagt tcaatgcatc   1920

agtttcattg cgcacacacc agaatcctac tgagttcgag tattatggca ttgggaaaca   1980

tgtttttctt gtaccatttg ttgtgcttgt aatttactgt gtttttttatt cggttttcgc   2040

tatcgaactg tgaaatggaa atggatggag aagagttaat gaatgatatg gtccttttgt   2100

tcattctcaa attaatatta tttgtttttt ctcttatttg ttgtgtgttg aatttgaaaa   2160

tataagagat atgcaaacat tttgttttga gtaaaaatgt gtcaaatcgt ggcctctaat   2220

gaccgaagtt aatatgagga gtaaaacact tgtagttgta ccattatgct tattcactag   2280

gcaacaaata tattttcaga cctagaaaag ctgcaaatgt tactgaatac aagtatgtcc   2340

tcttgtgttt tagacattta tgaactttcc tttatgtaat tttccagaat ccttgtcaga   2400

ttctaatcat tgctttataa ttatagttat actcatggat ttgtagttga gtatgaaaat   2460

attttttaat gcattttatg acttg                                          2485
```

<210> SEQ ID NO 67
<211> LENGTH: 2485
<212> TYPE: DNA
<213> ORGANISM: Artificial
<220> FEATURE:
<223> OTHER INFORMATION: Construct No. 011

<400> SEQUENCE: 67

```
atactgaaca ttatgttgca taacatgtag ataaggacac gaaaacatag aaagtttctc     60

agttatattt acccatcaac atgaaataaa aaacaacaaa gatgtcatag tgatgtttgt    120

ttcaacttac caagggtgac catgtcgtat ttataataat attatatatt tatatcgtca    180

atagaatatt agtgttacgg tgatatttta gcacaccgat tttttatatc atactgatgt    240

ttatcgtttt gtatctatat tttatatttg ttttataata atattagata tttatttcgt    300

caatagaata ttaatgttat gatgatactt tactatattg attttacata tgatagtgat    360
```

```
gttactcctt ccgtatctat attttatatt agtttttatc tcctggcaac acggtcacaa    420
cagaagagaa gtttttcaga ccgattccag gatcgatttt tttttatat ctgggctaag     480
acatcaggta gagattgttt aacctttgcg gctttccgca ctgacggacc cacccccacc    540
gcatcaacgg aacctaccaa ccacccccgt gctccgaccc cccatctgcc cgtcttccag    600
gttacgcccc gcgcggccgc gcgcgcggaa gctgtatcac cccacccgtc gacgtcgtct    660
tcgcttcgaa accccgcaaa accccgcgga aaaaacccac ctgctgcacg cacgcacccc    720
ctccctctcc ctccccatgg cgcctcccct cacccaactc tttgcttcca ttctttccat    780
ccacccgcca atgcgacgcc gacgccgcaa ctccacccac cgcctgccag cgccacctca    840
ccgcaccgct tccatcaccc cgcgatcatg ggctaccgct atatcaccac gcctccaacc    900
tccggcacgc ttagcctctc tctcccattc tctcacaccc aacacccagc tatcacaccc    960
tgatccccga ggccgcgcgt cggggtgagg aggaggggcc atggggaggt cgccgtgctg   1020
cgagaaggcg cacaccaaca agggcgcgtg gaccaaggag gaggacgagc gcctggtcgc   1080
gcacatcagg gcgcacggcg aggggtgctg gcgctcgctg cccaaggccg ccggcctcct   1140
gcgctgcggc aagagctgcc gcctccgctg gatcaactac ctccgccccg acctcaagcg   1200
cggcaacttc acggaggaag aggacgagct catcgtcaag ctgcacagcg tcctcggcaa   1260
caagtggtcc ctgatcgccg gaaggctgcc cggcaggacg gacaacgaga tcaagaacta   1320
ctggaacacg cacatccgga ggaagctgct gagcaggggg atcgacccgg tgacgcaccg   1380
cccggtcacg gagcaccacg cgtccaacat caccatatcg ttcgagacgg aagtggccgc   1440
cgctgcccgt gatgataaga agggcgccgt cttccggttg gaggacgagg aggaggagga   1500
gcgcaacaag gcgacgatgg tcgtcggccg cgaccggcag agccagagcc acagccacag   1560
ccaccccgcc ggcgagtggg gccaggggaa gaggccgctc aagtgccccg acctcaacct   1620
ggacctctgc atcagcccgc cgtgccagga ggaggaggag atggaggagg ctgcgatgag   1680
agtgagaccg gcggtgaagc gggaggccgg gctctgcttc ggctgcagcc tggggctccc   1740
caggaccgcg gactgcaagt gcagcagcag cagcttcctc gggctcagga ccgccatgct   1800
cgacttcaga agcctcgaga tgaaatgaca cgtgtgaatt acaggtgacc agctcgaatt   1860
tccccgatag ctttcgttcg tatcatcggt ttcgacaacg ttcgtcaagt tcaatgcatc   1920
agtttcattg cgcacacacc agaatcctac tgagttcgag tattatggca ttgggaaaca   1980
tgtttttctt gtaccatttg ttgtgcttgt aatttactgt gttttttatt cggttttcgc   2040
tatcgaactg tgaaatggaa atggatggag aagagttaat gaatgatatg gtccttttgt   2100
tcattctcaa attaatatta tttgtttttt ctcttatttg ttgtgtgttg aatttgaaaa   2160
tataagagat atgcaaacat tttgttttga gtaaaaatgt gtcaaatcgt ggcctctaat   2220
gaccgaagtt aatatgagga gtaaaacact tgtagttgta ccattatgct tattcactag   2280
gcaacaaata tattttcaga cctagaaaag ctgcaaatgt tactgaatac aagtatgtcc   2340
tcttgtgttt tagacattta tgaactttcc tttatgtaat tttccagaat ccttgtcaga   2400
ttctaatcat tgctttataa ttatagttat actcatggat ttgtagttga gtatgaaaat   2460
attttttaat gcattttatg acttg                                          2485
```

<210> SEQ ID NO 68
<211> LENGTH: 2626
<212> TYPE: DNA
<213> ORGANISM: Artificial
<220> FEATURE:

<223> OTHER INFORMATION: Construct No. 012

<400> SEQUENCE: 68

```
gagttaaatt gatatggttt tgtctgtcaa ggtgccgttt ctatggttgg aggaggaaaa      60
tgaaattagg ggaatagaac agtcgcaatc caaaagctat tgttctctct tctacggtag     120
ttgatagttc gatacgtgtg tttgatgtga gagactgaga ggagtgcacg gtgcacctgc     180
cccgtaagga cgcggaacta cattatcaga ggctaggccg gtactgttat acgcgacgtt     240
cacgaatcac gatgcgtaaa aaagtgaagc atgaaacagt actaggctct ccacgggcca     300
catcatgaaa aaactggtgc gacgccacgc ttaacaattt gtcggtcgta aactcgtaaa     360
gttaaaagcc ccacgacatt gtcaaccaat atctcagcac atgaacttct ctaacgagta     420
caacgaaacc gcatccgcaa aagcgccgtg aaccaaagct cttgccgtgc tgtgccgtgc     480
cggtggccgt gaacatgtgg aacacgaaga actcttgcgc gagatcggag cacctgacct     540
cccacctcgc gtccggcccg tcgccgtcgc agcaagcggg ctgtcaaaaa cgacgccaca     600
gcgcgagcgc tctcgccgat ccggcggacc caccctcctc acctcgcgca ccaaccgccc     660
gttcgctagt ccgatccccc acccctcatc cccccctacgc cttgcaggtt acgcgcctcg     720
ccgcggccaa cgcaaaccaa accaaatccc ccgtcacctt cgcttcgaaa ccccgcaaaa     780
ccccatggaa gaaaacaccg aacacctgcc gcgcgcacgc ctcctcctcc cccgcctctc     840
ctcctctctc ccgttccatg tccgctcaac cttgcttcca ttctttccat ccacccgccg     900
atcgacgcga tgccgacgcc ccaaccccac ccaccgcctg ccagcgccac cccacctcgc     960
gcctctgcgg ctatggctat atcaccatgc ctccaacctc cggtacgctt agcctctctc    1020
tctctccccc tcccattctg cgcattgctc tctgcgcgcg gtcgcgtgct gctgctcgcg    1080
gcgccccgga gcgtctcctt tgggggagag gagaggagag gagaggagag gggggtgagc    1140
catggggagg tcgccgtgct gcgagaaggc gcacaccaac aagggcgcgt ggaccaagga    1200
ggaggacgag cgcctggtcg cgcacatcag ggcgcacggc gaggggtgct ggcgctcgct    1260
gcccaaggcc gccggcctcc tgcgctgcgg caagagctgc cgcctccgct ggatcaacta    1320
cctccgcccc gacctcaagc gcggcaactt cacggaggaa gaggacgagc tcatcgtcaa    1380
gctgcacagc gtcctcggca acaagtggtc cctgatcgcc ggaaggctgc ccggcaggac    1440
ggacaacgag atcaagaact actggaacac gcacatccgg aggaagctgc tgagcagggg    1500
gatcgacccg gtgacgcacc gcccggtcac ggagcaccac gcgtccaaca tcaccatatc    1560
gttcgagacg gaagtggccg ccgctgcccg tgatgataag aagggcgccg tcttccggtt    1620
ggaggacgag gaggaggagg agcgcaacaa ggcgacgatg gtcgtcggcc gcgaccggca    1680
gagccagagc cacagccaca gccaccccgc cggcgagtgg ggccagggga agaggccgct    1740
caagtgcccc gacctcaacc tggacctctg catcagcccg ccgtgccagg aggaggagga    1800
gatggaggag gctgcgatga gagtgagacc ggcggtgaag cgggaggccg ggctctgctt    1860
cggctgcagc ctggggctcc ccaggaccgc ggactgcaag tgcagcagca gcagcttcct    1920
cgggctcagg accgccatgc tcgacttcag aagcctcgag atgaaatgac acgtgtgaat    1980
tacaggtgac cagctcgaat ttccccgata gctttcgttc gtatcatcgg tttcgacaac    2040
gttcgtcaag ttcaatgcat cagtttcatt gcgcacacac cagaatccta ctgagttcga    2100
gtattatggc attgggaaac atgtttttct tgtaccattt gttgtgcttg taatttactg    2160
tgtttttttat tcggttttcg ctatcgaact gtgaaatgga aatggatgga gaagagttaa    2220
tgaatgatat ggtccttttg ttcattctca aattaatatt atttgttttt tctcttattt    2280
```

gttgtgtgtt gaatttgaaa atataagaga tatgcaaaca ttttgttttg agtaaaaatg 2340
tgtcaaatcg tggcctctaa tgaccgaagt taatatgagg agtaaaacac ttgtagttgt 2400
accattatgc ttattcacta ggcaacaaat atattttcag acctagaaaa gctgcaaatg 2460
ttactgaata caagtatgtc ctcttgtgtt ttagacattt atgaactttc ctttatgtaa 2520
ttttccagaa tccttgtcag attctaatca ttgctttata attatagtta tactcatgga 2580
tttgtagttg agtatgaaaa tattttttaa tgcattttat gacttg 2626

<210> SEQ ID NO 69
<211> LENGTH: 2485
<212> TYPE: DNA
<213> ORGANISM: Artificial
<220> FEATURE:
<223> OTHER INFORMATION: Construct No. 013

<400> SEQUENCE: 69
ttcaatgcag gatgacgcca agagggagaa accaagcaga ggtggacggt acaacgtgta 60
agtcaccgca aaacgttgca gcttggatag tggccatcga gtggtgtgcc gataccggcg 120
cctgttcttt acagcctcag ctagtgttgt tgtccgaggc aatttttccg acctattgtg 180
ttgctttcct ctctgatagc ttatggtaaa agatacaaag atgttgagga gtttgtacgc 240
cacttaattt tgctcgtaac atacattgac aatcaagagg agccatggca ttgcgatctg 300
cttacacggc atattcttac tggatggtgt acactactta ccctttttaa tgcaagcatc 360
aatccattgc ttttctcact gcacacctga ttcgtactga aaacgtgaaa cataaaaaaa 420
aacaaaaatc tagctgatgt tggctctcgg ggcctcgagt ctagtttgtc ctagatggct 480
aacctgatat gtgttggtca cgctcacgtt tgaaccgaga aagagtgtgt gtgtgtgtgt 540
gtcggcgtgc tgctacacca gagcctccct gaatcgcaat gcgtgttaac gccagcatcg 600
caggatttca tctcacttga caggttcaga tggccttcct cctaccgtct gccatttata 660
cacgcagtga cttaacgctt acacgagccg gatggcccgg atctcccccc tgcaccatct 720
caccagaaaa acggtgaggc gtcaccgcaa cccacccacc aaacacatcc acgtcccttc 780
accgttggcc ttcgattttg cttcagctgc actacgaccc ctccaacaca tttccctcgc 840
gtctcgttgc gatctcacct tacgacgatc tcgttccagc agcagcagca tcggcagcgg 900
cggcttgctt ccgaagcgag caatgcatgg cgcgcgcggc cgcgtgcgtg cgtgccttgg 960
cttgcgctct aatcaaaccg ggacgcccca actcacggtt atggggaggt cgccgtgctg 1020
cgagaaggcg cacaccaaca agggcgcgtg gaccaaggag gaggacgagc gcctggtcgc 1080
gcacatcagg gcgcacggcg aggggtgctg gcgctcgctg cccaaggccg ccggcctcct 1140
gcgctgcggc aagagctgcc gcctccgctg gatcaactac ctccgccccg acctcaagcg 1200
cggcaacttc acggaggaag aggacgagct catcgtcaag ctgcacagcg tcctcggcaa 1260
caagtggtcc ctgatcgccg gaaggctgcc cggcaggacg gacaacgaga tcaagaacta 1320
ctggaacacg cacatccgga ggaagctgct gagcaggggg atcgacccgg tgacgcaccg 1380
cccggtcacg gagcaccacg cgtccaacat caccatatcg ttcgagacgg aagtggccgc 1440
cgctgcccgt gatgataaga agggcgccgt cttccggttg gaggacgagg aggaggagga 1500
gcgcaacaag gcgacgatgg tcgtcggccg cgaccggcag agccagagcc acagccacag 1560
ccaccccgcc ggcgagtggg gccaggggaa gaggccgctc aagtgccccg acctcaacct 1620
ggacctctgc atcagcccgc cgtgccagga ggaggaggag atggaggagg ctgcgatgag 1680

```
agtgagaccg gcggtgaagc gggaggccgg gctctgcttc ggctgcagcc tggggctccc   1740

caggaccgcg gactgcaagt gcagcagcag cagcttcctc gggctcagga ccgccatgct   1800

cgacttcaga agcctcgaga tgaaatgaca cgtgtgaatt acaggtgacc agctcgaatt   1860

tccccgatag ctttcgttcg tatcatcggt ttcgacaacg ttcgtcaagt tcaatgcatc   1920

agtttcattg cgcacacacc agaatcctac tgagttcgag tattatggca ttgggaaaca   1980

tgtttttctt gtaccatttg ttgtgcttgt aatttactgt gttttttatt cggttttcgc   2040

tatcgaactg tgaaatggaa atggatggag aagagttaat gaatgatatg gtccttttgt   2100

tcattctcaa attaatatta tttgtttttt ctcttatttg ttgtgtgttg aatttgaaaa   2160

tataagagat atgcaaacat tttgttttga gtaaaaatgt gtcaaatcgt ggcctctaat   2220

gaccgaagtt aatatgagga gtaaaacact tgtagttgta ccattatgct tattcactag   2280

gcaacaaata tattttcaga cctagaaaag ctgcaaatgt tactgaatac aagtatgtcc   2340

tcttgtgttt tagacattta tgaactttcc tttatgtaat tttccagaat ccttgtcaga   2400

ttctaatcat tgctttataa ttatagttat actcatggat ttgtagttga gtatgaaaat   2460

atttttaat gcattttatg acttg                                          2485
```

<210> SEQ ID NO 70
<211> LENGTH: 2440
<212> TYPE: DNA
<213> ORGANISM: Artificial
<220> FEATURE:
<223> OTHER INFORMATION: Construct No. 014

<400> SEQUENCE: 70

```
aggcggggcc ggaggagggc accagagagg ctgctcagga gagagaaata atagaatatg     60

tggtatagag taaacatgag tgcggatgat tgtggtatag agtaaagaat tttgctgact    120

aggacagaat attcttttta gggtagaaat ttagagtact atgagtgcgg atagcctaag    180

gaccacttta aatttgacac aatattgaaa tttgaatggt tttaacattt gaaggctgaa    240

aaccaaaata ctttgtagct aagtgttgga aacccgactc ggccaataag tcgacagacc    300

gtaaaataag gtcaatctaa actttatgat aaatattctt gtttgatagc aatagcattg    360

caggaccagg acccaaggga agagaagatg ccaaatccca tcgaggctaa agcaaaaacg    420

atccaattta tgagcaaacc cacactgaag tttcaaaatt gttttctgaa aaaaaagtaa    480

ccagcaagtt aaaaaatgag atggcgggaa agccaagtct cggttggtcg aggggttggt    540

tggggcgcag cctgacaagt gacaacggca gcaggatagt agcatcaggc gcaagccagc    600

gcaggcggca gcgcgaggat ttcgcttcac ttagcggcaa cggagacgct gcacccaacc    660

aacacgagct ccccctcacc cgctgcgacg cgcgcgtccc acgagcggaa gcccccgcg     720

ccgacgcgag cgcgggggct cgaccgaccg acccaacgcc tccatctcca ccgcgcgcac    780

caaatcgcac tcccgtccgc cccgccgatc gaacagccac cgctcacctc tcccacccgc    840

caaaaacctc cggcctcctc tcatattcat atagctagcc cctgccacaa ggtagagcgt    900

cgctcacacc tgcgtcgccc tgcctcgcaa tcgcgaatct gtcgagcacc tgaggggtcg    960

gaggccgaga gctagcctag cacgccggcc tccgcgcgcg atggggcggt cgccgtgctg   1020

cgagaaggcg cacaccaaca ggggcgcgtg gaccaaggag gaggacgagc ggctggtggc   1080

ctacgtccgc gcgcacggcg aagggtgctg gcgctcgctg cccagggcgg cgggcctgct   1140

gcgctgcggc aagagctgcc gcctgcgctg gatcaactac ctccgcccgg acctcaagcg   1200

aggcaacttc accgccgacg aggacgacct catcgtcaag ctgcacagcc tcctcgggaa   1260
```

caagtggtcg ctcatcgccg cgcggctccc ggggcggacg gacaacgaga tcaagaacta 1320
ctggaacacg cacatccggc gcaagctgct gggcagcggc atcgaccccg tcacgcaccg 1380
ccgcgtcgcg gggggcgccg cgaccaccat ctcgttccag cccagcccca actccgccgc 1440
cgccgccgcc gccgcagaaa cagcagcgca ggcgccgatc aaggccgagg agacggcggc 1500
cgtcaaggcg cccaggtgcc ccgacctcaa cctggacctc tgcatcagcc cgccgtgcca 1560
gcatgaggac gacggcgagg aggaggacga ggagctggac ctcaagcccg ccttcgtcaa 1620
gcgggaggcg ctgcaggccg gccacggcca cggccacggc ctctgcctcg gctgcggcct 1680
gggcggacag aagggagcgg ccgggtgcag ctgcagcaac ggccaccact tcctggggct 1740
caggaccagc gtgctcgact tcagaggcct ggagatgaag tgacacgtgt gaattacagg 1800
tgaccagctc gaatttcccc gatagctttc gttcgtatca tcggtttcga caacgttcgt 1860
caagttcaat gcatcagttt cattgcgcac acaccagaat cctactgagt tcgagtatta 1920
tggcattggg aaacatgttt ttcttgtacc atttgttgtg cttgtaattt actgtgtttt 1980
ttattcggtt ttcgctatcg aactgtgaaa tggaaatgga tggagaagag ttaatgaatg 2040
atatggtcct tttgttcatt ctcaaattaa tattatttgt tttttctctt atttgttgtg 2100
tgttgaattt gaaaatataa gagatatgca aacattttgt tttgagtaaa aatgtgtcaa 2160
atcgtggcct ctaatgaccg aagttaatat gaggagtaaa acacttgtag ttgtaccatt 2220
atgcttattc actaggcaac aaatatattt tcagacctag aaaagctgca aatgttactg 2280
aatacaagta tgtcctcttg tgttttagac atttatgaac tttcctttat gtaattttcc 2340
agaatccttg tcagattcta atcattgctt tataattata gttatactca tggatttgta 2400
gttgagtatg aaaatatttt ttaatgcatt ttatgacttg 2440

<210> SEQ ID NO 71
<211> LENGTH: 2440
<212> TYPE: DNA
<213> ORGANISM: Artificial
<220> FEATURE:
<223> OTHER INFORMATION: Construct No. 015

<400> SEQUENCE: 71
atactgaaca ttatgttgca taacatgtag ataaggacac gaaaacatag aaagtttctc 60
agttatattt acccatcaac atgaaataaa aaacaacaaa gatgtcatag tgatgtttgt 120
ttcaacttac caagggtgac catgtcgtat ttataataat attatatatt tatatcgtca 180
atagaatatt agtgttacgg tgatatttta gcacaccgat tttttatatc atactgatgt 240
ttatcgtttt gtatctatat tttatatttg ttttataata atattagata tttatttcgt 300
caatagaata ttaatgttat gatgatactt tactatattg attttacata tgatagtgat 360
gttactcctt ccgtatctat attttatatt agtttttatc tcctggcaac acggtcacaa 420
cagaagagaa gtttttcaga ccgattccag gatcgatttt ttttttatat ctgggctaag 480
acatcaggta gagattgttt aacctttgcg gctttccgca ctgacggacc cacccccacc 540
gcatcaacgg aacctaccaa ccacccccgt gctccgaccc cccatctgcc cgtcttccag 600
gttacgcccc gcgcggccgc gcgcgcggaa gctgtatcac ccccacccgtc gacgtcgtct 660 tcgcttcgaa accccgcaaa accccgcgga aaaaacccac ctgctgcacg cacgcacccc 720
ctccctctcc ctccccatgg cgcctcccct cacccaactc tttgcttcca ttctttccat 780
ccacccgcca atgcgacgcc gacgccgcaa ctccacccac cgcctgccag cgccacctca 840

```
ccgcaccgct tccatcaccc cgcgatcatg ggctaccgct atatcaccac gcctccaacc    900

tccggcacgc ttagcctctc tctcccattc tctcacaccc aacacccagc tatcacaccc    960

tgatccccga ggccgcgcgt cggggtgagg aggaggggcc atggggcggt cgccgtgctg   1020

cgagaaggcg cacaccaaca ggggcgcgtg gaccaaggag gaggacgagc ggctggtggc   1080

ctacgtccgc gcgcacggcg aagggtgctg gcgctcgctg cccagggcgg cgggcctgct   1140

gcgctgcggc aagagctgcc gcctgcgctg gatcaactac ctccgcccgg acctcaagcg   1200

aggcaacttc accgccgacg aggacgacct catcgtcaag ctgcacagcc tcctcgggaa   1260

caagtggtcg ctcatcgccg cgcggctccc ggggcggacg gacaacgaga tcaagaacta   1320

ctggaacacg cacatccggc gcaagctgct gggcagcggc atcgaccccg tcacgcaccg   1380

ccgcgtcgcg gggggcgccg cgaccaccat ctcgttccag cccagcccca actccgccgc   1440

cgccgccgcc gccgcagaaa cagcagcgca ggcgccgatc aaggccgagg agacggcggc   1500

cgtcaaggcg cccaggtgcc ccgacctcaa cctggacctc tgcatcagcc cgccgtgcca   1560

gcatgaggac gacggcgagg aggaggacga ggagctggac ctcaagcccg ccttcgtcaa   1620

gcgggaggcg ctgcaggccg gccacggcca cggccacggc ctctgcctcg gctgcggcct   1680

gggcggacag aagggagcgg ccgggtgcag ctgcagcaac ggccaccact tcctggggct   1740

caggaccagc gtgctcgact tcagaggcct ggagatgaag tgacacgtgt gaattacagg   1800

tgaccagctc gaatttcccc gatagctttc gttcgtatca tcggtttcga caacgttcgt   1860

caagttcaat gcatcagttt cattgcgcac acaccagaat cctactgagt tcgagtatta   1920

tggcattggg aaacatgttt ttcttgtacc atttgttgtg cttgtaattt actgtgtttt   1980

ttattcggtt ttcgctatcg aactgtgaaa tggaaatgga tggagaagag ttaatgaatg   2040

atatggtcct tttgttcatt ctcaaattaa tattatttgt tttttctctt atttgttgtg   2100

tgttgaattt gaaaatataa gagatatgca aacattttgt tttgagtaaa aatgtgtcaa   2160

atcgtggcct ctaatgaccg aagttaatat gaggagtaaa acacttgtag ttgtaccatt   2220

atgcttattc actaggcaac aaatatattt tcagacctag aaaagctgca aatgttactg   2280

aatacaagta tgtcctcttg tgttttagac atttatgaac tttcctttat gtaattttcc   2340

agaatccttg tcagattcta atcattgctt tataattata gttatactca tggatttgta   2400

gttgagtatg aaaatatttt ttaatgcatt ttatgacttg                        2440
```

<210> SEQ ID NO 72
<211> LENGTH: 2581
<212> TYPE: DNA
<213> ORGANISM: Artificial
<220> FEATURE:
<223> OTHER INFORMATION: Construct No. 016

<400> SEQUENCE: 72

```
gagttaaatt gatatggttt tgtctgtcaa ggtgccgttt ctatggttgg aggaggaaaa     60

tgaaattagg ggaatagaac agtcgcaatc caaaagctat tgttctctct tctacggtag    120

ttgatagttc gatacgtgtg tttgatgtga gagactgaga ggagtgcacg gtgcacctgc    180

cccgtaagga cgcggaacta cattatcaga ggctaggccg gtactgttat acgcgacgtt    240

cacgaatcac gatgcgtaaa aaagtgaagc atgaaacagt actaggctct ccacgggcca    300

catcatgaaa aaactggtgc gacgccacgc ttaacaattt gtcggtcgta aactcgtaaa    360

gttaaaagcc ccacgacatt gtcaaccaat atctcagcac atgaacttct ctaacgagta    420

caacgaaacc gcatccgcaa aagcgccgtg aaccaaagct cttgccgtgc tgtgccgtgc    480
```

```
cggtggccgt gaacatgtgg aacacgaaga actcttgcgc gagatcggag cacctgacct    540
cccacctcgc gtccggcccg tcgccgtcgc agcaagcggg ctgtcaaaaa cgacgccaca    600
gcgcgagcgc tctcgccgat ccggcggacc caccctcctc acctcgcgca ccaaccgccc    660
gttcgctagt ccgatccccc acccctcatc ccccctacgc cttgcaggtt acgcgcctcg    720
ccgcggccaa cgcaaaccaa accaaatccc ccgtcacctt cgcttcgaaa ccccgcaaaa    780
ccccatggaa gaaaacaccg aacacctgcc gcgcgcacgc ctcctcctcc cccgcctctc    840
ctcctctctc ccgttccatg tccgctcaac cttgcttcca ttctttccat ccacccgccg    900
atcgacgcga tgccgacgcc ccaaccccac ccaccgcctg ccagcgccac cccacctcgc    960
gcctctgcgg ctatggctat atcaccatgc ctccaacctc cggtacgctt agcctctctc   1020
tctctccccc tcccattctg cgcattgctc tctgcgcgcg gtcgcgtgct gctgctcgcg   1080
gcgccccgga gcgtctcctt tgggggagag gagaggagag gagaggagag gggggtgagc   1140
catggggcgg tcgccgtgct gcgagaaggc gcacaccaac aggggcgcgt ggaccaagga   1200
ggaggacgag cggctggtgg cctacgtccg cgcgcacggc gaagggtgct ggcgctcgct   1260
gcccagggcg gcgggcctgc tgcgctgcgg caagagctgc cgcctgcgct ggatcaacta   1320
cctccgcccg gacctcaagc gaggcaactt caccgccgac gaggacgacc tcatcgtcaa   1380
gctgcacagc ctcctcggga acaagtggtc gctcatcgcc gcgcggctcc cggggcggac   1440
ggacaacgag atcaagaact actggaacac gcacatccgg cgcaagctgc tgggcagcgg   1500
catcgacccc gtcacgcacc gccgcgtcgc ggggggcgcc gcgaccacca tctcgttcca   1560
gcccagcccc aactccgccg ccgccgccgc cgccgcagaa acagcagcgc aggcgccgat   1620
caaggccgag gagacggcgg ccgtcaaggc gcccaggtgc cccgacctca acctggacct   1680
ctgcatcagc ccgccgtgcc agcatgagga cgacggcgag gaggaggacg aggagctgga   1740
cctcaagccc gccttcgtca agcgggaggc gctgcaggcc ggccacggcc acggccacgg   1800
cctctgcctc ggctgcggcc tgggcggaca gaagggagcg gccgggtgca gctgcagcaa   1860
cggccaccac ttcctggggc tcaggaccag cgtgctcgac ttcagaggcc tggagatgaa   1920
gtgacacgtg tgaattacag gtgaccagct cgaatttccc cgatagcttt cgttcgtatc   1980
atcggtttcg acaacgttcg tcaagttcaa tgcatcagtt tcattgcgca cacaccagaa   2040
tcctactgag ttcgagtatt atggcattgg gaaacatgtt tttcttgtac catttgttgt   2100
gcttgtaatt tactgtgttt tttattcggt tttcgctatc gaactgtgaa atggaaatgg   2160
atggagaaga gttaatgaat gatatggtcc ttttgttcat tctcaaatta atattatttg   2220
ttttttctct tatttgttgt gtgttgaatt tgaaaatata agagatatgc aaacattttg   2280
ttttgagtaa aaatgtgtca aatcgtggcc tctaatgacc gaagttaata tgaggagtaa   2340
aacacttgta gttgtaccat tatgcttatt cactaggcaa caaatatatt ttcagaccta   2400
gaaaagctgc aaatgttact gaatacaagt atgtcctctt gtgttttaga catttatgaa   2460
ctttccttta tgtaattttc cagaatcctt gtcagattct aatcattgct ttataattat   2520
agttatactc atggatttgt agttgagtat gaaaatattt tttaatgcat tttatgactt   2580
g                                                                    2581
```

<210> SEQ ID NO 73
<211> LENGTH: 2440
<212> TYPE: DNA
<213> ORGANISM: Artificial
<220> FEATURE:

<223> OTHER INFORMATION: Construct No. 017

<400> SEQUENCE: 73

```
ttcaatgcag gatgacgcca agagggagaa accaagcaga ggtggacggt acaacgtgta     60
agtcaccgca aaacgttgca gcttggatag tggccatcga gtggtgtgcc gataccggcg    120
cctgttcttt acagcctcag ctagtgttgt tgtccgaggc aatttttccg acctattgtg    180
ttgctttcct ctctgatagc ttatggtaaa agatacaaag atgttgagga gtttgtacgc    240
cacttaattt tgctcgtaac atacattgac aatcaagagg agccatggca ttgcgatctg    300
cttacacggc atattcttac tggatggtgt acactactta cccttttttaa tgcaagcatc    360
aatccattgc ttttctcact gcacacctga ttcgtactga aaacgtgaaa cataaaaaaa    420
aacaaaaatc tagctgatgt tggctctcgg ggcctcgagt ctagtttgtc ctagatggct    480
aacctgatat gtgttggtca cgctcacgtt tgaaccgaga aagagtgtgt gtgtgtgtgt    540
gtcggcgtgc tgctacacca gagcctccct gaatcgcaat gcgtgttaac gccagcatcg    600
caggatttca tctcacttga caggttcaga tggccttcct cctaccgtct gccatttata    660
cacgcagtga cttaacgctt acacgagccg gatggcccgg atctccccccc tgcaccatct    720
caccagaaaa acggtgaggc gtcaccgcaa cccacccacc aaacacatcc acgtcccttc    780
accgttggcc ttcgattttg cttcagctgc actacgaccc ctccaacaca tttccctcgc    840
gtctcgttgc gatctcacct tacgacgatc tcgttccagc agcagcagca tcggcagcgg    900
cggcttgctt ccgaagcgag caatgcatgg cgcgcgcggc cgcgtgcgtg cgtgccttgg    960
cttgcgctct aatcaaaccg ggacgcccca actcacggtt atggggcggt cgccgtgctg   1020
cgagaaggcg cacaccaaca ggggcgcgtg gaccaaggag gaggacgagc ggctggtggc   1080
ctacgtccgc gcgcacggcg aagggtgctg gcgctcgctg cccagggcgg cgggcctgct   1140
gcgctgcggc aagagctgcc gcctgcgctg gatcaactac ctccgcccgg acctcaagcg   1200
aggcaacttc accgccgacg aggacgacct catcgtcaag ctgcacagcc tcctcgggaa   1260
caagtggtcg ctcatcgccg cgcggctccc ggggcggacg gacaacgaga tcaagaacta   1320
ctggaacacg cacatccggc gcaagctgct gggcagcggc atcgaccccg tcacgcaccg   1380
ccgcgtcgcg gggggcgccg cgaccaccat ctcgttccag cccagcccca actccgccgc   1440
cgccgccgcc gccgcagaaa cagcagcgca ggcgccgatc aaggccgagg agacggcggc   1500
cgtcaaggcg cccaggtgcc ccgacctcaa cctggacctc tgcatcagcc cgccgtgcca   1560
gcatgaggac gacggcgagg aggaggacga ggagctggac ctcaagcccg ccttcgtcaa   1620
gcgggaggcg ctgcaggccg gccacggcca cggccacggc ctctgcctcg gctgcggcct   1680
gggcggacag aagggagcgg ccgggtgcag ctgcagcaac ggccaccact tcctggggct   1740
caggaccagc gtgctcgact tcagaggcct ggagatgaag tgacacgtgt gaattacagg   1800
tgaccagctc gaatttcccc gatagctttc gttcgtatca tcggtttcga caacgttcgt   1860
caagttcaat gcatcagttt cattgcgcac acaccagaat cctactgagt tcgagtatta   1920
tggcattggg aaacatgttt ttcttgtacc atttgttgtg cttgtaattt actgtgtttt   1980
ttattcggtt ttcgctatcg aactgtgaaa tggaaatgga tggagaagag ttaatgaatg   2040
atatggtcct tttgttcatt ctcaaattaa tattatttgt tttttctctt atttgttgtg   2100
tgttgaattt gaaaatataa gagatatgca aacattttgt tttgagtaaa aatgtgtcaa   2160
atcgtggcct ctaatgaccg aagttaatat gaggagtaaa acacttgtag ttgtaccatt   2220
atgcttattc actaggcaac aaatatattt tcagacctag aaaagctgca aatgttactg   2280
```

aatacaagta tgtcctcttg tgttttagac atttatgaac tttcctttat gtaattttcc 2340
agaatccttg tcagattcta atcattgctt tataattata gttatactca tggatttgta 2400
gttgagtatg aaaatatttt ttaatgcatt ttatgacttg 2440

<210> SEQ ID NO 74
<211> LENGTH: 2428
<212> TYPE: DNA
<213> ORGANISM: Artificial
<220> FEATURE:
<223> OTHER INFORMATION: Construct No. 018

<400> SEQUENCE: 74
aggcggggcc ggaggagggc accagagagg ctgctcagga gagagaaata atagaatatg 60
tggtatagag taaacatgag tgcggatgat tgtggtatag agtaaagaat tttgctgact 120
aggacagaat attcttttta gggtagaaat ttagagtact atgagtgcgg atagcctaag 180
gaccacttta aatttgacac aatattgaaa tttgaatggt tttaacattt gaaggctgaa 240
aaccaaaata ctttgtagct aagtgttgga aacccgactc ggccaataag tcgacagacc 300
gtaaaataag gtcaatctaa actttatgat aaatattctt gtttgatagc aatagcattg 360
caggaccagg acccaaggga agagaagatg ccaaatccca tcgaggctaa agcaaaaacg 420
atccaattta tgagcaaacc cacactgaag tttcaaaatt gttttctgaa aaaaaagtaa 480
ccagcaagtt aaaaaatgag atggcgggaa agccaagtct cggttggtcg aggggttggt 540
tggggcgcag cctgacaagt gacaacggca gcaggatagt agcatcaggc gcaagccagc 600
gcaggcggca gcgcgaggat ttcgcttcac ttagcggcaa cggagacgct gcacccaacc 660
aacacgagct ccccctcacc cgctgcgacg cgcgcgtccc acgagcggaa gccccccgcg 720
ccgacgcgag cgcgggggct cgaccgaccg acccaacgcc tccatctcca ccgcgcgcac 780
caaatcgcac tcccgtccgc cccgccgatc gaacagccac cgctcacctc tcccacccgc 840
caaaaacctc cggcctcctc tcatattcat atagctagcc cctgccacaa ggtagagcgt 900
cgctcacacc tgcgtcgccc tgcctcgcaa tcgcgaatct gtcgagcacc tgaggggtcg 960
gaggccgaga gctagcctag cacgccggcc tccgcgcgcg atggggcgat cgccgtgctg 1020
cgagaaggcg cacacgaaca agggcgcctg gaccaaggag gaggacgacc gcctcgttgc 1080
ctacatccgg gcgcacggcg aggggtgctg gcgctccctc cccaaggccg cgggcctgct 1140
gcgctgcggc aagagctgcc gcctgcgctg gatcaactac ctccgcccgg acctcaagcg 1200
cggcaacttc accgccgacg aggacgacct catcgtcaag ctccacagcc tcctcggcaa 1260
caagtggtcg ctcatcgccg cgcgcctccc cggccgcacc gacaacgaga tcaagaacta 1320
ctggaacacg cacatcaagc gcaagctcct cagccgcggc atcgaccccg tcacacaccg 1380
ccccatcgcc gacgcagcca gaaacgtcac catctccttc cagcccgacg cgccgtcgca 1440
gcagcagctc agcgacgacg ccgaggcgcc gccgccgccg ccgccgcagc agcagcagca 1500
gctcaagccg ccgcccaggt gccccgacct caatctcgac ctctgcatca gcccgccctg 1560
ccacaaggaa gaagaggacc aggagctcgt caagcccgcc gccgtcaagc gcgagatgct 1620
gcaggccggc cacggcactc taggactctg cttcggctgc agcctgggcc tccagaaggg 1680
cgccgccggg tgcacctgca gcagcaacag ccacttcctg ggctcaggg tcggcatgct 1740 cctcgacttc agaggcctcg agatgaagtg acacgtgtga attacaggtg accagctcga 1800
atttccccga tagctttcgt tcgtatcatc ggtttcgaca acgttcgtca agttcaatgc 1860

```
atcagtttca ttgcgcacac accagaatcc tactgagttc gagtattatg gcattgggaa   1920

acatgttttt cttgtaccat ttgttgtgct tgtaatttac tgtgtttttt attcggtttt   1980

cgctatcgaa ctgtgaaatg gaaatggatg gagaagagtt aatgaatgat atggtccttt   2040

tgttcattct caaattaata ttatttgttt tttctcttat ttgttgtgtg ttgaatttga   2100

aaatataaga gatatgcaaa cattttgttt tgagtaaaaa tgtgtcaaat cgtggcctct   2160

aatgaccgaa gttaatatga ggagtaaaac acttgtagtt gtaccattat gcttattcac   2220

taggcaacaa atatattttc agacctagaa aagctgcaaa tgttactgaa tacaagtatg   2280

tcctcttgtg ttttagacat ttatgaactt tcctttatgt aattttccag aatccttgtc   2340

agattctaat cattgcttta taattatagt tatactcatg gatttgtagt tgagtatgaa   2400

aatatttttt aatgcatttt atgacttg                                      2428
```

<210> SEQ ID NO 75
<211> LENGTH: 2428
<212> TYPE: DNA
<213> ORGANISM: Artificial
<220> FEATURE:
<223> OTHER INFORMATION: Construct No. 019

<400> SEQUENCE: 75

```
atactgaaca ttatgttgca taacatgtag ataaggacac gaaaacatag aaagtttctc     60

agttatattt acccatcaac atgaaataaa aaacaacaaa gatgtcatag tgatgtttgt    120

ttcaacttac caagggtgac catgtcgtat ttataataat attatatatt tatatcgtca    180

atagaatatt agtgttacgg tgatatttta gcacaccgat tttttatatc atactgatgt    240

ttatcgtttt gtatctatat tttatatttg ttttataaata atattagata tttatttcgt    300

caatagaata ttaatgttat gatgatactt tactatattg attttacata tgatagtgat    360

gttactcctt ccgtatctat attttatatt agtttttatc tcctggcaac acggtcacaa    420

cagaagagaa gtttttcaga ccgattccag gatcgatttt ttttttatat ctgggctaag    480

acatcaggta gagattgttt aacctttgcg gctttccgca ctgacggacc cacccccacc    540

gcatcaacgg aacctaccaa ccacccccgt gctccgaccc cccatctgcc cgtcttccag    600

gttacgcccc gcgcggccgc gcgcgcggaa gctgtatcac cccacccgtc gacgtcgtct    660

tcgcttcgaa accccgcaaa accccgcgga aaaaacccac ctgctgcacg cacgcacccc    720

ctccctctcc ctccccatgg cgcctcccct cacccaactc tttgcttcca ttctttccat    780

ccacccgcca atgcgacgcc gacgccgcaa ctccacccac cgcctgccag cgccacctca    840

ccgcaccgct tccatcaccc cgcgatcatg ggctaccgct atatcaccac gcctccaacc    900

tccggcacgc ttagcctctc tctcccattc tctcacaccc aacacccagc tatcacaccc    960

tgatccccga ggccgcgcgt cggggtgagg aggaggggcc atggggcgat cgccgtgctg   1020

cgagaaggcg cacacgaaca agggcgcctg gaccaaggag gaggacgacc gcctcgttgc   1080

ctacatccgg gcgcacggcg aggggtgctg gcgctccctc cccaaggccg cgggcctgct   1140

gcgctgcggc aagagctgcc gcctgcgctg gatcaactac ctccgcccgg acctcaagcg   1200

cggcaacttc accgccgacg aggacgacct catcgtcaag ctccacagcc tcctcggcaa   1260

caagtggtcg ctcatcgccg cgcgcctccc cggccgcacc gacaacgaga tcaagaacta   1320

ctggaacacg cacatcaagc gcaagctcct cagccgcggc atcgaccccg tcacacaccg   1380

ccccatcgcc gacgcagcca gaaacgtcac catctccttc cagcccgacg cgccgtcgca   1440

gcagcagctc agcgacgacg ccgaggcgcc gccgccgccg ccgccgcagc agcagcagca   1500
```

```
gctcaagccg ccgcccaggt gccccgacct caatctcgac ctctgcatca gcccgccctg   1560

ccacaaggaa gaagaggacc aggagctcgt caagcccgcc gccgtcaagc gcgagatgct   1620

gcaggccggc cacggcactc taggactctg cttcggctgc agcctgggcc tccagaaggg   1680

cgccgccggg tgcacctgca gcagcaacag ccacttcctg ggctcaggg tcggcatgct    1740

cctcgacttc agaggcctcg agatgaagtg acacgtgtga attacaggtg accagctcga   1800

atttccccga tagctttcgt tcgtatcatc ggtttcgaca acgttcgtca agttcaatgc   1860

atcagtttca ttgcgcacac accagaatcc tactgagttc gagtattatg gcattgggaa   1920

acatgttttt cttgtaccat ttgttgtgct tgtaatttac tgtgtttttt attcggtttt   1980

cgctatcgaa ctgtgaaatg gaaatggatg gagaagagtt aatgaatgat atggtccttt   2040

tgttcattct caaattaata ttatttgttt tttctcttat ttgttgtgtg ttgaatttga   2100

aaatataaga gatatgcaaa cattttgttt tgagtaaaaa tgtgtcaaat cgtggcctct   2160

aatgaccgaa gttaatatga ggagtaaaac acttgtagtt gtaccattat gcttattcac   2220

taggcaacaa atatattttc agacctagaa aagctgcaaa tgttactgaa tacaagtatg   2280

tcctcttgtg ttttagacat ttatgaactt tcctttatgt aattttccag aatccttgtc   2340

agattctaat cattgcttta taattatagt tatactcatg gatttgtagt tgagtatgaa   2400

aatatttttt aatgcatttt atgacttg                                      2428
```

<210> SEQ ID NO 76
<211> LENGTH: 2569
<212> TYPE: DNA
<213> ORGANISM: Artificial
<220> FEATURE:
<223> OTHER INFORMATION: Construct No. 020

<400> SEQUENCE: 76

```
gagttaaatt gatatggttt tgtctgtcaa ggtgccgttt ctatggttgg aggaggaaaa     60

tgaaattagg ggaatagaac agtcgcaatc caaaagctat tgttctctct tctacggtag    120

ttgatagttc gatacgtgtg tttgatgtga gagactgaga ggagtgcacg gtgcacctgc    180

cccgtaagga cgcggaacta cattatcaga ggctaggccg gtactgttat acgcgacgtt    240

cacgaatcac gatgcgtaaa aaagtgaagc atgaaacagt actaggctct ccacgggcca    300

catcatgaaa aaactggtgc gacgccacgc ttaacaattt gtcggtcgta aactcgtaaa    360

gttaaaagcc ccacgacatt gtcaaccaat atctcagcac atgaacttct ctaacgagta    420

caacgaaacc gcatccgcaa aagcgccgtg aaccaaagct cttgccgtgc tgtgccgtgc    480

cggtggccgt gaacatgtgg aacacgaaga actcttgcgc gagatcggag cacctgacct    540

cccacctcgc gtccggcccg tcgccgtcgc agcaagcggg ctgtcaaaaa cgacgccaca    600

gcgcgagcgc tctcgccgat ccggcggacc caccctcctc acctcgcgca ccaaccgccc    660

gttcgctagt ccgatccccc acccctcatc cccccctacgc cttgcaggtt acgcgcctcg   720

ccgcggccaa cgcaaaccaa accaaatccc ccgtcacctt cgcttcgaaa ccccgcaaaa    780

ccccatggaa gaaaacaccg aacacctgcc gcgcgcacgc ctcctcctcc cccgcctctc    840

ctcctctctc ccgttccatg tccgctcaac cttgcttcca ttctttccat ccacccgccg    900

atcgacgcga tgccgacgcc ccaaccccac ccaccgcctg ccagcgccac cccacctcgc    960

gcctctgcgg ctatggctat atcaccatgc ctccaacctc cggtacgctt agcctctctc   1020

tctctccccc tcccattctg cgcattgctc tctgcgcgcg gtcgcgtgct gctgctcgcg   1080
```

gcgccccgga gcgtctcctt tgggggagag gagaggagag gagaggagag gggggtgagc 1140
catggggcga tcgccgtgct gcgagaaggc gcacacgaac aagggcgcct ggaccaagga 1200
ggaggacgac cgcctcgttg cctacatccg ggcgcacggc gaggggtgct ggcgctccct 1260
ccccaaggcc gcgggcctgc tgcgctgcgg caagagctgc cgcctgcgct ggatcaacta 1320
cctccgcccg gacctcaagc gcggcaactt caccgccgac gaggacgacc tcatcgtcaa 1380
gctccacagc ctcctcggca acaagtggtc gctcatcgcc gcgcgcctcc ccggccgcac 1440
cgacaacgag atcaagaact actggaacac gcacatcaag cgcaagctcc tcagccgcgg 1500
catcgacccc gtcacacacc gccccatcgc cgacgcagcc agaaacgtca ccatctcctt 1560
ccagcccgac gcgccgtcgc agcagcagct cagcgacgac gccgaggcgc cgccgccgcc 1620
gccgccgcag cagcagcagc agctcaagcc gccgcccagg tgccccgacc tcaatctcga 1680
cctctgcatc agcccgccct gccacaagga agaagaggac caggagctcg tcaagcccgc 1740
cgccgtcaag cgcgagatgc tgcaggccgg ccacggcact ctaggactct gcttcggctg 1800
cagcctgggc ctccagaagg gcgccgccgg gtgcacctgc agcagcaaca gccacttcct 1860
ggggctcagg gtcggcatgc tcctcgactt cagaggcctc gagatgaagt gacacgtgtg 1920
aattacaggt gaccagctcg aatttccccg atagctttcg ttcgtatcat cggtttcgac 1980
aacgttcgtc aagttcaatg catcagtttc attgcgcaca caccagaatc ctactgagtt 2040
cgagtattat ggcattggga aacatgtttt tcttgtacca tttgttgtgc ttgtaattta 2100
ctgtgttttt tattcggttt tcgctatcga actgtgaaat ggaaatggat ggagaagagt 2160
taatgaatga tatggtcctt ttgttcattc tcaaattaat attatttgtt ttttctctta 2220
tttgttgtgt gttgaatttg aaaatataag agatatgcaa acattttgtt ttgagtaaaa 2280
atgtgtcaaa tcgtggcctc taatgaccga agttaatatg aggagtaaaa cacttgtagt 2340
tgtaccatta tgcttattca ctaggcaaca aatatatttt cagacctaga aaagctgcaa 2400
atgttactga atacaagtat gtcctcttgt gttttagaca tttatgaact ttcctttatg 2460
taattttcca gaatccttgt cagattctaa tcattgcttt ataattatag ttatactcat 2520
ggatttgtag ttgagtatga aaatattttt taatgcattt tatgacttg 2569

<210> SEQ ID NO 77
<211> LENGTH: 2428
<212> TYPE: DNA
<213> ORGANISM: Artificial
<220> FEATURE:
<223> OTHER INFORMATION: Construct No. 021

<400> SEQUENCE: 77
ttcaatgcag gatgacgcca agagggagaa accaagcaga ggtggacggt acaacgtgta 60
agtcaccgca aaacgttgca gcttggatag tggccatcga gtggtgtgcc gataccggcg 120
cctgttcttt acagcctcag ctagtgttgt tgtccgaggc aatttttccg acctattgtg 180
ttgctttcct ctctgatagc ttatggtaaa agatacaaag atgttgagga gtttgtacgc 240
cacttaattt tgctcgtaac atacattgac aatcaagagg agccatggca ttgcgatctg 300
cttacacggc atattcttac tggatggtgt acactactta cccttttttaa tgcaagcatc 360 aatccattgc ttttctcact gcacacctga ttcgtactga aaacgtgaaa cataaaaaaa 420
aacaaaaatc tagctgatgt tggctctcgg ggcctcgagt ctagtttgtc ctagatggct 480
aacctgatat gtgttggtca cgctcacgtt tgaaccgaga aagagtgtgt gtgtgtgtgt 540
gtcggcgtgc tgctacacca gagcctccct gaatcgcaat gcgtgttaac gccagcatcg 600

```
caggatttca tctcacttga caggttcaga tggccttcct cctaccgtct gccatttata    660

cacgcagtga cttaacgctt acacgagccg gatggcccgg atctcccccc tgcaccatct    720

caccagaaaa acggtgaggc gtcaccgcaa cccacccacc aaacacatcc acgtcccttc    780

accgttggcc ttcgattttg cttcagctgc actacgaccc ctccaacaca tttccctcgc    840

gtctcgttgc gatctcacct tacgacgatc tcgttccagc agcagcagca tcggcagcgg    900

cggcttgctt ccgaagcgag caatgcatgg cgcgcgcggc cgcgtgcgtg cgtgccttgg    960

cttgcgctct aatcaaaccg ggacgcccca actcacggtt atggggcgat cgccgtgctg   1020

cgagaaggcg cacacgaaca agggcgcctg gaccaaggag gaggacgacc gcctcgttgc   1080

ctacatccgg gcgcacggcg aggggtgctg gcgctccctc cccaaggccg cgggcctgct   1140

gcgctgcggc aagagctgcc gcctgcgctg gatcaactac ctccgcccgg acctcaagcg   1200

cggcaacttc accgccgacg aggacgacct catcgtcaag ctccacagcc tcctcggcaa   1260

caagtggtcg ctcatcgccg cgcgcctccc cggccgcacc gacaacgaga tcaagaacta   1320

ctggaacacg cacatcaagc gcaagctcct cagccgcggc atcgaccccg tcacacaccg   1380

ccccatcgcc gacgcagcca gaaacgtcac catctccttc cagcccgacg cgccgtcgca   1440

gcagcagctc agcgacgacg ccgaggcgcc gccgccgccg ccgccgcagc agcagcagca   1500

gctcaagccg ccgcccaggt gccccgacct caatctcgac ctctgcatca gcccgccctg   1560

ccacaaggaa gaagaggacc aggagctcgt caagcccgcc gccgtcaagc gcgagatgct   1620

gcaggccggc cacggcactc taggactctg cttcggctgc agcctgggcc tccagaaggg   1680

cgccgccggg tgcacctgca gcagcaacag ccacttcctg ggctcaggg  tcggcatgct   1740

cctcgacttc agaggcctcg agatgaagtg acacgtgtga attacaggtg accagctcga   1800

atttccccga tagctttcgt tcgtatcatc ggtttcgaca acgttcgtca agttcaatgc   1860

atcagtttca ttgcgcacac accagaatcc tactgagttc gagtattatg gcattgggaa   1920

acatgttttt cttgtaccat ttgttgtgct tgtaatttac tgtgtttttt attcggtttt   1980

cgctatcgaa ctgtgaaatg gaaatggatg gagaagagtt aatgaatgat atggtccttt   2040

tgttcattct caaattaata ttatttgttt tttctcttat ttgttgtgtg ttgaatttga   2100

aaatataaga gatatgcaaa cattttgttt tgagtaaaaa tgtgtcaaat cgtggcctct   2160

aatgaccgaa gttaatatga ggagtaaaac acttgtagtt gtaccattat gcttattcac   2220

taggcaacaa atatattttc agacctagaa aagctgcaaa tgttactgaa tacaagtatg   2280

tcctcttgtg ttttagacat ttatgaactt tcctttatgt aattttccag aatccttgtc   2340

agattctaat cattgcttta taattatagt tatactcatg gatttgtagt tgagtatgaa   2400

aatatttttt aatgcatttt atgacttg                                      2428
```

<210> SEQ ID NO 78
<211> LENGTH: 2275
<212> TYPE: DNA
<213> ORGANISM: Artificial
<220> FEATURE:
<223> OTHER INFORMATION: Construct No. 022

<400> SEQUENCE: 78

```
aggcggggcc ggaggagggc accagagagg ctgctcagga gagagaaata atagaatatg     60

tggtatagag taaacatgag tgcggatgat tgtggtatag agtaaagaat tttgctgact    120

aggacagaat attcttttta gggtagaaat ttagagtact atgagtgcgg atagcctaag    180
```

```
gaccacttta aatttgacac aatattgaaa tttgaatggt tttaacattt gaaggctgaa    240

aaccaaaata ctttgtagct aagtgttgga aacccgactc ggccaataag tcgacagacc    300

gtaaaataag gtcaatctaa actttatgat aaatattctt gtttgatagc aatagcattg    360

caggaccagg acccaaggga agagaagatg ccaaatccca tcgaggctaa agcaaaaacg    420

atccaattta tgagcaaacc cacactgaag tttcaaaatt gttttctgaa aaaaaagtaa    480

ccagcaagtt aaaaaatgag atggcgggaa agccaagtct cggttggtcg aggggttggt    540

tggggcgcag cctgacaagt gacaacggca gcaggatagt agcatcaggc gcaagccagc    600

gcaggcggca gcgcgaggat ttcgcttcac ttagcggcaa cggagacgct gcacccaacc    660

aacacgagct ccccctcacc cgctgcgacg cgcgcgtccc acgagcggaa gccccccgcg    720

ccgacgcgag cgcgggggct cgaccgaccg acccaacgcc tccatctcca ccgcgcgcac    780

caaatcgcac tcccgtccgc cccgccgatc gaacagccac cgctcacctc tcccacccgc    840

caaaaacctc cggcctcctc tcatattcat atagctagcc cctgccacaa ggtagagcgt    900

cgctcacacc tgcgtcgccc tgcctcgcaa tcgcgaatct gtcgagcacc tgaggggtcg    960

gaggccgaga gctagcctag cacgccggcc tccgcgcgcg atggtacagc caaagaagaa   1020

gtttcgtgga gtcaggcagc ggcactgggg ctcctgggtc tctgagatca gacaccccct   1080

ccttaaaagg agggtgtggc tgggcacctt tgagacggcc gaggaggctg cgcgagccta   1140

cgatgaggct gctgtgctga tgagtggccg caacgccaag accaacttcc ccgtgcagag   1200

gaactccacc ggtgatctcg ccacggccgc agaccaggac gcccgtagca atggcggtag   1260

caggaactcc tccgcgggca acctgtcaca gattctcagt gctaagctcc gcaagtgctg   1320

caaggcgcca tctccgtcct taacctgcct ccgcctcgac cccgagaagt cccacattgg   1380

cgtgtggcaa aagcgcgcag gggcccgtgc tgactccaac tgggtgatga cggtggagct   1440

caacaaagag gtagaaccaa ctgaacctgc agctcagccc acatcaacag caacagcttc   1500

gcaagtgaca atggatgatg aggaaaagat tgcgctgcaa atgatcgagg agttgctgag   1560

caggagcagt ccagcttcac cctcacatgg agagggagag ggtagctttg tcatctgaca   1620

cgtgtgaatt acaggtgacc agctcgaatt tccccgatag ctttcgttcg tatcatcggt   1680

ttcgacaacg ttcgtcaagt tcaatgcatc agtttcattg cgcacacacc agaatcctac   1740

tgagttcgag tattatggca ttgggaaaca tgtttttctt gtaccatttg ttgtgcttgt   1800

aatttactgt gttttttatt cggttttcgc tatcgaactg tgaaatggaa atggatggag   1860

aagagttaat gaatgatatg gtccttttgt tcattctcaa attaatatta tttgtttttt   1920

ctcttatttg ttgtgtgttg aatttgaaaa tataagagat atgcaaacat tttgttttga   1980

gtaaaaatgt gtcaaatcgt ggcctctaat gaccgaagtt aatatgagga gtaaaacact   2040

tgtagttgta ccattatgct tattcactag gcaacaaata tattttcaga cctagaaaag   2100

ctgcaaatgt tactgaatac aagtatgtcc tcttgtgttt tagacattta tgaactttcc   2160

tttatgtaat tttccagaat ccttgtcaga ttctaatcat tgctttataa ttatagttat   2220

actcatggat ttgtagttga gtatgaaaat attttttaat gcattttatg acttg         2275
```

```
<210> SEQ ID NO 79
<211> LENGTH: 2275
<212> TYPE: DNA
<213> ORGANISM: Artificial
<220> FEATURE:
<223> OTHER INFORMATION: Construct No. 023

<400> SEQUENCE: 79
```

```
atactgaaca ttatgttgca taacatgtag ataaggacac gaaaacatag aaagtttctc     60
agttatattt acccatcaac atgaaataaa aaacaacaaa gatgtcatag tgatgtttgt    120
ttcaacttac caagggtgac catgtcgtat ttataataat attatatatt tatatcgtca    180
atagaatatt agtgttacgg tgatatttta gcacaccgat tttttatatc atactgatgt    240
ttatcgtttt gtatctatat tttatatttg ttttataata atattagata tttatttcgt    300
caatagaata ttaatgttat gatgatactt tactatattg attttacata tgatagtgat    360
gttactcctt ccgtatctat attttatatt agtttttatc tcctggcaac acggtcacaa    420
cagaagagaa gtttttcaga ccgattccag gatcgatttt ttttttatat ctgggctaag    480
acatcaggta gagattgttt aacctttgcg gctttccgca ctgacggacc cacccccacc    540
gcatcaacgg aacctaccaa ccacccccgt gctccgaccc cccatctgcc cgtcttccag    600
gttacgcccc gcgcggccgc gcgcgcggaa gctgtatcac cccacccgtc gacgtcgtct    660
tcgcttcgaa accccgcaaa accccgcgga aaaaacccac ctgctgcacg cacgcacccc    720
ctccctctcc ctccccatgg cgcctcccct cacccaactc tttgcttcca ttctttccat    780
ccacccgcca atgcgacgcc gacgccgcaa ctccacccac cgcctgccag cgccacctca    840
ccgcaccgct tccatcaccc cgcgatcatg ggctaccgct atatcaccac gcctccaacc    900
tccggcacgc ttagcctctc tctcccattc tctcacaccc aacacccagc tatcacaccc    960
tgatccccga ggccgcgcgt cggggtgagg aggaggggcc atggtacagc caaagaagaa   1020
gtttcgtgga gtcaggcagc ggcactgggg ctcctgggtc tctgagatca gacacccccct  1080
ccttaaaagg agggtgtggc tgggcacctt tgagacggcc gaggaggctg cgcgagccta   1140
cgatgaggct gctgtgctga tgagtggccg caacgccaag accaacttcc ccgtgcagag   1200
gaactccacc ggtgatctcg ccacggccgc agaccaggac gcccgtagca atggcggtag   1260
caggaactcc tccgcgggca acctgtcaca gattctcagt gctaagctcc gcaagtgctg   1320
caaggcgcca tctccgtcct taacctgcct ccgcctcgac cccgagaagt cccacattgg   1380
cgtgtggcaa aagcgcgcag ggcccgtgc tgactccaac tgggtgatga cggtggagct    1440
caacaaagag gtagaaccaa ctgaacctgc agctcagccc acatcaacag caacagcttc   1500
gcaagtgaca atggatgatg aggaaaagat tgcgctgcaa atgatcgagg agttgctgag   1560
caggagcagt ccagcttcac cctcacatgg agagggagag ggtagctttg tcatctgaca   1620
cgtgtgaatt acaggtgacc agctcgaatt tccccgatag ctttcgttcg tatcatcggt   1680
ttcgacaacg ttcgtcaagt tcaatgcatc agtttcattg cgcacacacc agaatcctac   1740
tgagttcgag tattatggca ttgggaaaca tgtttttctt gtaccatttg ttgtgcttgt   1800
aatttactgt gtttttttatt cggttttcgc tatcgaactg tgaaatggaa atggatggag  1860
aagagttaat gaatgatatg gtccttttgt tcattctcaa attaatatta tttgtttttt   1920
ctcttatttg ttgtgtgttg aatttgaaaa tataagagat atgcaaacat tttgttttga   1980
gtaaaaatgt gtcaaatcgt ggcctctaat gaccgaagtt aatatgagga gtaaaacact   2040
tgtagttgta ccattatgct tattcactag gcaacaaata tattttcaga cctagaaaag   2100
ctgcaaatgt tactgaatac aagtatgtcc tcttgtgttt tagacattta tgaactttcc   2160
tttatgtaat tttccagaat ccttgtcaga ttctaatcat tgctttataa ttatagttat   2220
actcatggat ttgtagttga gtatgaaaat attttttaat gcattttatg acttg        2275
```

<210> SEQ ID NO 80

<211> LENGTH: 2416
<212> TYPE: DNA
<213> ORGANISM: Artificial
<220> FEATURE:
<223> OTHER INFORMATION: Construct No. 024

<400> SEQUENCE: 80

```
gagttaaatt gatatggttt tgtctgtcaa ggtgccgttt ctatggttgg aggaggaaaa     60
tgaaattagg ggaatagaac agtcgcaatc caaaagctat tgttctctct tctacggtag    120
ttgatagttc gatacgtgtg tttgatgtga gagactgaga ggagtgcacg gtgcacctgc    180
cccgtaagga cgcggaacta cattatcaga ggctaggccg gtactgttat acgcgacgtt    240
cacgaatcac gatgcgtaaa aaagtgaagc atgaaacagt actaggctct ccacgggcca    300
catcatgaaa aaactggtgc gacgccacgc ttaacaattt gtcggtcgta aactcgtaaa    360
gttaaaagcc ccacgacatt gtcaaccaat atctcagcac atgaacttct ctaacgagta    420
caacgaaacc gcatccgcaa aagcgccgtg aaccaaagct cttgccgtgc tgtgccgtgc    480
cggtggccgt gaacatgtgg aacacgaaga actcttgcgc gagatcggag cacctgacct    540
cccacctcgc gtccggcccg tcgccgtcgc agcaagcggg ctgtcaaaaa cgacgccaca    600
gcgcgagcgc tctcgccgat ccggcggacc caccctcctc acctcgcgca ccaaccgccc    660
gttcgctagt ccgatccccc acccctcatc cccccctacgc cttgcaggtt acgcgcctcg    720
ccgcggccaa cgcaaaccaa accaaatccc ccgtcacctt cgcttcgaaa ccccgcaaaa    780
ccccatggaa gaaaacaccg aacacctgcc gcgcgcacgc ctcctcctcc cccgcctctc    840
ctcctctctc ccgttccatg tccgctcaac cttgcttcca ttctttccat ccacccgccg    900
atcgacgcga tgccgacgcc ccaaccccac ccaccgcctg ccagcgccac cccacctcgc    960
gcctctgcgg ctatggctat atcaccatgc ctccaacctc cggtacgctt agcctctctc   1020
tctctccccc tcccattctg cgcattgctc tctgcgcgcg gtcgcgtgct gctgctcgcg   1080
gcgccccgga gcgtctcctt tgggggagag gagaggagag gagaggagag gggggtgagc   1140
catggtacag ccaaagaaga agtttcgtgg agtcaggcag cggcactggg gctcctgggt   1200
ctctgagatc agacaccccc tccttaaaag gagggtgtgg ctgggcacct ttgagacggc   1260
cgaggaggct gcgcgagcct acgatgaggc tgctgtgctg atgagtggcc gcaacgccaa   1320
gaccaacttc cccgtgcaga ggaactccac cggtgatctc gccacggccg cagaccagga   1380
cgccccgtagc aatggcggta gcaggaactc ctccgcgggc aacctgtcac agattctcag   1440
tgctaagctc cgcaagtgct gcaaggcgcc atctccgtcc ttaacctgcc tccgcctcga   1500
ccccgagaag tcccacattg gcgtgtggca aaagcgcgca ggggcccgtg ctgactccaa   1560
ctgggtgatg acggtggagc tcaacaaaga ggtagaacca actgaacctg cagctcagcc   1620
cacatcaaca gcaacagctt cgcaagtgac aatggatgat gaggaaaaga ttgcgctgca   1680
aatgatcgag gagttgctga gcaggagcag tccagcttca ccctcacatg gagagggaga   1740
gggtagcttt gtcatctgac acgtgtgaat tacaggtgac cagctcgaat ttccccgata   1800
gctttcgttc gtatcatcgg tttcgacaac gttcgtcaag ttcaatgcat cagtttcatt   1860
gcgcacacac cagaatccta ctgagttcga gtattatggc attgggaaac atgtttttct   1920
tgtaccattt gttgtgcttg taatttactg tgttttttat tcggttttcg ctatcgaact   1980
gtgaaatgga aatggatgga gaagagttaa tgaatgatat ggtccttttg ttcattctca   2040
aattaatatt atttgttttt tctcttattt gttgtgtgtt gaatttgaaa atataagaga   2100
tatgcaaaca ttttgttttg agtaaaaatg tgtcaaatcg tggcctctaa tgaccgaagt   2160
```

taatatgagg agtaaaacac ttgtagttgt accattatgc ttattcacta ggcaacaaat 2220
atattttcag acctagaaaa gctgcaaatg ttactgaata caagtatgtc ctcttgtgtt 2280
ttagacattt atgaactttc ctttatgtaa ttttccagaa tccttgtcag attctaatca 2340
ttgctttata attatagtta tactcatgga tttgtagttg agtatgaaaa tattttttaa 2400
tgcattttat gacttg 2416

<210> SEQ ID NO 81
<211> LENGTH: 2275
<212> TYPE: DNA
<213> ORGANISM: Artificial
<220> FEATURE:
<223> OTHER INFORMATION: Construct No. 025

<400> SEQUENCE: 81
ttcaatgcag gatgacgcca agagggagaa accaagcaga ggtggacggt acaacgtgta 60
agtcaccgca aaacgttgca gcttggatag tggccatcga gtggtgtgcc gataccggcg 120
cctgttcttt acagcctcag ctagtgttgt tgtccgaggc aatttttccg acctattgtg 180
ttgctttcct ctctgatagc ttatggtaaa agatacaaag atgttgagga gtttgtacgc 240
cacttaattt tgctcgtaac atacattgac aatcaagagg agccatggca ttgcgatctg 300
cttacacggc atattcttac tggatggtgt acactactta cccttttaa tgcaagcatc 360 aatccattgc ttttctcact gcacacctga ttcgtactga aaacgtgaaa cataaaaaaa 420
aacaaaaatc tagctgatgt tggctctcgg ggcctcgagt ctagtttgtc ctagatggct 480
aacctgatat gtgttggtca cgctcacgtt tgaaccgaga aagagtgtgt gtgtgtgtgt 540
gtcggcgtgc tgctacacca gagcctccct gaatcgcaat gcgtgttaac gccagcatcg 600
caggatttca tctcacttga caggttcaga tggccttcct cctaccgtct gccatttata 660
cacgcagtga cttaacgctt acacgagccg gatggcccgg atctcccccc tgcaccatct 720
caccagaaaa acggtgaggc gtcaccgcaa cccacccacc aaacacatcc acgtcccttc 780
accgttggcc ttcgattttg cttcagctgc actacgaccc ctccaacaca tttccctcgc 840
gtctcgttgc gatctcacct tacgacgatc tcgttccagc agcagcagca tcggcagcgg 900
cggcttgctt ccgaagcgag caatgcatgg cgcgcgcggc cgcgtgcgtg cgtgccttgg 960
cttgcgctct aatcaaaccg ggacgcccca actcacggtt atggtacagc caaagaagaa 1020
gtttcgtgga gtcaggcagc ggcactgggg ctcctgggtc tctgagatca gacacccccct 1080 ccttaaaagg agggtgtggc tgggcacctt tgagacggcc gaggaggctg cgcgagccta 1140
cgatgaggct gctgtgctga tgagtggccg caacgccaag accaacttcc ccgtgcagag 1200
gaactccacc ggtgatctcg ccacggccgc agaccaggac gcccgtagca atggcggtag 1260
caggaactcc tccgcgggca acctgtcaca gattctcagt gctaagctcc gcaagtgctg 1320
caaggcgcca tctccgtcct taacctgcct ccgcctcgac cccgagaagt cccacattgg 1380
cgtgtggcaa aagcgcgcag gggcccgtgc tgactccaac tgggtgatga cggtggagct 1440
caacaaagag gtagaaccaa ctgaacctgc agctcagccc acatcaacag caacagcttc 1500
gcaagtgaca atggatgatg aggaaaagat tgcgctgcaa atgatcgagg agttgctgag 1560
caggagcagt ccagcttcac cctcacatgg agagggagag ggtagctttg tcatctgaca 1620
cgtgtgaatt acaggtgacc agctcgaatt tccccgatag ctttcgttcg tatcatcggt 1680
ttcgacaacg ttcgtcaagt tcaatgcatc agtttcattg cgcacacacc agaatcctac 1740

-continued

```
tgagttcgag tattatggca ttgggaaaca tgtttttctt gtaccatttg ttgtgcttgt   1800

aatttactgt gtttttttatt cggttttcgc tatcgaactg tgaaatggaa atggatggag   1860

aagagttaat gaatgatatg gtccttttgt tcattctcaa attaatatta tttgtttttt   1920

ctcttatttg ttgtgtgttg aatttgaaaa tataagagat atgcaaacat tttgttttga   1980

gtaaaaatgt gtcaaatcgt ggcctctaat gaccgaagtt aatatgagga gtaaaacact   2040

tgtagttgta ccattatgct tattcactag gcaacaaata tattttcaga cctagaaaag   2100

ctgcaaatgt tactgaatac aagtatgtcc tcttgtgttt tagacattta tgaactttcc   2160

tttatgtaat tttccagaat ccttgtcaga ttctaatcat tgctttataa ttatagttat   2220

actcatggat ttgtagttga gtatgaaaat attttttaat gcattttatg acttg        2275
```